(12) United States Patent
Denny et al.

(10) Patent No.: US 6,943,183 B2
(45) Date of Patent: Sep. 13, 2005

(54) 5-SUBSTITUTED TETRALONES AS INHIBITORS OF RAS FARNESYL TRANSFERASE

(75) Inventors: William Alexander Denny, Auckland (NZ); Richard H. Hutchings, Ann Arbor, MI (US); Douglas S. Johnson, Dexter, MI (US); James Stanley Kaltenbronn, Ann Arbor, MI (US); Ho Huat Lee, Auckland (NZ); Daniele Marie Leonard, Ann Arbor, MI (US); Jared Bruce John Milbank, Dexter, MI (US); Joseph Thomas Repine, Ann Arbor, MI (US); Gordon William Rewcastle, Auckland (NZ); Andrew David White, Pinckney, MI (US)

(73) Assignee: Pfizer Inc, New York, NY (US)

( * ) Notice: Subject to any disclaimer, the term of this patent is extended or adjusted under 35 U.S.C. 154(b) by 0 days.

(21) Appl. No.: 10/257,301

(22) PCT Filed: Apr. 16, 2001

(86) PCT No.: PCT/US01/12490

§ 371 (c)(1),
(2), (4) Date: May 19, 2003

(87) PCT Pub. No.: WO01/79180

PCT Pub. Date: Oct. 25, 2001

(65) Prior Publication Data

US 2004/0044057 A1 Mar. 4, 2004

Related U.S. Application Data

(60) Provisional application No. 60/197,485, filed on Apr. 17, 2000.

(51) Int. Cl.[7] ............... A61K 31/4164; A61K 31/4178; C07D 233/64; C07D 401/06

(52) U.S. Cl. ............... 514/341; 514/397; 514/399; 546/275.1; 546/178; 546/146; 548/315.4; 548/264.2; 548/341.1; 548/315.1; 548/236; 548/312.1; 548/314.7; 544/405

(58) Field of Search ............... 548/315.4, 264.2, 548/341.1, 315.1, 236, 312.1, 314.7; 546/275.1; 514/341, 397, 399

(56) References Cited

U.S. PATENT DOCUMENTS 6,265,422 B1 * 7/2001 Bikker et al. ............... 514/341

FOREIGN PATENT DOCUMENTS

WO WO 98/34921 A1 8/1998

OTHER PUBLICATIONS

PCT International Search Report PCT/US01/12490, Jan. 16, 2002.

* cited by examiner

Primary Examiner—Laura L. Stockton
(74) Attorney, Agent, or Firm—Peter C. Richardson; Garth Butterfield

(57) ABSTRACT

The present invention provides novel 5-substituted tetralones of Formulas I, II, III, and IV and pharmaceutically acceptable salts, esters, amides, and prodrugs thereof, which are useful for treating and preventing uncontrolled or abnormal proliferation of tissues, such as cancer, atherosclerosis, restenosis, and psoriasis. Specifically, the present invention relates to compounds that inhibit the farnesyl transferase enzyme

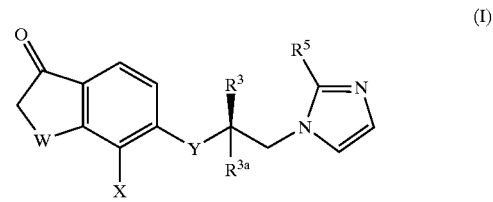

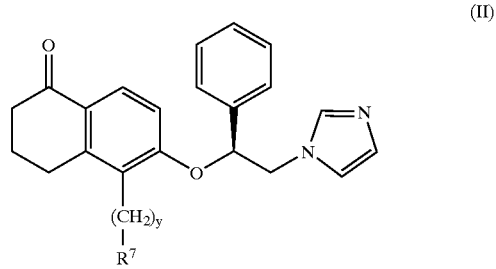

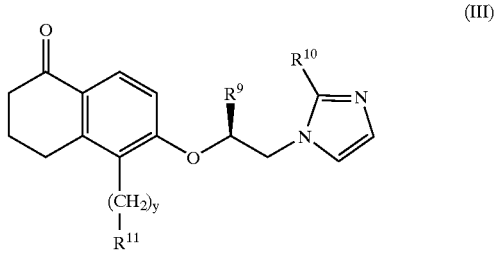

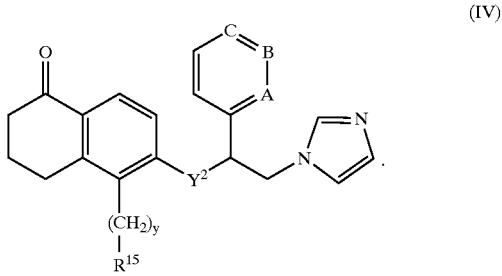

12 Claims, No Drawings

5-SUBSTITUTED TETRALONES AS INHIBITORS OF RAS FARNESYL TRANSFERASE

This application is a 371 application of PCT/US01/12490 filed Apr. 16, 2001, which claims the benefit of priority to U.S. provisional application Ser. No. 60/197,485 filed Apr. 17, 2000.

FIELD OF THE INVENTION

The present invention relates to compounds that can be used to treat, prophylactically or otherwise, uncontrolled or abnormal proliferation of tissues. Specifically, the present invention relates to compounds that inhibit the farnesyl transferase enzyme, which has been determined to activate ras proteins that in turn activate cellular division and are implicated in cancer, restenosis, and atherosclerosis.

SUMMARY OF THE RELATED ART

Ras protein (or p21) has been examined extensively because mutant forms are found in 20% of most types of human cancer and greater than 50% of colon and pancreatic carcinomas (Gibbs J. B., Cell, 1991,65:1, Cartwright T. et al., Chimica. Oggi., 1992;10:26). These mutant ras proteins are deficient in the capability for feedback regulation that is present in native ras, and this deficiency is associated with their oncogenic action since the ability to stimulate normal cell division cannot be controlled by the normal endogenous regulatory cofactors. The recent discovery that the transforming activity of mutant ras is critically dependent on post-translational modifications (Gibbs J. et al., Microbiol. Rev., 1989;53:171) has unveiled an important aspect of ras function and identified novel prospects for cancer therapy.

In addition to cancer, there are other conditions of uncontrolled cellular proliferation that may be related to excessive expression and/or function of native ras proteins. Post-surgical vascular restenosis and atherosclerosis are such conditions. The use of various surgical revascularization techniques such as saphenous vein bypass grafting, endarterectomy, and transluminal coronary angioplasty are often accompanied by complications due to uncontrolled growth of neointimal tissue, known as restenosis. The biochemical causes of restenosis are poorly understood and numerous growth factors and protooncogenes have been implicated (Naftilan A. J. et al., Hypertension, 1989;13:706 and J. Clin. Invest., 1989; 83:1419; Gibbons G. H. et al., Hypertension, 1989;14:358; Satoh T. et al., Molec. Cell. Biol., 1993;13:3706). The fact that ras proteins are known to be involved in cell division processes makes them a candidate for intervention in many situations where cells are dividing uncontrollably. In direct analogy to the inhibition of mutant ras related cancer, blockade of ras dependent processes has the potential to reduce or eliminate the inappropriate tissue proliferation associated with restenosis or atherosclerosis, particularly in those instances where normal ras expression and/or function is exaggerated by growth stimulatory factors. See, for example, Kohl et al., Nature Med., 1995;1(8):792–797.

Ras functioning is dependent upon the modification of the proteins in order to associate with the inner face of plasma membranes. Unlike other membrane-associated proteins, ras proteins lack conventional transmembrane or hydrophobic sequences and are initially synthesized in a cytosol soluble form. Ras protein membrane association is triggered by a series of post-translational processing steps that are signaled by a carboxyl terminal amino acid consensus sequence that is recognized by protein farnesyl transferase (PFT). This consensus sequence consists of a cysteine residue located four amino acids from the carboxyl terminus, followed by two lipophilic amino acids, and the C-terminal residue. The sulfhydryl group of the cysteine residue is alkylated by farnesyl pyrophosphate in a reaction that is catalyzed by protein farnesyl transferase. Following prenylation, the C-terminal three amino acids are cleaved by an endoprotease and the newly exposed alpha-carboxyl group of the prenylated cysteine is methylated by a methyl transferase.

The enzymatic processing of ras proteins that begins with farnesylation enables the protein to associate with the cell membrane. Mutational analysis of oncogenic ras proteins indicate that these post-translational modifications are essential for transforming activity. Replacement of the consensus sequence cysteine residue with other amino acids gives a ras protein that is no longer farnesylated, fails to migrate to the cell membrane, and lacks the ability to stimulate cell proliferation (Hancock J. F. et al., Cell, 1989;57:1617; Schafer W. R. et al., Science, 1989;245:379; Casey P. J., Proc. Natl. Acad. Sci. USA, 1989;86:8323).

Recently, protein farnesyl transferases (PFTs), also referred to as farnesyl protein transferases (FPTs), have been identified and a specific PFT from rat brain is purified to homogeneity (Reiss Y. et al., Bioch. Soc. Trans., 1992;20:487–88). The enzyme is characterized as a heterodimer composed of one alpha-subunit (49 kDa) and one beta-subunit (46 kDa), both of which are required for catalytic activity. High expression levels of mammalian PFT in a baculovirus system and purification of the recombinant enzyme in active form has also been accomplished (Chen W.-J. et al., J. Biol. Chem., 1993;268:9675).

In light of the foregoing, the discovery that the function of oncogenic ras proteins is critically dependent on their post-translational processing provides a means of cancer chemotherapy through inhibition of the processing enzymes. The identification and isolation of a protein farnesyl transferase that catalyzes the addition of a farnesyl group to ras proteins provides a promising target for such intervention. Ras farnesyl transferase inhibitors have been shown to have anticancer activity in several recent articles.

Ras inhibitor agents act by inhibiting farnesyl transferase, the enzyme responsible for the post-translational modification of the ras protein which helps to anchor the protein product of the ras gene to the cell membrane. The role of the ras mutation in transducing growth signals within cancer cells relies on the protein being in the cell membrane. Inhibition of farnesyl transferase will result in the ras protein remaining in the cytosol and, consequently, being unable to transmit growth signals. These facts are well-known in the literature.

A peptidomimetic inhibitor of farnesyl transferase B956 and its methyl ester B1086 at 100 mg/kg have been shown to inhibit tumor growth by EJ-1 human bladder carcinoma, HT1080 human fibrosarcoma, and human colon carcinoma xenografts in nude mice (Nagasu T. et al., Cancer Res., 1995;55:5310–5314). Furthermore, inhibition of tumor growth by B956 has been shown to correlate with inhibition of ras post-translational processing in the tumor. Other ras farnesyl transferase inhibitors have been shown to specifically prevent ras processing and membrane localization and are effective in reversing the transformed phenotype of mutant ras containing cells (Sepp-Lorenzino L. et al., Cancer Res., 1995;55:5302–5309).

In another report (Sun J. et al., Cancer Res., 1995;55:4243–4247), a ras farnesyl transferase inhibitor FTI276 has been shown to selectively block tumor growth in nude mice of a human lung carcinoma with K-ras mutation and p53 deletion. In yet another report, daily administration of a ras farnesyl transferase inhibitor L-744,832 caused tumor regression of mammary and salivary carcinomas in ras transgenic mice (Kohl et al., *Nature Med.*, 1995;1(8) :792–748). Thus, ras farnesyl transferase inhibitors have benefit in certain forms of cancer, particularly those dependent on oncogenic ras for their growth.

It is well-known, however, that human cancer is often manifested when several mutations in important genes occur, one or more of which mutations may be responsible for controlling growth and metastases. A single mutation may not be enough to sustain growth but after the occurrence of only two or three mutations, tumors can develop and grow. It is difficult, therefore, to determine which of these mutations may be primarily driving the growth in a particular type of cancer. Thus, ras farnesyl transferase inhibitors can have therapeutic utility in tumors not solely dependent on oncogenic forms of ras for their growth. For example, it has been shown that various ras FT-inhibitors have antiproliferative effects in vivo against tumor lines with either wild-type or mutant ras (Sepp-Lorenzino, supra.). In addition, there are several ras-related proteins that are prenylated. Proteins such as R-Ras2/TC21 are ras-related proteins that are prenylated in vivo by both farnesyl transferase and geranylgeranyl transferase I (Carboni et al., *Oncogene*, 1995;10: 1905–1913). Therefore, ras farnesyl transferase inhibitors could also block the prenylation of the above proteins and, therefore, would then be useful in inhibiting the growth of tumors driven by other oncogenes.

With regard to the restenosis and vascular proliferative diseases, it has been shown that inhibition of cellular ras prevents smooth muscle proliferation after vascular injury in vivo (Indolfi C. et al., *Nature Med.*, 1995;1(6):541–545). This report definitively supports a role for farnesyl transferase inhibitors in this disease, showing inhibition of accumulation and proliferation of vascular smooth muscle.

SUMMARY OF THE INVENTION

This invention provides certain 5-substituted tetralones of Formulas I, II, III, and IV that are useful for treating and preventing uncontrolled or abnormal proliferation of tissues, such as cancer, atherosclerosis, restenosis, psoriasis, and endometriosis. Specifically, the present invention relates to compounds that inhibit the farnesyl transferase enzyme. The compounds also inhibit amyloidoses, and are thus useful to treat conditions caused by amyloidoses, such as Alzheimer's' disease. The compounds are readily synthesized and can be administered by a variety of routes, including orally and parenterally.

The compounds of Formula I and Formula II are a sub-genus of the genus disclosed in WO 98/34921, which is PCT Application No. PCT/US98/03025. Surprisingly, the 5-substituted tetralones of the present invention have shown unexpected potency as inhibitors of the farnesyl transferase enzyme. Further, substitution at the 4 or, preferably, 5-position has also provided compounds with unexpected potency as farnesyl transferase inhibitors.

The present invention provides a compound of Formula I

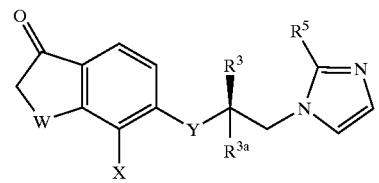

wherein:

W is $CH_2$ or $CH_2CH_2$;

$R^3$ is hydrogen, $C_1$–$C_6$ alkyl, phenyl, or substituted phenyl;

$R^{3a}$ is hydrogen or $C_1$–$C_6$ alkyl;

provided that $R^3$ and $R^{3a}$ cannot both be hydrogen;

further provided that when $R^3$ is phenyl or substituted phenyl that $R^{3a}$ is hydrogen;

X is halogen, amino, $C_1$–$C_6$ alkyl, $C_2$–$C_6$ alkenyl, aryl, substituted aryl, heteroaryl, arylalkyl, substituted arylalkyl, heteroarylalkyl, substituted heteroarylalkyl, —$CH_2OR^6$, —$CH_2NR^6R^{6a}$, —$CH_2SR^6$, or —$CH_2CH_2CO_2R^6$;

$R^6$ is hydrogen, $C_1$–$C_6$ alkyl, $C_2$–$C_6$ alkenyl, phenyl, benzyl, $C_3$–$C_6$ cycloalkyl, or substituted phenyl;

$R^{6a}$ is hydrogen or $C_1$–$C_6$ alkyl;

Y is O or S;

$R^5$ is hydrogen, $C_1$–$C_6$ allyl, or amino; and pharmaceutically acceptable salts, esters, amides, and prodrugs thereof, provided that the compound is not 5-[(Diisobutylamino)-methyl]-6-(imidazol-1-yl-phenyl-ethoxy)-3,4-dihydro-2H-napthalen-1-one;

5-Amino-6-((S)-imidazol-1-ylmethyl-2-methyl-propoxy)-3,4-dihydro-2H-napthalen-1-one;

5-(3,4-Dichloro-phenylsulfanylmethyl)6-((S)-2-imidazol-1-yl-1-phenyl-ethoxy)-3,4-dihydro-2H-napthalen-1-one;

Cyclopentylsulfanylmethyl-6-((S)-2-imidazol-1-yl-1-phenyl-ethoxy)-3,4-dihydro-2H-napthalen-1-one;

6-((S)-2-imidazol-1-yl-1-phenyl-ethoxy)-5-(isopropylamino-methyl)-3,4-dihydro-2H-napthalen-1-one;

5-Biphenyl-3-yl-6-((S)-2-imidazol-1-yl-1-phenyl-ethoxy)-3,4-dihydro-2H-napthalen-1-one;

6-((S)-2-Imidazol-1-yl-1-phenyl-ethoxy)-5-phenyl-3,4-dihydro-2H-napthalen-1-one;

6-((1S)-2-Imidazolyl-1-phenylethoxy)-5-prop-2-enyl-2,3,4-trihydronaphthalen-1-one; or 5-Bromo-6-(2-imidazol-1-yl-phenyl-ethoxy)-3,4-dihydro-2H-napthalen-1-one.

The present invention also provides a compound of Formula II:

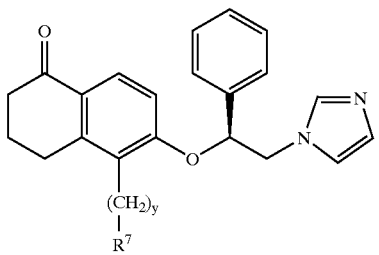

wherein:
y is 0, 1, 2, or 3;
R⁷ is $C_1$–$C_6$ alkyl, $C_2$–$C_6$ alkenyl, alkoxy, —O—($C_3$–$C_6$) cycloalkyl, —O—($C_2$–$C_6$)alkenyl, halogen, —$NH_2$, —$CO_2H$, —$CO_2$-alkyl, —O-phenyl, —O-substituted phenyl, —O-benzyl, —S—($C_1$–$C_6$)alkyl, —S—($C_3$–$C_6$)cycloalkyl, —S-phenyl, —S-substituted phenyl, —NH-phenyl, —NH-substituted phenyl, aryl, substituted aryl, heteroaryl, or substituted heteroaryl;
provided that when R⁷ is —$NH_2$ that y is 0;
further provided that when R⁷ is phenyl that y cannot be 0; and
pharmaceutically acceptable salts, esters, amides, and prodrugs thereof, provided that the compound is not
5-Bromo-6-(2-imidazol-1-yl-phenyl-ethoxy)-3,4-dihydro-2H-napthalen-1-one;
5-(3,4-Dichloro-phenylsulfanylmethyl)6-((S)-2-imidazol-1-yl-1-phenyl-ethoxy)-3,4-dihydro-2H-napthalen-1-one
Cyclopentylsulfanylmethyl-6-((S)-2-imidazol-1-yl-1-phenyl-ethoxy)-3,4-dihydro-2H-napthalen-1-one
5-Biphenyl-3-yl-6-((S)-2-imidazol-1-yl-1-phenyl-ethoxy)-3,4-dihydro-2H-napthalen-1-one; or
6-((1S)-2-Imidazolyl-1-phenylethoxy)-5-prop-2-enyl-2,3,4-trihydronaphthalen-1-one.

Additionally, the present invention provides a compound of Formula III:

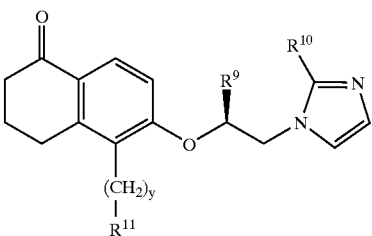

wherein:
R⁹ is phenyl, substituted phenyl, heteroaryl, or $C_1$–$C_6$ alkyl;
R¹⁰ is hydrogen, $C_1$–$C_6$ alkyl, or $C_1$–$C_6$ substituted alkyl;
y is 0, 1, 2, or 3;
R¹¹ is —O-substituted alkyl, —O-aryl, —O-substituted aryl, —O-aryl-heteroaryl, —O-heteroaryl, —O-substituted heteroaryl, —O-phenyl-O—$CF_3$, —O-phenyl-O-phenyl, —S-aryl, —S-substituted aryl, —S-arylalkyl, —S(O)z-substituted alkyl, —S(O)z-substituted arylalkyl, —S(O)z-heteroaryl, —S(O)z-heteroarylalkyl, —S(O)z-substituted heteroaryl, —SO-alkyl, —$SO_2$-alkyl, —SO-aryl, —$SO_2$-aryl, —SO-substituted aryl, —$SO_2$-substituted aryl, —SO-arylalkyl, —$SO_2$-arylalkyl, —S(O)z-phenyl-CONH—R¹³, —$NHSO_2$—R¹⁴, —NHCO—R¹⁴, NHCO-heteroaryl-O-aryl, NHCO-heteroaryl-substituted aryl, NHCOC(substituted alkyl)$NHCO_2$-alkyl, —NHCO—C(substituted alkyl)amino, —$NHCO_2$-alkyl, —NH-aryl, —NH-substituted aryl, —NH-heteroaryl, —NH—($CH_2$)$_2$—O-heteroaryl, —N(CO-alkyl) substituted aryl, -aryl-CO-alkyl,

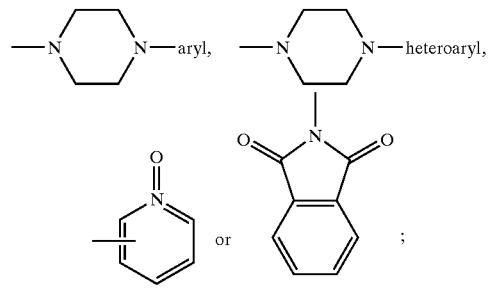

z is 0, 1 or 2;
R¹³ is alkyl, substituted alkyl, alkenyl, alkynyl, cycloalkyl, or heteroarylalkyl;
R14 is aryl, substituted aryl, arylalkyl, heteroaryl, heteroarylalkyl, or substituted heteroaryl; provided that when R¹¹ is —O-aryl, —O-substituted aryl, —S-aryl, —S-arylalkyl, S-substituted aryl, —NH-aryl, or —NH-substituted aryl that the aryl is not phenyl; and
pharmaceutically acceptable salts, esters, amides, and prodrugs thereof.

Furthermore, the present invention provides a compound of the Formula IV:

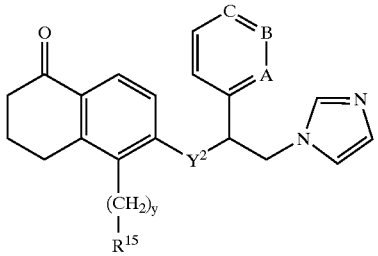

wherein:
y is 0, 1, 2, or 3;
R¹⁵ is lower alkyl, lower alkenyl, alkoxy, substituted alkoxy, arylalkoxy, —O-cycloalkyl, —O-alkenyl, alkylthio, hydroxy, thiol, cyano, halogen, —$CF_3$, —$NO_2$, —$NH_2$, —NH-alkyl, —NH-dialkyl, —NHCO-alkyl, —$CO_2H$, —$CO_2$-alkyl, —$SO_3H$, —O-aryl, —O-substituted aryl, —O-heteroaryl, —O-substituted heteroaryl, —S-alkyl, —S-substituted alkyl, —S-cycloalkyl, —S-aryl, —S-substituted aryl, —S-heteroaryl, —S-substituted heteroaryl, —$SO_2NH_2$, —$SO_2$NH-alkyl, —SO-aryl, —$SO_2$-aryl, —$SO_2$-substituted aryl, —$SO_2$-alkyl, —$SO_2$-heteroaryl, —$SO_2$-substituted heteroaryl, —$NHSO_2$-aryl, —NHCO-aryl, —NHCO-heteroaryl, —$NHCO_2$-alkyl, —NH-aryl, —NH-substituted aryl, aryl, substituted aryl, heteroaryl, and substituted, heteroaryl;
Y² is NR⁶, O, S, or $CR^{17}R^{17a}$;
R¹⁶ is hydrogen, lower alkyl, aryl, arylalkyl, heteroaryl, or cycloalkyl;

$R^{17}$ and $R^{17a}$ are each independently hydrogen, lower alkyl, lower alkenyl, cycloalkyl, aryl, substituted aryl, arylalkyl, substituted arylalkyl, heteroaryl, substituted heteroaryl, heteroarylalkyl, substituted heteroarylalkyl, heterocycloalkyl, substituted heterocycloalkyl, heterocyclalkylalkyl, substituted heterocycloalkylalkyl, halogen, trifluoromethyl, —$OR^{19}$, —$NR^{19}R^{19a}$, $NHSO_2R^{19}$, —$S(O)_zR^{19}$, —$SO_2NHR^{19}$, —$OCOR^{19}$, —$CH_2OR^{19}$, —$CH_2NR^{19}R^{19a}$, —$CH_2S(O)_zR^{19}$, —$CH_2NHSO_2R^{19}$, —$CH_2S(O)_zR^{19}$, —$CH_2SO_2NHR^{19}$, or —$CH_2OCOR^{19}$;

$R^{19}$ and $R^{19a}$ are each independently hydrogen, lower alkyl, aryl, arylalkyl, heteroaryl, or cycloalkyl;

provided that one of A, B, and C is N while the other two are CH; and pharmaceutically acceptable salts, esters, amides, and prodrugs thereof.

The present invention also provides a pharmaceutically acceptable composition that comprises a compound of Formulas I–IV and a pharmaceutically acceptable carrier.

The present invention also provides a method of treating or preventing restenosis, the method comprising administering to a patient having restenosis or at risk of having restenosis a therapeutically effective amount of a compound of Formulas I–IV.

The present invention also provides a method of treating cancer, the method comprising administering to a patient having cancer a therapeutically effective amount of a compound of Formulas I–IV. In a preferred embodiment of the method of treating cancer, the cancer is lung, colon, pancreatic, thyroid, or bladder cancer.

The present invention also provides a method of treating atherosclerosis, the method comprising administering to a patient having atherosclerosis a therapeutically effective amount of a compound of Formulas I–IV.

Also provided is a method of treating or preventing restenosis or atherosclerosis or treating cancer, the method of comprising administering to a patient having restenosis or atherosclerosis, or at risk of having restenosis or atherosclerosis, or having cancer a therapeutically effective amount of a compound of Formulas I–IV.

The present invention also provides a method of treating neurofibromin benign proliferative disorder, blindness related to retinal vascularization, hepatitis delta and related viruses, psoriasis, benign prostatic hypertrophy and polycystic kidney disease, the method comprising administering to a patient having such a condition a therapeutically effective amount of a compound of Formulas I–IV.

In addition, the present invention provides the use of a compound of Formulas I–IV, or a pharmaceutically acceptable salt thereof for the manufacture of a medicament for treating or preventing any of the diseases or disease states mentioned above.

Furthermore, the present invention provides the use of a compound of Formulas I–IV, or a pharmaceutically acceptable salt thereof for treating or preventing any of the diseases or disease states mentioned above.

DETAILED DESCRIPTION OF THE INVENTION

The novel compounds encompassed by the instant invention are those described by the general Formulas I–IV set forth above, and the pharmaceutically acceptable salts, esters, amides, and prodrugs thereof.

In addition to the compounds of Formulas I–IV, the present invention encompasses compounds of Formula V–VIII. The present invention provides compounds of Formula V:

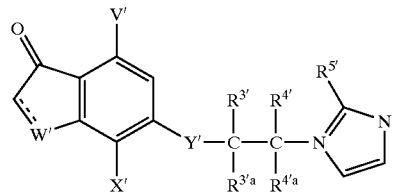

wherein:

- - - is a bond or absent;

W is $NR^{1'}$, $CR^{1'}R^{1'a}$, $CR^{1'}R^{1'a}CR^{2'}R^{2'a}$, $CR^{1'}R^{1'a}NR^{2'}$ or $CR^{1'}R^{1'a}O$;

$R^{1'}$, $R^{1'a}$, $R^{2'}$ and $R^{2'a}$ independently represent hydrogen, lower alkyl, lower alkenyl, cycloalkyl, aryl, substituted aryl, arylalkyl, substituted arylalkyl, heteroaryl, substituted heteroaryl, heteroarylalkyl, substituted heteroarylalkyl, heterocycloalkyl, substituted heterocycloalkyl, heterocycloalkylalkyl, substituted heterocycloalkylalkyl, halogen, trifluoromethyl, —$OR^{6'}$, —$NR^{6'}R^{6'a}$, $NHSO_2R^{6'}$, —$S(O)_zR^{6'}$, —$SO_2NHR^{6'}$, —$OCOR^{6'}$, —$CH_2OR^{6'}$, —$CH_2NR^{6'}R^{6'a}$, —$CH_2S(O)_zR^{6'}$, —$CH_2NHSO_2R^{6'}$, —$CH_2S(O)_zR^{6'}$, —$CH_2SO_2NHR^{6'}$, or —$CH_2OCOR^{6'}$;

z' is 0, 1, or 2;

V' is hydrogen, halogen, lower alkyl, $C_1$–$C_6$ lower alkoxy, hydroxy, amino or nitro;

$R^{3'}$, $R^{3'a}$, $R^{4'}$, and $R^{4'a}$ independently are hydrogen, halogen, lower alkyl, lower alkenyl, aryl, substituted aryl, heteroaryl, substituted heteroaryl, arylalkyl, substituted arylalkyl, heterocycloalkyl, substituted heterocycloalkyl, heterocycloalkylalkyl, substituted heterocycloalkylalkyl, heteroarylalkyl, or substituted heteroarylalkyl;

X' is hydrogen, halogen, amino, substituted amino, lower alkyl, substituted lower alkyl, lower alkenyl, cycloalkyl, substituted cycloalkyl, aryl, substituted aryl, heteroaryl, substituted heteroaryl, arylalkyl, substituted arylalkyl, heterocycloalkyl, substituted heterocycloalkyl, heterocycloalkylalkyl, substituted heterocycloalkylalkyl, heteroarylalkyl, substituted heteroarylalkyl, —$OR^{6'}$, —$NR^{6'}R^{6'a}$, $NHSO_2R^{6'}$, —$S(O)_zR^{6'}$, —$SO_2NHR^{6'}$,

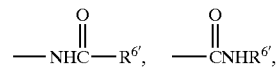

—$OCOR^{6'}$, —$CH_2OR^{6'}$, —$CH_2NR^{6'}R^{6'a}$, —$CH_2S(O)_zR^{6'}$, —$CH_2NHSO_2R^{6'}$, —$CH_2S(O)_zR^{6'}$, —$CH_2SO_2NHR^{6'}$, or —$CH_2OCOR^{6'}$;

$R^{6'}$ and $R^{6'a}$ independently represent hydrogen, lower alkyl, aryl, arylalkyl, heteroaryl or cycloalkyl;

Y' is $NR^{6'}$, O, S, or $CR^{1'}R^{1'a}$; and $R^{5'}$ is hydrogen, lower alkyl or substituted lower alkyl.

In addition to the compounds of Formula V, the invention encompasses compounds of Formula VI:

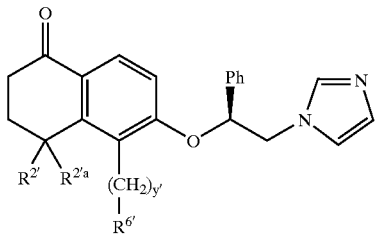

VI wherein $R^{2'}$ and $R^{2'a}$ are independently hydrogen or fluorine; y' is 0, 1, 2, or 3; and $R^{7'}$ is lower alkyl, lower alkenyl, alkoxy, substituted alkoxy, arylalkoxy, —O-cycloalkyl, —O-alkenyl, alkylthio, hydroxy, thiol, cyano, halogen, —$CF_3$, —$NO_2$, —NH-alkyl, —NH-dialkyl, —NHCO-alkyl, —$CO_2H$, —$CO_2$-alkyl, —$SO_3H$, —O-aryl, —O-substituted aryl, —O-heteroaryl, —O-substituted heteroaryl, —S-alkyl, —S-substituted alkyl, —S-cycloalkyl, —S-aryl, —S-substituted aryl, —S-heteroaryl, —S-substituted heteroaryl, —$SO_2NH_2$, —$SO_2NH$-alkyl, —SO-aryl, —$SO_2$-aryl, —$SO_2$-substituted aryl, —$SO_2$-alkyl, —$SO_2$-heteroaryl, —$SO_2$-substituted heteroaryl, $NHSO_2$-aryl, —NHCO-aryl, —NHCO-heteroaryl, —$NHCO_2$-alkyl, —NH-aryl, —NH-substituted aryl, aryl, substituted aryl, heteroaryl, and substituted heteroaryl.

Preferred compounds of Formula VI are those where y' is 0, 1, or 2.

The invention also encompasses compounds of Formula VII:

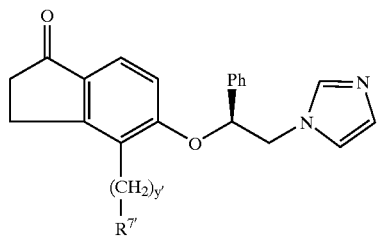

VII wherein y' and $R^{7'}$ are as defined above for Formula VI.

Preferred compounds of Formula VII are those where y' is 1 or 2, and $R^{7'}$ is lower aryl or heteroaryl.

The invention further encompasses compounds of the Formula VIII:

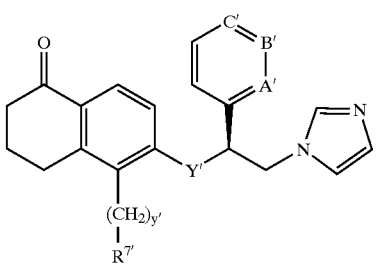

VIII wherein Y' is as defined above for Formula V; y' and $R^{7'}$ are as defined above for Formula VI; and one of A', B', and C' is N while the other two are CH.

Preferred compounds of Formula VIII are those where Y' is O or S, y' is 1 or 2, and $R^{7'}$ is lower alkyl, aryl or lower alkenyl.

The terms "alkyl," "lower alkyl," or "($C_1$–$C_{10}$)-alkyl" mean a straight or branched hydrocarbon having from 1 to 10 carbon atoms and includes, for example, methyl, ethyl, n-propyl, isopropyl, n-butyl, sec-butyl, isobutyl, tert-butyl, n-pentyl, n-hexyl, and the like. The alkyl group can also be substituted (and thus may be referred to as "substituted alkyl") with one or more of the substituents listed below for aryl. The term "($C_1$–$C_{10}$)-alkyl" includes within its definition the term "$C_1$–$C_6$ alkyl".

The term "cycloalkyl" or "($C_3$–$C_7$)-cycloalkyl" means a saturated hydrocarbon ring which contains from 3 to 7 carbon atoms, for example, cyclopropyl, cyclobutyl, cyclopentyl, cyclohexyl, adamantyl, and the like. The term "($C_3$–$C_7$)-cycloalkyl" includes within its definition the term "$C_3$–$C_6$ cycloalkyl".

By "alkoxy," "lower alkoxy," or "($C_1$–$C_{10}$)-alkoxy" in the present invention is meant straight or branched chain alkoxy groups having 1–10 carbon atoms, such as, for example, methoxy, ethoxy, propoxy, isopropoxy, n-butoxy, sec-butoxy, tertbutoxy, pentoxy, isopentoxy, neopentoxy, hexoxy, 2-hexoxy, 3-hexoxy, and 3-methylpentoxy. The alkoxy group can also be substituted (and thus may be referred to as "substituted alkoxy") with one or more of the substituents listed below for aryl.

The term "alkenyl," "lower alkenyl," or "($C_2$–$C_{10}$)-alkenyl" means a straight or branched hydrocarbon radical having from 1–10 carbon atoms and 1–2 double bonds and includes, for example, allyl, 3-methyl-but-2-enyl, 2-methyl-but-2-enyl, geranyl, and the like. The term "($C_2$–$C_{10}$)-alkenyl" includes within its definition the term "$C_2$–$C_6$ alkenyl".

The term "alkynyl" or "lower alkynyl" means a straight or branched hydrocarbon radical having from 2–10 carbon atoms and at least one triple bond and includes, for example, acetylene.

The term "aryl" means an unsubstituted aromatic carbocyclic group having a single ring (e.g., phenyl), multiple rings (e.g., biphenyl), or multiple condensed rings in which at least one is aromatic (e.g., 1,2,3,4-tetrahydronaphenyl, naphenyl, anthryl, or phenanthryl). The term "substituted aryl" means an aryl substituted by 1 to 4 substituents selected from alkyl, —O-alkyl, —S-alkyl, —OH, —SH, —CN, carboxy, guanidino, halogen, 1,3-dioxolanyl, —$CF_3$, —$NO_2$, —$(CH_2)_m$—NHCO-alkyl, —$(CH_2)_m$—N(alkyl)CO-alkyl —$CONH_2$, —CON-dialkyl-$SO_3H$, —$(CH_2)_mCO_2H$, —$(CH_2)_mCO_2$-alkyl, —$(CH_2)_mSO_3H$, —$(CH_2)_mNH_2$, —$(CH_2)_m$NH-alkyl, —$(CH_2)_m$—N-dialkyl, —$(CH_2)_mPO_3H_2$, —$(CH_2)_mPO_3$(alkyl)$_2$, —$(CH_2)_mSO_2NH_2$, —$(CH_2)_mSO_2NH$-alkyl wherein alkyl is defined as above and m is 0, 1, 2, 3, 4 or 5, and

The term "arylalkyl" means an alkyl moiety (as defined above) substituted with an aryl moiety (also as defined above). The term "substituted arylalkyl" means an arylalkyl moiety substituted by 1 to 3 substitutents selected from the group as defined above for "substituted aryl."

By halogen in the present invention is meant fluorine, bromine, chlorine, and iodine.

By heteroaryl (aromatic heterocycle) in the present invention is meant one or more aromatic ring systems of 5-, 6-, or 7-membered rings containing at least one and up to four hetero atoms selected from nitrogen, oxygen, or sulfur. Such heteroaryl groups include, for example, thienyl, furanyl, thiazolyl, imidazolyl, (is)oxazolyl, pyridyl, pyrimidinyl, (iso)quinolinyl, naphthyridinyl, benzimidazolyl, and benzoxazolyl. The term "substituted heteroaryl" means a heteroaryl substituted by 1 to 3 substituents selected from the group as found above for "substituted aryl".

The term "heteroarylalkyl" means an alkyl moiety (as defined above) substituted with an heteroaryl moiety (also as defined above). The term "substituted heteroarylalkyl means a heteroarylalkyl substituted by 1 to 3 substituents selected from the group as defined above for "substituted aryl."

The symbol "–" means a bond.

The following abbreviations are used in the application.

| | |
|---|---|
| HPLC | High pressure liquid chromatography |
| CI-MS | Chemical Ionization Mass Spectrometry |
| mp | Melting point |
| RT | Room temperature |
| THF | Tetrahydrofuran |
| APCI-MS | Atmospheric pressure chemical ionization mass spectrometry |
| dec | Decomposes |
| HOAc | Acetic acid |
| CDI | Carbonyl diimidazole |
| $CHCl_3$ | Chloroform |
| DCM | Dichloromethane |
| DEAD | Diethyl azodiacarboxylate |
| DMAP | 4-dimethylaminopyridine |
| DMF | N,N'-Dimethylformamide |
| DMSO | dimethyl sulfoxide |
| EtOAc | Ethyl acetate |
| EtOH | Ethanol |
| $Et_2O$ | Diethyl ether |
| $Et_3N$ | Triethylamine |
| HATU | O-(7-Azabenzotriazol-1-yl)-N,N,N',N'-tetramethyluronium hexafluorophosphate |
| HCl | Hydrochloric acid |
| $H_2O_2$ | Hydrogen peroxide |
| $H_2SO_4$ | Sulfuric acid |
| KOH | Potassium hydroxide |
| mCPBA | m-chloroperoxybenzoic acid |
| MeCN | Acetonitrile |
| MeOH | Methanol |
| NaH | Sodium hydride |
| NaOH | Sodium hydroxide |
| $NaHCO_3$ | Sodium bicarbonate |
| NBS | N-bromosuccinimide |
| iPrOH | iso-Propanol |
| pTSA | p-toluenesulfonic acid |
| TFAA | Trifluoroacetic acid |
| $Tf_2O$ | Trifluoromethanesulfonic anhydride |
| Boc | tertiary Butyloxycarbonyl |
| Ts | Tosylate |
| $Ph_3P$ | Triphenylphosphine |

The term "patient" means all animals, preferably mammals, including humans. Examples of patients include humans, cows, dogs, cats, goats, sheep, and pigs.

The term "treating" for purposes of the present invention refers to prophylaxis or prevention, amelioration or elimination of a named condition once the condition has been established.

A "therapeutically effective amount" is an amount of a compound of the present invention that when administered to a patient ameliorates a symptom of a disease state, such as restenosis, cancer, or atherosclerosis, or prevents a disease, such as restenosis. A therapeutically effective amount of a compound of the present invention can be easily determined by one skilled in the art by administering a quantity of a compound to a patient and observing the result. In addition, those skilled in the art are familiar with identifying patients having the diseases or disease states treated or prevented by a compound of the present invention, such as cancer, restenosis, or atherosclerosis or patients who are at risk of having restenosis.

The term "cancer" includes, but is not limited to, the following cancers: breast, ovary, uterine, fallopian tubes, endometrium, vagina, vulva, cervix, prostate, testis, penis, esophagus, glioblastoma, neuroblastoma, stomach, skin, keratoacanthoma, cutaneous or intraocular melanoma, lung, endocrine system, thyroid gland, parathyroid gland, adrenal gland, sarcoma of soft tissue, epidermoid carcinoma, large cell carcinoma, adenocarcinoma, bone, colon, adenocarcinoma, adenoma, pancreas, adenocarcinoma, thyroid, follicular carcinoma, undifferentiated carcinoma, papillary carcinoma, seminoma, melanoma, sarcoma, bladder carcinoma, liver carcinoma and biliary passages, kidney carcinoma, urethra, renal cell carcinoma, carcinoma of the renal pelvis, myeloid disorders, lymphoid disorders, Hodgkins, hairy cells, buccal cavity and pharynx (oral), lip, tongue, mouth, pharynx, small intestine, colon-rectum, cancer of the anal region, large intestine, rectum, cancer of the head or neck, brain and central nervous system, neoplasms of the central nervous system (CNS), primary CNS lymphona, spinal axis tumors, brain stem glioma, pituitary adenoma, chronic or acute leukemia, and lymphocytic lymphomas.

The term "pharmaceutically acceptable salts, esters, amides, and prodrugs" as used herein refers to those carboxylate salts, amino acid addition salts, esters, amides, and prodrugs of the compounds of the present invention which are, within the scope of sound medical judgment, suitable for use in contact with the tissues of patients without undue toxicity, irritation, allergic response, and the like, commensurate with a reasonable benefit/risk ratio, and effective for their intended use, as well as the zwitterionic forms, where possible, of the compounds of the invention. The term "salts" refers to the relatively non-toxic, inorganic and organic acid addition salts of compounds of the present invention. These salts can be prepared in situ during the final isolation and purification of the compounds or by separately reacting the purified compound in its free base form with a suitable organic or inorganic acid and isolating the salt thus formed. Representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphenylate methylate, glucoheptonate, lactobionate and laurylsulphonate salts, and the like. These may include cations based on the alkali and alkaline earth metals, such as sodium, lithium, potassium, calcium, magnesium and the like, as well as non-toxic ammonium, quaternary ammonium, and amine cations including, but not limited to ammonium, tetramethylammonium, tetraethylammonium, methylamine, dimethylamine, trimethylamine, triethylamine, ethylamine, and the like. (See, for example, Berge S. M. et al., "Pharmaceutical Salts," *J. Pharm. Sci.*, 1977;66:1–19 which is incorporated herein by reference.)

Examples of pharmaceutically acceptable, non-toxic esters of the compounds of this invention include $C_1$–$C_6$ alkyl esters wherein the alkyl group is a straight or branched chain. Acceptable esters also include $C_5$–$C_7$ cycloalkyl esters as well as arylalkyl esters such as, but not limited to benzyl. $C_1$–$C_4$ alkyl esters are preferred. Esters of the compounds of the present invention may be prepared according to conventional methods.

Examples of pharmaceutically acceptable, non-toxic amides of the compounds of this invention include amides derived from ammonia, primary $C_1$–$C_6$ alkyl amines and secondary $C_1$–$C_6$ dialkyl amines wherein the alkyl groups are straight or branched chain. In the case of secondary amines the amine may also be in the form of a 5- or 6-membered heterocycle containing one nitrogen atom. Amides derived from ammonia, $C_1$–$C_3$ alkyl primary amines and $C_1$–$C_2$ dialkyl secondary amines are preferred. Amides of the compounds of the invention may be prepared according to conventional methods.

The term "prodrug" refers to compounds that are rapidly transformed in vivo to yield the parent compound of the above formulae, for example, by hydrolysis in blood. A thorough discussion is provided in T. Higuchi and V. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987, both of which are hereby incorporated by reference.

Representative compounds of the invention are shown below in Table 1.

TABLE 1

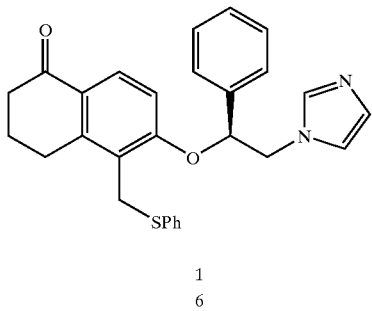

6

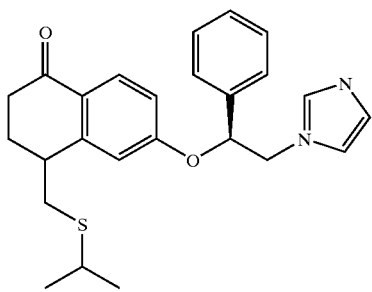

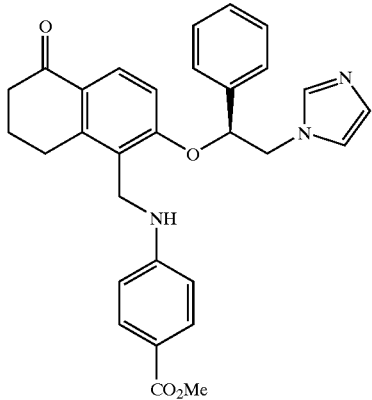

TABLE 1-continued

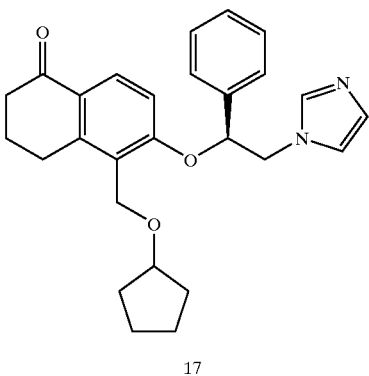

17

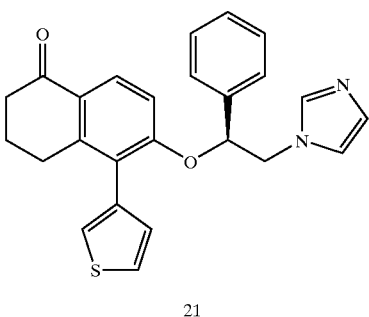

21

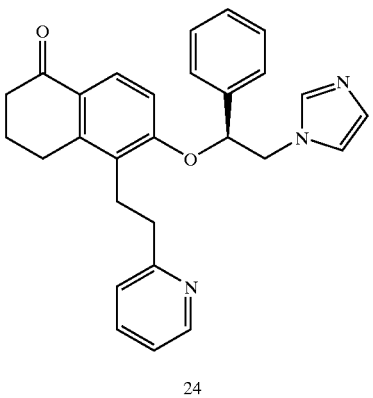

24

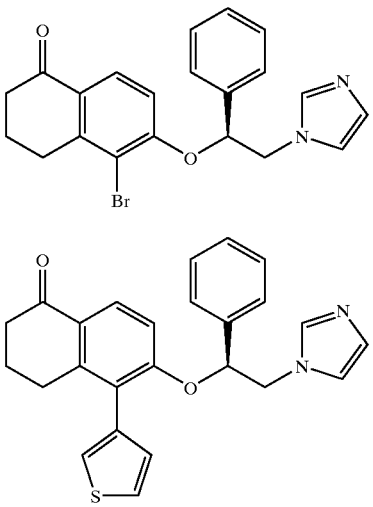

TABLE 1-continued

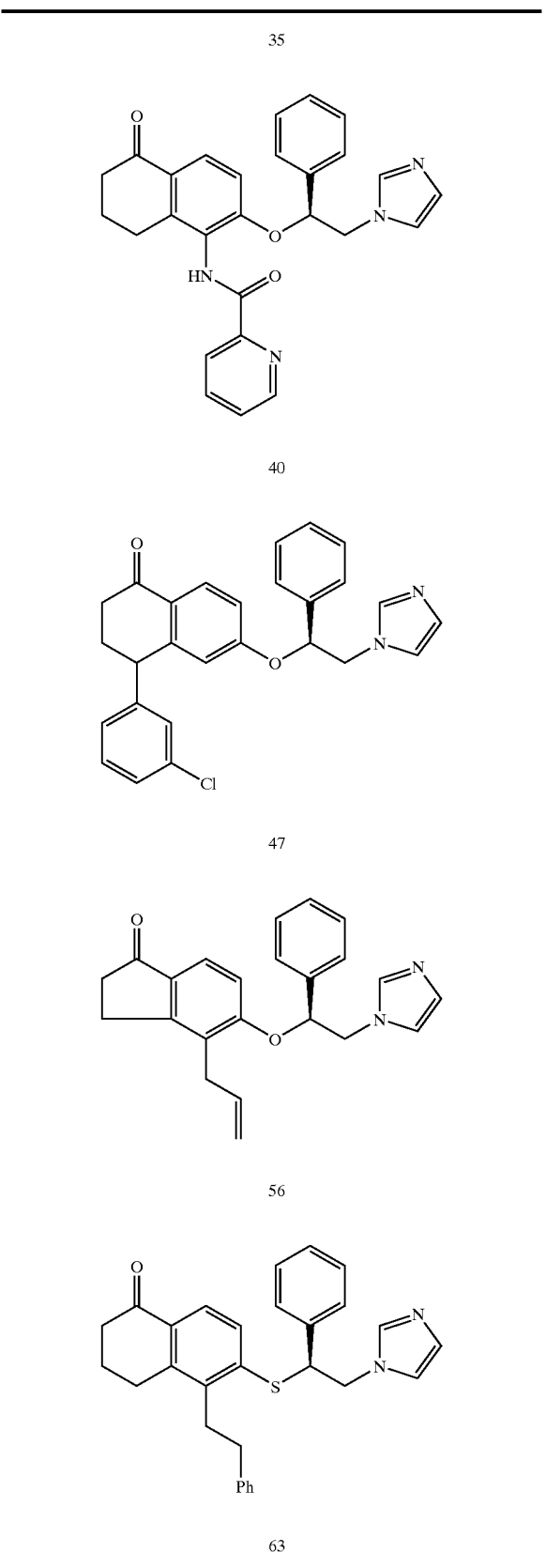

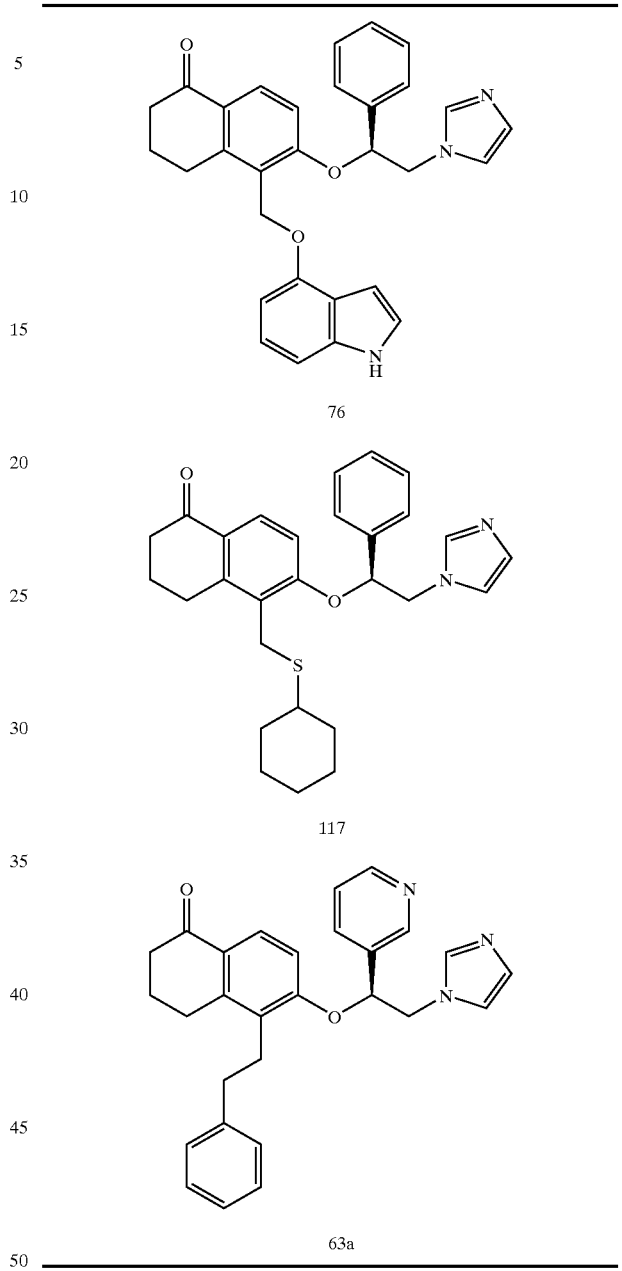

Representative compounds of the present invention, which are encompassed by Formulas I–VIII include, but are not limited to the compounds in Table 1 and their pharmaceutically acceptable acid or base addition salts, or amide or prodrugs thereof.

Preferred compounds of Formula I are those wherein W is $CH_2CH_2$; Y is O; $R^3$ is aryl; $R^{3a}$ is hydrogen; $R^5$ is hydrogen; and X is arylalkyl, substituted arylalkyl, heteroarylalkyl, substituted heteroarylalkyl, —$CH_2OR^6$, —$CH_2NR^6R^{6a}$, or —$CH_2SR^6$.

Preferred compounds of Formula II are those wherein $R^7$ is —O-phenyl, —O-substituted phenyl, —O-benzyl, —S—($C_1$–$C_6$)alkyl, —S—($C_3$–$C_6$)cycloalkyl, —S-phenyl, —S-substituted phenyl, —NH-phenyl, —NH-substituted phenyl, aryl, substituted aryl, heteroaryl, or substituted heteroaryl.

Preferred compounds of Formula III are those wherein $R^9$ is phenyl or heteroaryl; $R^{10}$ is hydrogen; y is 0 or 1; and $R^{11}$ is S(O)z-substituted alkyl, —S(O)$_z$-substituted arylalkyl, —S(O)z-heteroaryl, —S(O)z-heteroarylalkyl, —S(O)z-substituted heteroaryl, —SO$_2$-alkyl, —SO$_2$-aryl, —SO$_2$-substituted aryl, —SO$_2$-arylalkyl, —S(O)z-phenyl-CONH—$R^{13}$, —NHSO$_2$—$R^{14}$, or —NHCO—$R^{14}$; preferably $R^{11}$ is —S(O)z-phenyl-CONH—$R^{13}$, —NHSO$_2$—$R^{14}$, or —NHCO—$R^{14}$; and more preferably $R^{11}$ is —NHCO—$R^{14}$; and $R^{14}$ is heteroaryl.

Preferred compounds of Formula IV are those wherein A is N while B and C are CH; B is N while A and C are CH; $Y^2$ is O; y is 0, 1, or 2; preferably, 0 or 1; $R^{15}$ is —O-substituted aryl, —O-heteroaryl, —O-substituted heteroaryl, —S-alkyl, —S-substituted alkyl, —S-cycloalkyl, —S-aryl, —S-substituted aryl, —S-heteroaryl, —S-substituted heteroaryl, —SO$_2$NH$_2$, —SO$_2$NH-alkyl, —SO-aryl, —SO$_2$-aryl, —SO$_2$-substituted aryl, —SO$_2$-alkyl, —SO$_2$-heteroaryl, —SO$_2$-substituted heteroaryl, —NHSO$_2$-aryl, —NHCO-aryl, —NHCO-heteroaryl, —NHCO$_2$-alkyl, —NH-aryl, —NH-substituted aryl, aryl, substituted aryl, heteroaryl, or substituted heteroaryl; preferably, $R^{15}$ is aryl, heteroaryl, —SO$_2$-alkyl, —SO$_2$-heteroaryl, or —NHCO-heteroaryl; and more preferably, $R^{15}$ is —SO$_2$-alkyl, —SO$_2$-heteroaryl, or —NHCO-heteroaryl.

Illustrative of compounds encompassed by Formula I include the following list of compounds. This list is meant to be representative only and is not intended to limit the scope of the invention in any way:

6-((1S)-2-Imidazolyl-1-phenylethoxy)-5-(phenylthiomethyl)-2,3,4-trihydronaphthalen-1-one (Compound 1);

Methyl 2-{[2-((1S)-2-imidazolyl-1-phenylethoxy)-5-oxo-6,7,8-trihydronaphenyl]methylthio}benzoate (Compound 4);

2-{[2-((1S)-2-Imidazolyl-1-phenylethoxy)-5-oxo-6,7,8-trihydronaphenyl]methylthio}benzoic acid (Compound 5);

6-((S)-2-Imidazol-1-yl-1-phenyl-ethoxy)-5-isopropylsulfanylmethyl-2,3,4-trihydronaphthalen-1-one (Compound 6);

6-((1S)-2-Imidazolyl-1-phenylethoxy)-5-[(phenylamino)methyl]-2,3,4-trihydronaphthalen-1-one (Compound 11);

6-((1S)-2-Imidazolyl-1-phenylethoxy)-5-[(methylphenylamino)methyl]-2,3,4-trihydronaphthalen-1-one (Compound 12);

Methyl 4-({[2-((1S)-2-imidazolyl-1-phenylethoxy)-5-oxo(6,7,8-trihydronaphenyl)]methyl}methylamino)benzoate (Compound 13);

4-({[2-((1S)-2-imidazolyl-1-phenylethoxy)-5-oxo(6,7,8-trihydronaphenyl)]methyl}methylamino)benzoic acid, 2,2,2-trifluoroacetic acid (Compound 14);

6-((1S)-2-Imidazolyl-1-phenylethoxy)-5-[(methylethoxy)methyl]-2,3,4-trihydronaphthalen-1-one hydrochloride (Compound 15);

6-((1S)-2-Imidazolyl-1-phenylethoxy)-5-[(phenylmethoxy)methyl]-2,3,4-trihydronaphthalen-1-one (Compound 16);

6-((1S)-2-Imidazolyl-1-phenylethoxy)-5-(cyclopentyloxymethyl)-2,3,4-trihydronaphthalen-1-one (Compound 17);

6-((1S)-2-imidazolyl-1-phenylethoxy)-5-(prop-2-enyloxymethyl)-2,3,4-trihydronaphthalen-1-one (Compound 18);

6-((S)-2-Imidazol-1-yl-1-phenyl-ethoxy)-5-isobutoxymethyl-3,4-dihydro-2H-naphthalen-1-one (Compound 19a);

6-((S)-2-Imidazol-1-yl-1-phenyl-ethoxy)-5-propoxymethyl-3,4-dihydro-2H-naphthalen-1-one (Compound 19b);

5-(1-Ethyl-propoxymethyl)-6-((S)-2-imidazol-1-yl-1-phenyl-ethoxy)-3,4-dihydro-2H-naphthalen-1-one (Compound 19c);

(±)5-sec-Butoxymethyl-6-((S)-2-imidazol-1-yl-1-phenyl-ethoxy)-3,4-dihydro-2H-naphthalen-1-one (Compound 19d);

6-((1S)-2-Imidazolyl-1-phenylethoxy)-5-(2-phenylethyl)-2,3,4-trihydronaphthalen-1-one (Compound 20);

5-(2H-Benzo[d]1,3-dioxolan-5-yl)-6-((1S)-2-imidazolyl-1-phenylethoxy)2,3,4-trihydronaphthalen-1-one (Compound 21);

6-((1S)-2-Imidazolyl-1-phenylethoxy)-5-(3-chlorophenyl)-2,3,4-trihydronaphthalen-1-one (Compound 22);

6-((1S)-2-Imidazolyl-1-phenylethoxy)-5-(2-naphthyl)-2,3,4-trihydronaphthalen-1-one (Compound 23);

6-((1S)-2-Imidazolyl-1-phenylethoxy)-5-(2-(2-pyridyl)ethyl)-2,3,4-trihydronaphthalen-1-one (Compound 24);

6-((1S)-2-Imidazolyl-1-phenylethoxy)-5-(2-(4-pyridyl)ethyl)-2,3,4-trihydronaphthalen-1-one (Compound 26);

(S)-6-(-2-Imidazol-1-yl-1-phenyl-ethoxy)-5-(2-pyridin-3-yl-ethyl)-3,4-dihydro-2H-naphthalen-1-one (Compound 26b);

(S)-6-(-2-Imidazol-1-yl-1-phenyl-ethoxy)-5-(2-pyridin-3-yl-ethyl)-3,4-dihydro-2H-naphthalen-1-one (Compound 26c);

Methyl 4-{2-[2-((1S)-2-imidazolyl-1-phenylethoxy)-5-oxo-6,7,8-trihydronaphenyl]ethyl}benzoate (Compound 27);

Methyl 4-{2-[2-((1S)-2-imidazolyl-1-phenylethoxy)-5-oxo-6,7,8-trihydronaphenyl]ethyl}benzoate (Compound 28);

6-((1S)-2-Imidazolyl-1-phenylethoxy)-5-[2-(4-fluorophenyl)ethyl]-2,3,4-trihydronaphthalen-1-one (Compound 30);

Methyl 3-[2-((1S)-2-imidazolyl-1-phenylethoxy)-5-oxo-6,7,8-trihydronaphenyl]propanoate (Compound 31);

3-[2-((1S)-2-Imidazolyl-1-phenylethoxy)-5-oxo-6,7,8-trihydronaphenyl]propanoic acid (Compound 32);

4-{[2-((1S)-2-Imidazolyl-1-phenylethoxy)-5-oxo-6,7,8-trihydronaphenyl]methyl}benzenecarbonitrile (Compound 33);

6-((1S)-2-Imidazolyl-1-phenylethoxy)-5-bromo-2,3,4-trihydronaphthalen-1-one (Compound 34);

6-((1S)-2-Imidazolyl-1-phenylethoxy)-5-(3-thienyl)-2,3,4-trihydronaphthalen-1-one (Compound 35);

6-((1S)-2-Imidazolyl-1-phenylethoxy)-5-(3-furyl)-2,3,4-trihydronaphthalen-1-one, 2,2,2-trifluoroacetic acid (Compound 36);

5-Amino-6-((S)-2-imidazol-1-yl-1-phenyl-ethoxy)-3,4-dihydro-2H-naphthalen-1-one (Compound 37a);

6-((1S)-2-Imidazolyl-1-phenylethoxy)-5-(2-phenylpropyl)-2,3,4-trihydronaphthalen-1-one (Compound 44);

6-((S)-2-Imidazol-1-yl-1-phenyl-ethoxy)-5-(2-thiophen-3-yl-ethyl)-3,4-dihydro-2H-naphthalen-1-one (Compound 44a);

6-((S)-2-Imidazol-1-yl-1-phenyl-ethoxy)-5-(3-phenyl-propyl)-3,4-dihydro-2H-naphthalen-1-one (compound 44b);

6-((1S)-2-imidazolyl-1-phenylethoxy)-5-benzyl-2,3,4-trihydronaphthalen-1-one (Compound 45);

(6-((1S)-2-Imidazolyl-1-phenylethoxy)-5-propyl-2,3,4-trihydronaphthalen-1-one (Compound 53);

6-((1S)-2-Imidazolyl-1-phenylethoxy)-5-(2-methylprop-2-enyl)-2,3,4-trihydronaphthalen-1-one (Compound 54);

6-((1S)-2-Imidazolyl-1-phenylethoxy)-5-(2-methylpropyl)-2,3,4-trihydronaphthalen-1-one (Compound 55);

5-((1S)-2-Imidazolyl-1-phenylethoxy)-4-prop-2-enylindan-1-one (Compound 56);

6-[2-(1H-Imidazol-1-yl)-1,1-dimethylethoxy]-5-(2-phenylethyl)-3,4-dihydro-1(2H)-naphthalenone (Compound 58a);

6-((1S)-2-imidazolyl-1-phenylethylthio)-5-propyl-2,3,4-trihydronaphthalen-1-one (Compound 62);

6-((1S)-2-Imidazolyl-1-phenylethylthio)-5-(2-phenylethyl)-2,3,4-trihydronaphthalen-1-one (Compound 63);

(S)-6-(1-imidazol-1-ylmethyl-2-methyl-propoxy)-5-(2-pyridin-4-yl-ethyl)-3,4-dihydro-2H-naphthalen-1-one (Compound 63i);

(S)-6-[-1-(4-Fluoro-phenyl)-2-imidazol-1-yl-1-ethoxy]-5-(2-pyridin-4-yl-ethyl)-3,4-dihydro-2H-naphthalen-1-one (Compound 63k);

6-((1S)-2-Imidazolyl-1-phenylethoxy)-5-(methoxymethyl)-2,3,4-trihydronaphthalen-1-one (Compound 64);

6-((1S)-2-Imidazolyl-1-phenylethoxy)-5-(methoxymethyl)-2,3,4-trihydronaphthalen-1-one (Compound 65);

6-((1S)-2-Imidazolyl-1-phenylethoxy)-5-(phenoxymethyl)-2,3,4-trihydronaphthalen-1-one (Compound 66);

6-((1S)-2-Imidazolyl-1-phenylethoxy)-5-{[3-(tert-butyl)phenoxy]methyl}-2,3,4-trihydronaphthalen-1-one (Compound 67);

6-((1S)-2-Imidazolyl-1-phenylethoxy)-5-{[2-(methylethyl)phenoxy]methyl}-2,3,4-trihydronaphthalen-1-one (Compound 68);

6-((1S)-2-Imidazolyl-1-phenylethoxy)-5-[(3-chlorophenoxy)methyl]-2,3,4-trihydronaphthalen-1-one (Compound 69);

6-((1S)-2-Imidazolyl-1-phenylethoxy)-5-{[2-methyl-5-(methylethyl)phenoxy]methyl}-2,3,4-trihydronaphthalen-1-one (Compound 70);

6-((1S)-2-Imidazolyl-1-phenylethoxy)-5-[(3,5-dimethoxyphenoxy)methyl]-2,3,4-trihydronaphthalen-1-one (Compound 71);

6-((1S)-2-Imidazolyl-1-phenylethoxy)-5-{[4-(methylethyl)phenoxy]methyl}-2,3,4-trihydronaphthalen-1-one (Compound 72);

6-((1S)-2-Imidazolyl-1-phenylethoxy)-5-(2-5,6,7,8-tetrahydro-naphenyloxymethyl)-2,3,4-trihydronaphthalen-1-one (Compound 73);

6-((1S)-2-Imidazolyl-1-phenylethoxy)-5-{[3-(methylethyl)phenoxy]methyl}-2,3,4-trihydronaphthalen-1-one (Compound 74);

6-((1S)-2-Imidazolyl-1-phenylethoxy)-5-{[2-(methylethoxy)phenoxy]methyl}-2,3,4-trihydronaphthalen-1-one (Compound 77);

6-((1S)-2-Imidazolyl-1-phenylethoxy)-5-[(2-ethoxyphenoxy)methyl]-2,3,4-trihydronaphthalen-1-one (Compound 78);

6-((1S)-2-Imidazolyl-1-phenylethoxy)-5-[(4-ethoxyphenoxy)methyl]-2,3,4-trihydronaphthalen-1-one (Compound 79);

6-((1S)-2-Imidazolyl-1-phenylethoxy)-5-[(3-ethylphenoxy)methyl]-2,3,4-trihydronaphthalen-1-one (Compound 80);

Methyl 2-{[2-((1S)-2-imidazolyl-1-phenylethoxy)-5-oxo-6,7,8-trihydronaphenyl]methoxy}benzoate (Compound 81);

6-((1S)-2-Imidazolyl-1-phenylethoxy)-5-[(4-ethylphenoxy)methyl]-2,3,4-trihydronaphthalen-1-one (Compound 84);

6-((1S)-2-Imidazolyl-1-phenylethoxy)-5-(2-naphenyloxymethyl)-2,3,4-trihydronaphthalen-1-one (Compound 85);

6-((1S)-2-Imidazolyl-1-phenylethoxy)-5-[(2-chloro-5-methylphenoxy)methyl]-2,3,4-trihydronaphthalen-1-one (Compound 86);

6-((1S)-2-Imidazolyl-1-phenylethoxy)-5-{[2-(methylpropyl)phenoxy]methyl}-2,3,4-trihydronaphthalen-1-one (Compound 87);

Methyl 3-{[2-((1S)-2-imidazolyl-1-phenylethoxy)-5-oxo-6,7,8-trihydronaphthyl]methoxy}benzoate (Compound 88);

6-((1S)-2-Imidazolyl-1-phenylethoxy)-5-[(2,4,6-trimethylphenoxy)methyl]-2,3,4-trihydronaphthalen-1-one (Compound 89);

6-((1S)-2-Imidazolyl-1-phenylethoxy)-5-{[4-(methylpropyl)phenoxy]methyl}-2,3,4-trihydronaphthalen-1-one (Compound 90);

6-((1S)-2-Imidazolyl-1-phenylethoxy)-5-{[4-(trifluoromethyl)phenoxy]methyl}-2,3,4-trihydronaphthalen-1-one (Compound 91);

6-((1S)-2-Imidazolyl-1-phenylethoxy)-5-(2H-benzo[d]1,3-dioxolan-5-yloxymethyl)-2,3,4-trihydronaphthalen-1-one (Compound 92);

6-((1S)-2-Imidazolyl-1-phenylethoxy)-5-(2H-benzo[d]1,3-dioxolan-5-yloxymethyl)-2,3,4-trihydronaphthalen-1-one (Compound 93);

6-((1S)-2-Imidazolyl-1-phenylethoxy)-5-(8-quinolyloxymethyl)-2,3,4-trihydronaphthalen-1-one (Compound 95)

6-((1S)-2-Imidazolyl-1-phenylethoxy)-5-[(4-chlorophenoxy)methyl]-2,3,4-trihydronaphthalen-1-one (Compound 98);

6-((1S)-2-imidazolyl-1-phenylethoxy)-5-[(3-methylphenoxy)methyl]-2,3,4-trihydronaphthalen-1-one (Compound 99);

6-((1S)-2-Imidazolyl-1-phenylethoxy)-5-[(4-methylphenoxy)methyl]-2,3,4-trihydronaphthalen-1-one (Compound 100);

6-((1S)-2-Imidazolyl-1-phenylethoxy)-5-[(2-fluorophenoxy)methyl]-2,3,4-trihydronaphthalen-1-one (Compound 101);

6-((1S)-2-Imidazolyl-1-phenylethoxy)-5-[(3-fluorophenoxy)methyl]-2,3,4-trihydronaphthalen-1-one (Compound 102);

6-((1S)-2-Imidazolyl-1-phenylethoxy)-5-[(4-fluorophenoxy)methyl]-2,3,4-trihydronaphthalen-1-one (Compound 103);

6-((1S)-2-Imidazolyl-1-phenylethoxy)-5-(naphenyloxymethyl)-2,3,4-trihydronaphthalen-1-one (Compound 104);

6-((1S)-2-Imidazolyl-1-phenylethoxy)-5-[(3-methoxyphenoxy)methyl]-2,3,4-trihydronaphthalen-1-one (Compound 105);

6-((1S)-2-Imidazolyl-1-phenylethoxy)-5-[(2-chlorophenoxy)methyl]-2,3,4-trihydronaphthalen-1-one (Compound 106);

6-((1S)-2-Imidazolyl-1-phenylethoxy)-5-(6-quinolyloxymethyl)-2,3,4-trihydronaphthalen-1-one (Compound 108);

6-((1S)-2-Imidazolyl-1-phenylethoxy)-5-[(4-bromophenylthio)methyl]-2,3,4-trihydronaphthalen-1-one (Compound 109);

6-((1S)-2-Imidazolyl-1-phenylethoxy)-5-[(4-fluorophenylthio)methyl]-2,3,4-trihydronaphthalen-1-one (Compound 110);

N-(4-{[2-((1S)-2-Imidazolyl-1-phenylethoxy)-5-oxo-6,7,8-trihydronaphenyl]methylthio}phenyl)acetamide (Compound 111);

6-((1S)-2-Imidazolyl-1-phenylethoxy)-5-[(4-hydroxyphenylthio)methyl]-2,3,4-trihydronaphthalen-1-one (Compound 112);

6-((1S)-2-Imidazolyl-1-phenylethoxy)-5-[(4-methylphenylthio)methyl]-2,3,4-trihydronaphthalen-1-one (Compound 113);

6-((1S)-2-Imidazolyl-1-phenylethoxy)-5-[(2-methylpropylthio)methyl]-2,3,4-trihydronaphthalen-1-one (Compound 114);

6-((1S)-2-Imidazolyl-1-phenylethoxy)-5-(cyclohexylthiomethyl)-2,3,4-trihydronaphthalen-1-one (Compound 117);

6-((1S)-2-Imidazolyl-1-phenylethoxy)-5-[(2-bromophenylthio)methyl]-2,3,4-trihydronaphthalen-1-one (Compound 130);

6-((1S)-2-Imidazolyl-1-phenylethoxy)-5-[(2-chlorophenylthio)methyl]-2,3,4-trihydronaphthalen-1-one (Compound 131);

6-((1S)-2-Imidazolyl-1-phenylethoxy)-5-[(2,6-dichlorophenylthio)methyl]-2,3,4-trihydronaphthalen-1-one (Compound 132);

6-((1S)-2-Imidazolyl-1-phenylethoxy)-5-[(2-methoxyphenylthio)methyl]-2,3,4-trihydronaphthalen-1-one (Compound 133);

6-((1S)-2-Imidazolyl-1-phenylethoxy)-5-[(2-methylphenylthio)methyl]-2,3,4-trihydronaphthalen-1-one (Compound 134);

6-((1S)-2-Imidazolyl-1-phenylethoxy)-5-[(4-methoxyphenylthio)methyl]-2,3,4-trihydronaphthalen-1-one (Compound 135);

6-((1S)-2-Imidazolyl-1-phenylethoxy)-5-[(4-nitrophenylthio)methyl]-2,3,4-trihydronaphthalen-1-one (Compound 137);

6-((1S)-2-Imidazolyl-1-phenylethoxy)-5-[(3-methoxyphenylthio)methyl]-2,3,4-trihydronaphthalen-1-one (Compound 138);

6-((1S)-2-Imidazolyl-1-phenylethoxy)-5-[(4-chlorophenylthio)methyl]-2,3,4-trihydronaphthalen-1-one (Compound 139);

2-{[2-((S)-2-Imidazol-1-yl-1-phenyl-ethoxy)-5-oxo-5,6,7,8-tetrahydro-napthalen-1-ylmethyl]-amino}-benzonitrile (Compound 149);

5-[(4-Bromo-phenylamino)-methyl]-6-((S)-2-imidazol-1-yl-1-phenyl-ethoxy)-3,4-dihydro-2H-napthalen-1-one (Compound 150);

5-[(4-Fluoro-phenylamino)-methyl]-6-((S)-2-imidazol-1-yl-1-phenyl-ethoxy)-3,4-dihydro-2H-napthalen-1-one (Compound 151);

5-[(2,3-Dihydro-benzo[1,4]dioxin-6-ylamino)-methyl]-6-((S)-2-imidazol-1-yl-1-phenyl-ethoxy)-3,4-dihydro-2H-napthalen-1-one (Compound 152);

Methyl 4-{[(2-{[(1S)-2-(1H-Imidazol-1-yl)-1-phenylethyl]oxy}-5-oxo-5,6,7,8-tetrahydro-1-naphthalenyl)methyl]sulfanyl}benzoate (Compound 157);

Methyl 3-{[(2-{[(1S)-2-(1H-Imidazol-1-yl)-1-phenylethyl]oxy}-5-oxo-5,6,7,8-tetrahydro-1-naphthalenyl)methyl]sulfanyl}benzoate (Compound 158);

4-{[(2-{[(1S)-2-(1H-Imidazol-1-yl)-1-phenylethyl]oxy}-5-oxo-5,6,7,8-tetrahydro-1-naphthalenyl)methyl]sulfanyl}benzoic Acid. (Compound 162); and 3-{[(2-{[(1S)-2-(1H-Imidazol-1-yl)-1-phenylethyl]oxy}-5-oxo-5,6,7,8-tetrahydro-1-naphthalenyl)methyl]sulfanyl}benzoic Acid. (Compound 163).

Illustrative of compounds encompassed by Formula III include the following list of compounds. This list is meant to be representative only and is not intended to limit the scope of the invention in any way:

6-((1S)-2-Imidazolyl-1-phenylethoxy)-5-[(phenylsulfinyl)methyl]-2,3,4-trihydronaphthalen-1-one (Compound 2);

6-((1S)-2-Imidazolyl-1-phenylethoxy)-5-[(phenylsulfonyl)methyl]-2,3,4-trihydronaphthalen-1-one (Compound 3);

6-((1S)-2-Imidazolyl-1-phenylethoxy)-5-{[(methylethyl)sulfonyl]methyl}-2,3,4-trihydronaphthalen-1-one (Compound 7);

6-((1S)-2-Imidazolyl-1-phenylethoxy)-5-(4-pyridylthiomethyl)-2,3,4-trihydronaphthalen-1-one (Compound 8);

6-((1S)-2-Imidazolyl-1-phenylethoxy)-5-(2-pyridylthiomethyl)-2,3,4-trihydronaphthalen-1-one (Compound 9);

6-((1S)-2-Imidazolyl-1-phenylethoxy)-5-[(2-pyridylsulfonyl)methyl]-2,3,4-trihydronaphthalen-1-one hydrochloride (Compound 10);

6-((S)-2-Imidazol-1-yl-1-phenyl-ethoxy)-5-(naphthalen-1-ylsulfanylmethyl)-3,4-dihydro-2H-naphthalen-1-one (Compound 10a);

[2-(2-Imidazol-1-yl-1(S)-phenyl-ethoxy)-5-oxo-5,6,7,8-tetrahydro-naphthalen-1-ylmethylsulfanyl]-acetic acid methyl ester (Compound 10b);

5-(3,4-Dichloro-benzylsulfanylmethyl)-6-((1S)-2-imidazol-1-yl-1-phenyl-ethoxy)-3,4-dihydro-2H-naphthalen-1-one (Compound 10c);

(S)-6-{2-[2-(Hydroxymethyl)-1H-imidazol-1-yl]-1-phenylethoxy}-5-[(phenylsulfonyl)methyl]-3,4-dihydro-1(2H)-naphthalenone (Compound 10d);

6-((1S)-2-Imidazolyl-1-phenylethoxy)-5-[(2-methoxyethoxy)-methyl]-2,3,4-trihydronaphthalen-1-one (Compound 19);

6-((1S)-2-Imidazolyl-1-phenylethoxy)-5-[2-(1-oxy(2-pyridyl))ethyl]-2,3,4-trihydronaphthalen-1-one (Compound 25);

(S)-6-(2-Imidazol-1-y-1-phenyl-ethoxy)-5-[2-(1-oxy-pyridin-4-yl)-ethyl]-3,4-dihydro-2H-naphthalen-1-one (Compound 26a);

(4-{2-[2-((1S)-2-Imidazolyl-1-phenylethoxy)-5-oxo(6,7,8-trihydronaphenyl)]ethyl}phenyl)-N-methylcarboxamide (Compound 29);

N-[2-((S)-2-Imidazol-1-yl-1-phenyl-ethoxy)-5-oxo-5,6,7,8-tetrahydro-naphthalen-1-yl]-benzenesulfonamide (Compound 38);

N-[2-((S)-2-Imidazol-1-yl-1-phenyl-ethoxy)-5-oxo-5,6,7,8-tetrahydro-naphthalen-1-yl]-1-phenyl-methanesulfonamide (Compound 39);

N-[2-((S)-2-Imidazol-1-yl-1-phenyl-ethoxy)-5-oxo-5,6,7,8-tetrahydro-naphthalen-1-yl]-2-pyridin-2-yl-acetamide (Compound 39a);

Pyridine-2-carboxylic acid [2-((S)-2-imidazol-1-yl-1-phenyl-ethoxy)-5-oxo-5,6,7,8-tetrahydro-naphthalen-1-yl]-amide (Compound 40);

Isoquinoline-1-carboxylic acid [2-((S)-2-imidazol-1-yl-1-phenyl-ethoxy)-5-oxo-5,6,7,8-tetrahydro-naphthalen-1-yl]-amide (Compound 40a);

Isoquinoline-3-carboxylic acid [2-((S)-2-imidazol-1-yl-1-phenyl-ethoxy)-5-oxo-5,6,7,8-tetrahydro-naphthalen-1-yl]-amide (Compound 40b);

Pyrazine-2-carboxylic acid [2-((S)-2-imidazol-1-yl-1-phenyl-ethoxy)-5-oxo-5,6,7,8-tetrahydro-naphthalen-1-yl]-amide (Compound 40c);

5-(4-Chloro-phenyl)-oxazole-4-carboxylic acid [2-((S)-2-imidazol-1-yl-1-phenyl-ethoxy)-5-oxo-5,6,7,8-tetrahydro-naphthalen-1-yl]-amide (Compound 40d);

N-[2-((S)-2-Imidazol-1-yl-1-phenyl-ethoxy)-5-oxo-5,6,7,8-tetrahydro-naphthalen-1-yl]-2-chloro-nicotinamide (Compound 40e);

N-[2-((S)-2-Imidazol-1-yl-1-phenyl-ethoxy)-5-oxo-5,6,7,8-tetrahydro-naphthalen-1-yl]-2-phenoxy-nicotinamide (Compound 40f);

Quinoline-8-carboxylic acid [2-((S)-2-imidazol-1-yl-1-phenyl-ethoxy)-5-oxo-5,6,7,8-tetrahydro-naphthalen-1-yl]-amide (Compound 40g)

[2-((S)-2-Imidazol-1-yl-1-phenyl-ethoxy)-5-oxo-5,6,7,8-tetrahydro-naphthalen-1-ylmethyl]-carbamic acid tert-butyl ester (Compound 41);

N-[2-((S)-2-Imidazol-1-yl-1-phenyl-ethoxy)-5-oxo-5,6,7,8-tetrahydro-naphthalen-1-ylmethyl]-benzenesulfonamide (Compound 42);

N-[2-((S)-2-Imidazol-1-yl-1-phenyl-ethoxy)-5-oxo-5,6,7,8-tetrahydro-naphthalen-1-ylmethyl]-4-methoxy-benzenesulfonamide (Compound 42a);

2,4-Difluoro-N-[2-((S)-2-imidazol-1-yl-1-phenyl-ethoxy)-5-oxo-5,6,7,8-tetrahydro-naphthalen-1-ylmethyl]-benzenesulfonamide; compound with trifluoro-acetic acid (Compound 42b);

2-{[2-((S)-2-Imidazol-1-yl-1-phenyl-ethoxy)-5-oxo-5,6,7,8-tetrahydro-naphthalen-1-ylmethyl]-sulfamoyl}-benzoic acid methyl ester; compound with trifluoro-acetic acid (Compound 42c);

2,5-Dichloro-thiophene-3-sulfonic acid [2-((S)-2-imidazol-1-yl-1-phenyl-ethoxy)-5-oxo-5,6,7,8-tetrahydro-naphthalen-1-ylmethyl]-amide; compound with trifluoro-acetic acid (Compound 42d);

3-Chloro-N-[2-((S)-2-imidazol-1-yl-1-phenyl-ethoxy)-5-oxo-5,6,7,8-tetrahydro-naphthalen-1-ylmethyl]-benzenesulfonamide; compound with trifluoro-acetic acid (Compound 42e);

Naphthalen-2-sulfonic acid [2-((S)-2-imidazol-1-yl-1-phenyl-ethoxy)-5-oxo-5,6,7,8-tetrahydro-naphthalen-1-ylmethyl]-amide; compound with trifluoro-acetic acid (Compound 42f);

N-[2-((S)-2-Imidazol-1-yl-1-phenyl-ethoxy)-5-oxo-5,6,7,8-tetrahydro-naphthalen-1-ylmethyl]-C-phenyl-methanesulfonamide (Compound 42g);

Pyridine-2-carboxylic acid [2-((S)-2-imidazol-1-yl-1-phenyl-ethoxy)-5-oxo-5,6,7,8-tetrahydro-naphthalen-1-ylmethyl]-amide (Compound 42h);

N-[2-((S)-2-Imidazol-1-yl-1-phenyl-ethoxy)-5-oxo-5,6,7,8-tetrahydro-naphthalen-1-ylmethyl]-benzamide (Compound 42i);

((S)-1-{[2-((S)-2-Imidazol-1-yl-1-phenyl-ethoxy)-5-oxo-5,6,7,8-tetrahydro-naphthalen-1-ylmethyl]-carbamoyl}-3-methylsulfanyl-propyl)carbamic acid tert-butyl ester (Compound 42j);

(S)-2-Amino-N-[2-((S)-2-imidazol-1-yl-1-phenyl-ethoxy)-5-oxo-5,6,7,8-tetrahydro-naphthalen-1-ylmethyl]-4-methylsulfanyl-butyramide (Compound 42k);

2-[2-((S)-2-Imidazol-1-yl-1-phenyl-ethoxy)-5-oxo-5,6,7,8-tetrahydro-naphthalen-1-ylmethyl]-isoindole-1,3-dione (Compound 43);

6-((1S)-2-Imidazolyl-1-phenylethoxy)-5-phenoxy-2,3,4-trihydronaphthalen-1-one (Compound 46);

6-((S)-1-Imidazol-1-ylmethyl-2-methyl-propoxy)-5-(propane-2-sulfonylmethyl)-3,4-dihydro-2H-napthalen-1-one (Compound 63g);

Isoquinoline-1-carboxylic acid [2-((S)-1-imidazol-1-ylmethyl-2-methyl-propoxy)-5-oxo-5,6,7,8-tetrahydro-naphthalen-1-yl]-amide (Compound 63h);

(S)-6-[-1-(2,4-Difluoro-phenyl)-2-imidazol-1-yl-1-ethoxy]-5-(pyridin-2-ylsulfonylmethyl)-3,4-dihydro-2H-naphthalen-1-one (Compound 63j);

6-{[1-(1H-Imidazol-1-ylmethyl)pentyl]oxy}-5-[(phenylsulfonyl)methyl]3,4-dihydro-1(2H)-naphthalenone (Compound 63m);

6-((1S)-2-Imidazolyl-1-phenylethoxy)-5-[(4-pyrrolylphenoxy)methyl]-2,3,4-trihydronaphthalen-1-one (Compound 75);

6-((1S)-2-Imidazolyl-1-phenylethoxy)-5-(indol-4-yloxymethyl)-2,3,4-trihydronaphthalen-1-one (Compound 76);

6-((1S)-2-Imidazolyl-1-phenylethoxy)-5-[(6-methyl(3-pyridyloxy))methyl]-2,3,4-trihydronaphthalen-1-one (Compound 82);

6-((1S)-2-Imidazolyl-1-phenylethoxy)-5-[(6-methyl(3-pyridyloxy))methyl]-2,3,4-trihydronaphthalen-1-one (Compound 83);

6-((1S)-2-Imidazolyl-1-phenylethoxy)-5-(8-quinolyloxymethyl)-2,3,4-trihydronaphthalen-1-one (Compound 94);

6-((1S)-2-Imidazolyl-1-phenylethoxy)-5-{[4-(trifluoromethoxy)phenoxy]methyl}-2,3,4-trihydronaphthalen-1-one (Compound 96);

6-((1S)-2-Imidazolyl-1-phenylethoxy)-5-{[4-(phenoxy)phenoxy]methyl}-2,3,4-trihydronaphthalen-1-one (Compound 97);

6-((1S)-2-Imidazolyl-1-phenylethoxy)-5-(6-quinolyloxymethyl)-2,3,4-trihydronaphthalen-1-one (Compound 107);

6-((1S)-2-Imidazolyl-1-phenylethoxy)-5-[(2-hydroxyethylthio)methyl]-2,3,4-trihydronaphthalen-1-one (Compound 115);

6-((1S)-2-Imidazolyl-1-phenylethoxy)-5-[(2-phenylethylthio)methyl]-2,3,4-trihydronaphthalen-1-one (Compound 116);

Methyl 3-{[2-((1S)-2-Imidazolyl-1-phenylethoxy)-5-oxo-6,7,8-trihydronaphenyl]methylthio}propanoate (Compound 118);

6-((1S)-2-Imidazolyl-1-phenylethoxy)-5-(imidazol-2-ylthiomethyl)-2,3,4-trihydronaphthalen-1-one (Compound 119);

6-((1S)-2-Imidazolyl-1-phenylethoxy)-5-(1H-1,2,4-triazol-3-ylthiomethyl)-2,3,4-trihydronaphthalen-1-one (Compound 120);

6-((1S)-2-Imidazolyl-1-phenylethoxy)-5-[(1-methylimidazol-2-ylthio)methyl]-2,3,4-trihydronaphthalen-1-one (Compound 121);

6-((1S)-2-Imidazolyl-1-phenylethoxy)-5-(benzothiazol-2-ylthiomethyl)-2,3,4-trihydronaphthalen-1-one (Compound 122);

6-((1S)-2-Imidazolyl-1-phenylethoxy)-5-[(5-chlorobenzothiazol-2-ylthio)methyl]-2,3,4-trihydronaphthalen-1-one (Compound 123);

6-((1S)-2-Imidazolyl-1-phenylethoxy)-5-(2-furylthiomethyl)-2,3,4-trihydronaphthalen-1-one (Compound 124);

6-((1S)-2-Imidazolyl-1-phenylethoxy)-5-[(5-nitrobenzimidazol-2-ylthio)methyl]-2,3,4-trihydronaphthalen-1-one (Compound 125);

2-{[2-((1S)-2-Imidazolyl-1-phenylethoxy)-5-oxo-6,7,8-trihydronaphenyl]methylthio}pyridine-3-carboxylic acid (Compound 126);

6-((1S)-2-Imidazolyl-1-phenylethoxy)-5-[(1-methyl(1,2,3,4-tetraazol-5-ylthio))methyl]-2,3,4-trihydronaphthalen-1-one (Compound 127);

6-((1S)-2-Imidazolyl-1-phenylethoxy)-5-[(2,2,2-trifluoroethylthio)methyl]-2,3,4-trihydronaphthalen-1-one (Compound 128);

6-((1S)-2-Imidazolyl-1-phenylethoxy)-5-(2-naphenylthiomethyl)-2,3,4-trihydronaphthalen-1-one (Compound 129);

6-((1S)-2-Imidazolyl-1-phenylethoxy)-5-[(4-methyl(1,2,4-triazol-3-ylthio))methyl]-2,3,4-trihydronaphthalen-1-one (Compound 136);

6-((1S)-2-Imidazolyl-1-phenylethoxy)-5-(2-quinolylthiomethyl)-2,3,4-trihydronaphthalen-1-one (Compound 140);

6-((S)-2-Imidazol-1-yl-1-phenyl-ethoxy)-5-(4-methoxy-benzenesulfinylmethyl)-3,4-dihydro-2H-napthalen-1-one (Compound 141);

6-((S)-2-Imidazol-1-yl-1-phenyl-ethoxy)-5-(pyridine-2-sulfinylmethyl)-3,4-dihydro-2H-naptalen-1-one (Compound 142);

6-((S)-2-Imidazol-1-yl-1-phenyl-ethoxy)-5-(propane-2-sulfinylmethyl)-3,4-dihydro-2H-naptalen-1-one (Compound 143);

N-[2-((S)-2-Imidazol-1-yl-1-phenyl-ethoxy)-5-oxo-5,6,7,8-tetrahydro-naphthalen-1-ylmethyl]-N-β-tolyl-acetamide (Compound 144);

6-((S)-2-Imidazol-1-yl-1-phenyl-ethoxy)-5-[1H-indazol-5-ylamino)-methyl]-3,4-dihydro-2H-naptalen-1-one (Compound 145);

6-((S)-2-Imidazol-1-yl-1-phenyl-ethoxy)-5-(4-phenyl-piperazin-1-ylmethyl)-3,4-dihydro-2H-naptalen-1-one (Compound 146);

6-((S)-2-Imidazol-1-yl-1-phenyl-ethoxy)-5-(4-pyridin-2-yl-piperazin-1-ylmethyl)-3,4-dihydro-2H-naptalen-1-one (Compound 147);

6-((S)-2-Imidazol-1-yl-1-phenyl-ethoxy)-5-(quinolin-8-ylaminomethyl)-3,4-dihydro-2H-naptalen-1-one (Compound 148);

5-(3,4-Dichloro-benzylsulfanylmethyl)-6-((1S)-2-imidazol-1-yl-1-phenyl-ethoxy)-3,4-dihydro-2H-naphthalen-1-one (Compound 153);

Methyl 2-{[(2-{[(1S)-2-(1H-Imidazol-1-yl)-1-phenylethyl]oxy}-5-oxo-5,6,7,8-tetrahydro-1-naphthalenyl)methyl]sulfonyl}benzoate (Compound 154);

Methyl 4-{[(2-{[(1S)-2-(1H-Imidazol-1-yl)-1-phenylethyl]oxy}-5-oxo-5,6,7,8-tetrahydro-1-naphthalenyl)methyl]sulfonyl}benzoate (Compound 155);

Methyl 4-{[(2-{[(1S)-2-(1H-Imidazol-1-yl)-1-phenylethyl]oxy}-5-oxo-5,6,7,8-tetrahydro-1-naphthalenyl)methyl]sulfonyl}benzoate (Compound 156);

2-{[(2-{[(1S)-2-(1H-Imidazol-1-yl)-1-phenylethyl]oxy}-5-oxo-5,6,7,8-tetrahydro-1-naphthalenyl)methyl]sulfonyl}benzoic Acid (Compound 159);

4-{[(2-{[(1S)-2-(1H-Imidazol-1-yl)-1-phenylethyl]oxy}-5-oxo-5,6,7,8-tetrahydro-1-naphthalenyl)methyl]sulfonyl}benzoic Acid (Compound 160);

3-{[(2-{[(1S)-2-(1H-Imidazol-1-yl)-1-phenylethyl]oxy}-5-oxo-5,6,7,8-tetrahydro-1-naphthalenyl)methyl]sulfonyl}benzoic Acid (Compound 161);

2-{[(2-{[(1S)-2-(1H-Imidazol-1-yl)-1-phenylethyl]oxy}-5-oxo-5,6,7,8-tetrahydro-1-naphthalenyl)methyl]sulfonyl)-N-methylbenzamide (Compound 164);

N-(2-Hydroxyethyl)-2-{[(2-{[(1S)-2-(1H-imidazol-1-yl)-1-phenylethyl]oxy}-5-oxo-5,6,7,8-tetrahydro-1-naphthalenyl)methyl]sulfonyl}benzamide (Compound 165);

N-4-{[(2-{[(1S)-2-(1H-Imidazol-1-yl)-1-phenylethyl]oxy}-5-oxo-5,6,7,8-tetrahydro-1-naphthalenyl)methyl]sulfonyl}benzoyl-β-alanine (Compound 166);

N-2-{[(2-{[(1S)-2-(1H-Imidazol-1-yl)-1-phenylethyl]oxy}-5-oxo-5,6,7,8-tetrahydro-1-naphthalenyl)methyl]sulfonyl}benzoyl-β-alanine (Compound 167);

N-3-{[(2-{[(1S)-2-(1H-Imidazol-1-yl)-1-phenylethyl]oxy}-5-oxo-5,6,7,8-tetrahydro-1-naphthalenyl)methyl]sulfonyl}benzoyl-β-alanine (Compound 168)

N-2-{[(2-{[(1S)-2-(1H-Imidazol-1-yl)-1-phenylethyl]oxy}-5-oxo-5,6,7,8-tetrahydro-1-naphthalenyl)methyl]sulfanyl}benzoyl-β-alanine (Compound 169);

N-4-{[(2-{[(1S)-2-(1H-Imidazol-1-yl)-1-phenylethyl]oxy}-5-oxo-5,6,7,8-tetrahydro-1-naphthalenyl)methyl]sulfanyl}benzoyl-β-alanine (Compound 170);

N-3-{[(2-{[(1S)-2-(1H-Imidazol-1-yl)-1-phenylethyl]oxy}-5-oxo-5,6,7,8-tetrahydro-1-naphthalenyl)methyl]sulfanyl}benzoyl-β-alanine (Compound 171);

N-(2-Hydroxyethyl)-3-{[(2-{[(1S)-2-(1H-imidazol-1-yl)-1-phenylethyl]oxy}-5-oxo-5,6,7,8-tetrahydro-1-naphthalenyl)methyl]sulfanyl}benzamide (Compound 172);

N-(2-Hydroxyethyl)-2-{[(2-{[(1S)-2-(1H-imidazol-1-yl)-1-phenylethyl]oxy}-5-oxo-5,6,7,8-tetrahydro-1-naphthalenyl)methyl]sulfanyl}benzamide (Compound 173);

N-(2-Hydroxyethyl)-4-{[(2-{[(1S)-2-(1H-imidazol-1-yl)-1-phenylethyl]oxy}-5-oxo-5,6,7,8-tetrahydro-1-naphthalenyl)methyl]sulfanyl}benzamide (Compound 174);

N-(2-Hydroxyethyl)-4-{[(2-{[(1S)-2-(1H-imidazol-1-yl)-1-phenylethyl]oxy}-5-oxo-5,6,7,8-tetrahydro-1-naphthalenyl)methyl]sulfonyl}benzamide (Compound 175);

N-(2-Hydroxyethyl)-3-{[(2-{[(1S)-2-(1H-imidazol-1-yl)-1-phenylethyl]oxy}-5-oxo-5,6,7,8-tetrahydro-1-naphthalenyl)methyl]sulfonyl}benzamide (Compound 176);

N-[2-(Dimethylamino)ethyl]-4-{[(2-{[(1S)-2-(1H-imidazol-1-yl)-1-phenylethyl]oxy}-5-oxo-5,6,7,8-tetrahydro-1-naphthalenyl)methyl]sulfanyl}benzamide (Compound 177);

N-[2-(Dimethylamino)ethyl]-3-{[(2-{[(1S)-2-(1H-imidazol-1-yl)-1-phenylethyl]oxy}-5-oxo-5,6,7,8-tetrahydro-1-naphthalenyl)methyl]sulfanyl}benzamide (Compound 178);

N-[2-(Dimethylamino)ethyl]-2-{[(2-{[(1S)-2-(1H-imidazol-1-yl)-1-phenylethyl]oxy}-5-oxo-5,6,7,8-tetrahydro-1-naphthalenyl)methyl]sulfanyl}benzamide (Compound 179);

N-[2-(Dimethylamino)ethyl]-2-{[(2-{[(1S)-2-(1H-imidazol-1-yl)-1-phenylethyl]oxy}-5-oxo-5,6,7,8-tetrahydro-1-naphthalenyl)methyl]sulfonyl}benzamide (Compound 180);

N-[2-(Dimethylamino)ethyl]-4-{[(2-{[(1S)-2-(1H-imidazol-1-yl)-1-phenylethyl]oxy}-5-oxo-5,6,7,8-tetrahydro-1-naphthalenyl)methyl]sulfonyl}benzamide (Compound 181);

N-[2-(Dimethylamino)ethyl]-3-{[(2-{[(1S)-2-(1H-imidazol-1-yl)-1-phenylethyl]oxy}-5-oxo-5,6,7,8-tetrahydro-1-naphthalenyl)methyl]sulfonyl}benzamide (Compound 182);

Ethyl 3-[(2-{[(2-{[(1S)-2-(1H-Imidazol-1-yl)-1-phenylethyl]oxy}-5-oxo-5,6,7,8-tetrahydro-1-naphthalenyl)methyl]sulfonyl}benzoyl)amino]propanoate (Compound 183);

Ethyl 4-[(2-{[(2-{[(1S)-2-(1H-Imidazol-1-yl)-1-phenylethyl]oxy}-5-oxo-5,6,7,8-tetrahydro-1-naphthalenyl)methyl]sulfonyl}benzoyl)amino]propanoate (Compound 184);

Ethyl 2-[(2-{[(2-{[(1S)-2-(1H-Imidazol-1-yl)-1-phenylethyl]oxy}-5-oxo-5,6,7,8-tetrahydro-1-naphthalenyl)methyl]sulfonyl}benzoyl)amino]propanoate (Compound 185);

Ethyl 2-[(2-{[(2-{[(1S)-2-(1H-Imidazol-1-yl)-1-phenylethyl]oxy}-5-oxo-5,6,7,8-tetrahydro-1-naphthalenyl)methyl]sulfanyl}benzoyl)amino]propanoate (Compound 186);

Ethyl 3-[(2-{[(2-{[(1S)-2-(1H-Imidazol-1-yl)-1-phenylethyl]oxy}-5-oxo-5,6,7,8-tetrahydro-1-naphthalenyl)methyl]sulfanyl}benzoyl)amino]propanoate (Compound 187);

Ethyl 4-[(2-{[(2-{[(1S)-2-(1H-Imidazol-1-yl)-1-phenylethyl]oxy}-5-oxo-5,6,7,8-tetrahydro-1-naphthalenyl)methyl]sulfanyl}benzoyl)amino]propanoate (Compound 188);

4-{[(2-{[(1S)-2-(1H-2-Imidazol-1-yl)-1-phenylethyl]oxy}-5-oxo-5,6,7,8-tetrahydro-1-naphthalenyl)methyl]sulfonyl}-N-methylbenzamide (Compound 189);

3-{[(2-{[(1S)-2-(1H-imidazol-1-yl)-1-phenylethyl]oxy}-5-oxo-5,6,7,8-tetrahydro-1-naphthalenyl)methyl]sulfonyl}-N-methylbenzamide (Compound 190);

4-{[(2-{[(1S)-2-(1H-Imidazol-1-yl)-1-phenylethyl]oxy}-5-oxo-5,6,7,8-tetrahydro-1-naphthalenyl)methyl]sulfanyl}-N-methylbenzamide (Compound 191);

3-{[(2-{[(1S)-2-(1H-Imidazol-1-yl)-1-phenylethyl]oxy}-5-oxo-5,6,7,8-tetrahydro-1-naphthalenyl)methyl]sulfanyl}-N-methylbenzamide (Compound 192);

2-{[(2-{[(1S)-2-(1H-Imidazol-1-yl)-1-phenylethyl]oxy}-5-oxo-5,6,7,8-tetrahydro-1-naphthalenyl)methyl]sulfanyl}-N-methylbenzamide (Compound 193);

N-[(2R)-2-Hydroxypropyl]-2-{[(2-{[(1S)-2-(1H-imidazol-1-yl)-1-phenylethyl]oxy}-5-oxo-5,6,7,8-tetrahydro-1-naphthalenyl)methyl]sulfanyl}benzamide (Compound 194);

N-[(2R)-2-Hydroxypropyl]-4-{[(2-{[(1S)-2-(1H-imidazol-1-yl)-1-phenylethyl]oxy}-5-oxo-5,6,7,8-tetrahydro-1-naphthalenyl)methyl]sulfanyl}benzamide (Compound 195);

N-[(2S)-2-Hydroxypropyl]-4-{[(2-{[(1S)-2-(1H-imidazol-1-yl)-1-phenylethyl]oxy}-5-oxo-5,6,7,8-tetrahydro-1-naphthalenyl)methyl]sulfanyl}benzamide (Compound 196);

N-[(2S)-2-Hydroxypropyl]-3-{[(2-{[(1S)-2-(1H-imidazol-1-yl)-1-phenylethyl]oxy}-5-oxo-5,6,7,8-tetrahydro-1-naphthalenyl)methyl]sulfanyl}benzamide (Compound 197);

N-[(2S)-2-Hydroxypropyl]-2-{[(2-{[(1S)-2-(1H-imidazol-1-yl)-1-phenylethyl]oxy}-5-oxo-5,6,7,8-tetrahydro-1-naphthalenyl)methyl]sulfanyl}benzamide (Compound 198);

N-[(2S)-2-Hydroxypropyl]-4-{[(2-{[(1S)-2-(1H-imidazol-1-yl)-1-phenylethyl]oxy}-5-oxo-5,6,7,8-tetrahydro-1-naphthalenyl)methyl]sulfonyl}benzamide (Compound 199);

N-[(2S)-2-Hydroxypropyl]-3-{[(2-{[(1S)-2-(1H-imidazol-1-yl)-1-phenylethyl]oxy}-5-oxo-5,6,7,8-tetrahydro-1-naphthalenyl)methyl]sulfonyl}benzamide (Compound 200);

N-[(2S)-2-Hydroxypropyl]-2-{[(2-{[(1S)-2-(1H-imidazol-1-yl)-1-phenylethyl]oxy}-5-oxo-5,6,7,8-tetrahydro-1-naphthalenyl)methyl]sulfonyl}benzamide (Compound 201);

N-[(2R)-2-Hydroxypropyl]-2-{[(2-{[(1S)-2-(1H-imidazol-1-yl)-1-phenylethyl]oxy}-5-oxo-5,6,7,8-tetrahydro-1-naphthalenyl)methyl]sulfonyl}benzamide (Compound 202);

N-[(2R)-2-Hydroxypropyl]-4-{[(2-{[(1S)-2-(1H-imidazol-1-yl)-1-phenylethyl]oxy}-5-oxo-5,6,7,8-tetrahydro-1-naphthalenyl)methyl]sulfonyl}benzamide (Compound 203);

N-[(2R)-2-Hydroxypropyl]-3-{[(2-{[(1S)-2-(1H-imidazol-1-yl)-1-phenylethyl]oxy}-5-oxo-5,6,7,8-tetrahydro-1-naphthalenyl)methyl]sulfonyl}benzamide (Compound 204);

N-Allyl-3-{[(2-{[(1S)-2-(1H-imidazol-1-yl)-1-phenylethyl]oxy}-5-oxo-5,6,7,8-tetrahydro-1-naphthalenyl)methyl]sulfonyl}benzamide (Compound 205);

N-Allyl-4-{[(2-{[(1S)-2-(1H-imidazol-1-yl)-1-phenylethyl]oxy}-5-oxo-5,6,7,8-tetrahydro-1-naphthalenyl)methyl]sulfonyl}benzamide (Compound 206);

N-Allyl-2-{[(2-{[(1S)-2-(1H-imidazol-1-yl)-1-phenylethyl]oxy}-5-oxo-5,6,7,8-tetrahydro-1-naphthalenyl)methyl]sulfonyl}benzamide (Compound 207);

N-Allyl-2-{[(2-{[(1S)-2-(1H-imidazol-1-yl)-1-phenylethyl]oxy}-5-oxo-5,6,7,8-tetrahydro-1-naphthalenyl)methyl]sulfanyl}benzamide (Compound 208);

N-Allyl-4-{[(2-{[(1S)-2-(1H-imidazol-1-yl)-1-phenylethyl]oxy}-5-oxo-5,6,7,8-tetrahydro-1-naphthalenyl)methyl]sulfanyl}benzamide (Compound 209);

N-Allyl-3-{[(2-{[(1S)-2-(1H-imidazol-1-yl)-1-phenylethyl]oxy}-5-oxo-5,6,7,8-tetrahydro-1-naphthalenyl)methyl]sulfanyl}benzamide (Compound 210);

2-{[(2-{[(1S)-2-(1H-Imidazol-1-yl)-1-phenylethyl]oxy}-5-oxo-5,6,7,8-tetrahydro-1-naphthalenyl)methyl]sulfanyl}-N-(2-propynyl)benzamide (Compound 211);

4-{[(2-{[(1S)-2-(1H-Imidazol-1-yl)-1-phenylethyl]oxy}-5-oxo-5,6,7,8-tetrahydro-1-naphthalenyl)methyl]sulfanyl}-N-(2-propynyl)benzamide (Compound 212);

3-{[(2-{[(1S)-2-(1H-Imidazol-1-yl)-1-phenylethyl]oxy}-5-oxo-5,6,7,8-tetrahydro-1-naphthalenyl)methyl]sulfanyl}-N-(2-propynyl)benzamide (Compound 213);

4-{[(2-{[(1S)-2-(1H-Imidazol-1-yl)-1-phenylethyl]oxy}-5-oxo-5,6,7,8-tetrahydro-1-naphthalenyl)methyl]sulfonyl}-N-(2-propynyl)benzamide (Compound 214);

3-{[(2-{[(1S)-2-(1H-Imidazol-1-yl)-1-phenylethyl]oxy}-5-oxo-5,6,7,8-tetrahydro-1-naphthalenyl)methyl]sulfonyl}-N-(2-propynyl)benzamide (Compound 215);

2-{[(2-{[(1S)-2-(1H-Imidazol-1-yl)-1-phenylethyl]oxy}-5-oxo-5,6,7,8-tetrahydro-1-naphthalenyl)methyl]sulfonyl}-N-(2-propynyl)benzamide (Compound 216);

N-Cyclopentyl-4-{[(2-{[(1S)-2-(1H-imidazol-1-yl)-1-phenylethyl]oxy}-5-oxo-5,6,7,8-tetrahydro-1-naphthalenyl)methyl]sulfonyl}benzamide (Compound 217);

N-Cyclopentyl-3-{[(2-{[(1S)-2-(1H-imidazol-1-yl)-1-phenylethyl]oxy}-5-oxo-5,6,7,8-tetrahydro-1-naphthalenyl)methyl]sulfonyl}benzamide (Compound 218);

N-Cyclopentyl-2-{[(2-{[(1S)-2-(1H-imidazol-1-yl)-1-phenylethyl]oxy}-5-oxo-5,6,7,8-tetrahydro-1-naphthalenyl)methyl]sulfonyl}benzamide (Compound 219);

N-Cyclopentyl-4-{[(2-{[(1S)-2-(1H-imidazol-1-yl)-1-phenylethyl]oxy}-5-oxo-5,6,7,8-tetrahydro-1-naphthalenyl)methyl]sulfanyl}benzamide (Compound 220);

N-Cyclopentyl-3-{[(2-{[(1S)-2-(1H-imidazol-1-yl)-1-phenylethyl]oxy}-5-oxo-5,6,7,8-tetrahydro-1-naphthalenyl)methyl]sulfanyl}benzamide (Compound 221);

N-Cyclopentyl-2-{[(2-{[(1S)-2-(1H-imidazol-1-yl)-1-phenylethyl]oxy}-5-oxo-5,6,7,8-tetrahydro-1-naphthalenyl)methyl]sulfanyl}benzamide (Compound 222);

N-Cyclopropyl-4-{[(2-{[(1S)-2-(1H-imidazol-1-yl)-1-phenylethyl]oxy}-5-oxo-5,6,7,8-tetrahydro-1-naphthalenyl)methyl]sulfonyl}benzamide (Compound 223);

N-Cyclopropyl-3-{[(2-{[(1S)-2-(1H-imidazol-1-yl)-1-phenylethyl]oxy}-5-oxo-5,6,7,8-tetrahydro-1-naphthalenyl)methyl]sulfonyl}benzamide (Compound 224);

N-Cyclopropyl-2-{[(2-{[(1S)-2-(1H-imidazol-1-yl)-1-phenylethyl]oxy}-5-oxo-5,6,7,8-tetrahydro-1-naphthalenyl)methyl]sulfonyl}benzamide (Compound 225);

N-Cyclopropyl-4-{[(2-{[(1S)-2-(1H-imidazol-1-yl)-1-phenylethyl]oxy}-5-oxo-5,6,7,8-tetrahydro-1-naphthalenyl)methyl]sulfanyl}benzamide (Compound 226);

N-Cyclopropyl-3-{[(2-{[(1S)-2-(1H-imidazol-1-yl)-1-phenylethyl]oxy}-5-oxo-5,6,7,8-tetrahydro-1-naphthalenyl)methyl]sulfanyl}benzamide (Compound 227);

N-Cyclopropyl-2-{[(2-{[(1S)-2-(1H-imidazol-1-yl)-1-phenylethyl]oxy}-5-oxo-5,6,7,8-tetrahydro-1-naphthalenyl)methyl]sulfanyl}benzamide (Compound 228);

N-(2-Furylmethyl)-4-{[(2-{[(1S)-2-(1H-imidazol-1-yl)-1-phenylethyl]oxy}-5-oxo-5,6,7,8-tetrahydro-1-naphthalenyl)methyl]sulfonyl}benzamide (Compound 229);

N-(2-Furylmethyl)-3-{[(2-{[(1S)-2-(1H-imidazol-1-yl)-1-phenylethyl]oxy}-5-oxo-5,6,7,8-tetrahydro-1-naphthalenyl)methyl]sulfonyl}benzamide (Compound 230);

N-(2-Furylmethyl)-2-{[(2-{[(1S)-2-(1H-imidazol-1-yl)-1-phenylethyl]oxy}-5-oxo-5,6,7,8-tetrahydro-1-naphthalenyl)methyl]sulfonyl}benzamide (Compound 231);

N-[2-Hydroxy-1-(hydroxymethyl)ethyl]-2-{[(2-{[(1S)-2-(1H-imidazol-1-yl)-1-phenylethyl]oxy}-5-oxo-5,6,7,8-tetrahydro-1-naphthalenyl)methyl]sulfanyl}benzamide (Compound 232);

N-[2-Hydroxy-1-(hydroxymethyl)ethyl]-4-{[(2-{[(1S)-2-(1H-imidazol-1-yl)-1-phenylethyl]oxy}-5-oxo-5,6,7,8-tetrahydro-1-naphthalenyl)methyl]sulfanyl}benzamide (Compound 233);

N-[2-Hydroxy-1-(hydroxymethyl)ethyl]-3-{[(2-{[(1S)-2-(1H-imidazol-1-yl)-1-phenylethyl]oxy}-5-oxo-5,6,7,8-tetrahydro-1-naphthalenyl)methyl]sulfanyl}benzamide (Compound 234);

N-[2-Hydroxy-1-(hydroxymethyl)ethyl]-4-{[(2-{[(1S)-2-(1H-imidazol-1-yl)-1-phenylethyl]oxy}-5-oxo-5,6,7,8-tetrahydro-1-naphthalenyl)methyl]sulfonyl}benzamide (Compound 235);

N-[2-Hydroxy-1-(hydroxymethyl)ethyl]-3-{[(2-{[(1S)-2-(1H-imidazol-1-yl)-1-phenylethyl]oxy}-5-oxo-5,6,7,8-tetrahydro-1-naphthalenyl)methyl]sulfonyl}benzamide (Compound 236);

N-[2-Hydroxy-1-(hydroxymethyl)ethyl]-2-{[(2-{[(1S)-2-(1H-imidazol-1-yl)-1-phenylethyl]oxy}-5-oxo-5,6,7,8-tetrahydro-1-naphthalenyl)methyl]sulfonyl}benzamide (Compound 237);

N-(2-Furylmethyl)-4-{[(2-{[(1S)-2-(1H-imidazol-1-yl)-1-phenylethyl]oxy}-5-oxo-5,6,7,8-tetrahydro-1-naphthalenyl)methyl]sulfanyl}benzamide (Compound 238);

N-(2-Furylmethyl)-3-{[(2-{[(1S)-2-(1H-imidazol-1-yl)-1-phenylethyl]oxy}-5-oxo-5,6,7,8-tetrahydro-1-naphthalenyl)methyl]sulfanyl}benzamide (Compound 239);

N-(2-Furylmethyl)-2-{[(2-{[(1S)-2-(1H-imidazol-1-yl)-1-phenylethyl]oxy}-5-oxo-5,6,7,8-tetrahydro-1-naphthalenyl)methyl]sulfanyl}benzamide (Compound 240);

N-[(1R)-1-(Hydroxymethyl)propyl]-4-{[(2-{[(1S)-2-(1H-imidazol-1-yl)-1-phenylethyl]oxy}-5-oxo-5,6,7,8-tetrahydro-1-naphthalenyl)methyl]sulfonyl}benzamide (Compound 241);

N-[(1R)-1-(Hydroxymethyl)propyl]-3-{[(2-{[(1S)-2-(1H-imidazol-1-yl)-1-phenylethyl]oxy}-5-oxo-5,6,7,8-tetrahydro-1-naphthalenyl)methyl]sulfonyl}benzamide (Compound 242);

N-[(1R)-1-(Hydroxymethyl)propyl]-2-{[(2-{[(1S)-2-(1H-imidazol-1-yl)-1-phenylethyl]oxy}-5-oxo-5,6,7,8-tetrahydro-1-naphthalenyl)methyl]sulfonyl}benzamide (Compound 243);

N-[(1R)-1-(Hydroxymethyl)propyl]-2-{[(2-{[(1S)-2-(1H-imidazol-1-yl)-1-phenylethyl]oxy}-5-oxo-5,6,7,8-tetrahydro-1-naphthalenyl)methyl]sulfanyl}benzamide (Compound 244);

N-[(1R)-1-(Hydroxymethyl)propyl]-4-{[(2-{[(1S)-2-(1H-imidazol-1-yl)-1-phenylethyl]oxy}-5-oxo-5,6,7,8-tetrahydro-1-naphthalenyl)methyl]sulfanyl}benzamide (Compound 245);

N-[(1R)-1-(Hydroxymethyl)propyl]-3-{[(2-{[(1S)-2-(1H-imidazol-1-yl)-1-phenylethyl]oxy}-5-oxo-5,6,7,8-tetrahydro-1-naphthalenyl)methyl]sulfanyl}benzamide (Compound 246);

4-{[(2-{[(1S)-2-(1H-Imidazol-1-yl)-1-phenylethyl]oxy}-5-oxo-5,6,7,8-tetrahydro-1-naphthalenyl)methyl]sulfonyl}-N-[(2S)-2-methylbutyl]benzamide (Compound 247);

3-{[(2-{[(1S)-2-(1H-Imidazol-1-yl)-1-phenylethyl]oxy}-5-oxo-5,6,7,8-tetrahydro-1-naphthalenyl)methyl]sulfonyl}-N-[(2S)-2-methylbutyl]benzamide (Compound 248);

2-{[(2-{[(1S)-2-(1H-Imidazol-1-yl)-1-phenylethyl]oxy}-5-oxo-5,6,7,8-tetrahydro-1-naphthalenyl)methyl]sulfonyl}-N-[(2S)-2-methylbutyl]benzamide (Compound 249);

2-{[(2-{[(1S)-2-(1H-Imidazol-1-yl)-1-phenylethyl]oxy}-5-oxo-5,6,7,8-tetrahydro-1-naphthalenyl)methyl]sulfanyl}-N-[(2S)-2-methylbutyl]benzamide (Compound 250);

4-{[(2-{[(1S)-2-(1H-Imidazol-1-yl)-1-phenylethyl]oxy}-5-oxo-5,6,7,8-tetrahydro-1-naphthalenyl)methyl]sulfanyl}-N-[(2S)-2-methylbutyl]benzamide (Compound 251);

3-{[(2-{[(1S)-2-(1H-Imidazol-1-yl)-1-phenylethyl]oxy}-5-oxo-5,6,7,8-tetrahydro-1-naphthalenyl)methyl]sulfanyl}-N-[(2S)-2-methylbutyl]benzamide (Compound 252);

N-(2-Hydroxypropyl)-4-{[(2-{[(1S)-2-(1H-imidazol-1-yl)-1-phenylethyl]oxy}-5-oxo-5,6,7,8-tetrahydro-1-naphthalenyl)methyl]sulfonyl}benzamide (Compound 253);

N-(2-Hydroxypropyl)-3-{[(2-{[(1S)-2-(1H-imidazol-1-yl)-1-phenylethyl]oxy}-5-oxo-5,6,7,8-tetrahydro-1-naphthalenyl)methyl]sulfonyl}benzamide (Compound 254);

N-(2-Hydroxypropyl)-2-{[(2-{[(1S)-2-(1H-imidazol-1-yl)-1-phenylethyl]oxy}-5-oxo-5,6,7,8-tetrahydro-1-naphthalenyl)methyl]sulfonyl}benzamide (Compound 255);

N-(2-Hydroxypropyl)-4-{[(2-{[(1S)-2-(1H-imidazol-1-yl)-1-phenylethyl]oxy}-5-oxo-5,6,7,8-tetrahydro-1-naphthalenyl)methyl]sulfanyl}benzamide (Compound 256);

N-(2-Hydroxypropyl)-2-{[(2-{[(1S)-2-(1H-imidazol-1-yl)-1-phenylethyl]oxy}-5-oxo-5,6,7,8-tetrahydro-1-naphthalenyl)methyl]sulfanyl}benzamide (Compound 257);

N-(2-Hydroxypropyl)-3-{[(2-{[(1S)-2-(1H-imidazol-1-yl)-1-phenylethyl]oxy}-5-oxo-5,6,7,8-tetrahydro-1-naphthalenyl)methyl]sulfanyl}benzamide (Compound 258);

3-{[(2-{[(1S)-2-(1H-Imidazol-1-yl)-1-phenylethyl]oxy}-5-oxo-5,6,7,8-tetrahydro-1-naphthalenyl)methyl]sulfanyl}-N-(2-methoxyethyl)benzamide (Compound 259);

2-{[(2-{[(1S)-2-(1H-Imidazol-1-yl)-1-phenylethyl]oxy}-5-oxo-5,6,7,8-tetrahydro-1-naphthalenyl)methyl]sulfanyl}-N-(2-methoxyethyl)benzamide (Compound 260);

4-{[(2-{[(1S)-2-(1H-Imidazol-1-yl)-1-phenylethyl]oxy}-5-oxo-5,6,7,8-tetrahydro-1-naphthalenyl)methyl]sulfanyl}-N-(2-methoxyethyl)benzamide (Compound 261);

4-{[(2-{[(1S)-2-(1H-Imidazol-1-yl)-1-phenylethyl]oxy}-5-oxo-5,6,7,8-tetrahydro-1-naphthalenyl)methyl]sulfonyl}-N-(2-methoxyethyl)benzamide (Compound 262);

3-{[(2-{[(1S)-2-(1H-Imidazol-1-yl)-1-phenylethyl]oxy}-5-oxo-5,6,7,8-tetrahydro-1-naphthalenyl)methyl]sulfonyl}-N-(2-methoxyethyl)benzamide (Compound 263); and 2-{[(2-{[(1S)-2-(1H-Imidazol-1-yl)-1-phenylethyl]oxy}-5-oxo-5,6,7,8-tetrahydro-1-naphthalenyl)methyl]sulfonyl}-N-(2-methoxyethyl)benzamide (Compound 264).

Illustrative of compounds encompassed by Formula IV include the following list of compounds. This list is meant to be representative only and is not intended to limit the scope of the invention in any way:

(±)-6-(2-Imidazolyl-1-(2-pyridyl)ethoxy)-5-(2-phenylethyl)-2,3,4-trihydronaphthalen-1-one (Compound 57);

(±)-6-(2-Imidazolyl-1-(3-pyridyl)ethoxy)-5-(2-phenylethyl)-2,3,4-trihydronaphthalen-1-one (Compound 58);

6-((S)-2-Imidazol-1-yl-1-pyridin-3-yl-ethoxy)-5-phenethyl-3,4-dihydro-2H-naphthalen-1-one (Compound 63a);

6-((S)-2-Imidazol-1-yl-1-pyridin-3-yl-ethoxy)-5-(propane-2-sulfonylmethyl)-3,4-dihydro-2H-napthalen-1-one (Compound 63b);

6-((S)-2-Imidazol-1-yl-1-pyridin-3-yl-ethoxy)-5-(pyridin-2-ylsulfonylmethyl)-3,4-dihydro-2H-napthalen-1-one (Compound 63ba);

6-((S)-2-Imidazol-1-yl-1-pyridin-3-ethoxy)-5-(2-pyridin-2-yl-ethyl)-3,4-dihydro-2H-naphthalen-1-one (Compound 63c);

Isoquinoline-1-carboxylic acid [2-((S)-2-imidazol-1-yl-1-pyridin-3-yl-ethoxy)-5-oxo-5,6,7,8-tetrahydro-naphthalen-1-yl]-amide (Compound 63d);

Pyrazine-2-carboxylic acid [2-((S)-2-imidazol-1-yl-1-pyridin-3-yl-ethoxy)-5-oxo-5,6,7,8-tetrahydro-naphthalen-1-yl]-amide (Compound 63e); and Cinnoline-4-carboxylic acid [2-((S)-2-imidazol-1-yl-1-pyridin-3-yl-ethoxy)-5-oxo-5,6,7,8-tetrahydro-naphthalen-1-yl]-amide (Compound 63f).

Additional representative compounds of the present invention include the following list of compounds. This list is meant to be representative only and is not intended to limit the scope of the invention in any way:

6-((1S)-2-Imidazolyl-1-phenylethoxy)-4-(3-chlorophenyl)-2,3,4-trihydronaphthalen-1-one (Compound 47);

(±)-6-(2-Imidazolyl-1-phenylethoxy)-4-phenyl-2,3,4-trihydro-naphthalen-1-one (Compound 48);

(±)-6-[1-(2-Chlorophenyl)-2-imidazolylethoxy]-5-prop-2-enyl-2,3,4-trihydronaphthalen-1-one (Compound 59);

(±)-6-[1-(2,6-Dichlorophenyl)-2-imidazolylethoxy]-5-prop-2-enyl-2,3,4-trihydronaphthalen-1-one, trifluoroacetic acid (Compound 60);

(±)-6-(2-imidazolyl-1-(2-thienyl)ethoxy)-5-prop-2-enyl-2,3,4-trihydronaphthalen-1-one (Compound 61);

6-[1-(1H-Imidazol-1-ylmethyl)-2-methylpropoxy]-5-[(phenylsulfonyl)methyl]-3,4-dihydro-1(2H)-naphthalenone (Compound 63l);

6-[1-(1H-Imidazol-1-ylmethyl)propoxy]-5-[(phenylsulfonyl)methyl]-3,4-dihydro-1(2H)-naphthalenone (Compound 63n);

(±)-6-[2-(2-Methyl-imidazol-1-yl)-1-phenyl-ethoxy]-5-phenethyl-3,4-dihydro-2H-naphthalen-1-one (Compound 63o);

6-(2-Imidazol-1-yl-1-thiophen-2-yl-ethoxy)-5-(pyridine-2-sulfonylmethyl)-3,4-dihidro-2H-naphthalen-1-one (Compound 63p);

6-(2-Imidazol-1-yl-1-thiazol-2-yl-ethoxy)-5-(pyridine-2-sulfonylmethyl)-3,4-dihidro-2H-naphthalen-1-one (Compound 63q); and 6-[2-(2-Amino-imidazol-1-yl)-1-phenyl-ethoxy]-5-phenethyl-3,4-dihydro-2H-naphthalen-1-one (Compound 63r).

The compounds of the present invention can be administered to a patient alone or as part of a composition that contains other components such as excipients, diluents, and carriers, all of which are well-known in the art. The compositions can be administered to humans and animals either orally, rectally, parenterally (intravenously, intramuscularly, or subcutaneously), intracisternally, intravaginally, intraperitoneally, intravesically, locally (powders, ointments, or drops), or as a buccal or nasal spray. The present invention includes a pharmaceutical composition comprising a compound of Formulas I–VIII and a pharmaceutically acceptable excipients, diluents, and carriers thereof.

Compositions suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil), and injectable organic esters such as ethyl oleate. Proper fluidity can be maintained, for example, by the use of a coating such as lecithin, by the maintenance of the required particle size in the case of dispersions and by the use of surfactants.

These compositions may also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monostearate and gelatin.

Solid dosage forms for oral administration include capsules, tablets, pills, powders, and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol, and silicic acid; (b) binders, as for example, carboxymethylcellulose, alignates, gelatin, polyvinylpyrrolidone, sucrose, and acacia; (c) humectants, as for example, glycerol; (d) disintegrating agents, as for example, agar-agar, calcium carbonate, potato or tapioca starch, alginic acid, certain complex silicates, and sodium carbonate; (e) solution retarders, as for example paraffin; (f) absorption accelerators, as for example, quaternary ammonium compounds; (g) wetting agents, as for example, cetyl alcohol and glycerol monostearate; (h) adsorbents, as for example, kaolin and bentonite; and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid compositions of a similar type may also be employed as fillers in soft and hard-filled gelatin capsules using such excipients as lactose or milk sugar as well as high molecular weight polyethyleneglycols, and the like.

Solid dosage forms such as tablets, dragees, capsules, pills, and granules can be prepared with coatings and shells, such as enteric coatings and others well-known in the art. They may contain opacifying agents, and can also be of such composition that they release the active compound or compounds in a certain part of the intestinal tract in a delayed manner. Examples of embedding compositions which can be used are polymeric substances and waxes. The active compounds can also be in micro-encapsulated form, if appropriate, with one or more of the above-mentioned excipients.

Liquid dosage forms for oral administration include pharmaceutically acceptable emulsions, solutions, suspensions, syrups, and elixirs. In addition to the active compounds, the liquid dosage forms may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan or mixtures of these substances, cremophor and the like.

Besides such inert diluents, the composition can also include adjuvants, such as wetting agents, emulsifying and suspending agents, sweetening, flavoring, and perfuming agents.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions for rectal administrations are preferably suppositories which can be prepared by mixing the compounds of the present invention with suitable non-irritating excipients or carriers such as cocoa butter, polyethyleneglycol, or a suppository wax, which are solid at ordinary temperatures but liquid at body temperature and therefore, melt in the rectum or vaginal cavity and release the active component.

Dosage forms for topical administration of a compound of this invention include ointments, powders, sprays, and inhalants. The active component is admixed under sterile conditions with a physiologically acceptable carrier and any preservatives, buffers, or propellants as may be required. Ophthalmic formulations, eye ointments, powders, and solutions are also contemplated as being within the scope of this invention.

The compounds of the present invention can be administered to a patient at dosage levels in the range of about 0.1 to about 2,000 mg per day. For a normal human adult having a body weight of about 70 kilograms, a dosage in the range of about 0.01 to about 100 mg per kilogram of body weight per day is preferable. The specific dosage used, however, can vary. For example, the dosage can depended on a numbers of factors including the requirements of the patient, the severity of the condition being treated, and the pharmacological activity of the compound being used. The determination of optimum dosages for a particular patient is well known to those skilled in the art.

The compounds of the present invention can exist in different stereoisomeric forms by virtue of the presence of asymmetric centers in the compounds. It is contemplated that all stereoisomeric forms of the compounds as well as mixtures thereof, including racemic mixtures, form part of this invention.

In addition, the compounds of the present invention can exist in unsolvated as well as solvated forms with pharmaceutically acceptable solvents such as water, ethanol, and the like. In general, the solvated forms are considered equivalent to the unsolvated forms for the purposes of the present invention.

The examples presented below are intended to illustrate particular embodiments of the invention, and are not intended to limit the scope of the specification or the claims in any way.

An illustration of the preparation of compounds of the present invention is shown below in Schemes 1 to 23. Q through $Q^{13}$ are defined below. L is an appropriate leaving group, such as a halide or equivalent. W, $R^3$, $R^{3a}$, X, $R^5$, Y, $R^6$, and $R^{6a}$ refer to the substituents in Formula I. $R^7$ refers to the substituents in Formula II. $R^9$, $R^{10}$, $R^{11}$, $R^{13}$, $R^{14}$ refer to the substituents in Formula III. $R^{15}$ refers to the substituents in Formula IV. X' and Y' refer to the substituents in Formula V. R" represents any of the substituents listed for "substituted aryl" above.

Armed with the disclosure provided herein (particularly the schemes and the synthetic examples that follow) and knowledge common to all who practice in the field, those of ordinary skill in the art will be able to make and use the entire scope of compounds disclosed herein.

Scheme 1

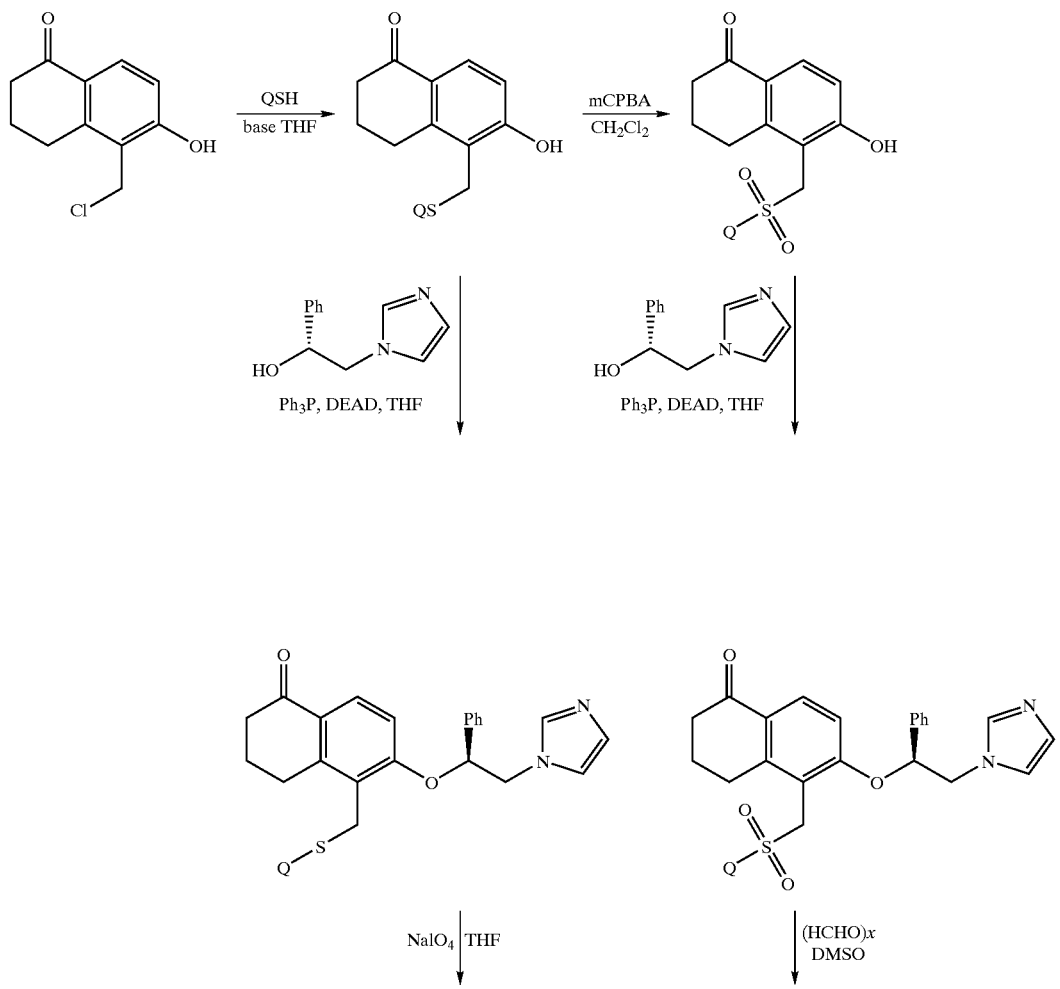

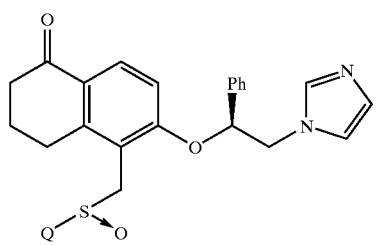
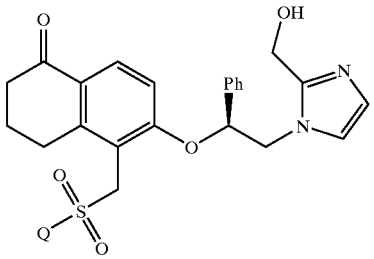
Q is lower alkyl, substituted alkyl, aryl, substituted aryl, arylalkyl substituted arylalkyl, or heteroaryl
Scheme 2
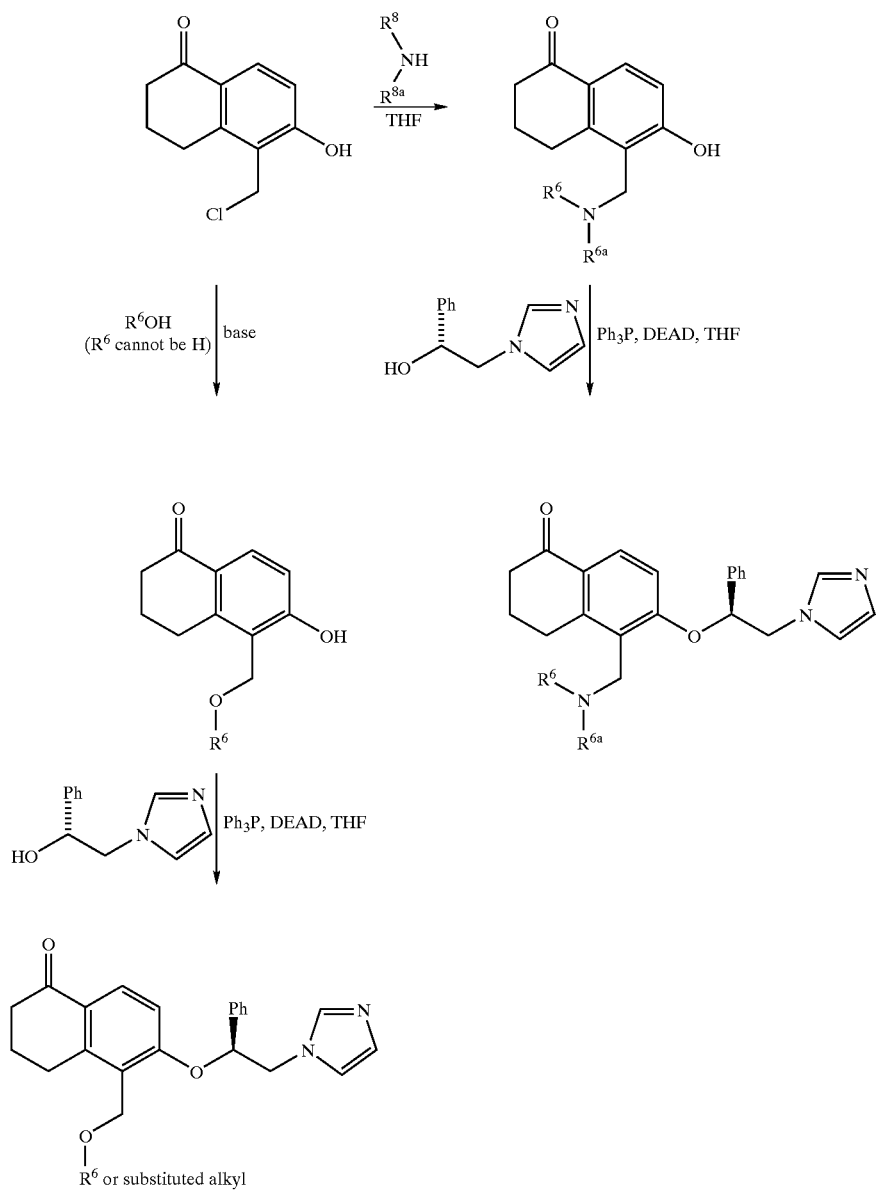

Scheme 3
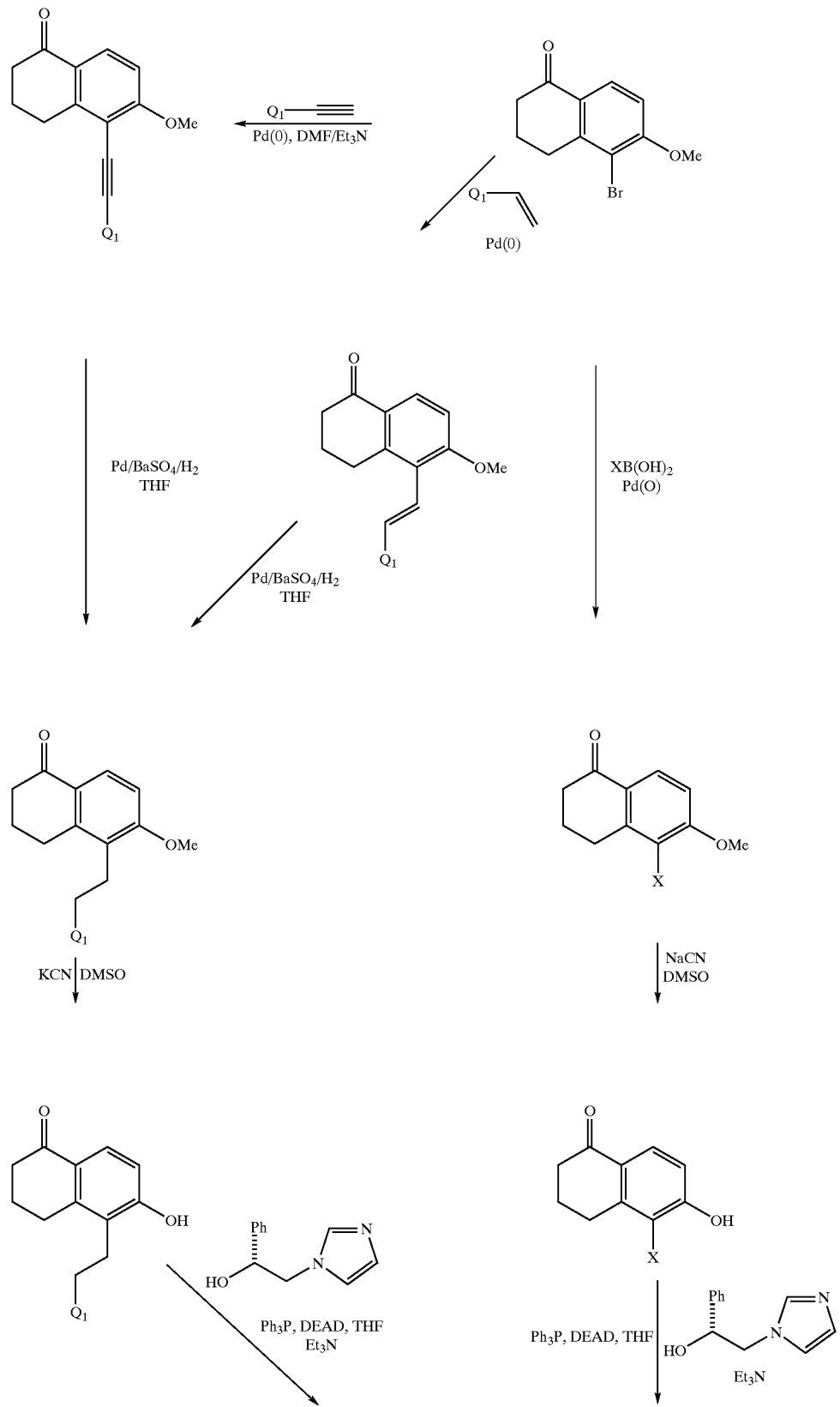

-continued
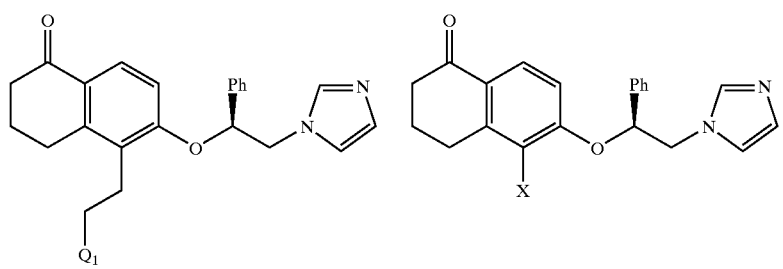
┌── Q₁ = Nheterocycle
mCPBA
└─▶ Q₁ = N(O)heterocycle
Scheme 4
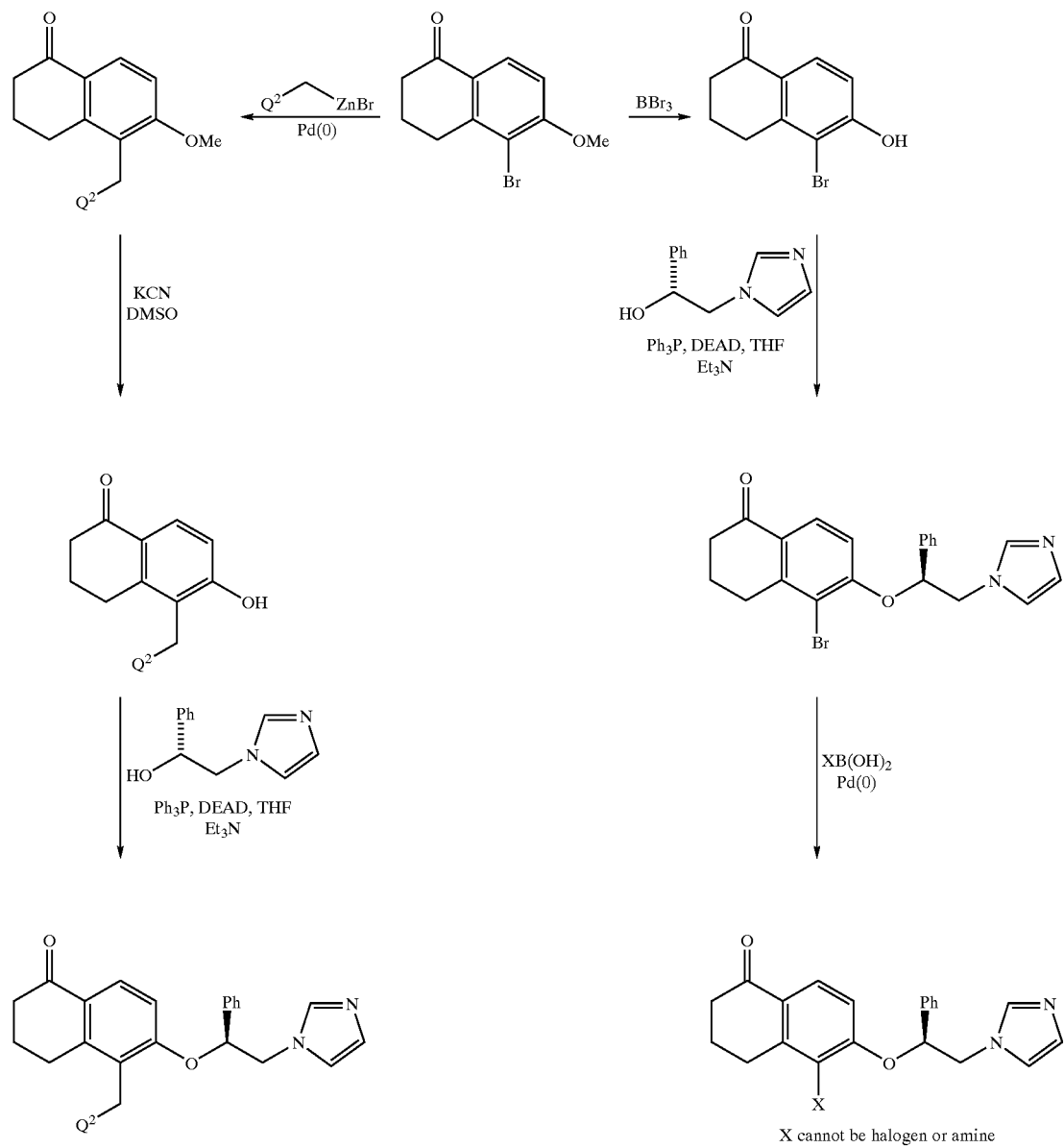

Scheme 5
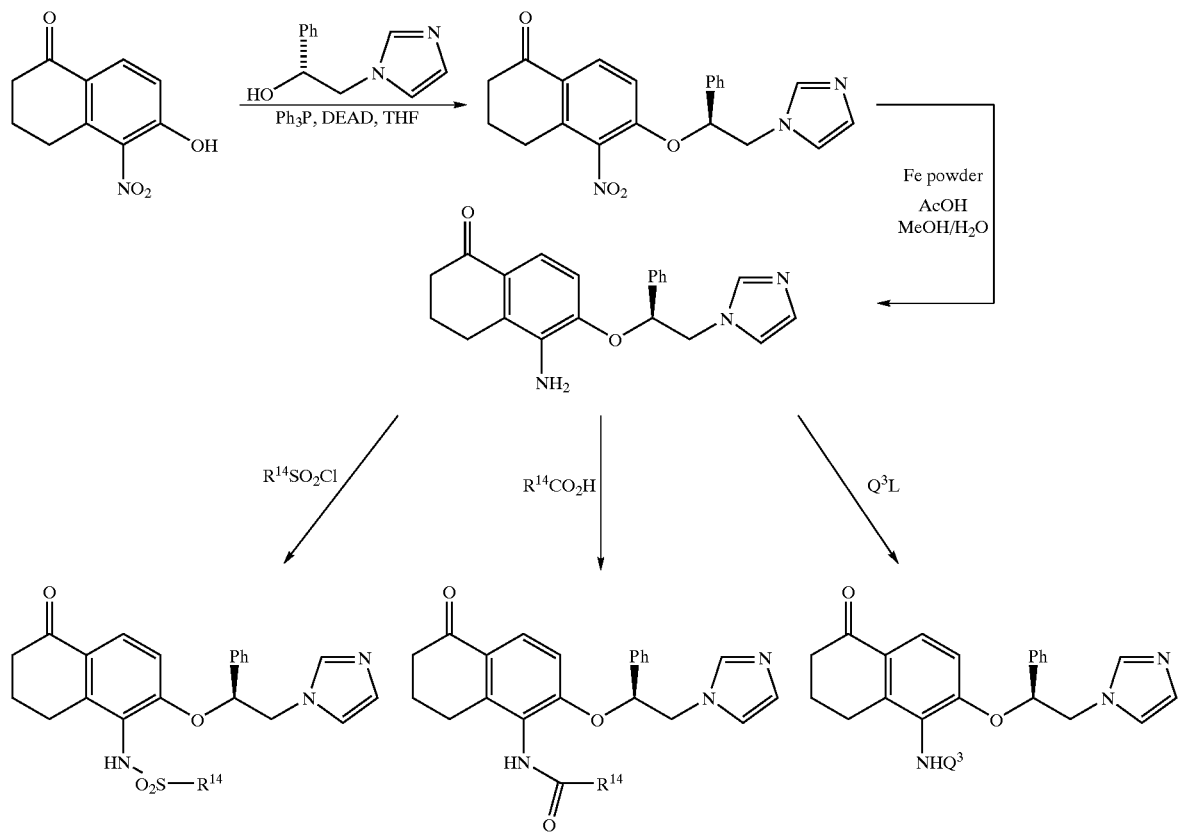
Scheme 6
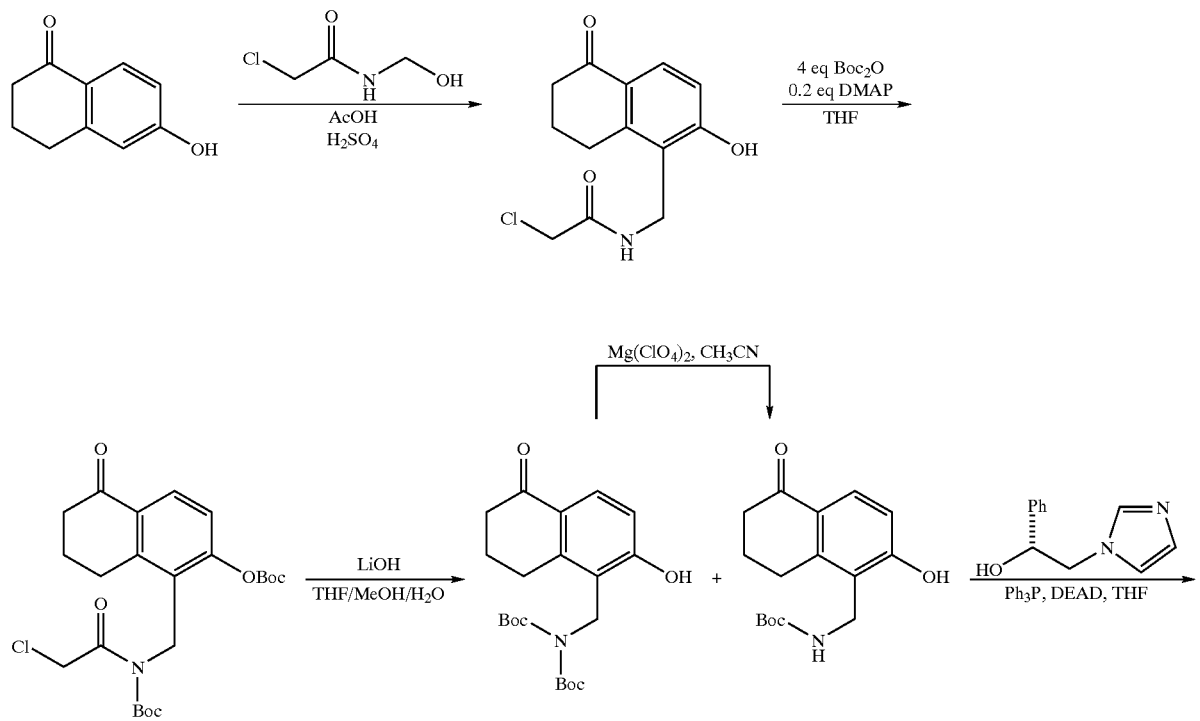

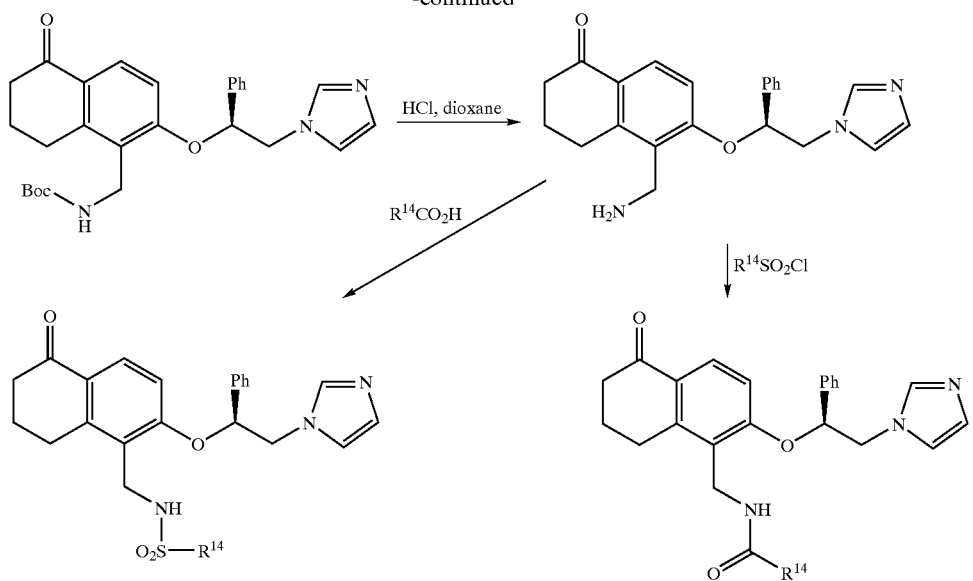
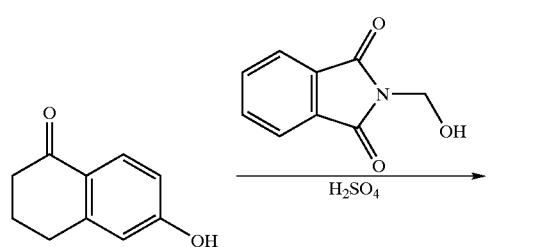
Scheme 7
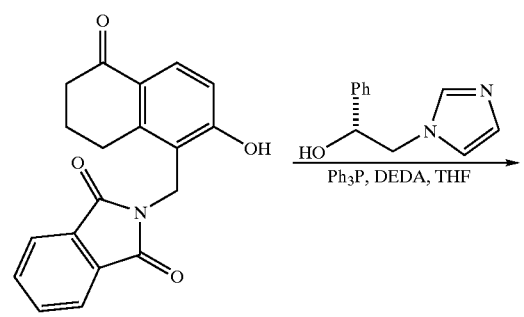
Scheme 8
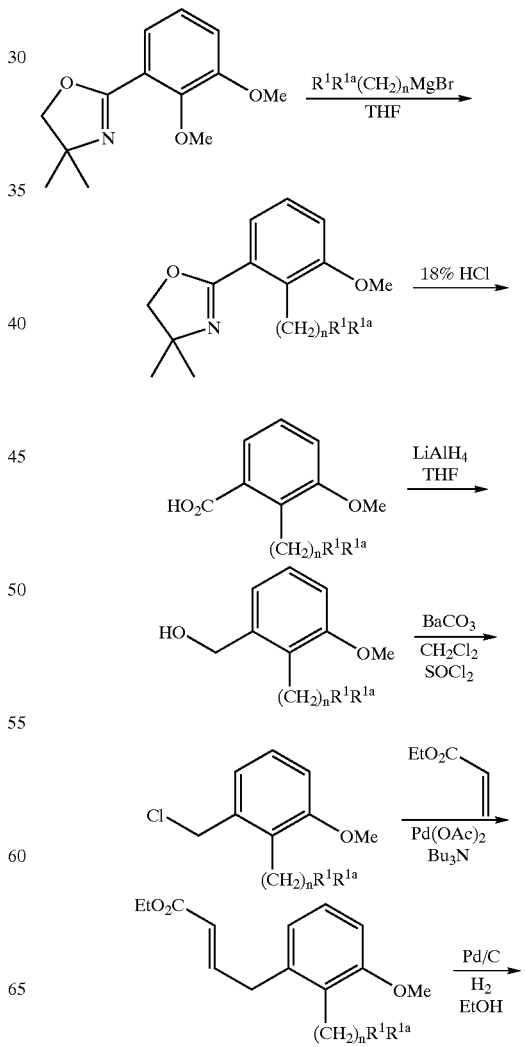

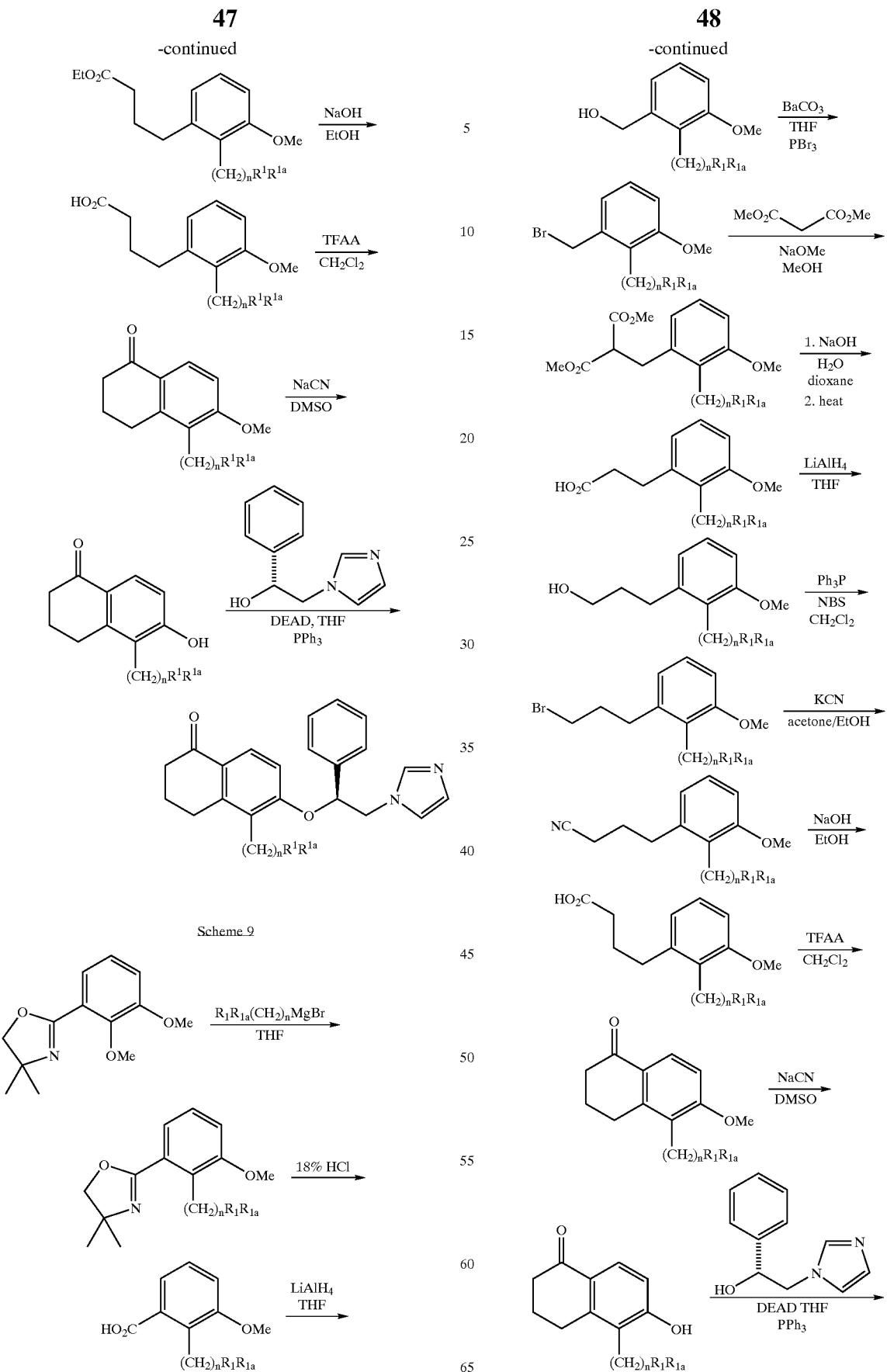

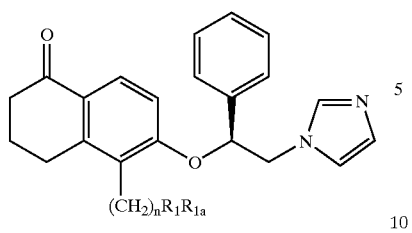
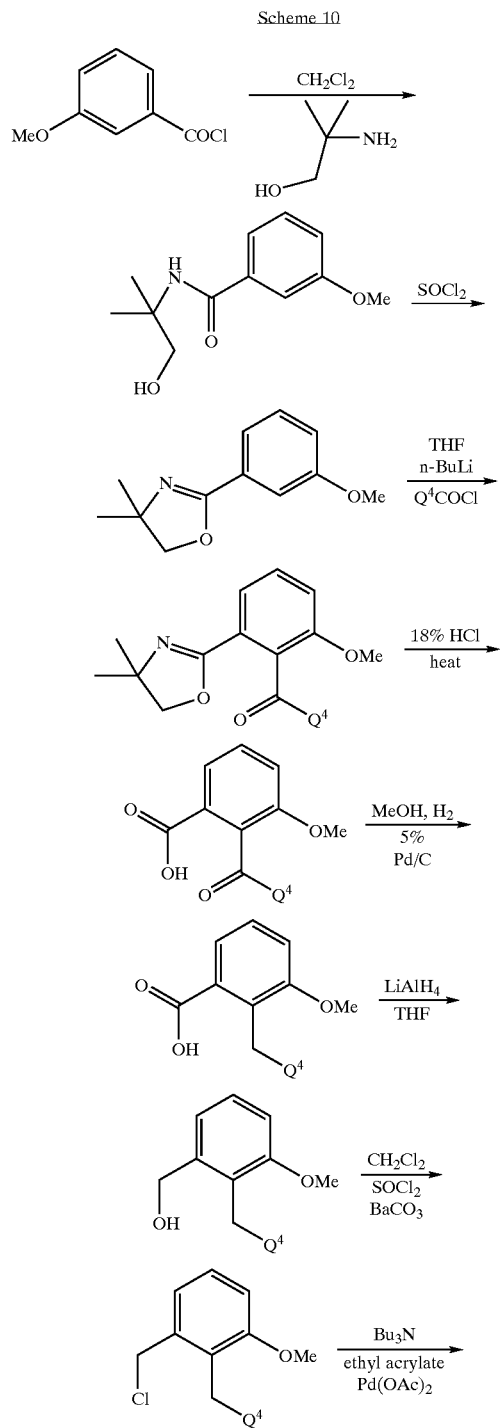
Scheme 10
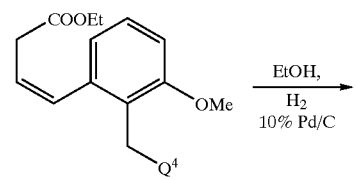
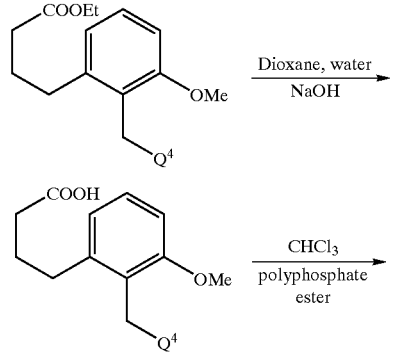
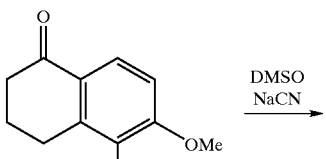
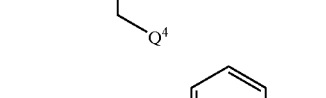
Scheme 11
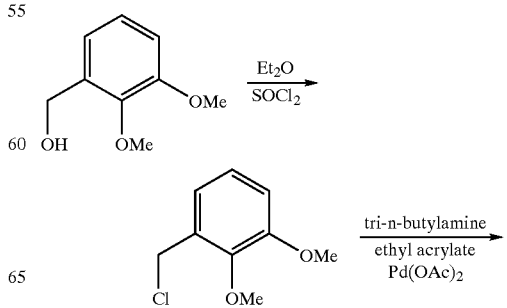

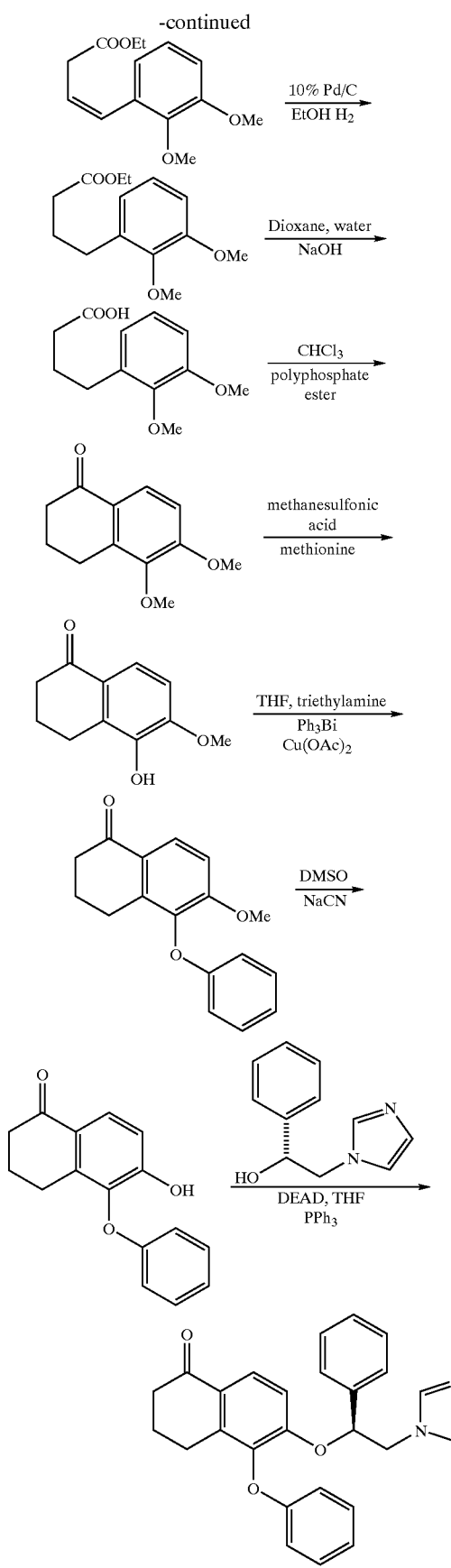
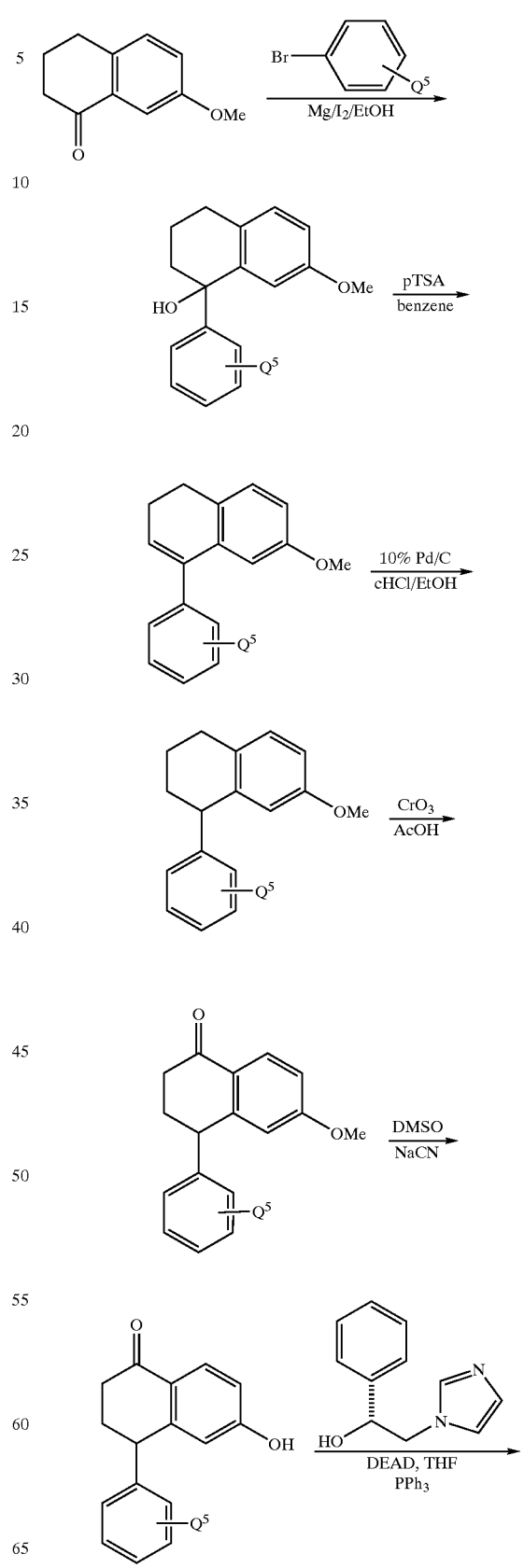
Scheme 12

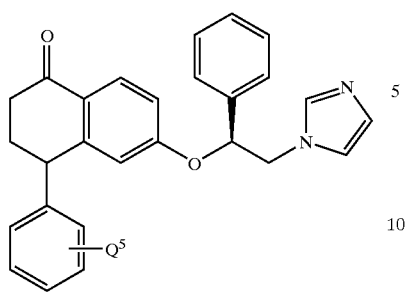
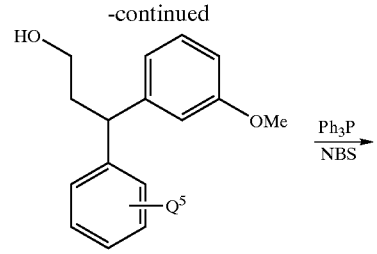
Scheme 13
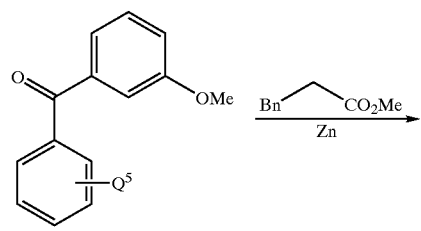
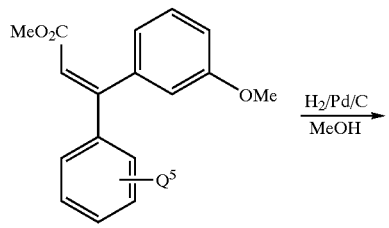
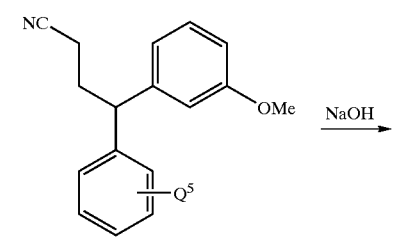
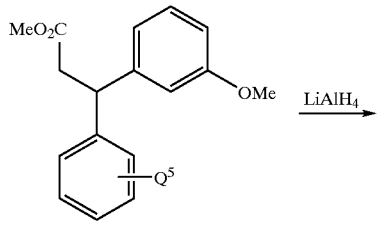
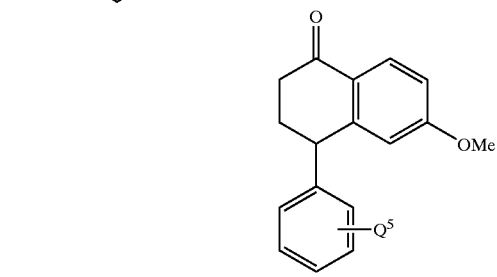
Scheme 14
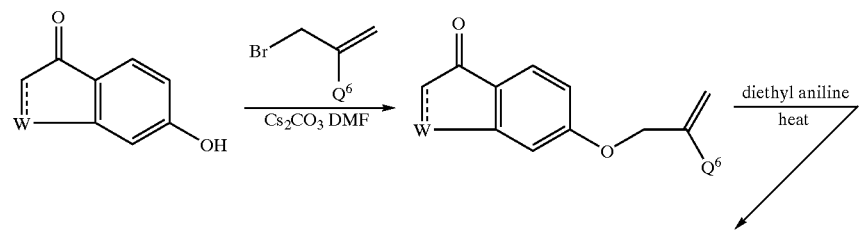

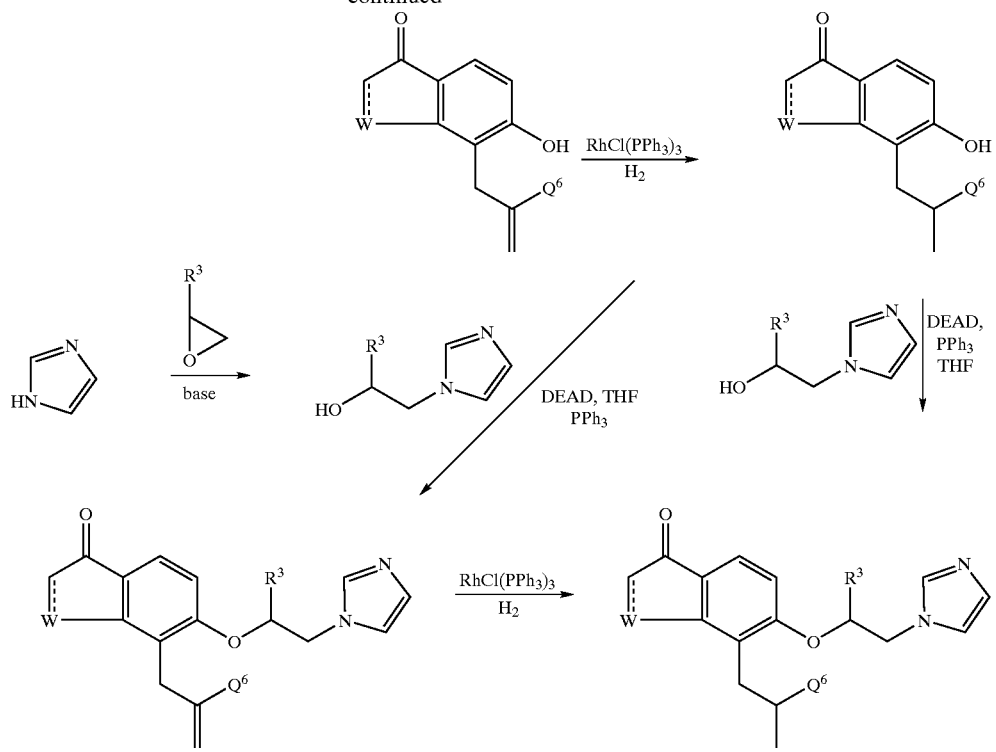
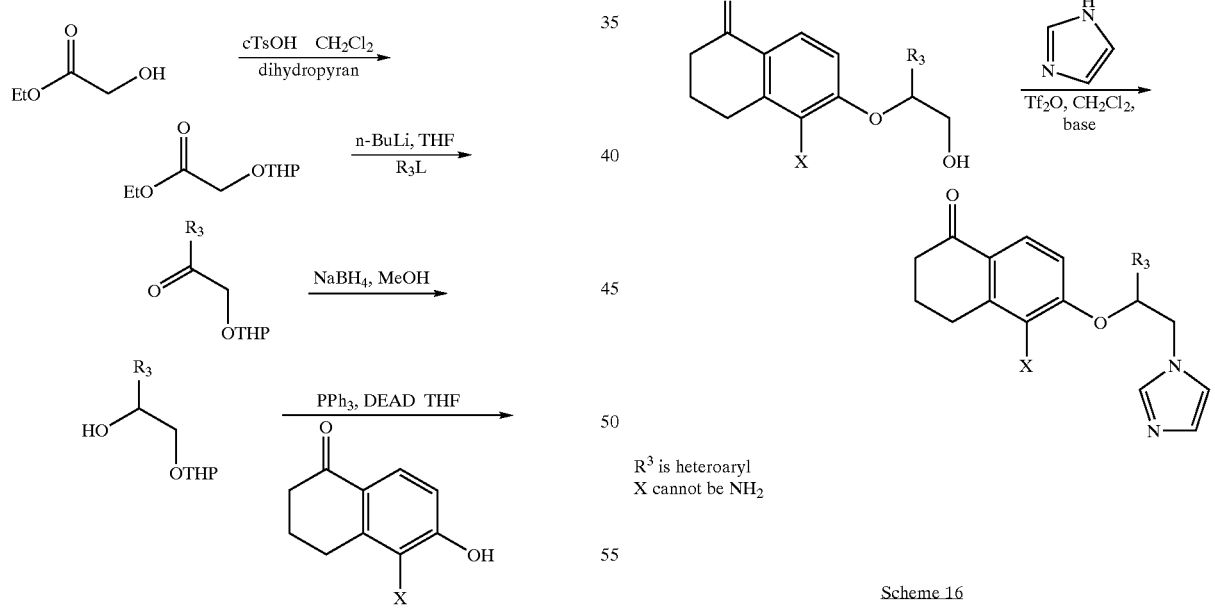
R³ is heteroaryl
X cannot be NH₂
Scheme 16
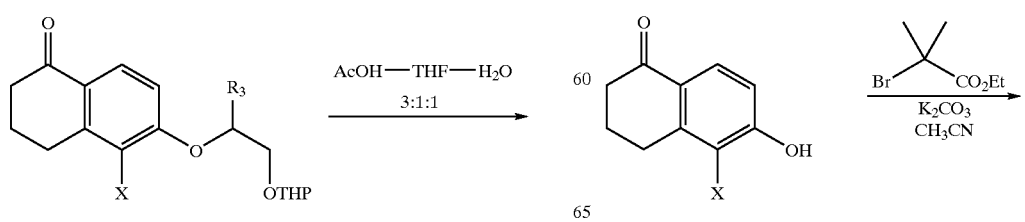

-continued
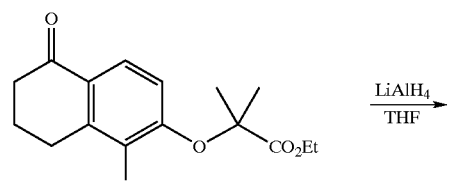
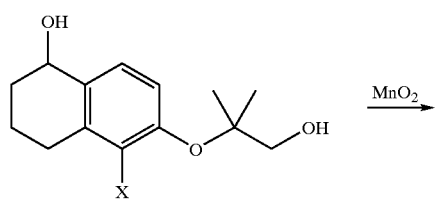
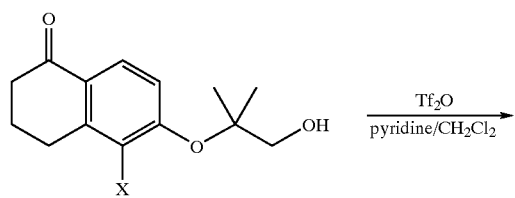
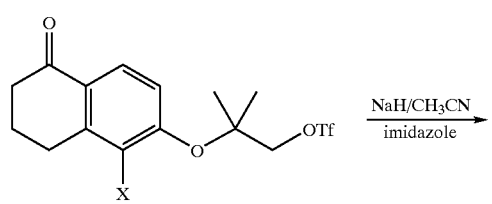
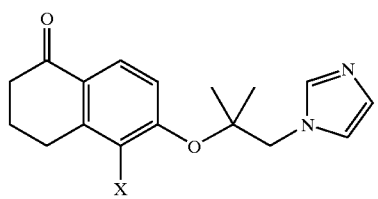
X cannot be NH$_2$
Scheme 17
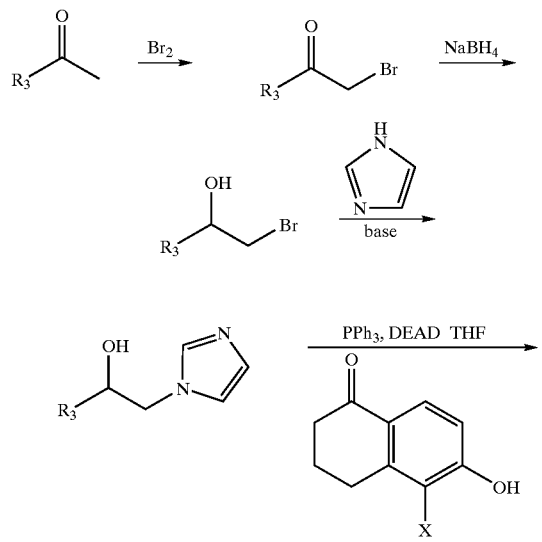
-continued
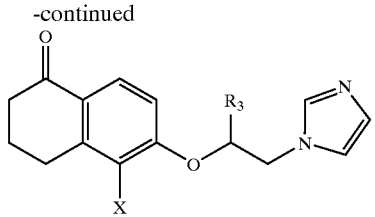
R$^3$ is heteroaryl or substituted heteroaryl
X cannot be NH$_2$
Scheme 18
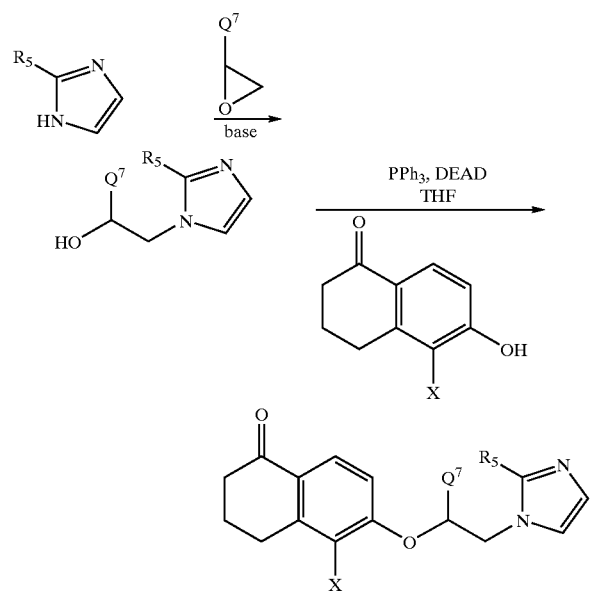
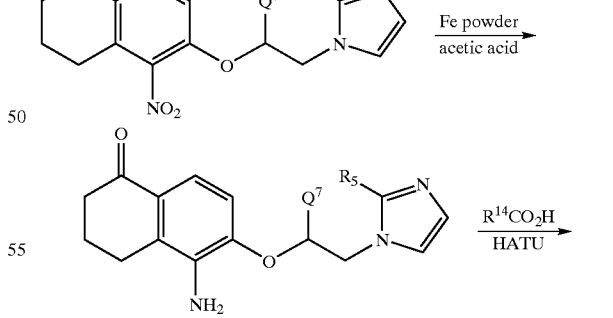
Q$^7$ is R$^3$, R$^9$, heteroaryl, or substituted heteroaryl Scheme 19
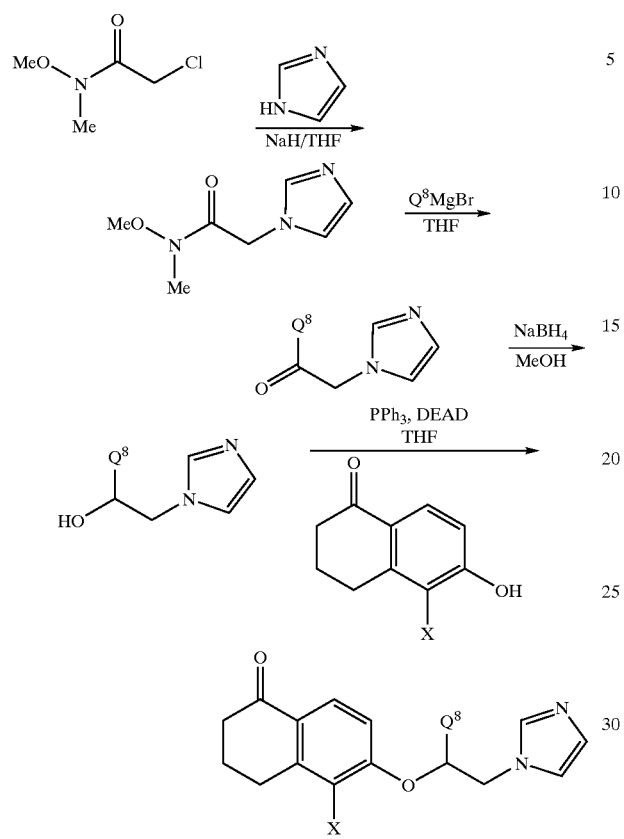
$Q^8$ is phenyl, substituted phenyl, heteroaryl, substituted heteroaryl
X cannot be $NH_2$
Scheme 20
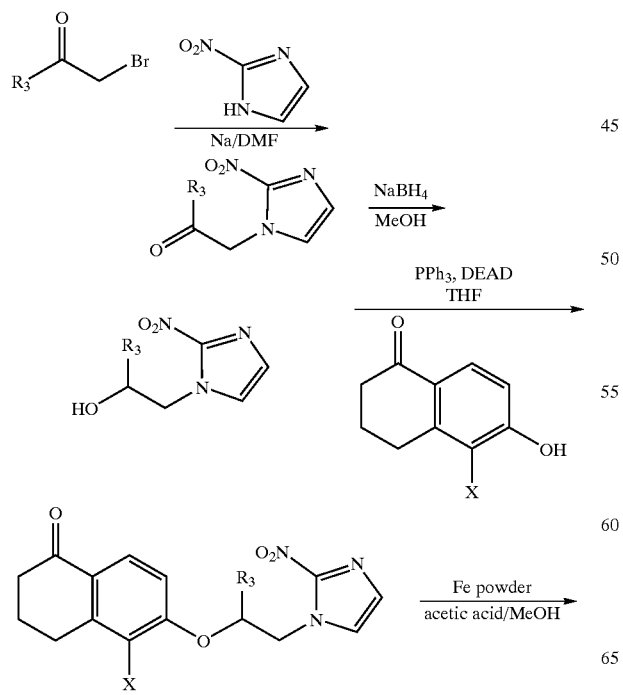
-continued
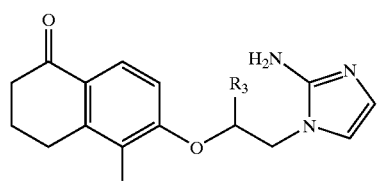
Scheme 21
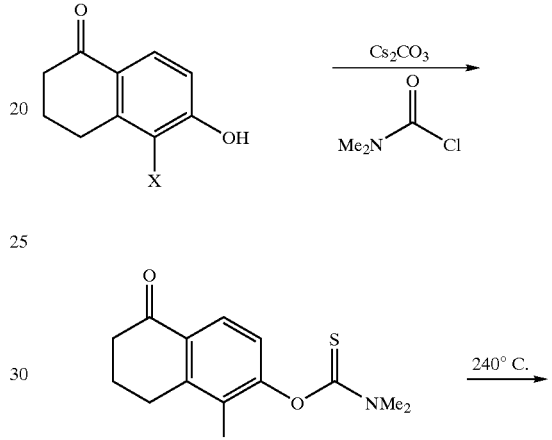
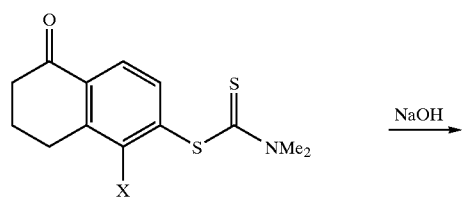
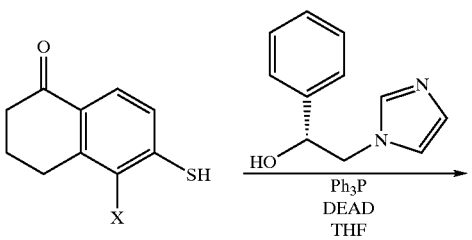
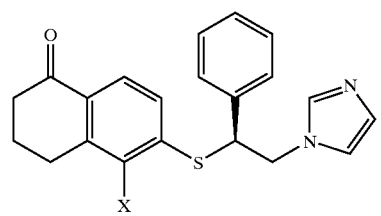

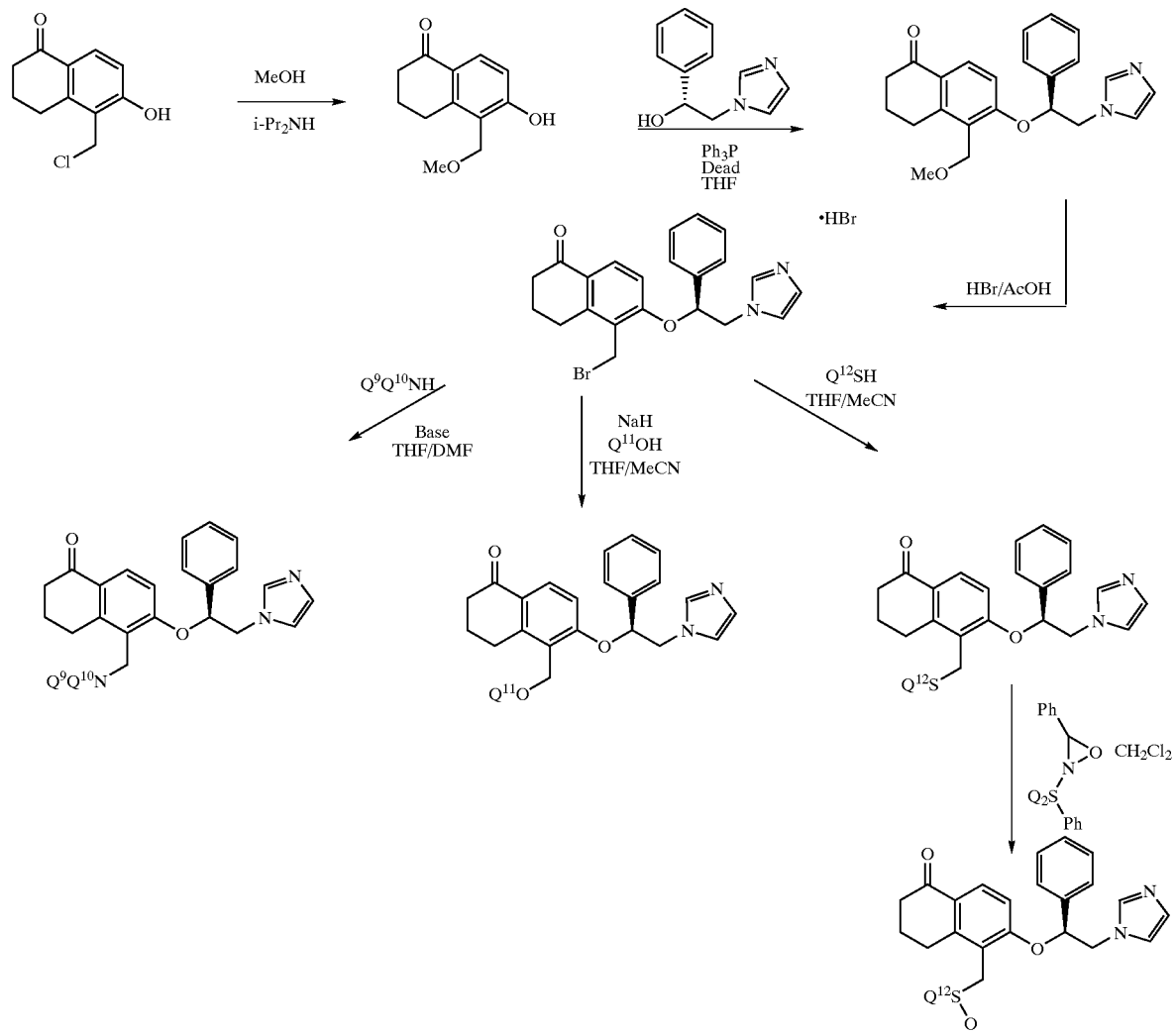
Scheme 22
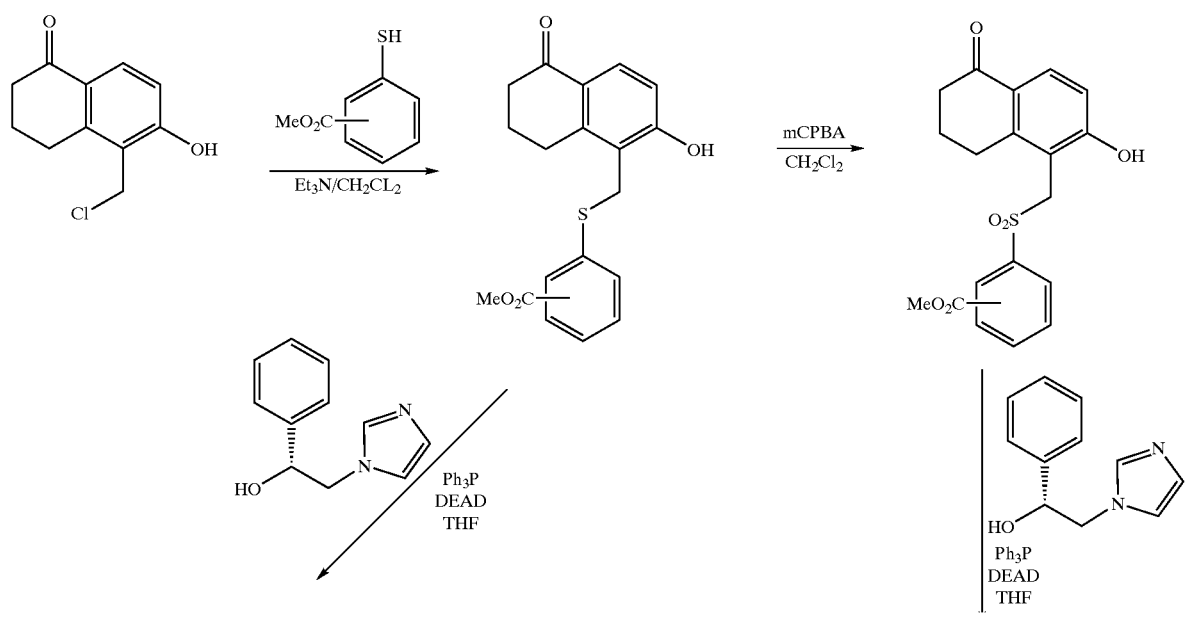
Scheme 23

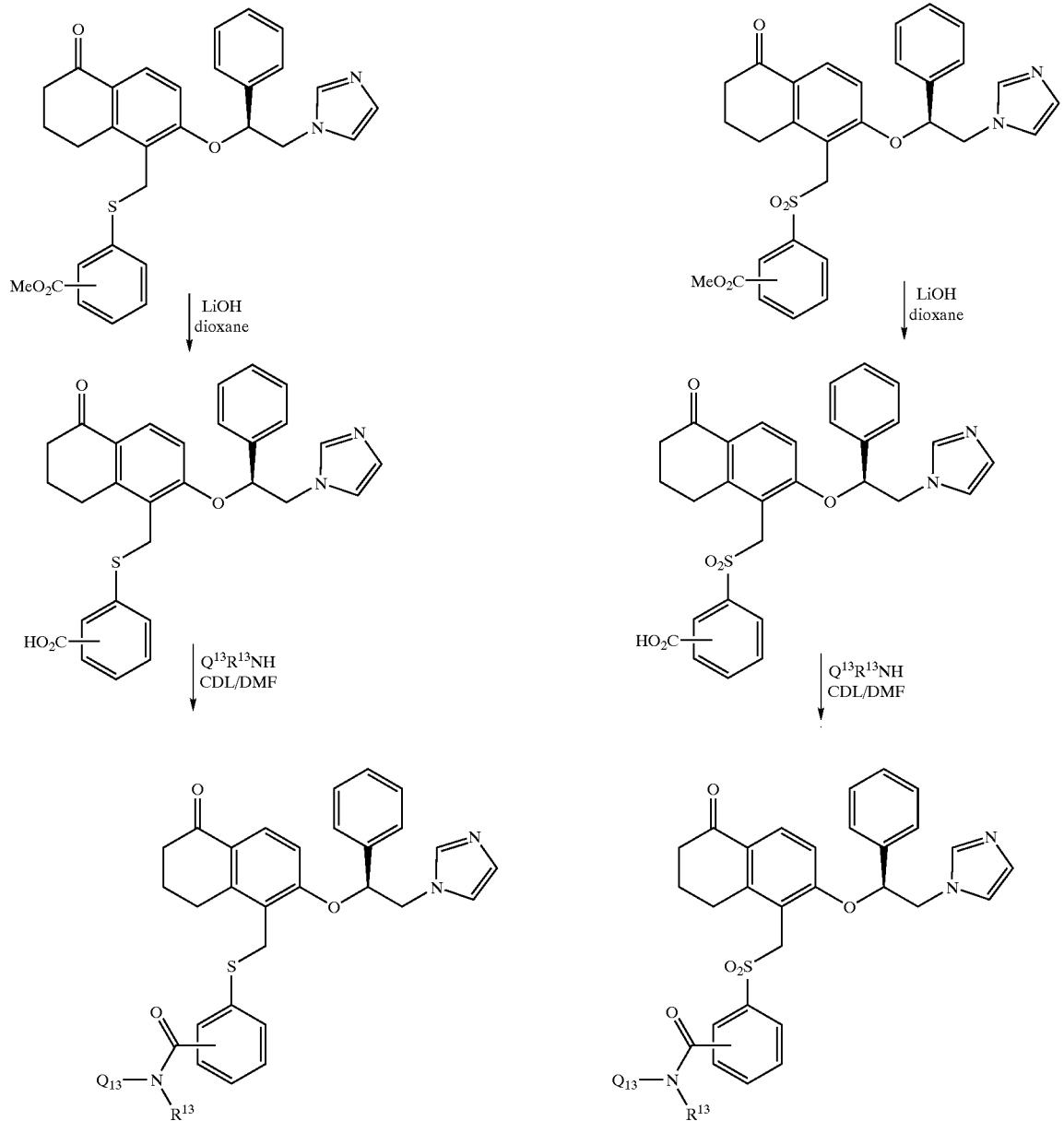

The compounds of Formulas I–V are synthesized according to the above Schemes.

Accordingly, Scheme 1 depicts the synthesis of those compounds of Formula I wherein W=$CH_2CH_2$, $R^3$=phenyl, $R^{3a}$=hydrogen, $R^5$=hydrogen, X=$CH_2SR^6$, $R^6$ is hydrogen, $C_1$-$C_6$-alkyl, phenyl, benzyl or substituted phenyl, and Y=O. Scheme 1 also depicts the synthesis of those compounds of Formula II wherein $R^7$ is —S—($C_1$-$C_6$)alkyl, —S-phenyl, or —S-substituted phenyl. Finally, Scheme 1 depicts the synthesis of those compounds of Formula III wherein $R^9$=phenyl, $R^{10}$=hydrogen or —$CH_2OH$ and $R^{11}$ is —SO-aryl, —$SO_2$-aryl, —$SO_2$-alkyl, —S(O)z-heteroaryl, —S-aryl, —S(O)z-substituted alkyl, and —S(O)z-substituted arylalkyl.

Chloromethyltetralone (*Chem. Pharm. Bull.* 1977;25(11):2988) is treated with a thiol or thiophenol in the presence of a base in a solvent such as THF to yield a thioether. Oxidation with an oxidant such as mCPBA in a solvent such as dichloromethane affords the sulfone. Mitsunobu reaction of the sulfone with the imidazole alcohol in the presence of triphenylphosphine/diethyl azodicarboxylate (DEAD) in a solvent such as THF affords the 6-((1S)-2-imidazolyl-1-phenylethoxy)-sulfone. Treatment of the sulfoxide with paraformaldehyde in a solvent such as DMSO affords the methylene alcohol substituted imidazole. Similarly, Mitsunobu reaction of the thioether with the imidazole alcohol in the presence of triphenylphosphine/DEAD in a solvent such as THF affords the thioether. Oxidation of the thioether with an oxidant such as sodium periodate in a solvent such as THF yields the corresponding sulfoxide.

Compounds such as those of Formula I wherein W=$CH_2CH_2$, $R^3$=phenyl, X=$CH_2NR^6R^{6a}$ and Y=O can be synthesized as set forth in Scheme 2. Scheme 2 also depicts the synthesis of those compounds of Formula II wherein $R^7$ is —NH-phenyl or —NH-substituted phenyl. 5-chloromethyltetralone is treated with an amine in a solvent such as THF to afford the aminomethyl tetralone. Mitsunobu reaction of the aminomethyl tetralone with the imidazole alcohol in the presence of triphenylphosphine/DEAD in a solvent such as THF affords the 6-((1S)-2-imidazolyl-1-phenylethoxy)-5-substituted aminomethyl tetralone.

Compounds such as those of Formula I wherein W=$CH_2CH_2$, $R^3$=phenyl, X=$CH_2OR^6$, $R^6$ cannot be hydrogen, and Y=O can also be synthesized as set forth in Scheme 2. Scheme 2 also depicts the synthesis of those compounds of Formula II wherein $R^7$ is alkoxy, —O—($C_3$–$C_6$)cycloalkyl, —O—($C_2$–$C_6$)alkenyl, —O-phenyl, —O-substituted phenyl, or —O-benzyl. Additionally, Scheme 2 depicts the synthesis of those compounds of Formula III wherein $R^9$=phenyl and $R^{11}$=—O-substituted alkyl. 5-Chloromethyltetralone is treated with an alcohol in a solvent such as THF in the presence of a base to afford the ether. Mitsunobu reaction of the ether with the imidazole alcohol in the presence of triphenylphosphine/DEAD in a solvent such as THF affords the 6-((1S)-2-imidazolyl-1-phenylethoxy)-ether.

Scheme 3 depicts the synthesis of 6-((1S)-2-imidazolyl-1-phenylethoxy)-5-substituted alkyl tetralones. Compounds such as those of Formula I wherein W=$CH_2CH_2$, $R^3$=phenyl, Y=O and X is arylalkyl, substituted arylalkyl, heteroarylalkyl or —$CH_2CH_2CO_2R^6$ can be synthesized as set forth in Scheme 3. $Q_1$ includes aryl, heteroaryl, substituted aryl and $CO_2R^6$. 5-Bromotetralone (Z. Chem. 1970; 10:70) is treated with an acetylene in the presence of a palladium catalyst such as $Pd(PPh_3)_2Cl_2$ and copper iodide in a solvent such as DMF/$Et_3N$ to afford the 5-substituted acetylene tetralone. Alternatively, the 5-bromotetralone is treated with an alkene in the presence of a palladium catalyst such as $Pd(PhCN)_2Cl_2$, sodium acetate and N,N-dimethylglycine and heated in a solvent such as methanol to afford the 5-substituted alkenyl tetralone. Reduction of either the 5-substituted acetylene tetralone or the 5-substituted alkenyl tetralone with a catalyst such as Pd/$BaSO_4$ in the presence of $H_2$ in a solvent such as THF yields the 5-substituted alkyl tetralone. Removal of the methoxy protecting group with potassium cyanide in a solvent such as DMSO yields the corresponding phenol. Mitsunobu reaction of the ether with the imidazole alcohol in the presence of triphenylphosphine/DEAD in a solvent such as THF affords the 6-((1S)-2-imidazolyl-1-phenylethoxy)-5-substituted alkyl tetralone.

Scheme 3 also shows the synthesis of generally 6-((1S)-2-imidazolyl-1-phenylethoxy)-5-X substituted tetralones. Compounds such as those of Formula I wherein W=$CH_2CH_2$, $R^3$=phenyl, Y=O and X is aryl or substituted aryl can be synthesized as set forth in Scheme 3. 5-Bromotetralone is treated with a boronic acid derivative in the presence of a palladium catalyst such as $Pd(PPh_3)_4$ in a solvent such as DME to afford tetralone derivative. Removal of the methoxy protecting group with sodium cyanide in a solvent such as DMSO yields the phenol. Mitsunobu reaction of the ether with the imidazole alcohol in the presence of triphenylphosphine/DEAD in a solvent such as TIF affords the 6-((1S)-2-imidazolyl-1-phenylethoxy)-5-X substituted tetralone. When the sidechain of the 5-substituted alkyl tetralone contains a nitrogen heterocycle such as pyridyl, or isoquinoline it can be oxidized to the N-oxide with mCPBA in a solvent such as dichloromethane.

Compounds such as those of Formula I wherein W=$CH_2CH_2$, $R^3$=phenyl, Y=O and X is substituted arylalkyl can be synthesized as set forth in Scheme 4. $Q^2$ includes substituted aryl. In Scheme 4, 5-bromotetralone is treated with a zinc reagent in the presence of a palladium catalyst such as palladium bis(dibenzylideneacetone) or bis diphenylphosphino) ferrocene in a solvent such as THF in an inert atmosphere to afford a tetralone derivative. Removal of the methoxy protecting group with sodium cyanide in a solvent such as DMSO yields the phenol. Mitsunobu reaction of the ether with the imidazole alcohol in the presence of triphenylphosphine/DEAD in a solvent such as THF affords the 6-[(1S)-2-imidazolyl-1-phenylethoxy]-5-substituted methyl tetralone.

Compounds such as those of Formula I wherein W=$CH_2CH_2$, $R^3$=phenyl, Y=O and X is halogen or heteroaryl can be synthesized as set forth in Scheme 4. Also in Scheme 4, 5-bromotetralone is converted to a phenol by treatment with boron tribromide. The Mitsunobu reaction then affords the 5-bromo-tetralone. The 5-bromo-tetralone is coupled with a boronic acid derivative in the presence of a palladium catalyst such as $Pd(PPh_3)_4$ in a solvent such as DME to afford a 5-X substituted tetralone.

The compounds of Formula I wherein X=amino are synthesized as set forth in Scheme 5. Scheme 5 depicts the synthesis of those compounds of Formula III wherein $R^9$=phenyl and $R^{11}$=—$NHSO_2$—$R^{14}$, —NHCO—$R^{14}$, NHCO-heteroaryl-O-aryl, or NHCO-heteroaryl-substituted aryl. $Q^3$ includes the definition of $R^{6'}$ for Formula V. 5-Nitro-tetralone is converted to the 6-[(1S)-2-imidazolyl-1-phenylethoxy]-5-nitro tetralone via the Mitsunobu reaction. This compound is reduced to the aniline in the presence of iron/acetic acid in a solvent such as methanol/water. The aniline is treated with sulfonyl chloride in the presence of a base such as pyridine in a solvent such as dichloromethane to afford the 5-sulfonamide-tetralone. Alternatively, the aniline is treated with a carboxylic acid in the presence of a coupling agent such as EDCI or CDI in a solvent such as DMF to afford a 5-amido-tetralone. Finally, the aniline is also treated with an alkylhalide or equivalent in the presence of a base such as $Et_3N$ to afford the 5-amino-tetralone.

Scheme 6 depicts the synthesis of compounds such as those of Formula III wherein $R^9$=phenyl and $R^{11}$ is —$NHCO_2$-alkyl, —$NHSO_2$—$R^{14}$, —NHCO—$R^{14}$, NHCOC(substituted alkyl)$NHCO_2$-alkyl, or —NHCO—C(substituted alkyl)amino. 6-Hydroxytetralone is aminoalkylated with hydroxymethyl derivative in the presence of $H_2SO_4$ in acetic acid to afford the aminoalkylated tetralone. The Bis Boc protected tetralone is obtained via treatment of the aminoalkylated tetralone with Boc anhydride in the presence of DMAP in THF. Hydrolysis of the Bis Boc protected tetralone with LiOH in THF/MeOH/$H_2O$ affords a mixture of mono and bis N-Boc derivatives. Treatment of this latter mixture with $Mg(ClO_4)_2$ in acetonitrile affords the mono Boc product. The subsequent Mitsunobu reaction affords the Boc protected amine which is deprotected under acidic conditions such as HCl in a solvent such as dioxane to afford the 5-aminomethyl-tetralone. This compound is then treated with sulfonyl chloride in the presence of a base such as pyridine in a solvent such as dichloromethane to afford the 5-sulfonamidomethyl-tetralone. Alternatively, the 5-aminomethyl-tetralone is treated with a carboxylic acid in the presence of a coupling agent such as EDCI or CDI in a solvent such as DMF to afford the 5-amidomethyl-tetralone.

The synthesis of Compound 43 is depicted in Scheme 7. 6-Hydroxytetralone is aminoalkylated with hydroxymethyl phthalimide in the presence of $H_2SO_4$ to afford the 5-phthalimido methyl tetralone. Subsequent Mitsunobu reaction affords 2-{[2-((1S)-2-imidazolyl-1-phenylethoxy)-5-oxo-6,7,8-trihydronaphenyl]methyl}isoindoline-1,3-dione (Compound 43).

The compounds disclosed in Formula V wherein X'=$(CH_2)_nR^1R^{1'a}$ and Y'=O are synthesized as set forth in Scheme 8. Compounds such as those of Formula I wherein W=$CH_2CH_2$, $R^3$=phenyl, Y=O and X is arylalkyl can be synthesized as set forth in Scheme 8. $(CH_2)_nR^1R^{1a}$ is defined as shown above for $(CH_2)_nR^{1'}R^{1'a}$ in Formula V. $(CH_2)_nR^1R^{1a}$ can also be defined as arylalkyl. The oxazoline (*J. Org. Chem.* 1978;43:1372) is treated with a Grignard reagent prepared by methods known by those skilled in the art, in a solvent such as THF to afford the 5-$(CH_2)_nR^1R^{1a}$ oxazoline. Removal of the oxazoline under acidic conditions such as 18% HCl affords the corresponding carboxylic acid. The carboxylic acid can be 3-carbon homologated by methods known to those skilled in the art to afford the butyric acid compound via reduction, halogenation, acrylate coupling, another reduction, and finally hydrolysis. Intramolecular Friedel-Crafts acylation of the butyric acid by treatment with trifluoroacetic acid anhydride in dichloromethane gives the tetralone. Removal of the methoxy protecting group of with sodium cyanide in a solvent such as DMSO yields the phenol. Mitsunobu reaction of the phenol affords the 5-$(CH_2)_nR^1R^{1a}$ tetralone.

The compounds disclosed in Formula V wherein X'=$(CH_2)_nR^1R^{1'a}$ and Y'=O are synthesized as set forth in Scheme 9. Compounds such as those of Formula I wherein W=$CH_2CH_2$, $R^3$=phenyl, Y=O and X is arylalkyl or heteroarylalkyl can be synthesized as set forth in Scheme 9. $(CH_2)_nR^1R^{1a}$ is defined as shown above for $(CH_2)_nR^{1'}R^{1'a}$ in Formula V. $(CH_2)_nR^1R^{1a}$ can also be defined as arylalkyl or heteroarylalkyl. The oxazoline as shown in scheme 9 (*J. Org. Chem.* 1978;43:1372) is treated with a Grignard reagent prepared by methods known by those skilled in the art, in a solvent such as THF to afford the 5-$(CH_2)_nR^1R^{1a}$ oxazoline. Removal of the oxazoline under acidic conditions such as 18% HCl affords the corresponding carboxylic acid. The carboxylic acid can be 3-carbon homologated by methods known to those skilled in the art to afford the butyric acid compound via reduction, halogenation, malonate displacement, hydrolysis, another reduction, halogenation, displacement with cyanide and finally hydrolysis. Intramolecular Friedel-Crafts acylation of the bytyric acid by treatment with trifluoroacetic acid anhydride in dichloromethane gives the tetralone. Removal of the methoxy protecting group of with sodium cyanide in a solvent such as DMSO yields the phenol. Mitsunobu reaction of the phenol affords the 5-$(CH_2)_nR^1R^{1a}$ tetralone.

The compounds of Formula I wherein W=$CH_2CH_2$, $R^3$=phenyl, Y=O and X is arylalkyl or substituted arylalkyl can be synthesized as set forth in Scheme 10. Scheme 10 also depicts the synthesis of Compound 45. $Q^4$ includes aryl, arylalkyl, substituted aryl, and substituted arylalkyl. Condensation of 3-methoxybenzoyl chloride with 2-amino-2-methyl-1-propanol in dichloromethane affords the corresponding amide. Cyclization of the amide to the oxazolidine is achieved with thionyl chloride. Acylation of the oxazolidine with an acid chloride in the presence of a base such as butyl lithium and in a solvent such as THF affords a 2-substituted carboxy phenyl. Deprotection under acidic conditions such as 18% HCl affords the carboxylic acid. Reduction of the benzylic ketone is achieved in the presence of a catalyst such as 5% Pd/C in the presence of $H_2$ and in a solvent such as MeOH to afford the 2-$CH_2R''$-3-methoxy benzoic acid. This compound is 3-carbon homologated to the butyric acid using the 5-step method described above for Scheme 8. Intramolecular Friedel-Crafts acylation of the resulting 3-(2-$CH_2Q^4$-3-methoxyphenyl)butyric acid is achieved by treatment with polyphosphate ester in chloroform to give the tetralone. Removal of the methoxy protecting group with sodium cyanide in a solvent such as DMSO yields the phenol. The subsequent Mitsunobu reaction affords the 5-$CH_2Q^4$ tetralone.

Scheme 11 outlines the synthesis of Compound 46, which is a compound of Formula III. 2,3-Dimethoxybenzyl alcohol is 3-carbon homologated to the butyric acid using the 4-step method described above in Scheme 8 (i.e. from benzyl alcohol to butyric acid). Intramolecular Friedel-Crafts acylation of the acid by treatment with polyphosphate ester in chloroform gives the tetralone. Selective removal of the 5-methoxy protecting group with methane sulfonic acid/methionine affords the phenol. O-Phenylation of the phenol is carried out with triphenylbismuth in the presence of $Cu(OAc)_2$, a base such as $Et_3N$ and a solvent such as THF. Removal of the methoxy protecting group with sodium cyanide in a solvent such as DMSO yields 6-hydroxy-5-phenoxy-2,3,4-trihydronaphthalen-1-one. The standard Mitsunobu reaction then affords 6-((1S)-2-imidazolyl-1-phenylethoxy)-5-phenoxy-2,3,4-trihydronaphthalen-1-one (Compound 46).

Compounds such as Compound 47 and Compound 48 are synthesized as set forth in Scheme 12. $Q^5$ represents any of the substituents listed for "substituted aryl" above. 7-Methoxytetralone is treated with a Grignard reagent, obtained by those skilled in the art from, for example, an arylbromide and magnesium, to yield the alcohol. Elimination with catalytic tosic acid in benzene and reduction with 10% Pd/C affords the 7-methoxy-1-phenyl-1,2,3,4-tetrahydronaphthalene. Subsequent oxidation with an oxidant such as $CrO_3$ in a solvent such as acetic acid affords the corresponding tetralone. Removal of the methoxy protecting group with sodium cyanide in a solvent such as DMSO yields the phenol, which is then converted to the 6-((1S)-2-imidazolyl-1-phenylethoxy)-4-phenyl-2,3,4-trihydronaphthalen-1-one via the Mitsunobu reaction.

The synthesis of compounds described in Scheme 12 are alternatively prepared by the route depicted in Scheme 13. A benzophenone is condensed with methylbromoacetate in the presence of zinc and catalytic iodine to afford a methyl-3-(3-methoxyphenyl)-3-phenylprop-2-enoate. Catalytic reduction with Pd/C in the presence of $H_2$ in a solvent such as MeOH yields the ester. One carbon homologation of the ester to the butyric acid is achieved by methods known in the art, via reduction, bromination, conversion to nitrile, and hydrolysis. Intramolecular Friedel-Crafts acylation of the acid gives the tetralone of Scheme 12. Conversion of the tetralone to the 6-((1S)-2-imidazolyl-1-phenylethoxy)-4-phenyl-2,3,4-trihydronaphthalen-1-one is as described above.

Preparation of 2-imidazolyl-1-R3-ethoxy prop-2-enyl tetralone and indanone derivatives of Formula I and Formula V are depicted in Scheme 14. The compounds of Formula I wherein Y=O and X is lower alkyl or lower alkenyl can be synthesized as set forth in Scheme 14. $Q^6$ represents any of the substituents listed for "substituted aryl" above. Initially, imidazole is reacted with a chiral epoxide, either obtained commercially or synthesized (*Science*, 1977;277:936), in the presence of a base such as pyridine in a solvent such as EtOH, DMF or DMSO to yield the desired imidazole alcohol.

A commercially available hydroxy-tetralone or hydroxy-indanone is treated with an allyl bromide in the presence of a base such as $Cs_2CO_3$ in a solvent such as DMF to afford the ether. Claisen rearrangement in a solvent such as diethylaniline affords the substituted tetralone or indanone. The Mitsunobu reaction then affords the 2-imidazolyl-1-$R^3$- ethoxy)prop-2-enyl compound. Alternatively, the substituted tetralone or indanone is reduced with a catalyst such as RhCl(PPh$_3$)$_3$ in the presence of H$_2$ neat to afford a (prop-2-enyl)phenol derivative. Mitsunobu reaction of the phenol the desired imidazole alcohol affords the 2-imidazolyl-1-R3-ethoxy prop-2-enyl tetralone or indanone derivative.

The compounds of Formula IV wherein Y=O and X cannot be NH$_2$ are synthesized as set forth in Scheme 15. Scheme 15 depicts the synthesis of compounds such as Compound 57 and 58. Glycolic acid ethyl ester is protected as a tetrahydropyranyl ether via coupling under acidic conditions such as Tosic acid, with dihydropyran in a solvent such as dichloromethane to afford an ester. A heteroaryl halide is treated with an organometalic reagent such as butyl lithium in a solvent such as TBF to afford the heteroaryl-lithium reagent, which is subsequently treated with the ether in situ to afford a ketone. Reduction of the ketone with a reducing agent such as sodium borohydride in a solvent such as methanol affords the alcohol. Mitsunobu reaction of the alcohol with a phenolic tetralone, synthesized according to several previous Schemes, in the presence of triphenylphosphine/DEAD and in a solvent such as THF affords the 5,6-substituted-tetralone. Deprotection of the THP ether under acidic conditions such as acetic acid/THF/H$_2$O yields the 6-[2-(hydroxy)-1-R$^3$-ethoxy]-5-X-2,3,4-trihydronaphthalen-1-one. Treatment of this compound with a mixture of imidazole and a base such as sodium hydride in the presence of trifluoromethanesulfonic acid anhydride in a solvent such as THF affords a 6-(2-imidazolyl-1-R$^3$-ethoxy)-5-X-2,3,4-trihydronaphthalen-1-one.

Compounds such as those of Formula I wherein Y=O and X cannot be NH$_2$ are synthesized as set forth in Scheme 16. Compounds such as Compound 58a are synthesized as depicted in Scheme 16. 6-Hydroxy-5-(2-phenylethyl)-3,4-dihydro-1(2H)-naphthalenone synthesized as set forth in Scheme 3 is condensed with 2-bromo-2-methylpropionate in the presence of a base such as potassium carbonate in a solvent such as acetonitrile to afford an ether. The ester is converted to the diol with lithium aluminum hydride in THF and the secondary alcohol is reoxidized to the ketone with manganese dioxide in THF. The resulting alcohol is then converted to the trifluoromethanesulfonate via treatment with trifluromethanesulfonic anhydride. Displacement of the trifluoromethanesulfonate with imidazole affords compound 58a.

The compounds of Scheme 15 are alternatively prepared according to the route depicted in Scheme 17. Acetophenone is treated with bromine to afford bromoketone. Reduction of the ketone with a reducing agent such as sodium borohydride in a solvent such as methanol affords the bromoalcohol. Imidazole is then reacted with the bromoalcohol in the presence of a base such as pyridine and in a solvent such as EtOH, DMF or DMSO to yield an imidazole alcohol. Mitsunobu reaction of this alcohol with a desired phenol affords the corresponding 6-(2-imidazolyl-1-R$^3$-ethoxy)-5-X-2,3,4-trihydronaphthalen-1-one.

Compounds such as those of Formula IV wherein Y=O, X is represented by (CH$_2$)y-R$^{15}$, R$^{15}$ is —SO$_2$-alkyl or —SO$_2$-heteroaryl, and R$^{14}$ is heteroaryl are synthesized as set forth in Scheme 18. Scheme 18 also depicts the compounds of Formula III wherein R$^9$ is C$_1$–C$_6$ alkyl or substituted phenyl, X is represented by (CH$_2$)y-R$^{11}$ and R$^{11}$ is —SO$_2$-alkyl, —SO$_2$-aryl, or —S(O)z-heteroaryl, and R$^{14}$ is heteroaryl. Finally, Scheme 18 depicts compounds such as those of Formula I wherein R$^3$ is substituted phenyl or R$^5$ is C$_1$–C$_6$ alkyl. Imidazole or substituted imidazole is condensed with an epoxide, the synthesis of which is known to those skilled in the art. The subsequent imidazole alcohol is then subjected to Mitsunobu reaction as described previously with a tetralone, the synthesis of which has been shown in several schemes. When the tetralone where X=NO$_2$ is used. The product can be reduced with iron powder in acetic acid to give the aniline. The aniline is then reacted with carboxylic acids to afford the amides of Formula I wherein X=NHCOR$^6$ or the compounds of Formula III or IV wherein R$^{14}$ is heteroaryl.

The compounds of Formula I wherein R$^3$=phenyl or substituted phenyl, Formula III wherein R$^9$=phenyl or substituted phenyl, Formula IV wherein Q$^8$=heteroaryl, and Formula V wherein Q$^8$=phenyl, substituted phenyl, heteroaryl, or substituted heteroaryl are synthesized as set forth in Scheme 19. For the compounds of Scheme 19, X cannot be NH$_2$. Scheme 19 also depicts compounds such as Compound 63p and 63q. Imidazole is reacted with 2-chloro-N-methoxy-N-methylacetamide to afford 2-imidazol-1-yl-N-methoxy-N-methyl-acetamide. The acetamide is reacted with a Grignard reagent prepared from magnesium and aryl or heteroaryl halide to give the corresponding ketone. Reduction of the ketone is accomplished with NaBH$_4$ in a solvent such as methanol to afford the alcohol which is subjected to Mitsunobu reaction with a tetralone as described previously.

Scheme 20 sets forth the synthesis of compounds such as those of Formula I wherein R$^5$ is amino. The anion obtained from reacting 2-nitro imidazole with sodium metal is reacted with an acylbromide known in the art. The subsequent ketone is reduced with sodium borohydride in a solvent such as methanol to give the alcohol which is subjected to Mitsunobu reaction with a tetralone as described previously. The resultant 2-nitroimidazole is reduced to the 2-amino imidazole with iron powder in acetic acid.

The compounds of Formula I and Formula V wherein Y=S are synthesized as set forth in Scheme 21. A desired phenol reacted with N,N-dimethylthiocarbamoyl chloride in the presence of a base such as cesium carbonate in a solvent such as DMF gives a thiocarbamate. Thermal rearrangement of the thiocarbamate is achieved by heating it neat at 240° C. to afford the corresponding thiocarboxamide. Hydrolysis of the thiocarboxamide is carried out in the presence of a base such as sodium hydroxide in a solvent such as methanol to afford a thiophenol. The Mitsunobu reaction of the imidazole alcohol with the thiophenol affords the 6-((1S)-2-imidazolyl-1-phenyl-ethylsulfanyl)-5-X-2,3,4-trihydronaphthalen-1-one.

Compounds such as those of Formula I wherein X=—CH$_2$NR$^6$R$^{6a}$ are set forth in Scheme 22. Compounds such as those of Formula III wherein R$^{11}$=—SO-substituted aryl, —S(O)z-heteroaryl, SO-alkyl, —NH-substituted aryl, NH-heteroaryl, —NH—(CH$_2$)$_2$—O-heteroaryl, or —N(CO-alkyl)substituted aryl are also depicted in Scheme 22. Finally, the compounds of Formula V wherein X'=CH$_2$OR$^{6'}$, —CH$_2$NR$^{6'}$R$^{6'a}$, or CH$_2$S(O)$_z$R$^{6'}$ and Y'=O can be synthesized as set forth in Scheme 22. Q$^9$ includes substituted aryl, heteroaryl, —(CH$_2$)$_2$—O-heteroaryl and the definition of R$^6$ and R$^{6'}$. Q$^{10}$ includes CO-alkyl and the definition of R$^{6a}$. Q$^{11}$ includes the definition of R$^{6'}$. Q$^{12}$ includes substituted aryl, heteroaryl and alkyl and the definition of R$^{6'}$. Chloromethyltetralone (*Chem. Pharm. Bull.* 1977;25(11):2988) is treated with methanol in diisopropylamine to yield methoxymethyltetralone. Mitsunobu reaction of this tetralone with the imidazole affords 6-((1S)-2-imidazolyl-1-phenylethoxy)-5-(methoxymethyl)-2,3,4-trihydronaphthalen-1-one. Conversion to the bromide is achieved via treatment with HBr in acetic acid. The bromide is treated either with an amine, a thiol or an alcohol in a solvent such as THF to yield an amine, a thioether or an ether, respectively. Selective oxidation of the thioether with an oxaziridine affords the sulfoxides.

Compounds such as those of Formula I wherein X=CH$_2$SR$^6$ are set forth in Scheme 23. Scheme 23 also depicts compounds such as those of Formula III wherein R$^{11}$=—SO$_2$-substituted aryl, or —S(O)z-phenyl-CONH—R$^{13}$. Q$^{13}$ is generally hydrogen.-5-chloromethyl-6-hydroxy-3,4-dihydro-2H-napthalen-1-one is reacted with methyl-2,3 or 4-mercaptobenzoate in the presence of a base such as triethylamine in a solvent such as dichloromethane to afford the thioether. The thioether is oxidized with mCPBA in a solvent such as dichloromethane to afford the sulfone. Coupling of the tetralone sulfone with an alcohol under previously described Mitsunobu conditions afford the compounds of Formula III wherein R$^{11}$=—S$_2$-substituted aryl, wherein the substituent is CO$_2$CH$_3$. Subsequent hydrolysis of the ester under conditions known in the art affords the carboxylic acids which are coupled with amines under conditions known in the art to give the amides.

In addition, the compounds of Formula I wherein X=CH$_2$SR$^6$ can be synthesized from the thioether shown in Scheme 23. The coupling of the tetralone thioether with an alcohol under previously described Mitsunobu conditions followed by hydrolysis and amide coupling as described previously affords the thioether amides.

The disclosures in this application of all articles and references, including patents, are incorporated herein by reference.

The invention is illustrated further by the following examples which are not to be construed as limiting the invention in scope or spirit to the specific procedures described in them.

The starting materials and various intermediates may be obtained from commercial sources, prepared from commercially available organic compounds, or prepared using well known synthetic methods.

Representative examples of methods for preparing intermediates of the invention are set forth below.

EXAMPLE 1

Synthesis of 6-((1S)-2-Imidazolyl-1-phenylethoxy)-5-(phenylthiomethyl)-2,3,4-trihydronaphthalen-1-one (Compound 1)

1. 6-Hydroxy-5-phenylthiomethyl-2,3,4-trihydronaphthalen-1-one

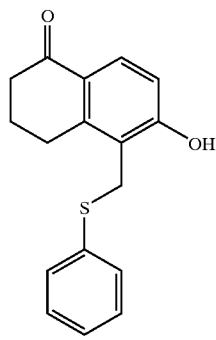

To a solution of thiophenol (9.42 g, 0.0855 mol) in oxygen-free tetrahydrofuran (100 mL) is added diisopropylamine (3.68 g, 0.0285 mol). 5-Chloromethyl-6-hydroxy-2,3,4-trihydronaphthalen-1-one, prepared as described in *Chem. Pharm. Bull.* 1977;25(11):2988–3002 (6.0 g, 0.0285 mol) is dissolved in tetrahydrofuran (200 mL) and the solution added dropwise to the preceding solution at 25° C. The mixture is stirred for 2 hours, concentrated in vacuo and the residue layered with ethyl ether. The suspension is extracted with 1N NaOH, which is separated and washed with ethyl ether. Upon standing a solid precipitate forms within the aqueous phase. The solid is filtered, dissolved in ethyl acetate, and the solution is washed with 1N citric acid, brine and dried over anhydrous magnesium sulfate. The suspension is filtered and the filtrate is evaporated in vacuo giving a white solid, 4.68 g, 58% yield. MS: APCI: M+1: 285.1 (M: 284.4). NMR spectrum is consistent with structure.

2. 6-((1S)-2-Imidazolyl-1-phenylethoxy)-5-(phenylthiomethyl)-2,3,4-trihydronaphthalen-1-one (R)-2-Imidazol-1-yl-1-phenyl-ethanol (1.45 g, 7.73 mmol), triphenylphosphine (2.77 g, 10.5 mmol), and 6-hydroxy-5-phenylsulfanylmethyl-2,3,4-trihydronaphthalen-1-one (2.0 g, 7.03 mmol) are suspended in dry tetrahydrofuran (100 mL). To the suspension is added a solution of diethyl azodicarboxylate (1.83 g, 10.5 mmol) in tetrahydrofuran (25 mL). After stirring for 3 hours at 25° C., the mixture is evaporated to a syrup in vacuo. To the residue is added ethyl ether and 1N citric acid which gives a solution that precipitates a white solid. The solid is filtered and added to a mixture of saturated sodium bicarbonate solution and ethyl ether. The ether phase of the resulting solution is separated, washed with brine, dried over anhydrous magnesium sulfate and filtered. The filtrate is evaporated in vacuo to a white solid (1.0 g, 31% yield). MS: APCI: M+1: 455.1 (M: 454.6). NMR spectrum is consistent with structure (Compound 1). Calcd. for C$_{28}$H$_{26}$N$_2$O$_2$S.0.20H$_2$O:

| Theory: | C 73.40, | H 5.72, | N 6.11, | H$_2$O 0.79. |
| Found: | C 73.07, | H 5.91, | N 6.15, | H$_2$O 0.45. |

EXAMPLE 2

Synthesis of 6-((1S)-2-Imidazolyl-1-phenylethoxy)-5-[(phenylsulfinyl)methyl]-2,3,4-trihydronaphthalen-1-one (Compound 2)

To an ice cold solution of compound 1 (0.60 g, 1.32 mmol) in 10 mL tetrahydrofuran is added a solution of NaIO$_4$ (3.3 mL 0.5M in H$_2$O). The mixture is stirred 3 days at 25° C. Another portion of NaIO$_4$ solution (6.6 mL 0.5M in H$_2$O) is added and after stirring for 6 hours at 25° C., the mixture is filtered and the filtrate is extracted with chloroform. The organic phase is washed with brine, dried over anhydrous magnesium sulfate, and filtered. The filtrate is evaporated to a solid (550 mg). The mixture is purified by reverse phase silica gel chromatography giving the product (Compound 2) as a trifluoroacetate salt (100 mg, 16% yield). MS: APCI: M+1: 471.1 (M: 470.6). NMR spectrum is consistent with structure. Calcd. for C$_{28}$H$_{26}$N$_2$O$_3$S.0.10H$_2$O.1.45 TFA:

| Theory: | C 58.20, | H 4.34, | N 4.39, | H$_2$O 0.28 | F 12.96. |
| Found: | C 58.51, | H 4.61, | N 4.23, | H$_2$O <0.1 | F 13.00. |

EXAMPLE 3

Synthesis of 6-((1S)-2-Imidazolyl-1-phenylethoxy)-5-[(phenylsulfinyl)methyl]-2,3,4-trihydronaphthalen-1-one (Compound 3)

1. 5-Benzenesulfonylmethyl-6-hydroxy-2,3,4-dihydronaphthalen-1-one

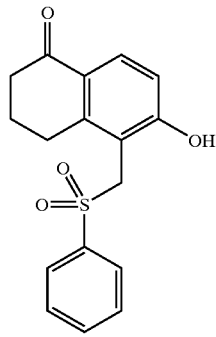

To a suspension of 6-hydroxy-5-phenylsulfanylmethyl-2,3,4-trihydronaphthalen-1-one (7.0 g, 0.025 mol) in 300 mL dichloromethane is added a solution of 73% meta-chloroperbenzoic acid (11.82 g, 0.05 mol) in 150 mL dichloromethane. The suspended solids dissolve, followed by precipitation of another white solid. After stirring 3 hours at 25° C., an additional portion of 73% meta-chloroperbenzoic acid (2.95 g, 0.0125 mol) in 11 mL dichloromethane is added. The mixture is then stirred for 1 hour and extracted with saturated potassium carbonate solution (475 mL). The organic phase is washed with brine, dried over anhydrous magnesium sulfate, filtered, and evaporated to a solid. The pH of the carbonate is adjusted to 8 with concentrated HCl and washed with ethyl acetate. The ethyl acetate is washed with brine, dried over anhydrous magnesium sulfate, filtered and evaporated to a solid. The solids from both organic phases are combined and crystallized from ethyl acetate, filtered, and dried giving a white solid (5.07 g, 64% yield). MS: APCI: M+1: 317 (M: 316.4). NMR spectrum is consistent with structure.

2. 6-((1S)-2-Imidazolyl-1-phenylethoxy)-5-[(phenylsulfonyl)methyl]-2,3,4-trihydronaphthalen-1-one (R)-2-Imidazol-1-yl-1-phenyl-ethanol (3.27 g, 17.4 mmol), triphenylphosphine (6.22 g, 23.7 mmol), and 5-benzenesulfonylmethyl-6-hydroxy-2,3,4-trihydronaphthalen-1-one (5.0 g, 15.8 mmol) are suspended in dry tetrahydrofuran (250 mL). To the suspension is added a solution of diethyl azodicarboxylate (4.13 g, 23.7 mmol) in tetrahydrofuran (50 mL) over 45 minutes. After stirring for 23 hours at 25° C., the mixture is evaporated to a syrup in vacuo. The residue is dissolved in ethyl ether and 1N citric acid. The ether phase is decanted from the mixture and the citric acid phase is washed exhaustively with ethyl ether. The pH of the citric acid phase is adjusted to 13 with 6N NaOH giving a white solid precipitate. The solid is filtered and dissolved in dichloromethane, which is washed with brine, dried over anhydrous magnesium sulfate and filtered. The filtrate is evaporated in vacuo to give a foam. The product is purified by chromatography on 200 g silica gel eluted with chloroform/1% methanol. The product (Compound 3) is obtained from chloroform/ethyl ether as a crystalline solid (3.53 g, 46% yield). MS: NMR spectrum is consistent with structure. Calcd. for $C_{28}H_{26}N_2O_4S$:

| | | | |
|---|---|---|---|
| Theory: | C 69.12, | H 5.39, | N 5.76. |
| Found: | C 68.80, | H 5.44, | N 5.68. |

EXAMPLE 4

Synthesis of Methyl 2-{[2-((1S)-2-imidazolyl-1-phenylethoxy)-5-oxo-6,7,8-trihydronaphthyl]methylthio}benzoate (Compound 4)

1. Methyl 2-(2-hydroxy-5-oxo-6,7,8-trihydronaphthalenylmethylthio) benzoate

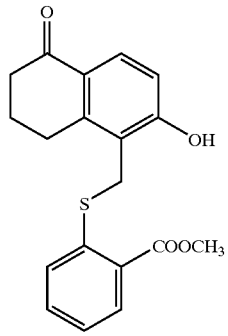

To a solution of methyl thiosalicylate (14.38 g, 85.5 mmol) in oxygen-free tetrahydrofuran (100 mL) is added diisopropylamine (3.68 g, 0.0285 mol) 5-chloromethyl-6-hydroxy-2,3,4-trihydronaphthalen-1-one, prepared as described in Chem. Pharm. Bull. 1977;25(11):2988–3002 (6.0 g, 0.0285 mol) is dissolved in tetrahydrofuran (125 mL) and the solution added dropwise to the preceding solution at 25° C. over 45 minutes. The mixture is stirred for 22 hours, concentrated in vacuo, and the residue layered with ethyl ether. Water is added to the mixture giving a solid precipitate. The solid is filtered, washed with water, and dried at 25° C. The solid is recrystallized from ethyl acetate and dried in vacuo giving a white solid (7.3 g, 75% yield). MS: APCI: M+1: 343.1 (M: 342.41). NMR spectrum is consistent with the structure.

2. Methyl 2-{[2-((1S)-2-Imidazolyl-1-phenylethoxy)-5-oxo-6,7,8-trihydronaphthyl]methylthio}benzoate (R)-2-Imidazol-1-yl-1-phenyl-ethanol (2.42 g, 12.9 mmol), triphenylphosphine (4.60 g, 17.5 mmol), and 2-(2-hydroxy-5-oxo-5,6,7,8-tetrahydro-naphthalen-1-ylmethylsulfanyl)-benzoic acid methyl ester (4.0 g, 11.7 mmol) are suspended in dry tetrahydrofuran (250 mL). To the suspension is added a solution of diethyl azodicarboxylate (3.05 g, 17.5 mmol) in tetrahydrofuran (50 mL) over 30 minutes. After stirring for 18 hours at 25° C., the mixture is evaporated to a syrup in vacuo. The residue is added to ethyl ether and 1N citric acid, which subsequently gives a solution. The ether phase is decanted from the mixture, and the citric acid phase is washed exhaustively with ethyl ether. The citric acid phase is layered with ethyl acetate, and the pH of the citric acid phase is adjusted to 13 with 6N NaOH giving a yellow oily precipitate. The oil is dissolved in chloroform, washed with brine, dried over anhydrous magnesium sulfate and filtered. The filtrate is evaporated in vacuo to a foam. The product is purified by chromatography on 200 g silica gel eluted with chloroform/1% methanol. The product (Compound 4) is obtained from chloroform/ethyl ether as a foam (1.88 g, 31% yield). MS: APCI: M+1: 513.2 (M: 512.6). NMR spectrum is consistent with structure.

Calcd. For $C_{30}H_{28}N_2O_4S \cdot 0.23\ CHCl_3, 0.275\ H_2O$:

| Theory: | C 67.31, | H 5.27, | N 5.20, | Cl 3.36, | $H_2O$, 1.00. |
|---|---|---|---|---|---|
| Found: | C 67.21, | H 5.38, | N 4.72, | Cl 3.42, | $H_2O$, 1.12. |

EXAMPLE 5

Synthesis of 2-{[2-((1S)-2-Imidazolyl-1-phenylethoxy)-5-oxo-6,7,8-trihydronaphenyl]methylthio}benzoic acid (Compound 5)

To dioxane (20 mL) is added compound 4 (0.5 g, 0.975 mmol), followed by the addition of a 1N solution of NaOH (3.0 mL). After the mixture is stirred for 72 hours, the dioxane is evaporated in vacuo, and the residue is washed twice with ethyl ether. The residue is layered with ethyl ether and acidified with 1N HCl to pH 4 giving a solid precipitate. The ether is removed from the suspension in vacuo, and the residue is taken up in dichloromethane giving a two phase solution. The dichloromethane phase is dried over anhydrous magnesium sulfate, filtered, and evaporated to an oil (325 mg). The oil is layered with ethyl ether, and 1N NaOH is added. The pH is adjusted to 5 by addition of 1N HCl resulting in an off-white precipitate. The solid is filtered, dried and purified by silica gel chromatography and eluted with chloroform/methanol (90:10). A white solid (compound 5) is recovered (120 mg, 25% yield).

Calcd. for $C_{29}H_{26}N_2O_4S$, 0.23 $CHCl_3$, 0.6 $H_2O$:

| Theory: | C 65.40, | H 4.92, | N 5.22, | Cl 4.56, | $H_2O$, 2.01. |
|---|---|---|---|---|---|
| Found: | C 65.24, | H 5.12, | N 5.23, | Cl 3.72, | $H_2O$, 1.72. |

EXAMPLE 6

Synthesis of 6-((S)-2-Imidazol-1-yl-1-phenyl-ethoxy)-5-isopropylsulfanylmethyl-2,3,4-trihydronaphthalen-1-one (Compound 6)

1. 6-Hydroxy-5-isopropylsulfanylmethyl-2,3,4-trihydronaphthalen-1-one

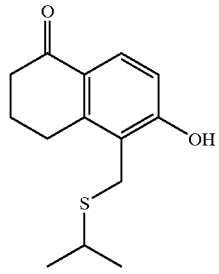

Tetrahydrofuran (100 mL, anhydrous, distilled) is sparged with nitrogen gas followed by addition of triethylamine (6.97 mL, 50 mmol) and 2-propanethiol (7 mL, 150 mmol). A solution of 5-chloromethyl-6-hydroxy-2,3,4-trihydronaphthalen-1-one, prepared as described in Chem. Pharm. Bull. 1977;25(11):2988–3002 (10.53 g, 50 mmol) in tetrahydrofuran (175 mL) is added. The mixture is stirred for 1 hour at 25° C. followed by heating at 85° C. for 3 hours. The mixture is filtered and the filtrate is evaporated under vacuum giving a solid. The solid is dissolved in ethyl acetate and then washed with 1N citric acid and brine. The organic phase is separated, dried over anhydrous magnesium sulfate and filtered. The filtrate is concentrated in vacuo giving a solid which is filtered, washed with ethyl ether, and dried in vacuo to a solid (8.69 g, 69.4% yield). NMR spectrum is consistent with structure. MS: APCI: M+1: 251.2 (M: 250.4).

2. 6-((S)-2-Imidazol-1-yl-1-phenyl-ethoxy)-5-isopropylsulfanylmethyl-2,3,4-trihydronaphthalen-1-one (R)-2-Imidazol-1-yl-1-phenyl-ethanol (3.05 g, 21.1 mmol), triphenylphosphine (5.54 g, 21.1 mmol), and 6-hydroxy-5-isopropylsulfanyl methyl-2,3,4-trihydronaphthalen-1-one (3.5 g, 14 mmol) are suspended in dry tetrahydrofuran (75 mL). To the suspension is added a solution of diethyl azodicarboxylate (3.68 g, 21.1 mmol) in tetrahydrofuran (30 mL) over 30 minutes at 25° C. After stirring for 3 hours at 25° C., the mixture is evaporated to a solid in vacuo. To the residue is added ethyl ether and 1N citric acid which gives a precipitate. The ether phase is decanted from the mixture and the mixed precipitate and citric acid phases are washed exhaustively with ethyl ether. The citric acid phase is layered with ethyl ether and the pH of the citric acid phase is adjusted to 5.5 with 6N NaOH. The product is extracted into a mixture of ethyl acetate and ethyl ether, washed with brine, dried over anhydrous magnesium sulfate and filtered. The filtrate is concentrated in vacuo and is purified by chromatography on 150 g silica gel eluted with a gradient of chloroform to 2% methanol. The product (Compound 6) is obtained as a solid (3.12 g, 53% yield). MS: APCI: M+1: 425.1 (M: 420.6). NMR spectrum is consistent with structure. Calcd. for $C_{25}H_{28}N_2O_2S$, 0.125 $CHCl_3$, 0.0125 $H_2O$:

| Theory: | C 69.26, | H 6.15, | N 6.43, | Cl 3.05, | $H_2O$ 0.52. |
|---|---|---|---|---|---|
| Found: | C 69.12, | H 6.61, | N 6.38, | Cl 2.85, | $H_2O$ 0.51. |

EXAMPLE 7

Synthesis of 6-(1S)-2-Imidazolyl-1-phenylethoxy)-5-{[(methylethyl)sulfonyl]methyl}-2,3,4-trihydronaphthalen-1-one (Compound 7)

1. 6-Hydroxy-5-isopropylsulfonylmethyl-2,3,4-trihydronaphthalen-1-one

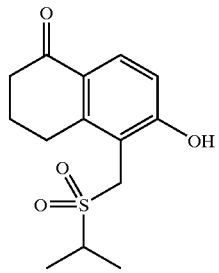

To dichloromethane (100 mL) is added 6-hydroxy-5-isopropylsulfanyl methyl-2,3,4-trihydronaphthalen-1-one, (3.74 g, 14.9 mmol). The mixture is cooled to 15° C., followed by the addition of m-chloroperbenzoic acid (70% with water, 7.36 g, 29.9 mmol) over 2 minutes. The mixture is stirred for 5 hours at 25° C. giving a suspended solid. The suspension is evaporated under vacuum. The resulting solid is dissolved in warm ethyl acetate (700 mL) and washed with saturated sodium bicarbonate and brine. The organic phase is separated, dried over anhydrous magnesium sulfate and filtered. The filtrate is concentrated in vacuo to 150 mL in volume at 2° C. giving a suspended solid. The solid is filtered, washed with ethyl ether, and dried in vacuo (2.64 g, 63% yield). NMR spectrum is consistent with structure. MS: APCI: M+1: 283.0 (M: 282.36).

2. 6-((1S)-2-Imidazolyl-1-phenylethoxy)-5-{[(methylethyl)sulfonyl]methyl}-2,3,4-trihydronaphthalen-1-one (R)-2-Imidazol-1-yl-1-phenyl-ethanol (1.95 g, 10.3 mmol), triphenyl-phosphine (3.54 g, 13.5 mmol), and 6-hydroxy-5-isopropylsulfonylmethyl-2,3,4-trihydronaphthalen-1-one (2.54 g, 9.0 mmol) are suspended in dry tetrahydrofuran (50 mL). To the suspension is added a solution of diethyl azodicarboxylate (2.35 g, 13.5 mmol) in tetrahydrofuran (20 mL) over 30 minutes at 25° C. After stirring for 5 hours at 25° C., the mixture is evaporated in vacuo. To the residue is added ethyl ether and 1N citric acid which gives a precipitate. The ether phase is decanted from the mixture and the mixed precipitate and citric acid phases are washed exhaustively with ethyl ether. The citric acid phase and the suspended oil are layered with ethyl acetate and the pH of the citric acid phase is adjusted to 6.5 with 6N NaOH. The product is extracted into the ethyl acetate, washed with brine, dried over anhydrous magnesium sulfate and filtered. The filtrate is concentrated in vacuo and is purified by chromatography on 150 g silica gel eluted with a gradient of chloroform to 2% methanol. The product (Compound 7) is obtained as a solid (3.12 g, 53% yield). MS: APCI: M+1 (M: 452.58). NMR spectrum is consistent with structure.

Calcd. for $C_{25}H_{28}N_2O_4S$, 0.125 $CHCl_3$, 0.0125$H_2O$:

| Theory: | C 69.26, | H 6.15, | N 6.43, | Cl 3.05, | $H_2O$ 0.52. |
|---|---|---|---|---|---|
| Found: | C 69.12, | H 6.61, | N 6.38, | Cl 2.85, | $H_2O$ 0.51. |

EXAMPLE 8

Synthesis of 6-((1S)-2-Imidazolyl-1-phenylethoxy)-5-(4-pyridylthiomethyl)-2,3,4-trihydronaphthalen-1-one (Compound 8)

1. 6-Hydroxy-5-(pyridin-4-ylsulfanylmethyl)-2,3,4-trihydronaphthalen-1-one

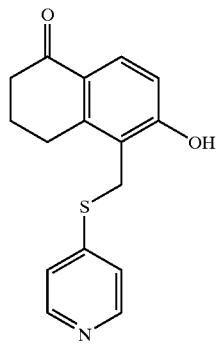

To tetrahydrofuran (50 mL) is added 4-mercaptopyridine (3.33 g, 30 mmol) and triethylamine (2.08 mL, 15 mmol). The mixture is warmed to 30° C., followed by the addition of a solution of 5-chloromethyl-6-hydroxy-2,3,4-trihydronaphthalen-1-one, prepared as described in *Chem. Pharm. Bull.* 1977;25(11):2988–3002 (2.11 g, 10 mmol) in tetrahydrofuran (25 mL) giving a suspension. The mixture is stirred for 18 hours at 55° C. The suspension is filtered, and the filtrate is evaporated under vacuum giving a solid. The solid is dissolved in 1N NaOH (100 mL), washed with ethyl ether, and separated. The pH of the aqueous phase is adjusted to 10 with 6N HCl giving a solid precipitate. The suspension is with ethyl acetate, washed with minimal amounts of water, brine, dried over anhydrous magnesium sulfate, and filtered. The filtrate is concentrated in vacuo to a small volume, giving a suspended solid. The solid is filtered, washed with ethyl acetate, and dried in vacuo to give desired product (1.42 g, 49.8% yield). NMR spectrum is consistent with structure. MS: APCI: M+1: 286.1 (M: 285.37).

2. 6-((1S)-2-Imidazolyl-1-phenylethoxy)-5-(4-pyridylthiomethyl)-2,3,4-trihydronaphthalen-1-one (R)-2-Imidazol-1-yl-1-phenyl-ethanol (1.03 g, 5.47 mmol), triphenylphosphine (1.87 g, 7.13 mmol), and 6-hydroxy-5-(pyridin-4-yl-sulfanylmethyl)-2,3,4-trihydronaphthalen-1-one (1.35 g, 4.73 mmol) are suspended in dry tetrahydrofuran (25 mL). To the suspension is added a solution of diethyl azodicarboxylate (1.24 g, 4.73 mmol) in tetrahydrofuran (10 mL) over 30 minutes at 25° C. After stirring for 3 hours at 25° C., the mixture is evaporated in vacuo. The residue is added to ethyl ether and 1N citric acid. The ether phase is decanted from the mixture, and the mixed precipitate and citric acid phases are washed exhaustively with ethyl ether. The citric acid phase and the suspended oil are layered with a mixture of ethyl acetate and ethyl ether, and the pH of the citric acid phase is adjusted to 6.5 with 6N NaOH giving an oily precipitate. The product is dissolved into the organic phase by addition of ethyl acetate, washed with brine, dried over anhydrous magnesium sulfate, and filtered. The filtrate is concentrated in vacuo and is purified by chromatography on 100 g silica gel eluted with a gradient of chloroform to 5% methanol. The product (Compound 8) is obtained as a solid (1.5 g, 49.8% yield). MS: APCI: M+1, 456.3 (M: 455.6). NMR spectrum is consistent with structure.

Calcd. for $C_{27}H_{25}N_3O_2S$, 0.125 $CHCl_3$, 0.1$H_2O$:

| Theory: | C 68.98, | H 5.40, | N 8.89, | Cl 2.81, | $H_2O$ 0.38. |
|---|---|---|---|---|---|
| Found: | C 68.87, | H 5.62, | N 9.08, | Cl 3.16, | $H_2O$ 0.68. |

EXAMPLE 9

Synthesis of 6-((1S)-2-Imidazolyl-1-phenylethoxy)-5-(2-pyridylthiomethyl)-2,3,4-trihydronaphthalen-1-one (Compound 9)

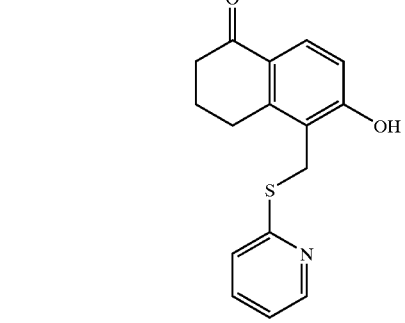

1. 6-Hydroxy-5-(pyridin-2-ylsulfanylmethyl)-2,3,4-trihydronaphthalen-1-one

To tetrahydrofuran (500 mL) is added 2-mercaptopyridine (16 g, 0.14 mol) and triethylamine (20.8 mL, 0.15 mol). The mixture is warmed to 30° C., followed by the addition of a solution of 5-chloromethyl-6-hydroxy-2,3,4-trihydronaphthalen-1-one, prepared as described in *Chem.*

*Pharm. Bull.* 1977;25(11):2988–3002 (29.5 g, 0.143 mol) in tetrahydrofuran (300 mL) giving a suspension. The mixture stirred for 18 hours at 25° C. The suspension is filtered, and the filtrate is evaporated under vacuum giving a solid. The solid is dissolved in warm ethyl acetate, washed with 300 mL of water and then brine, dried over anhydrous magnesium sulfate, and filtered. The filtrate is concentrated in vacuo to a small volume, giving a suspended solid. The solid is filtered, washed with ethyl acetate, and dried in vacuo to afford product (22.26 g, 56% yield). NMR spectrum is consistent with structure. MS: APCI: M+1: 286.1 (M: 285.4).

2. 6-[(S)-2-(2,5-Dihydro-imidazol-1-yl)-1-phenyl-ethoxy]-5-(pyridin-2-ylsulfanylmethyl)-2,3,4-trihydronaphthalen-1-one (R)-2-Imidazol-1-yl-1-phenyl-ethanol (1.80 g, 9.6 mmol), triphenylphosphine (3.27 g, 12.5 mmol), and 6-hydroxy-5-(pyridin-2-yl-sulfanylmethyl)-2,3,4-trihydronaphthalen-1-one (2.36 g, 8.29 mmol) are suspended in dry tetrahydrofuran (45 mL). To the suspension is added a solution of diethyl azodicarboxylate (2.18 g, 12.5 mmol) in tetrahydrofuran (20 mL) over 30 minutes at 25° C. After stirring for 3 hours at 25° C., the mixture is evaporated in vacuo. To the residue is added ethyl ether and 1N citric acid. The ether phase is decanted from the mixture, and the mixed precipitate and citric acid phases are washed exhaustively with ethyl ether. The citric acid phase and the suspended oil are layered with a mixture of ethyl acetate and ethyl ether, and the pH of the citric acid phase is adjusted to 9 with 6N NaOH giving an oily precipitate. The product is dissolved into the organic phase by addition of ethyl acetate, washed with brine, dried over anhydrous magnesium sulfate, and filtered. The filtrate is concentrated in vacuo and is purified by chromatography on 100 g silica gel eluted with a gradient of chloroform to 5% methanol. The product (Compound 9) is obtained as a solid (1.5 g, 49.8% yield). MS: APCI: M+1, 456.3 (M: 455.6). NMR spectrum is consistent with structure.

Calcd. for $C_{27}H_{25}N_3O_2S$, 0.125 $CHCl_3$, 0.1 $H_2O$:

| | | | | | |
|---|---|---|---|---|---|
| Theory: | C 68.98, | H 5.40, | N 8.89, | Cl 2.81, | $H_2O$ 0.38. |
| Found: | C 68.87, | H 5.62, | N 9.08, | Cl 3.16, | $H_2O$ 0.68. |

EXAMPLE 10

Synthesis of 6-(1S)-2-Imidazolyl-1-phenylethoxy)-5-[(2-pyridylsulfonyl)methyl]-2,3,4-trihydronaphthalen-1-one hydrochloride (Compound 10)

1. 6-Hydroxy-5-(pyridine-2-sulfonylmethyl)-3,4-dihydro-2H-naphthalen-1-one

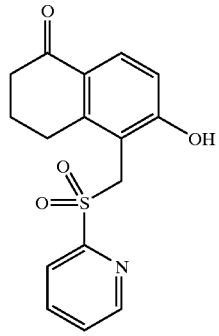

6-Hydroxy-5-(pyridin-2-ylsulfanylmethyl)-2,3,4-trihydronaphthalen-1-one (18 g, 0.063 mol) is added to dichloromethane (400 mL). A solution of m-chloroperbenzoic acid (70%, 33.6 g, 0.136 mol) in dichloromethane (250 mL) is added over 2 hours, after which the mixture is allowed to stir for 18 hours at 25° C. The mixture is filtered, and the solid is resuspended in hot ethyl acetate and extracted with saturated sodium bicarbonate solution. The organic phase is washed with brine, dried over anhydrous magnesium sulfate, and filtered. The filtrate is concentrated giving a solid, which is subsequently filtered, washed with ethyl acetate and dried, 6.8 g, 34% yield. MS: APCI: M+1, 318.3 (M: 317.4). NMR spectrum is consistent with structure.

2. 6-((1S)-2-Imidazolyl-1-phenylethoxy)-5-[(2-pyridylsulfonyl)methyl]-2,3,4-trihydronaphthalen-1-one (R)-2-Imidazol-1-yl-1-phenyl-ethanol (1.80 g, 9.6 mol), triphenylphosphine (3.27 g, 12.5 mmol), and 6-hydroxy-5-(pyridine-2-sulfonylmethyl)-3,4-dihydro-2H-naphthalen-1-one (2.63 g, 8.29 mmol) are suspended in dry tetrahydrofuran (50 mL). To the suspension is added a solution of diethyl azodicarboxylate (2.18 g, 12.5 mmol) in tetrahydrofuran (20 mL) over 40 minutes at 25° C. After stirring for 68 hours at 25° C., the mixture is evaporated in vacuo. The residue is added to ethyl ether and 1N citric acid. The ether phase is decanted from the mixture, and the mixed precipitate and citric acid phases are washed exhaustively with ethyl ether. The citric acid phase is layered with a mixture of ethyl acetate and ethyl ether, and the pH of the citric acid phase is adjusted to 8 with 6N NaOH giving an oily precipitate. The product is dissolved into the organic phase by addition of ethyl acetate, washed with brine, dried over anhydrous magnesium sulfate, and filtered. The filtrate is concentrated in vacuo and is purified by chromatography on 100 g silica gel eluted with a gradient of chloroform to 5% methanol. The product is obtained as a solid 1.0 g, 43% yield. MS: APCI: M+1, 488.2 (M: 487.5). The product was stirred with one equivalent of 1M HCl solution in ether. The solution was concentrated and the hydrochloride (Compound 10) was collected by filtration. NMR spectrum is consistent with structure.

Calcd. for $C_{22}H_{25}N_3O_2S$, 0.125 $CHCl_3$, 0.1 $H_2O$:

| | | | | | |
|---|---|---|---|---|---|
| Theory: | C 68.98, | H 5.40, | N 8.89, | Cl 2.81, | $H_2O$ 0.38. |
| Found: | C 68.87, | H 5.62, | N 9.08, | Cl 3.16, | $H_2O$ 0.68. |

EXAMPLE 10a

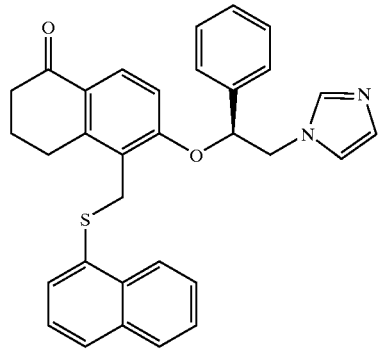

Synthesis of 6-((S)-2-Imidazol-1-yl-1-phenyl-ethoxy)-5-(naphthalen-1-ylsulfanylmethyl)-3,4-dihydro-2H-naphthalen-1-one (Compound 10a)

1. 6-Hydroxy-5-(naphthalen-1-ylsulfanylmethyl)-3,4-dihydro-2H-naphthalen-1-one

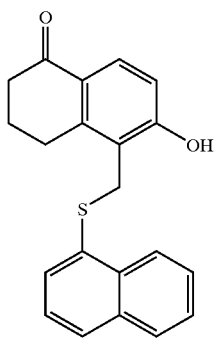

To a solution of 1-naphthalenethiol (19.38 g, 0.092 mol) in oxygen-free tetrahydrofuran (500 ml) was added diisopropylamine (12.74 g, 0.098 mol). 5-Chloromethyl-6-hydroxy-3,4-dihydro-2H-naphthalen-1-one, prepared as described Chem. Pharm. Bull. 25(11)2988–3002(1977), (6.0 g, 0.0285 mol) was dissolved in tetrahydrofuran (300 ml) and the solution added dropwise to the preceding solution at 25° C. over 2 hours. The mixture was stirred for 16 hours, concentrated in vacuo and the residue layered with ethyl acetate. The suspension was filtered and washed with hot chloroform, a small amount of ethyl ether, 1N citric acid and water. The solid was dried in vacuo at 70° C. giving a solid, 18.5 g, 59% yield. MS: APCI: M+1: 335.0 (M: 334.4).

2. 6-((S)-2-Imidazol-1-yl-1-phenyl-ethoxy)-5-(naphthalen-1-ylsulfanylmethyl)-3,4-dihydro-2H-naphthalen-1-one

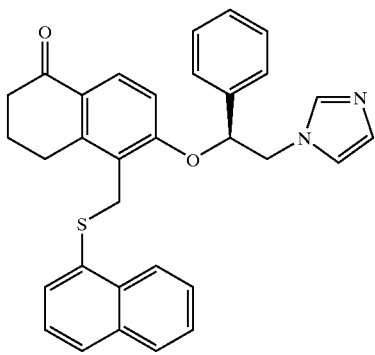

In a manner similar to that of Example 7, step(b), (R)-2-Imidazol-1-yl-1-phenyl-ethanol (0.565 g, 3.0 mmol) and 6-Hydroxy-5-(naphthalen-1-ylsulfanylmethyl)-3,4-dihydro-2H-naphthalen-1-one (0.84 g, 2.5 mmol) gave a solid, 0.79 g, 62% yield. MS: APCI: M+1: 505.1 (M: 504.7). Calcd. for C32H28N2O2S 0.05CHCl3: Theory: C, 75.38; H, 5.54; N, 5.48; Cl, 0.10. Found: C, 75.67; H, 5.81; N, 5.41; Cl, 0.35.

EXAMPLE 10b

Synthesis of [2-(2-Imidazol-1-yl-1(S)-phenyl-ethoxy)-5-oxo-5,6,7,8-tetrahydro-naphthalen-1-ylmethylsulfanyl]-acetic acid methyl ester (Compound 10b)

1. (2-Hydroxy-5-oxo-5,6,7,8-tetrahydro-naphthalen-1-ylmethylsulfanyl)acetic acid methyl ester 5-Chloromethyl-6-hydroxy-1-tetralone (315 mg, 1.5 mmol) and methyl thioglycolate (2.0 mL, 22 mmol) were combined in a septum capped round bottomed flask and heated to 40° C. overnight. The excess methyl thioglycolate was removed in vacuo and the pot residue was purified by silica gel chromatography ($R_f$=0.18, hexanes/ethyl acetate/acetic acid, 58:40:2) to give 219 mg (52%) of the desired compound as a colorless glass: $^1$H NMR (CDCl$_3$) δ 2.02 (p, 2H, J=6.01 Hz); 2.50 (t, 2H, J=6.01 Hz); 2.89 (t, 2H, J=6.01 Hz); 3.19 (s, 2H); 3.64 (s, 3H); 3.85 (s, 2H); 6.79 (d, 1H, J=8.7 Hz); 7.83 (d, 1H, J=8.7 Hz); 8.59 (br s, 1H).

2. [2-(2-Imidazol-1-yl-(S)-phenyl-ethoxy)-5-oxo-5,6,7,8-tetrahydro-naphthalen-1-ylmethylsulfanyl]-acetic acid methyl ester (2-Hydroxy-5-oxo-5,6,7,8-tetrahydro-naphthalen-1-ylmethylsulfanyl)-acetic acid methyl ester (200 mg, 0.71 mmol), (R)2-imidazol-1-yl-1-phenyl-ethanol (141 mg, 0.75 mmol), and triphenylphosphine resin (1.5 g, loading 1.41 mmol/g) were combined in dry tetrahydrofuran (10 mL) and treated with diethyl azodicarboxylate (337 μL, 2.1 mmol). The resulting orange-brown heterogeneous mixture was allowed to stir at ambient temperature overnight. The spent triphenylphosphine resin was removed by filtration, washing sequentially with ethyl acetate, methanol, and chloroform. The filtrate was concentrated in vacuo and the crude material was purified by silica gel chromatography (hexanes/ethyl acetate/triethylamine 20:75:5) to give 84 mg (26%) of the desired product as a light yellow glass: (LC-MS, APCI) m/z 450 M+H]+; $^1$H NMR (CDCl$_3$) δ 2.10 (p, 2H, J=6.01 Hz); 2.54 (t, 2H, J=6.01 Hz); 3.02 (t, 2H, J=6.01 Hz); 3.37 (s, 2H); 3.75 (s, 3H); 4.06 (apparent q, 2H); 4.40 (dd, 1H, J=11.1, 3.0 Hz); 4.50 (dd, 1H, J=11.1, 5.4 Hz); 5.46 (dd, 1H, J=5.4, 3.0 Hz); 6.52 (d, 1H, J=6.6 Hz); 6.97 (s, 1H); 7.02 (s, 1H); 7.25–7.36 (m, 6H); 7.51 (s, 1H); 7.80 (d, 1H, J=6.6 Hz); $^{13}$C NMR (CDCl$_3$) 22.6, 26.1, 27.9, 34.1, 38.2, 52.4, 53.1, 79.5, 111.3, 119.7, 123.0, 125.9, 127.1, 128.6, 128.9, 129.2, 129.4, 136.6, 137.9, 145.3, 158.6, 170.9, 197.1.

EXAMPLE 10c

Synthesis of 5-(3,4-Dichloro-benzylsulfanylmethyl)-6-((1S)-2-imidazol-1-yl-1-phenyl-ethoxy)-3,4-dihydro-2H-naphthalen-1-one (Compound 10c)

1. 5-(3,4-Dichloro-benzylsulfanylmethyl)-6-hydroxy-3,4-dihydro-2H-naphthalen-1-one 5-Chloromethyl-6-hydroxy-1-tetralone (315 mg, 1.5 mmol) and (3,4-Dichloro-phenyl)-methanethiol (1.0 mL, 6.0 mmol) were sealed in a 16×120 mm screw capped tube and heated to 40° C. overnight. The excess (3,4-Dichlorophenyl)-methanethiol was removed in vacuo and the residue was purified by silica gel chromatography (hexanes/ethyl acetate/acetic acid, 58:40:2) to give 350 mg (63%) of the desired product as a tan powder: (LC-MS, APCI) m/z 367/369 [M+H]+.

2. 5-(3,4-Dichloro-benzylsulfanylmethyl)-6-((1S)-2-imidazol-1-yl-1-phenyl-ethoxy)-3,4-dihydro-2H-naphthalen-1-one 5-(3,4-Dichloro-benzylsulfanylmethyl)-6-hydroxy-3,4-dihydro-2H-naphthalen-1-one (256 mg, 0.69 mmol), (R)-2-imidazol-1-yl-1-phenyl-ethanol (144 mg, 0.75 mmol), and triphenylphosphine resin (1.46 g, loading 1.41 mmol/g) were combined in dry tetrahydrofuran (10 mL) and treated with diisopropyl azodicarboxylate (271 μL, 2.0 mmol). The resulting orange-brown heterogeneous mixture was allowed to stir at ambient temperature overnight. The spent triphenylphosphine resin was removed by filtration, washing sequentially with ethyl acetate, methanol, and chloroform. The filtrate was concentrated in vacuo and the crude material was purified by silica gel chromatography (hexanes/ethyl acetate/triethylamine 28:70:2) to give 280 mg (75%) of the desired product as a colorless solid: (LC-MS, APCI) m/z 553/555 [M+H]+.

EXAMPLE 10d

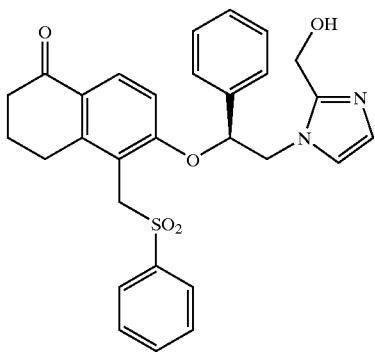

Synthesis of (S)-6{2-[2-(Hydroxymethyl)-1H-imidazol-1-yl]-1-phenylethoxy}-5-[(phenylsulfonyl)methyl]-3,4-dihydro-1(2H)-naphthalenone (Compound 10d)

A mixture of (S)-6-[2-(1H-imidazol-1-yl)-1-phenylethoxy]-5-[(phenylsulfonyl)methyl]-3,4-dihydro-1(2H)-naphthalenone (see example 3, 250 mg, 0.51 mmol), paraformaldehyde (1.5 g) and dimethylsulfoxide (6 mL) was stirred at 130° C. for 24 h. The mixture was diluted with ethanol (10 mL), filtered, concentrated, diluted with water (50 mL) and extracted with ethyl acetate (4×10 mL). The combined extracts were washed with water (3×10 mL), dried (brine, $Na_2SO_4$), and concentrated. The residue was purified by dry-flash column chromatography ($SiO_2$, 2.5–22.5% 2-propanol-dichloromethane) to give (S)-6-{2-[2-(hydroxymethyl)-1H-imidazol-1-yl]-1-phenylethoxy}-5-[(phenylsulfonyl)methyl]-3,4-dihydro-1(2H)-naphthalenone as a white solid, 161 mg, 61% yield. NMR spectrum was consistent with structure. MS EI: $M^{+*}$ 517.1816 ($M^{+*}$ 517.1797).

EXAMPLE 11

Synthesis of 6-((1S)-2-Imidazolyl-1-phenylethoxy)-5-[(phenylamino)methyl]-2,3,4-trihydronaphthalen-1-one (Compound 11)

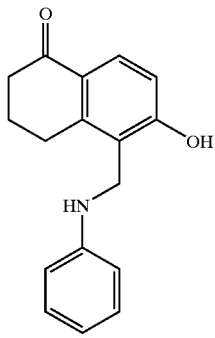

1. 6-Hydroxy-5-phenylaminomethyl-2,3,4-trihydronaphthalen-1-one

To a solution of aniline (13.27 g, 0.1425 mol) in tetrahydrofuran (100 mL) is added a solution of 5-chloromethyl-6-hydroxy-2,3,4-trihydronaphthalen-1-one (*Chem. Pharm. Bull.* 1977;25(11):2988–3002) (6.0 g, 0.0285 mol) in tetrahydrofuran (150 mL) at 25° C. The mixture is stirred for 3 hours, concentrated in vacuo and the residue layered with ethyl ether. The mixture is extracted with 1N citric acid and the ether layer is washed with brine. Upon standing, a solid precipitates from the organic phase. The ether is concentrated in vacuo and the solid is filtered and dried in vacuo giving 4.47 g (59% yield). MS: APCI: M+1: 268.1 (M: 267.3). NMR spectrum is consistent with structure.

2. 6-((1S)-2-Imidazolyl-1-phenylethoxy)-5-[(phenylamino)methyl]-2,3,4-trihydronaphthalen-1-one (R)-2-Imidazol-1-yl-1-phenyl-ethanol (3.42 g, 18.2 mmol), triphenylphosphine (6.49 g, 24.8 mmol), and 6-hydroxy-5-phenylaminomethyl-2,3,4-trihydronaphthalen-1-one (4.4 g, 16.5 mmol) are suspended in dry tetrahydrofuran (250 mL). To the suspension is added a solution of diethyl azodicarboxylate (4.31 g, 24.8 mmol) in tetrahydrofuran (50 mL) over 45 minutes. After stirring for 18 hours at 25° C., the mixture is evaporated to a syrup in vacuo. To the residue is added ethyl ether and 1N citric acid. The ether phase is decanted from the mixture, and the citric acid phase is washed exhaustively with ethyl ether. The citric acid phase is layered with ethyl acetate, and the pH of the citric acid phase is adjusted to 13 with 6N NaOH giving a yellow solid precipitate. The solid is dissolved by addition of chloroform, washed with brine, dried over anhydrous magnesium sulfate, and filtered. The filtrate is concentrated in vacuo and crystallized by addition of ethyl ether. The solid is filtered, washed with ethyl ether and dried giving a solid, 6.95 g, 96% yield. The product is purified by chromatography on 200 g silica gel eluted with chloroform/1% methanol. The product (Compound 11) is obtained from chloroform/ethyl ether as a brittle foam (1.5 g, 21% yield). NMR spectrum is consistent with structure.

Calcd. for $C_{28}H_{27}N_3O_2S$ 0.075 $CHCl_3$, 0.15$H_2O$:

| | | | | | |
|---|---|---|---|---|---|
| Theory: | C 75.07, | H 6.08, | N 9.35, | Cl 1.78, | $H_2O$, 0.60. |
| Found: | C 75.02, | H 6.24, | N 9.32, | Cl 1.52, | $H_2O$, 0.57. |

EXAMPLE 12

Synthesis of 6-((1S)-2-Imidazolyl-1-phenylethoxy)-5-[(methylphenylamino)methyl]-2,3,4-trihydronaphthalen-1-one (Compound 12)

1. 6-Hydroxy-5-[(methyl-phenylamino)methyl]-2,3,4-trihydronaphthalen-1-one

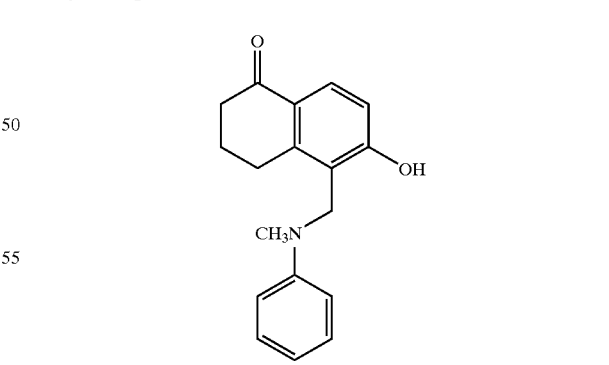

To a solution of n-methylaniline (3.81 g, 0.0356 mol) in tetrahydrofuran (80 mL) is added a solution of 5-chloromethyl-6-hydroxy-2,3,4-trihydro-naphthalen-1-one (*Chem. Pharm. Bull.* 1977;25(11):2988–3002) (2.5 g, 0.0119 mol) in tetrahydrofuran (80 mL) at 25° C. over 30 minutes. The mixture is concentrated in vacuo and is extracted with 1N citric acid. The aqueous phase is layered with ethyl ether and the pH is adjusted to 10 with 1N NaOH. The product is extracted into the ethyl ether phase, washed with brine, dried over anhydrous magnesium sulfate and filtered. Upon concentration of the filtrate in vacuo, a solid precipitates from the organic phase. The solid is filtered and dried in vacuo giving a white solid (3.33 g, 67% yield). MS: APCI: M+1: 282.1 (M: 281.3). NMR spectrum is consistent with structure.

2. 6-((1S)-2-Imidazolyl-1-phenylethoxy)-5-[(methyl-phenylamino)methyl]-2,3,4-trihydronaphthalen-1-one (R)2-Imidazol-1-yl-1-phenyl-ethanol (2.28 g, 12.1 mmol), triphenylphosphine (4.17 g, 15.9 mmol), and 6-hydroxy-5-[(methyl-phenyl-amino)-methyl]-2,3,4-trihydronaphthalen-1-one (3.0 g, 10.7 mmol) are suspended in dry tetrahydrofuran (50 mL). To the suspension is added a solution of diethyl azodicarboxylate (2.77 g, 15.9 mmol) in tetrahydrofuran (25 mL) over 2 hours at 25° C. After stirring for 2 hours at 25° C., the mixture is evaporated to a foam in vacuo. To the residue is added ethyl ether and 1N citric acid. The ether phase is decanted from the mixture and the citric acid phase is washed exhaustively with ethyl ether. The citric acid phase is layered with ethyl acetate and the pH of the citric acid phase is adjusted to 12 with 6N NaOH. The product is extracted into ethyl acetate, washed with brine, dried over anhydrous magnesium sulfate and filtered. The filtrate is concentrated in vacuo and is purified by chromatography on 200 g silica gel eluted with chloroform/1% methanol. The product is obtained from ethyl ether as a brittle foam, which become a glass (Compound 12) upon drying in vacuo at 65° C. (2.4 g, 50% yield). MS: APCI: M+1: 452.1 (M: 451.6). NMR spectrum is consistent with structure.

Calcd. for $C_{29}H_{29}N_3O_2S$ 0.1 $CHCl_3$:

| Theory: | C 75.41, | H 6.33, | N 9.07, | Cl 2.29, | $H_2O$, 0.00. |
| Found: | C 75.11, | H 6.41, | N 9.09, | Cl 1.83, | $H_2O$, 0.34. |

EXAMPLE 13

Synthesis of Methyl 4-({[2-((1S)-2-imidazolyl-1-phenylethoxy)-5-oxo(6,7,8-trihydronaphthyl)]methyl}methylamino)benzoate (Compound 13)

1. Methyl 4-[(2-Hydroxy-5-oxo-5,6,7,8-tetrahydronaphthalen-1-ylmethyl)methyl-amino]benzoate

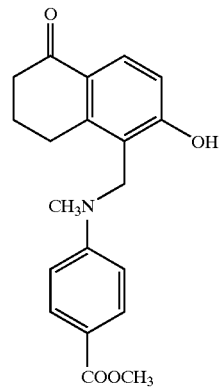

To a solution of methyl-4(methylamino)benzoate (5.88 g, 0.0356 mol) in tetrahydrofuran (80 mL) is added a solution of 5-chloromethyl-6-hydroxy-2,3,4-trihydronaphthalen-1-one (*Chem. Pharm. Bull.* 1977;25(11):2988–3002) (2.5 g, 0.0119 mol) in tetrahydrofuran (80 mL) at 25° C. over 30 minutes. After stirring for 18 hours, the mixture is concentrated in vacuo, taken up in ethyl ether, and washed with 1N citric acid. A solid precipitates from the organic phase, which is filtered and dried in vacuo giving a white solid (2.16 g, 54% yield). MS: APCI: M11: 338.1 (M: 339.4). NMR spectrum is consistent with structure.

2. Methyl 4-({[2-((1S)-2-imidazolyl-1-phenylethoxy)-5-oxo (6,7,8-trihydro naphenyl)]methyl}methylamino)benzoate (R)-2-Imidazol-1-yl-1-phenyl-ethanol (1.22 g, 6.48 mmol), triphenyl-phosphine (2.32 g, 8.84 mmol), and 4-[(2-hydroxy-5-oxo-5,6,7,8-tetrahydro-naphthalen-1-ylmethyl)-methyl-amino]-benzoic acid methyl ester (2.0 g, 5.89 mmol) are suspended in dry tetrahydrofuran (85 mL). To the suspension is added a solution of diethyl azodicarboxylate (1.54 g, 8.84 mmol) in tetrahydrofuran (25 mL) over 30 minutes at 25° C. After stirring for 18 hours at 25° C., the mixture is evaporated to an oil in vacuo. To the residue is added ethyl ether and 1N citric acid. The ether phase is decanted from the mixture, and the citric acid phase is washed exhaustively with ethyl ether. The citric acid phase is layered with ethyl ether, and the pH of the citric acid phase is adjusted to 13 with 6N NaOH. The product is extracted into ethyl ether, washed with brine, dried over anhydrous magnesium sulfate, and filtered. The filtrate is concentrated in vacuo and is purified by chromatography on 200 g silica gel eluted with chloroform/1% methanol. The product is obtained from ethyl ether as a solid (Compound 13) (1.33 g, 44% yield). MS: APCI: M+1: 510.2 (M: 509.6). NMR spectrum is consistent with structure.

Calcd. for $C_{31}H_{31}N_3O_4S$ 0.05 $CHCl_3$, 0.05$H_2O$:

| Theory: | C 72.09, | H 6.05, | N 8.14, | Cl 1.03, | $H_2O$, 0.17. |
| Found: | C 71.88, | H 6.08, | N 8.01, | Cl 0.95, | $H_2O$, 0.37. |

EXAMPLE 14

Synthesis of 4-({[2-((1S)-2-imidazolyl-1-phenylethoxy)-5-oxo(6,7,8-trihydronaphthyl)]methyl}methylamino)benzoic acid, 2,2,2-trifluoroacetic acid (Compound 14)

To a mixture of dioxane (10 mL) and water (10 mL) is added methyl 4-({[2-((1S)-2-imidazolyl-1-phenylethoxy)-5-oxo(6,7,8-trihydronaphthyl)]methyl}methylamino)benzoate (Compound 13) (1.10 g, 2.16 mmol) and 1N NaOH (9 mL). The mixture is stirred at 25° C. for 18 hours, and the dioxane is removed in vacuo. The mixture is layered with ethyl ether and acidified by the addition of 1N HCl (9 mL). The resulting solid precipitate is filtered, washed with ethyl ether, and dried at 25° C. The solid is purified by reverse phase chromatography, eluting with acetonitrile/water, 0.1% trifluoroacetic acid. The product is recovered as a foam (Compound 14) (175 mg, 16.3% yield). NMR spectrum is consistent with structure.

Calcd. for $C_{30}H_{29}N_3O_4$ 1.3 TFA, 0.75$H_2O$:

| Theory: | C 59.57, | H 4.88, | N 6.39, | $H_2O$, 2.05. |
| Found: | C 59.34, | H 4.76, | N 6.23, | $H_2O$, 1.29. |

EXAMPLE 15

Synthesis of 6-((1S)-2-Imidazolyl-1-phenylethoxy)-5-[(methylethoxy)methyl]-2,3,4-trihydronaphthalen-1-one hydrochloride (Compound 15)

1. 6-Hydroxy-5-isopropoxymethyl-2,3,4-trihydronaphthalen-1-one

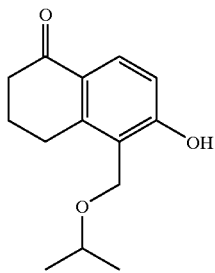

To a solution of diisopropylamine (6.46 g, 0.05 mol) in isopropanol (250 mL) is added 5-chloromethyl-6-hydroxy-2,3,4-trihydronaphthalen-1-one (*Chem. Pharm. Bull.* 1977;25(11):2988–3002) (10.53 g, 0.05 mol). After stirring for 3 hours at 100° C. followed by stirring at 25° C. for 18 hours, the mixture is concentrated in vacuo and taken up in a mixture of ethyl ether, ethyl acetate, and 1N citric acid. The mixture is filtered through celite to remove a small amount of insoluble material. The organic phase is separated, washed with saturated sodium bicarbonate solution and then brine, and dried over anhydrous magnesium sulfate. The organic phase is filtered and the filtrate is concentrated in vacuo. Upon concentration in vacuo, solid precipitates from the organic phase, which is filtered and dried in vacuo giving a white solid. Repeated crystallization gives a pure solid (6.64 g, 57% yield). NMR spectrum is consistent with structure.

2. 6-((1S)-2-imidazolyl-1-phenylethoxy)-5-[(methylethoxy)methyl]-2,3,4-trihydronaphthalen-1-one (R)-2-Imidazol-1-yl-1-phenyl-ethanol (3.05 g, 16.2 mmol), triphenylphosphine (5.54 g, 21.1 mmol), and 6-hydroxy-5-isopropoxymethyl-2,3,4-trihydronaphthalen-1-one (3.3 g, 14 mmol) are suspended in dry tetrahydrofuran (75 mL). To the suspension is added a solution of diethyl azodicarboxylate (3.68 g, 21.1 mmol) in tetrahydrofuran (30 mL) over 30 minutes at 30° C. After stirring for 18 hours at 25° C., the mixture is evaporated to an oil in vacuo. To the residue is added ethyl ether and 1N citric acid. The ether phase is decanted from the mixture and the citric acid phase is washed exhaustively with ethyl ether. The citric acid phase is layered with ethyl ether and the pH of the citric acid phase is adjusted to 5 with 2N NaOH. The product is extracted into ethyl ether, washed with 1N NaOH and brine, dried over anhydrous magnesium sulfate and filtered. The filtrate is concentrated in vacuo and is purified by chromatography on 300 g silica gel eluted with chloroform/2% methanol. The free base product is obtained from ethyl ether as a solid (4.92 g, 86% yield). MS: APCI: M+1: 405.6). The hydrochloride salt is prepared by adding the free base prepared above (2.0 g, 4.94 mmol) to 1N HCl (4.94 mL) giving a solution. The solution is diluted to 100 mL with deionized water, filtered, at 45μ pore size, and lyophilized to a white solid (Compound 15) (2.04 g, 94% yield). MS: APCI: M+1: 404.5 (M: 405.6). NMR spectrum is consistent with structure.

Calcd. for $C_{25}H_{28}N_2O_3$, 1.0 HCl, 0.5$H_2O$:

| | | | | | |
|---|---|---|---|---|---|
| Theory: | C 66.81, | H 6.78, | N 6.22, | Cl 7.58, | $H_2O$, 2.28. |
| Found: | C 66.73, | H 6.72, | N 6.23, | Cl 7.88, | $H_2O$, 2.00. |

EXAMPLE 16

Synthesis of 6-((1S)-2-Imidazolyl-1-phenylethoxy)-5-[(phenylmethoxy)methyl]-2,3,4-trihydronaphthalen-1-one (Compound 16)

1. 5-Benzyloxymethyl-6-hydroxy-2,3,4-trihydronaphthalen-1-one

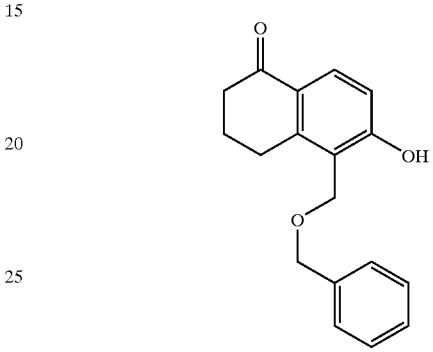

To benzyl alcohol (100 mL) is added 5-chloromethyl-6-hydroxy-2,3,4-trihydronaphthalen-1-one (*Chem. Pharm. Bull.* 1977;25(11):2988–3002) (1.0 g, 4.75 mmol). After slightly warming the suspension, a solution occurs. To the mixture is added triethylamine (0.48 g, 4.75 mmol) followed by heating to 80° C. for 3 hours. The excess benzyl alcohol is distilled from the mixture under 2 mm Hg vacuum until the distillate temperature reaches 65° C. The residue is taken up in a mixture of ethyl ether and washed repeatedly with water. The product is extracted into water by adjusting the pH to 12.5 by addition of 2N NaOH. The aqueous extract is washed with ethyl ether, layered with ether and acidified by addition of 1N HCl. The organic phase is separated, washed with brine, dried over anhydrous magnesium sulfate and filtered. The filtrate is concentrated in vacuo giving a solid that is filtered and dried in vacuo (1.12 g, 83% yield). NMR spectrum is consistent with structure. MS: APCI: M+1: 282.3 (M: 283.1).

2. 6-((1S)-2-Imidazolyl-1-phenylethoxy)-5-[(phenylmethoxy)methyl]-2,3,4-trihydronaphthalen-1-one (R)-2-Imidazol-1-yl-1-phenyl-ethanol (0.733 g, 3.89 mmol), triphenyl-phosphine (1.39 g, 5.31 mmol), and 5-benzyloxymethyl-6-hydroxy-2,3,4-trihydronaphthalen-1-one (1.0 g, 3.54 mmol) are suspended in dry tetrahydrofuran (75 mL). To the suspension is added a solution of diethyl azodicarboxylate (0.925 g, 5.31 mmol) in tetrahydrofuran (20 mL) over 20 minutes at 25° C. After stirring for 18 hours at 25° C., the mixture is evaporated to an oil in vacuo. To the residue is added ethyl ether and 1N citric acid. The ether phase is decanted from the mixture, and the citric acid phase is washed exhaustively with ethyl ether. The citric acid phase is layered with ethyl ether and the pH of the citric acid phase is adjusted to 13 with 2N NaOH. The product is extracted into a mixture of ethyl ether and chloroform, washed with brine, dried over anhydrous magnesium sulfate, and filtered. The filtrate is concentrated in vacuo and is purified by chromatography on 300 g silica gel eluted with chloroform. The product is further purified by reverse phase chromatography, eluted with a mixture of acetonitrile, water, and 0.1% trifluoroacetic acid. The product is obtained as a solid (Compound 16) (280 mg, 18% yield). MS: APCI: M+1: 452.6 (M: 453.3). NMR spectrum is consistent with structure.

Calcd. for C$_{29}$H$_{28}$N$_2$O$_3$, 1.25 TFA, 0.25H$_2$O:

| Theory: | C 63.10, | H 5.00, | N 4.67, | F 11.88, | H$_2$O, 0.75. |
|---|---|---|---|---|---|
| Found: | C 62.94, | H 5.12, | N 4.57, | F 11.49, | H$_2$O, 0.62. |

EXAMPLE 17

Synthesis of 6-((1S)-2-Imidazolyl-1-phenylethoxy)-5-(cyclopentyloxymethyl)-2,3,4-trihydronaphthalen-1-one (Compound 17)

1. 5-Cyclopentyloxymethyl-6-hydroxy-2,3,4-trihydronaphthalen-1-one

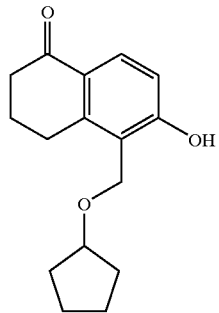

To cyclopentyl alcohol (30 mL) is added 5-chloromethyl-6-hydroxy-2,3,4-trihydronaphthalen-1-one (*Chem. Pharm. Bull.* 1977;25(11):2988–3002) (1.0 g, 4.75 mmol). To the mixture is added triethylamine (3.5 mL, 23.7 mmol) followed by stirring for 3 hours at 25° C. The excess cyclopentyl alcohol is distilled from the mixture under 2 mm Hg vacuum until the pot temperature reached 110° C. The residue is taken up in a mixture of ethyl acetate and ethyl ether and then washed with 1N citric acid, water, and brine. The organic phase is separated, dried over anhydrous magnesium sulfate, and filtered. The filtrate is concentrated in vacuo giving an oil which is purified by silica gel chromatography, eluted with a gradient of ethyl acetate/hexane (5:95) to (20:80). The product is recovered as a solid from hexane, dried in vacuo (2.19 g, 28% yield). NMR spectrum is consistent with structure. MS: APCI: M+1: 260.3 (M: 261.1).

2. 6-((1S)-2-Imidazolyl-1-phenylethoxy)-5-(cyclopentyloxymethyl)-2,3,4-trihydronaphthalen-1-one (R)-2-Imidazol-1-yl-1-phenyl-ethanol (1.82 g, 9.67 mmol), triphenyl-phosphine (3.11 g, 11.9 mmol), and 5-cyclopentyloxymethyl-6-hydroxy-2,3,4-trihydronaphthalen-1-one (2.06 g, 8.79 mmol) are suspended in dry tetrahydrofuran (40 mL). To the suspension is added a solution of diethyl azodicarboxylate (2.07 g, 11.9 mmol) in tetrahydrofuran (20 mL) over 15 minutes at 25° C. After stirring for 3 hours at 25° C., the mixture is evaporated to an oil in vacuo. To the residue is added ethyl ether and 1N citric acid, resulting in a precipitate. The ether phase is decanted from the mixture, and the mixed precipitate and citric acid phases are washed exhaustively with ethyl ether giving solution of the precipitates gum. The citric acid phase is layered with ethyl ether, and the pH of the citric acid phase is adjusted to 5 with 6N NaOH. The product is extracted into a mixture of ethyl ether and ethyl acetete, washed with brine, dried over anhydrous magnesium sulfate, and filtered. The filtrate is concentrated in vacuo and is purified by chromatography on 200 g silica gel eluted with chloroform. The product (Compound 17) is obtained as a solid (2.39 g, 63% yield). MS: APCI: M+1: 430.6 (M: 431.2). NMR spectrum is consistent with structure.

Calcd. for C$_{27}$H$_{30}$N$_2$O$_3$, 0.075 CHCl$_3$:

| Theory: | C 73.99, | H 6.89, | N 6.37, | Cl 1.81. |
|---|---|---|---|---|
| Found: | C 73.85, | H 6.98, | N 6.84, | Cl 1.11. |

EXAMPLE 18

Synthesis of 6-((1S)-2-imidazolyl-1-phenylethoxy)-5-(prop-2-enyloxymethyl)-2,3,4-trihydronaphthalen-1-one (Compound 18)

1. 5-(Prop-2-enyloxymethyl)-6-hydroxy-2,3,4-trihydronaphthalen-1-one

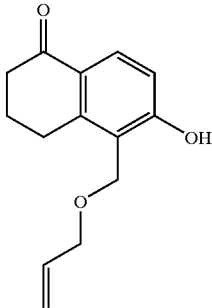

To allyl alcohol (50 mL) is added 5-chloromethyl-6-hydroxy-2,3,4-trihydronaphthalen-1-one (*Chem. Pharm. Bull.* 1977;25(11):2988–3002) (5.0 g, 23.7 mmol). To the mixture is added diisopropylamine (5.6 mL, 32 mmol) followed by stirring for 4 hours at 70° C., then 25° C. for 18 hours. The excess allyl alcohol is evaporated from the mixture under vacuum. The residue is taken up in a mixture of ethyl ether and 1N citric acid. The organic phase is washed with 1N citric acid, water, and brine. The organic phase is then separated, dried over anhydrous magnesium sulfate, and filtered. The filtrate is concentrated in vacuo giving an oil which is purified by silica gel chromatography, eluted with ethyl acetate/hexane (25:75). The product is recovered as a solid from hexane, dried in vacuo (2.19 g, 28% yield). NMR spectrum is consistent with structure. MS: APCI: M+1: 233.1 (M: 232.3).

2. 6-((1S)-2-Imidazolyl-1-phenylethoxy)-5-(prop-2-enyloxymethyl)-2,3,4-trihydronaphthalen-1-one (R)-2-Imidazol-1-yl-1-phenyl-ethanol (2.64 g, 17.7 mmol), triphenyl-phosphine (4.65 g, 17.7 mmol), and 5-(prop-2-enyloxymethyl)-6-hydroxy-2,3,4-trihydronaphthalen-1-one (2.94 g, 12.6 mmol) are suspended in dry tetrahydrofuran (25 mL). To the suspension is added a solution of diethyl azodicarboxylate (2.97 g, 17.1 mmol) in tetrahydrofuran (10 mL) over 25 minutes at 10° C. After stirring for 3 hours at 25° C., the mixture is evaporated to an oil in vacuo. The residue is added to ethyl ether and 1N citric acid, resulting in a precipitate. The ether phase is decanted from the mixture, and the mixed precipitate and citric acid phases are washed exhaustively with ethyl ether. The citric acid phase is layered with ethyl ether, and the pH of the citric acid phase is adjusted to 5.5 with 6N NaOH. The product is extracted into ethyl ether, washed with 1N NaOH and brine, dried over anhydrous magnesium sulfate, and filtered. The filtrate is concentrated in vacuo and is purified by chromatography on 150 g silica gel eluted with chloroform. The product (Compound 18) is obtained as a solid (4.07 g, 80% yield). MS: APCI: M+1: 403.1 (M: 402.5). NMR spectrum is consistent with structure.

Calcd. for $C_{25}H_{26}N_2O_3$, 0.2 $CHCl_3$:

| Theory: | C 70.90, | H 6.28, | N 6.55, | Cl 4.98. |
|---|---|---|---|---|
| Found: | C 71.05, | H 6.26, | N 6.47, | Cl 5.29. |

EXAMPLE 19

Synthesis of 6-((1S)-2-Imidazolyl-1-phenylethoxy)-5-[(2-methoxyethoxy)-methyl]-2,3,4-trihydronaphthalen-1-one (Compound 19)

1. 6-Hydroxy-5-(2-methoxyethoxymethyl)-2,3,4-trihydronaphthalen-1-one

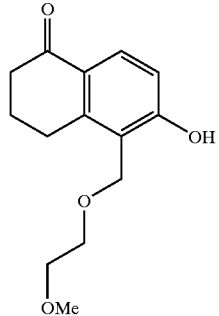

To 2-methoxyethanol (50 mL) is added 5-chloromethyl-6-hydroxy-2,3,4-trihydronaphthalen-1-one (*Chem. Pharm. Bull.* 1977;25(11):2988–3002) (5.0 g, 23.7 mmol). To the mixture is added diisopropylamine (4.42 mL, 25.3 mmol) followed by stirring for 4 hours at 70° C. The excess 2-methoxyethanol is evaporated from the mixture under vacuum. The residue is taken up in a mixture of ethyl ether and water. The organic phase is separated, washed with brine, dried over anhydrous magnesium sulfate, and filtered. The filtrate is concentrated in vacuo giving a solid that is purified by silica gel chromatography, eluted with ethyl acetate/hexane (25:75). The product is recovered as a solid from hexane, dried in vacuo (3.10 g, 52% yield). NMR spectrum is consistent with structure. MS: APCI: M+1: 251.1 (M: 250.3).

2. 6-((1S)-2-Imidazolyl-1-phenylethoxy)-5-[(2-methoxyethoxy)methyl]-2,3,4-trihydronaphthalen-1-one (R)-2-Imidazol-1-yl-1-phenyl-ethanol (2.56 g, 13.6 mmol), triphenyl-phosphine (4.88 g, 18.6 mmol), and 6-hydroxy-5-(2-methoxyethoxymethyl)-2,3,4-trihydronaphthalen-1-one (3.10 g, 12.4 mmol) are suspended in dry tetrahydrofuran (25 mL). To the suspension is added a solution of diethyl azodicarboxylate (3.24 g, 18.6 mmol) in tetrahydrofuran (50 mL) over 45 minutes at 25° C. After stirring for 18 hours at 25° C., the mixture is evaporated to an oil in vacuo. The residue is added to ethyl ether and 1N citric acid, resulting in a precipitate. The ether phase is decanted from the mixture, and the mixed precipitate and citric acid phases are washed exhaustively with ethyl ether. The citric acid phase is layered with ethyl ether, and the pH of the citric acid phase is adjusted to 13 with 6N NaOH. The product is extracted into a mixture of ethyl acetate and ethyl ether, washed with brine, dried over anhydrous magnesium sulfate, and filtered. The filtrate is concentrated in vacuo and is purified by chromatography on 200 g silica gel eluted with chloroform. The product (Compound 19) is obtained as a solid (1.88 g, 36% yield). MS: APCI: M+1: 421.4 (M: 420.5). NMR spectrum is consistent with structure.

Calcd. for $C_{25}H_{28}N_2O_4$, 0.23 $CHCl_3$, 0.275$H_2O$:

| Theory: | C 66.91, | H 6.28, | N 6.19, | Cl 5.40, | $H_2O$, 1.09. |
|---|---|---|---|---|---|
| Found: | C 67.05, | H 6.35, | N 6.13, | Cl 5.68, | $H_2O$, 1.07. |

EXAMPLE 19a

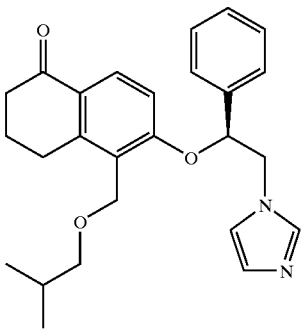

Synthesis of 6-((S)-2-Imidazol-1-yl-1-phenylethoxy)-5-isobutoxymethyl-1-3,4-dihydro-2H-naphthalen-1-one (Compound 19a)

1. Synthesis of 6-Hydroxy-5-isobutoxymethyl-3,4-dihydro-2H-naphthalen-1-one

To a solution of 5-Chloromethyl-6-hydroxy-3,4-dihydro-2H-naphthalen-1-one, prepared as described Chem. Pharm. Bull. 25(11)2988–3002(1077), (0.211 g, 0.001 mol) and triethylamine (0.167 ml, 0.0012 mol, Mallinckrodt) contained in a 16×125 mm screw top glass tube, was added isobutyl alcohol (3 ml, Aldrich Chemical). The tube was capped with a teflon lined cap and placed on an orbital mixing heat block at reflux temperature (~108° C.) for 16 hrs. The reaction mixture was concentrated in vacuo to a pink-red syrup. On addition of ethyl ether, a pinkish solid precipitated from the syrup. Washed mixture with 5% citric acid, brine, and dried organic phase over anhydrous sodium sulfate. Evaporated mixture in vacuo to yield a red-pink powder, 0.210 g, 85% crude yield. Low resolution mass spectroscopy (APCI) 249 [M+H]$^+$.

2. 6-((S)-2-Imidazol-1-yl-1-phenyl-ethoxy)-5-isobutoxymethyl-3,4-dihydro-2H-naphthalen-1-one To a solution of 6-Hydroxy-5-isobutoxymethyl-3,4-dihydro-2H-naphthalen-1-one (0.21 g, 0.85 mmol and freshly distilled tetrahydrofuran in an Ar(g) purged flask, was added triphenylphosphine resin (0.823 g, loading 1.24 mmol/g, Argonaut Technologies) and (R)-2-Imidazol-1-yl-1-phenyl-ethanol (0.16 g, 0.85 mmol). To this stirring mixture was added a solution of diethyl diazodicarboxylate (0.161 g, 1.02 mmol, Aldrich Chemical) in THF (1 ml). After stirring for 16 hrs. at 25° C. the resin was removed by filtration and the mixture concentrated in vacuo to yield a yellow oil. The oil was dissolved in methanol (10 ml) and Macroporous polystyrene sulfonic acid resin (1.13 g, loading 1.5 mmol/g, Argonaut Technologies) added. After stirring for 2 hrs. at 25° C., the resin was collected by gravity filtration, washed with methanol (2×5 ml). Elution of product from the resin with 2.0 M ammonia in methanol (5 ml, Aldrich) and concentration in vacuo yielded 120 mg yellow glass-like compound. High resolution mass spectroscopy m/z (APCI) 419 [M+H]$^+$.

EXAMPLE 19b

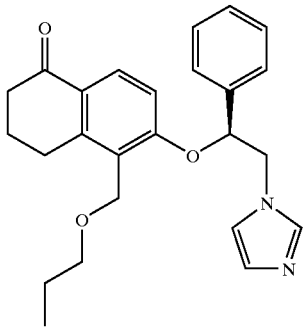

Synthesis of 6-((S)-2-Imidazol-1-yl-1-phenyl-ethoxy)-5-propoxymethyl-3,4-dihydro-2H-naphthalen-1-one (Compound 19b)

1. Synthesis of 6-Hydroxy-5-propoxymethyl-3,4-dihydro-2H-naphthalen-1-one.

According to step 1 in the method of example 19a, 5-Chloromethyl-6-hydroxy-3,4-dihydro-2H-naphthalen-1-one (0.211 g, 1.0 mmol) was combined with triethylamine (0.167 ml, 1.2 mmol) in propan-1-ol (3.0 ml, Aldrich Chemical) to produce 123 mg of desired product as yellow crystals. Low resolution mass spectrum (APCI) m/z 235 [M+H]+.

2. 6-((S)-2-Imidazol-1-yl-1-phenyl-ethoxy)-5-propoxymethyl-3,4-dihydro-2H-naphthalen-1-one According to step 2 in the method of example 19a, 6-Hydroxy-5-propoxymethyl-3,4-dihydro-2H-naphthalen-1-one (0.123 g, 0.53 mmol), (R)-2-Imidazol-1-yl-1-phenyl-ethanol (0.131 g, 0.7 mmol), triphenylphosphine resin (0.620 g, loading 1.24 mmol/g, Argonaut Technologies), diethyl diazodicarboxylate (0.121 ml, 0.77 mmol, Aldrich Chemical) and freshly distilled tetrahydrofuran (5 ml, Aldrich Chemical) were combined in a 2 dram screw topped vial with a teflon lined cap. After mixing on an inverting mixer at 25° C. for 16 hrs., the resin was removed by gravity filtration and mixture concentrated in vacuo to a yellow-brown syrup. The residue was dissolved in methanol (5 ml) and macroporous polystyrene sulfonic acid resin (0.583 g, loading 1.5 mmol/g, Argonaut Technologies) added. After mixing for 2 hrs. at 25° C., the resin was collected by gravity filtration, washed with methanol (2×5 ml). Elution of product from the resin with 2.0 M ammonia in methanol (5 ml, Aldrich) and concentration in vacuo yielded 158 mg yellow glass compound. Low resolution mass spectroscopy m/z (APCI) 405 [M+H]+.

EXAMPLE 19c

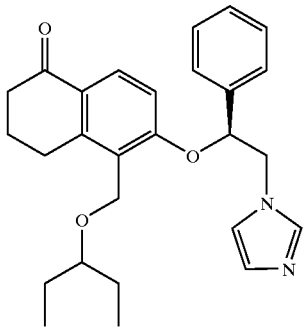

Synthesis of 5-(1-Ethyl-propoxymethyl)-6-((S)-2-imidazol-1-yl-1-phenyl-ethoxy)-3,4-dihydro-2H-naphthalen-1-one (Compound 19c)

1. Synthesis of 5-(1-Ethyl-propoxymethyl)-6-hydroxy-3,4-dihydro-2H-naphthalen-1-one.

According to step (a) in the method of example 19a, 5-Chloromethyl-6-hydroxy-3,4-dihydro-2H-naphthalen-1-one (0.211 g, 1.0 mmol) was combined with triethylamine (0.167 ml, 1.2 mmol) in pentan-3-ol (3 ml, Aldrich Chemical) to produce 248 mg of desired product as an orange-red oil. Low resolution mass spectrum (APCI) m/z 263 [M+H]+.

2. 5-(1-Ethyl-propoxymethyl)-6-((S)-2-imidazol-1-yl-1-phenyl-ethoxy)-3,4-dihydro-2H-naphthalen-1-one According to step 2 in the method of example 19, 5-(1-Ethyl-propoxymethyl)-6-hydroxy-3,4-dihydro-2H-naphthalen-1-one (0.123 g, 0.53 mmol), (R)-2-Imidazol-1-yl-1-phenyl-ethanol (0.131 g, 0.7 mmol), triphenylphosphine resin (0.620 g, loading 1.24 mmol/g, Argonaut Technologies), diethyl diazodicarboxylate (0.121 ml, 0.77 mmol, Aldrich Chemical) and freshly distilled tetrahydrofuran (5 ml, Aldrich Chemical) were combined in a 2 dram screw topped vial with a teflon lined cap. After mixing on an inverting mixer at 25° C. for 16 hrs., the resin was removed by gravity filtration and mixture concentrated in vacuo to a yellow-brown syrup. The residue was dissolved in methanol (5 ml) and macroporous polystyrene sulfonic acid resin (0.583 g, loading 1.5 mmol/g, Argonaut Technologies) added. After mixing for 2 hrs. at 25° C., the resin was collected by gravity filtration, washed with methanol (2×5 ml). Elution of product from the resin with 2.0 M ammonia in methanol (5 ml, Aldrich) and concentration in vacuo yielded 139 mg brown glass compound. Low resolution mass spectroscopy m/z (APCI) 433 [M+H]+.

EXAMPLE 19d

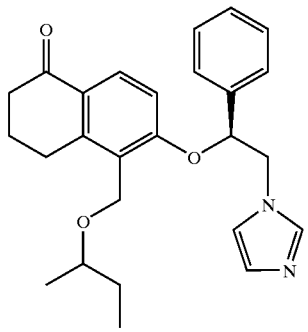

Synthesis of (±)5-sec-Butoxymethyl-6-((S)-2-imidazol-1-yl-1-phenyl-ethoxy)-3,4-dihydro-2H-naphthalen-1-one (Compound 19d)

1. (±)5-sec-Butoxymethyl-6-hydroxy-3,4-dihydro-2H-naphthalen-1-one.

According to step (a) in the method of example A, 5-Chloromethyl-6-hydroxy-3,4-dihydro-2H-naphthalen-1-one (0.211 g, 1.0 mmol) was combined with triethylamine (0.167 ml, 1.2 mmol) in (±)butan-2-ol (3 ml, Aldrich Chemical) to produce 159 mg of desired product as an orange oil. Low resolution mass spectrum (APCI) m/z 249 [M+H]+.

2. (±)5-sec-Butoxymethyl-6-((S)-2-imidazol-1-yl-1-phenyl-ethoxy)-3,4-dihydro-2H-naphthalen-1-one According to step (b) in the method of example A, (±)5-sec-Butoxymethyl-6-hydroxy-3,4-dihydro-2H-naphthalen-1-one (0.159 g, 0.64 mmol), (R)-2-Imidazol-1-yl-1-phenyl-ethanol (0.131 g, 0.7 mmol), triphenylphosphine resin (0.620 g, loading 1.24 mmol/g, Argonaut Technologies), diethyl diazodicarboxylate (0.121 ml, 0.77 mmol, Aldrich Chemical) and freshly distilled tetrahydrofuran (5 ml, Aldrich Chemical) were combined in a 2 dram screw topped vial with a teflon lined cap. After mixing on an inverting mixer at 25° C. for 16 hrs., the resin was removed by gravity filtration and mixture concentrated in vacuo to a yellow-brown syrup. The residue was dissolved in methanol (5 ml) and macroporous polystyrene sulfonic acid resin (0.583 g, loading 1.5 mmol/g, Argonaut Technologies) added. After mixing for 2 hrs. at 25° C., the resin was collected by gravity filtration, washed with methanol (2×5 ml). Elution of product from the resin with 2.0 M ammonia in methanol (5 ml, Aldrich) and concentration in vacuo yielded 139 mg dark brown glass compound. Low resolution mass spectroscopy m/z (APCI) 419 [M+H]+.

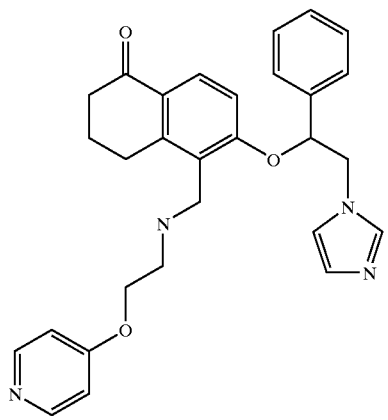

6-(2-Imidazol-1-yl-1-phenyl-ethoxy)-5-{[2-(pyridin-4-yloxy)-ethylamino]-methyl}-3,4-dihydro-2H-naphthalen-1-one 2-(Pyridin-4-yloxy)-ethylamine (1.0 mL, 0.4 mmol, 0.4 M in α,α,α-trifluorotoluene) and 6-((1S)-2-imidazoyl-1-phenylethoxy)-5-(bromomethyl)-2,3,4-trihydronapthalen-1-one (Example 65, step 1)(100 mg, 0.198 mmol) were sealed in a 16×120 mm screw capped tube and heated to 50° C. (45 min). Reaction mixture was cooled to rt and partitioned between 2N sodium hydroxide and ethyl acetate. The organic layer was separated, washed (brine), dried (Na₂SO₄), and concentrated in vacuo. The residue was purified by flash silica gel chromatography (ethyl acetate/triethylamine/methanol, 17:2:1) to give 31 mg (32%) of the desired product as a colorless glass: (LC-MS, APCI) m/z 483 [M+H]+.

EXAMPLE 20

Synthesis of 6-((1S)-2-Imidazolyl-1-phenylethoxy)-5-(2-phenylethyl)-2,3,4-trihydronaphthalen-1-one (Compound 20)

1. 6-Methoxy-5-phenylethynyl-2,3,4-trihydronapthalen-1-one

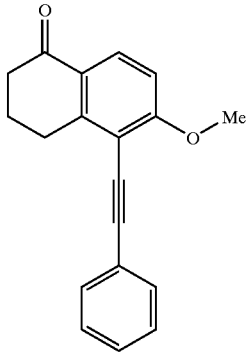

5-Bromo-6-methoxy-2,3,4-trihydronapthalen-1-one (10.7 g, 0.04 mol) (Z. Chem. 1970;10:70) and phenylacetylene (8.2 g, 0.08 mol) are added to a mixture of dimethylformamide (80 mL) and triethylamine (40 mL). The mixture is sparged with nitrogen gas, and copper iodide (228 mg) is added. Dichlorobis-(triphenyl-phosphine)palladium (II) (1.12 g) and butylated hydroxytoluene (0.08 g) are added, and the resulting reaction mixture is heated to 108° C. for 2 hours. Another portion of phenylacetylene (16 g, 0.16 mol) is slowly added over 3 hours followed by heating to 108° C. for 18 hours. The mixture is then evaporated in vacuo, and the residue is taken up into ethyl ether. Insoluble material is decanted. The organic phase is washed with 1N citric acid and then brine, dried over anhydrous magnesium sulfate, filtered and evaporated in vacuo to a crude solid (32 g). The material is purified by chromatography on 400 g silica gel, eluted with a mixture of ethyl acetate/hexane (10:90). The product is obtained as a solid (5.89 g, 53% yield). NMR spectrum is consistent with structure. MS: APCI: M+1, 277.2 (M: 276.34).

2. 6-Methoxy-5-phenethyl-2,3,4-trihydronapthalen-1-one

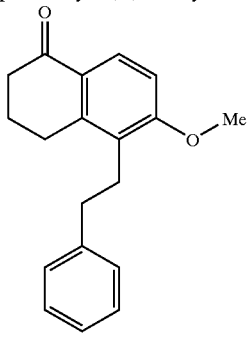

6-Methoxy-5-phenylethynyl-2,3,4-trihydronapthalen-1-one (5.69 g, 0.021 mol) and 5% palladium on barium sulfate (1.0 g) are added to tetrahydrofuran (100 mL) followed by pressurization to 49 psi with hydrogen gas. At regular intervals, 3 additional 1 g portions of 5% palladium on barium sulfate are added over 36 hours during additional treatment with hydrogen gas at 49 psi. The mixture is then filtered and evaporated in vacuo to a solid (5.68 g, 98% yield). NMR spectrum is consistent with structure. MS: APCI: M+1, 281.2 (M: 280.37).

3. 6-Hydroxy-5-phenethyl-2,3,4-trihydronapthalen-1-one

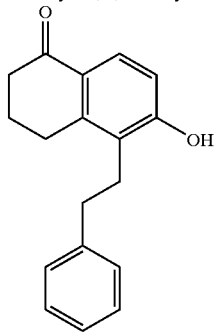

6-Methoxy-5-phenethyl-2,3,4-trihydronapthalen-1-one (5.39 g, 0.192 mol) and sodium cyanide (4.71 g, 0.096 mol) are added to dimethylsulfoxide (30 mL) and heated to 180° C. for 18 hours. The mixture is poured, while hot, into water (200 mL), washed with ethyl ether, and acidified to pH 1 with conc. HCl. The mixture is extracted with ethyl ether, washed with brine, dried over anhydrous magnesium sulfate, and filtered. The filtrate is concentrated in vacuo, giving a solid (2.87 g, 56% yield). NMR spectrum is consistent with structure. MS: APCI: M+1, 267.1 (M: 266.3).

4. 6-((1S)-2-Imidazolyl-1-phenylethoxy)-5-(2-phenylethyl)-2,3,4-trihydronaphthalen-1-one To tetrahydrofuran (50 mL) is added 6-hydroxy-5-phenethyl-2,3,4-trihydronapthalen-1-one (2.67 g, 10 mmol), (R)-2-imidazol-1-yl-1-phenyl-ethanol (2.15 g, 11.4 mmol), and triphenylphosphine (3.94 g, 15 mmol). A solution of diethylazodicarboxylate (2.61 g, 15 mmol) in tetrahydrofuran (25 ML) is added over 1 hour with cooling to 5° C. After stirring for 18 hours at 25° C., the mixture is evaporated in vacuo, and the residue is suspended in ethyl ether and 1N citric acid, washed exhaustively with ethyl ether and the pH adjusted to 14 with 6N NaOH. The aqueous phase is extracted with ethyl ether, which is subsequently separated, washed with brine, dried over anhydrous magnesium sulfate and filtered. The filtrate is evaporated to a solid (Compound 20) that is purified by recrystallization and obtained as a solid (2.22 g, 51% yield). NMR spectrum is consistent with structure. MS: APCI: M+1, 437.3 (M: 436.6).

Calcd. for $C_{25}H_{28}N_2O_2$, 0.1 $CHCl_3$, 0.25$H_2O$:

| Theory: | C 79.79, | H 6.46, | N 6.36. |
|---|---|---|---|
| Found: | C 79.47, | H 6.52, | N 6.42. |

EXAMPLE 21

Synthesis of 5-(2H-Benzo[d]-1,3-dioxolan-5-yl)-6-((1S)-2-imidazolyl-1-phenylethoxy)-2,3,4-trihydronaphthalen-1-one (Compound 21)

1. 5-(2H-Benzo[d]1,3-dioxolan-5-yl)-6-methoxy-2,3,4-trihydronaphthalen-1-one

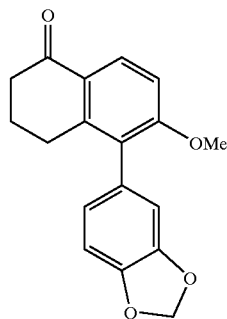

Under nitrogen, a suspension of 0.35 g (0.3 mmol) of tetrakis(triphenyl-phosphine)palladium (0) in 25 mL dimethoxyethane is treated with 2.55 g (10 mmol), of 5-bromo-6-methoxy-2,3,4-trihydronapthalen-1-one [Example 20, step 1] and stirred at room temperature for 10 minutes. To this is added a solution of 2.5 g (15 mmol) of 3,4-methylenedioxyphenylboronic acid, and the mixture is heated at reflux overnight. The reaction is then diluted with EtOAc and filtered through Celite. The filtrate is washed with sat. NaHCO₃ and sat. NaCl. Drying over MgSO₄ and removal of the solvent under reduced pressure gives the crude product. Chromatography on silica gel, eluting with $CH_2Cl_2$ gives 2.88 g (97.3% yield) of the product as a white foam. The structure is confirmed by NMR and mass spectroscopy.

2. 5-(2H-Benzo[d]1,3-dioxolan-5-yl)-6-hydroxy-2,3,4-trihydronaphthalen-1-one

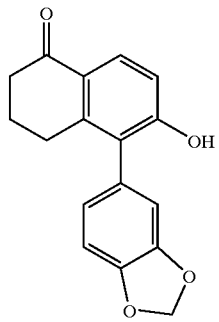

A solution of 2.88 g (9.7 mmol) of the methoxy compound [Example 21; step 1] in 15 mL DMSO is treated with 2.4 g (4.8.6 mmol) of crushed NaCN and heated at 180° C. overnight. The mixture is poured into $H_2O$, acidified with dil. HCl and extracted twice with EtOAc. The EtOAc is washed with sat. NaCl, dried over $MgSO_4$, and the solvent removed under reduced pressure giving the crude product. This is taken up in $Et_2O$ containing a small amount of acetone and washed twice with 5% NaOH. The NaOH solution is back washed with $Et_2O$ and acidified with dil. HCl. The product is extracted into EtOAc and the EtOAc washed with sat. NaCl. Drying over $MgSO_4$ and removal of the solvent under reduced pressure leaves 2.59 g of a dark oil. This is taken up in $CHCl_3$/MeOH (98:2) and passed through a plug of silica gel. Removal of the solvent under reduced pressure leaves 1.94 g (70.8% yield) of the crude product, which is used directly in the next reaction.

3. 5-(2H-Benzo [d]1,3-dioxolan-5-yl)-6-((1S)-2-imidazolyl-1-phenylethoxy)-2,3,4-trihydronaphthalen-1-one Under nitrogen, a solution of 1.94 g (6.9 mmol) of the phenol [Example 21; step 2] in 35 mL THF is treated with 1.42 g (7.6 mmol) of (R)-1-phenyl-2-(1-imidazoyl)ethanol and 2.16 g (8.2 mmol) of triphenylphosphine. This is treated dropwise over 20 minutes with a solution of 1.3 mL (8.2 mmol) of diethyl azodicarboxylate in 10 mL THF. After stirring at room temperature for 4 days, the mixture is diluted with EtOAc, washed twice with $H_2O$, and then sat. NaHCO₃ followed by sat. NaCl. Drying over $MgSO_4$ and removal of the solvent under pressure gives the crude product. Chromatography on silica gel, eluting with $CH_2Cl_2$/acetone (80:20) gives 1.55 g (50% yield) of the product (Compound 21) as light tan foam. The structure is confirmed by NMR.

Calcd for $C_{28}H_{24}N_2O_4 \cdot 0.2CH_2Cl_2$ (MW 469.77):

| Theory: | C, 72.14 | H, 5.24 | N, 5.97. |
|---|---|---|---|
| Found: | C, 71.94 | H, 5.45 | N, 6.17. |

EXAMPLE 22

Synthesis of 6-((1S)-2-Imidazolyl-1-phenylethoxy)-5-(3-chlorophenyl)-2,3,4-trihydronaphthalen-1-one (Compound 22)

Following the procedure of Example 21, steps 1–3 but using 2.4 g (15 mmol) of 3-chlorophenylboronic acid, the crude product is obtained. Two chromatographies on silica gel, eluting with $CH_2Cl_2$/acetone (80:20) gives 0.95 g of the title product (Compound 22) as a cream foam. The structure is confirmed by NMR and mass spectroscopy.

Calcd for $C_{27}H_{23}N_2O_2Cl \cdot 0.1 CH_2Cl_2$ (MW 451.42):

| Theory: | C, 72.10 | H, 5.18 | N, 6.21. |
|---|---|---|---|
| Found: | C, 72.15 | H, 5.04 | N, 6.11. |

EXAMPLE 23

Synthesis of 6-((1S)-2-Imidazolyl-1-phenylethoxy)-5-(2-naphthyl)-2,3,4-trihydronaphthalen-1-one (Compound 23)

1. 6-Methoxy-5-(2-naphthyl)-2,3,4-trihydronaphthalen-1-one

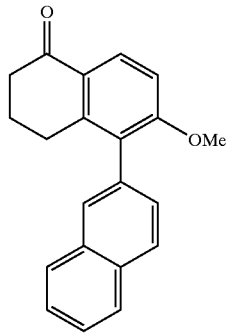

5-Bromo-6-methoxy-2,3,4-trihydronapthalen-1-one (6.1 g, 0.024 mol) and palladium tetrakis(triphenylphosphine) (0.7 g, 0.06 mmol) is added to dimethoxyethane (40 mL). A suspension of 2-naphthylboronic acid (5.16 g, 0.03 mol) in absolute ethanol (20 mL) is added, followed by addition of a solution of potassium carbonate (5.52 g, 0.04 mol) in water (25 mL). The mixture is heated with vigorous stirring to 85° C. for 2.5 hours, followed by stirring at 25° C. for 18 hours. The mixture is poured into ethyl acetate, filtered, and washed with 0.5M NaOH, 1N citric acid, and brine. The organic phase is stripped to an oil. Addition of ethyl ether induces crystallization. A solid is obtained (4.31 g, 71% yield). NMR spectrum is consistent with structure. MS: APCI: M+1, 303.1 (M: 302.4).

2. 6-Hydroxy-5-(2-naphthyl)-2,3,4-trihydronaphthalen-1-one

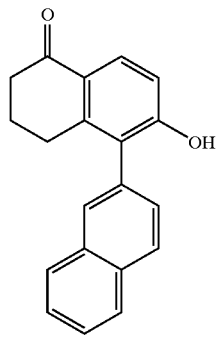

6-Methoxy-5-(2-naphthyl)-2,3,4-trihydronaphthalen-1-one (4.31 g, 0.143 mol) and sodium cyanide (3.5 g, 0.071 mol) are added to dimethylsulfoxide (25 mL) and heated to 180° C. for 18 hours. The mixture is poured while hot into water (200 mL) and acidified by addition of conc. HCl to give a solid precipitate. The mixture is filtered, and the damp solid is dissolved in ethyl acetate and washed with brine. The solution is filtered, dried over anhydrous magnesium sulfate, and evaporated to an oil. The material is purified by passing it through a short plug of silica gel as a dichloromethane solution, giving a crystalline solid by addition of ethyl ether (1.5 g, 36% yield). NMR spectrum is consistent with structure. MS: APCI: M+1, 289.1 (M: 288.4).

3. 6-((1S)-2-Imidazolyl-1-phenylethoxy)-5-(2-naphthyl)-2,3,4-trihydronaphthalen-1-one To tetrahydrofuran (25 mL) is added 6-hydroxy-5-(2-naphthyl)-2,3,4-trihydronaphthalen-1-one (1.74 g, 5.1 mmol), (R)-2-imidazol-1-yl-1-phenyl-ethanol (1.09 g, 5.8 mmol), and triphenylphosphine (2.01 g, 7.6 mmol). A solution of diethylazodicarboxylate (1.33 g, 7.6 mmol) in tetrahydrofuran (10 mL) is added over 30 minutes. After stirring for 3 hours at 25° C., the mixture is evaporated in vacuo and the residue is suspended in ethyl ether and 1N citric acid, washed exhaustively with ethyl ether, and the pH adjusted to 14 with 4N NaOH. The aqueous phase is extracted with ethyl ether which is separated, washed with brine, dried over anhydrous magnesium sulfate, and filtered. The filtrate is evaporated to a solid (Compound 23) that is purified by recrystallization and obtained as a solid (1.03 g, 44% yield). NMR spectrum is consistent with structure. MS: APCI: M+1, 459.1 (M: 458.6).

Calcd. for $C_{31}H_{26}N_2O_2$:

| Theory: | C 81.20, | H 5.72, | N 6.11. |
|---|---|---|---|
| Found: | C 80.35, | H 5.83, | N 6.06. |

EXAMPLE 24

Synthesis of 6-((1S)-2-Imidazolyl-1-phenylethoxy)-5-(2-(2-pyridyl)ethyl)-2,3,4-trihydronaphthalen-1-one (Compound 24)

1. 6-Methoxy-5-(2-pyridin-2-yl-ethenyl)-2,3,4-trihydronapthalen-1-one

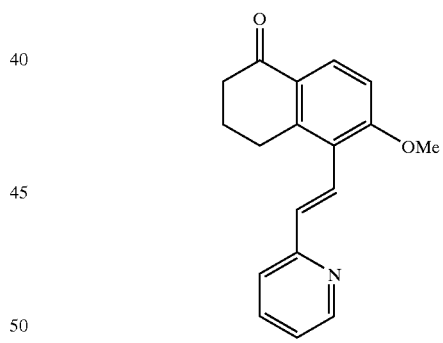

A Pyrex glass pressure tube is charged with 5-bromo-6-methoxy-2,3,4-trihydronapthalen-1-one (30 g, 0.12 mol), 2-vinylpyridine (38 mL, 0.35 mol), sodium acetate (19.7 g, 0.24 mol), N,N-dimethylglycine (7.22 g, 0.07 mol), methanol (300 mL), and bis(benzonitrile)dichloropalladium (II) (2.8 g, 0.007 mol). The tube is sealed and heated to 130° C. for 10 hours. After cooling, diethylether is added, and the reaction mixture is filtered through a bed of celite. The organic layer is washed with saturated sodium bicarbonate solution and then brine, dried over magnesium sulfate, and the solvent removed in vacuo. The black residue is chromatographed using 20% ethyl acetate/80% hexanes to 50% ethyl acetate/50% hexanes. A tan solid (4 g) is obtained, which is recrystallized using hexane/ethyl acetate as the solvent (3.6 g, 10.6% yield). MS: APCI 280.1 [M+1].

2. 6-Methoxy-5-(2-pyridin-2-yl-ethyl)-2,3,4-trihydronapthalen-1-one

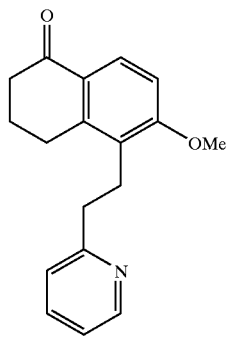

6-Methoxy-5-(2-pyridin-2-yl-ethenyl)-2,3,4-trihydronapthalen-1-one (3.6 g, 0.13 mol) in tetrahydrofuran (75 mL) is treated with 5% Pd/BaSO$_4$ (0.5 g) in a Parr shaker under a Hydrogen atmosphere of 50 psi. After 10 hours, there is no further uptake of hydrogen gas and the calculated ΔP=54.9#. The solvent is removed in vacuo. The residue is recrystallized using hexanes and ethyl acetate giving a light green solid (2.65 g, 73% yield). MS: APCI 282 [M+1].

3. 6-Hydroxy-5-(2-pyridin-2-yl-ethyl)-2,3,4-trihydronapthalen-1-one

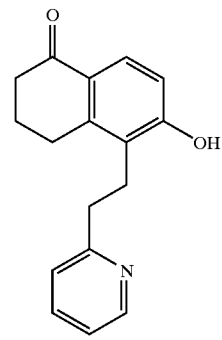

6-Methoxy-5-(2-pyridin-2-yl-ethyl)-2,3,4-trihydronapthalen-1-one (2.65 g, 0.0094 mol) is dissolved in DMSO (10 mL). Crushed sodium cyanide (2.31 g, 0.047 mol) is added, and the reaction is heated to 180° C. for 3 hours. The reaction mixture is poured into water and cooled in an ice-water bath. Using a pH meter, the aqueous solution is acidified with concentrated HCl to pH 5 and subsequently extracted with ethyl acetate (3×). The organic solution is washed with brine, dried over MgSO$_4$, and the solvent removed in vacuo. A green solid is obtained (2.9 g, 65% yield). MS: APCI 268.2 [M+1].

4. 6-((1S)-2-imidazolyl-1-phenylethoxy)-5-(2-(2-pyridyl)ethyl)-2,3,4-trihydronaphthalen-1-one 6-Hydroxy-5-(2-pyridin-2-yl-ethyl)-2,3,4-trihydronapthalen-1-one (2.75 g, 0.0103 mol), (R)-2-imidazol-1-yl-1-phenyl-ethanol (2.08 g, 0.012 mol), and triphenylphosphine (4.05 g, 0.015 mol) are dissolved in dry THF (50 mL) under a nitrogen atmosphere and cooled in an ice-water bath. DEAD reagent (2.36 mL, 0.015 mol) in dry THF (20 mL) is added over 0.5 hour. The reaction mixture is stirred for an additional 2 hours after the DEAD reagent is added. Solvent is removed in vacuo. The residue is partitioned between diethyl ether and 1N citric acid. The aqueous solution is washed with diethyl ether several times. Then, the aqueous solution is made basic using 50% sodium hydroxide solution and extracted with ethyl acetate (3×). The organic layer is washed with brine, dried over MgSO$_4$, and the solvent removed in vacuo. The residue is chromatographed using dichloromethane to 97% dichloromethane/3% methanol as eluent. A tan solid is obtained as the final product (Compound 24) (2.5 g, 56% yield) MS: APCI 438.1 [M+1].

Anal. Calcd. $C_{28}H_{27}N_3O_2 \cdot 0.16$ mol DCM, MWC= 451.14:

| | | | |
|---|---|---|---|
| Theory: | C 74.97, | H 6.10, | N 9.31. |
| Found: | C 74.97, | H 6.34, | N 9.06. |

EXAMPLE 25

Synthesis of 6-((1S)-2-Imidazolyl-1-phenylethoxy)-5-[2-(1-oxy(2-pyridyl))ethyl]-2,3,4-trihydronaphthalen-1-one (Compound 25)

Compound 24 (0.4 g, 0.0015 mol) is dissolved in dichloromethane (10 mL) and cooled in an ice-water bath under N$_2$ atmosphere. Meta-chloroperbenzoic acid (0.42 g, 0.0024 mol) is added and the reaction is warmed to room temperature and stirred for 2 hours. Solvent is removed in vacuo. Chromatography using DCM to DCM/MeOH 5% affords a white foam (Compound 25) (0.24 g, 56% yield); MS: APCI 454.2 [M+1].

Anal. Calcd. $C_{28}H_{27}N_3O_3 \cdot 0.0.56$ mol DCM, MWC= 501.47:

| | | | |
|---|---|---|---|
| Theory: | C 68.41, | H 5.66, | N 8.38. |
| Found: | C 68.78, | H 5.80, | N 7.96. |

EXAMPLE 26

Synthesis of 6-((1S)-2-Imidazolyl-1-phenylethoxy)-5-(2-(4-pyridyl)ethyl)-2,3,4-trihydronaphthalen-1-one (Compound 26)

The title compound (Compound 26) is obtained in a manner similar to Example 24, steps 1–4 using 4-vinylpyridine. MS: APCI 438.2 [M+1].

Anal. Calcd. $C_{28}H_{27}N_3O_2 \cdot 1.12H_2O/0.06$ DCM, MWC= 462.82:

| | | | |
|---|---|---|---|
| Theory: | C 72.82, | H 6.39, | N 9.08. |
| Found: | C 72.81, | H 6.38, | N 8.94. |

EXAMPLE 26a

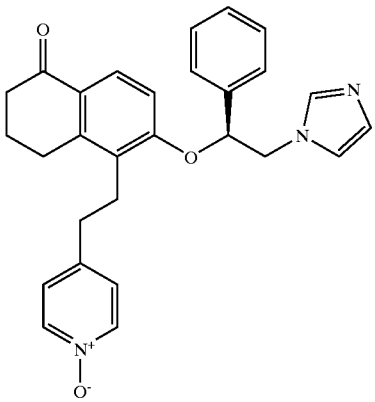

Synthesis of (S)-6-(-2-Imidazol-1-yl-1-phenylethoxy)-5-[2-(4-pyridyl-4-yl)ethyl]-3,4-dihydro-2H-naphthalen-1-one (Compound 26a)

The title compound was obtained in a manner similar to Example 25, using (S)-6-(-2-Imidazol-1-yl-1-phenylethoxy)-5-(2-pyridin-4-yl-ethyl)-3,4-dihydro-2H-naphthalen-1-one (Example 26). NMR (CDCl$_3$); MS APCI 454, [M+1]$^+$; anal. calcd. C$_{28}$H$_{27}$N$_3$O$_3$ 0.24 EtOAc/1.73H$_2$O MWC=505.90, C, 68.76%; H, 6.45%; N, 8.31%. found C, 68.81%; H, 6.48%; N, 8.30%.

EXAMPLE 26b

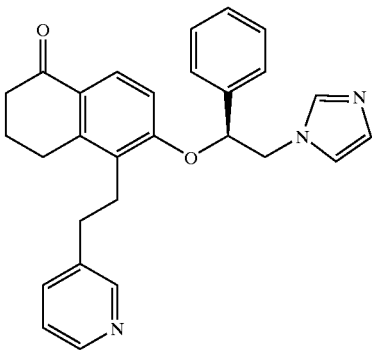

Synthesis of (S)-6-(-2-imidazol-1-yl-phenyl-ethoxy)-5-(2-pyridin-3-yl-ethyl)-3,4-dihydro-2H-naphthalen-1-one (Compound 26b)

The title compound was obtained in a manner similar to Example 24, 1–4 using 3-vinylpyridine (Chirex). Obtained a white solid (1.15 g, 91% yield). NMR MS APCI 438, [M+1]$^+$; HPLC RT=13.87 min. 100% pure, 254 nm; anal. calcd. for C$_{28}$H$_{27}$N$_3$O$_2$.2HCl/1.52H$_2$O, MWC=537.85, C, 62.53%; H, 6.00%; N, 7.81%. found C, 62.54%; H, 5.80%; N, 7.77%.

EXAMPLE 26c

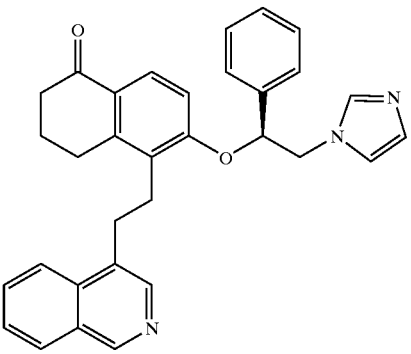

Synthesis of (S)-6-(-2-Imidazol-1-yl-1-phenyl-ethoxy)-5-(2-pyridin-2-3-yl-ethyl)-3,4-dihydro-2H-naphthalen-1-one (Compound 26c)

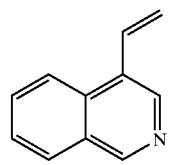

1. 4-vinylisoquinoline

4-Bromoisoquinoline (10 g, 0.048 mol), Pd(OAc)$_2$ (1.07 g, 0.0048 mol), (o-tol)$_3$P (2.95 g, 0.0096 mol), Et$_3$N (13.06 mL, 0.096 mol) and a saturated soln. of ethylene in MeCN (100 mL) were placed in a seal reaction apparatus and heated to 100° C. for 2 days. Solvent was removed in vacuo and EtOAc was added. Washed the organic layer with H$_2$O (2x), sat. NaHCO$_3$ (2x), and brine. The organic solution was dried over MgSO$_4$ and the solvent was removed in vacuo. A brown oil (7.0 g) was obtained and chromatographed using SiO$_2$, DCM/1% MeOH to DCM/2%MeOH giving a yellow oil (5.57 g, 75% yield). MS APCI (156), [M+H]$^+$; anal. calcd. for C$_{11}$H$_9$N$_1$.0.07H$_2$O, MWC=156.46, C, 84.44%; H, 5.89%; N, 8.95%. found C, 84.48%; H, 5.84%; N, 8.66%.

2. (S)-6-(-2-Imidazol-1-yl-1-phenyl-ethoxy)-5-(2-isoquinolin-4-yl-ethyl)-3,4-dihydro-2H-naphthalen-1-one The title compound was obtained in a manner similar to Example 24, 1–4 using 4-vinylisoquinoline. Obtained a brown solid (0.15 g, 89% yield). MS APCI 488 [M+H]$^+$; anal. calcd. C$_{32}$H$_{29}$N$_3$O$_2$.2.57 HCl/2.39H$_2$O MWC=624.4, C, 61.56%; H, 5.87%; N, 6.73%. found C, 61.16%; H, 5.90%; N, 7.97%.

EXAMPLE 27

Synthesis of Methyl 4-(2-[2-((1S)-2-imidazolyl-1-phenylethoxy)-5-oxo-6,7,8-trihydronaphthyl]ethyl}benzoate (Compound 27)

The title compound (Compound 27) is obtained in a manner similar to Example 24, steps 1–4 using 4-vinylbenzoic acid methyl ester. MS: APCI 495.1 [M+1].

Anal. Calcd. C$_{31}$H$_{30}$N$_2$O$_4$.0.3 mol EtOAc, MWC=525.4:

| Theory: | C 74.06, | H 6.29, | N 5.33. |
| Found: | C 74.04, | H 6.27, | N 5.33. |

EXAMPLE 28

Synthesis of Methyl 4-{2-[2-((1S)-2-imidazolyl-1-phenylethoxy)-5-oxo-6,7,8-trihydronaphthyl]ethyl}benzoate (Compound 28)

Compound 27 (0.55 g, 0.0011 mol) is dissolved in THF (10 mL)/MeOH (10 mL) and 1N NaOH (4.4 mL) is added. The reaction mixture is stirred at room temperature over the weekend. Solvent is removed in vacuo. 1N HCl (4.4 mL) is added and extracted with EtOAc. The organic layer is washed with brine, dried over MgSO$_4$, and the solvent removed in vacuo. Et$_2$O is added, triturating a white foam (Compound 28) (0.44 g, 83% yield); MS: APCI 481 [M+1].

Anal. Calcd. $C_{30}H_{28}N_2O_2 \cdot 0.52H_2O$ MWC=489.94:

| | | | |
|---|---|---|---|
| Theory: | C 73.55, | H 5.97, | N 5.72. |
| Found | C 73.55, | H 5.91, | N 5.52. |

EXAMPLE 29

Synthesis of (4-{2-[2-((1S)-2-Imidazolyl-1-phenylethoxy)-5-oxo(6,7,8-trihydronaphthyl)]ethyl}phenyl)-N-methylcarboxamide (Compound 29)

Compound 28 (0.3 g, 0.63 mmol) is dissolved in dry THF (10 mL). Carbonyl diimidazole (0.11 g, 0.69 mmol) and 2M methylamine in THF (0.35 mL, 0.69 mmol) are added. The reaction is refluxed overnight. Solvent is removed in vacuo. Ethyl acetate is added, and the reaction mixture is washed with sat. NaHCO$_3$ and brine, dried over MgSO$_4$, and the solvent removed in vacuo. Chromatography using DCM to DCM/MeOH 3% affords a white foam (Compound 29) (0.13 g, 42% yield). MS: APCI 495.2 [M+1].

Anal. Calcd. $C_{31}H_{31}N_3O_3 \cdot 0.16$ mol DCM/0.52 mol H$_2$O:

| | | | |
|---|---|---|---|
| Theory: | C 72.45, | H 6.31, | N 8.13. |
| Found | C 72.47, | H 6.33, | N 8.51. |

EXAMPLE 30

Synthesis of 6-((1S)-2-Imidazolyl-1-phenylethoxy)-5-[2-(4-fluorophenyl)ethyl]-2,3,4-trihydronaphthalen-1-one (Compound 30)

The title compound (Compound 30) is obtained in a manner similar to Example 24, steps 1–4 using 4-fluorostyrene. A white solid is obtained (1.3 g, 38% yield), mp=106–108° C.; MS: APCI 455 [M+1].

Anal. Calcd. $C_{29}H_{27}F_1N_2O_2$: Theory: C, 76.63; H, 5.99; N, 6.16. Found: C, 76.53; H, 6.08; N, 6.08.

EXAMPLE 31

Synthesis of Methyl 3-[2-((1S)-2-imidazolyl-1-phenylethoxy)-5-oxo-6,7,8-trihydronaphthyl]propanoate (Compound 31)

1. 5-[Ethylacrylate]-6-methoxy-1-tetralone

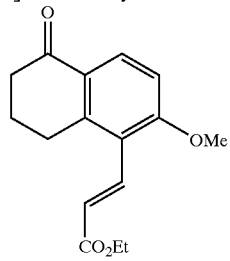

Ethyl acrylate (2.12 mL, 20 mmol) and bis(triphenylphosphine)-palladium (II) chloride (0.27 g, 0.39 mmol) are heated to reflux in triethylamine (5 mL) and N,N-dimethylformamide for 1 hour. 6-Methoxy-5-bromo-1-tetralone (1.0 g, 3.9 mmol) is added to the mixture and heated at reflux overnight. The reaction mixture is filtered through a bed of celite, washing with ethyl acetate. The organic solution is washed with water (5×), sat. sodium bicarbonate solution and brine. Subsequent drying over MgSO$_4$ and removal of the solvent in vacuo affords crude product Chromatography using 25% EtOAc/hexanes affords a yellow solid (0.91 g, 85% yield). MS: APCI 275.1 [M+1].

2. 5-[2-Ethyl-ethylcarboxylate]-6-methoxy-1-tetralone

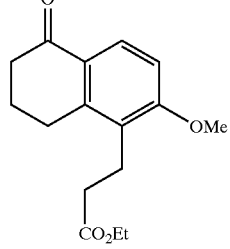

The title compound is obtained in a manner similar to Example 24, step 2 using a Parr shaker to yield a yellow oil (2.32 g, 79% yield). MS: APCI 277.1 [M+1].

3. 5-[2-ethylcarboxylic acid]-6-hydroxy-1-tetralone

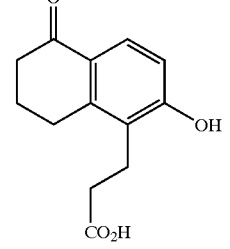

The title compound is obtained in a manner similar to Example 24, step 3 using sodium cyanide in DMSO to yield a brown solid (1.64 g, 83% yield).

MS: APCI 235.1 [M+1].

4. 5-[2-Methyl-ethylcarboxylate]-1-6-hydroxy-1-tetralone

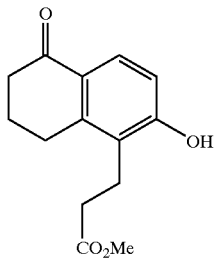

5-[2-ethylcarboxylic acid]-6-hydroxy-1-tetralone (1.6 g, 6.8 mmol) was dissolved in MeOH (10 mL)/toluene (10 mL) and cooled in an ice-water bath. (Trimethylsilyl) diazomethane (3.4 mL, 6.8 mmol, 2.0M solution in hexanes) was added dropwise and the mixture stirred for 18 h. TLC and MS indicated incomplete reaction. Additional (trimethylsilyl)diazomethane (3.4 mL, 6.8 mmol, 2.0M soln in hexanes) was added and the mixture refluxed for 2 h. Acetic acid (1 mL) was added and after 10 min all solvent removed in vacuo to afford a brown oily solid (0.8 g, 47% yield). NMR (DMSO) was consistent with the product, MS APCI 249 [M+H]+.

5. Methyl 3-[2-((1S)-2-imidazolyl-1-phenylethoxy)-5-oxo-6,7,8-trihydronaphthyl]propanoate The title compound (Compound 31) is obtained in a manner similar to Example 25, step 4 using 5–5-[2-methyl-ethylcarboxylate]-6-hydroxy-1-tetralone to yield a yellow solid (0.35 g, 26%). MS: APCI 419.6 [M+1].

Anal. Calcd. $C_{25}H_{26}N_2O_4 \cdot 0.11$ DCM MWC=427.84:

| Theory: | C 70.49, | H 6.18, | N 6.55. |
| --- | --- | --- | --- |
| Found: | C 70.14, | H 6.18, | N 6.95. |

EXAMPLE 32

Synthesis of 3-[2-((1S)-2-Imidazolyl-1-phenylethoxy)-5-oxo-6,7,8-trihydronaphthyl] propanoic acid (Compound 32)

The title compound (Compound 32) is obtained in a manner similar to Example 28 using compound 31 to yield a yellow solid (0.22 g, 88% yield).

MS: APCI 405.1 [M+1]. Anal. Calcd. $C_{24}H_{24}N_2O_4 \cdot EtOAc$ (0.1)/water (0.76) MWC=426.97:

| Theory: | C 68.64, | H 6.21, | N 6.56. |
| --- | --- | --- | --- |
| Found: | C 68.63, | H 6.43, | N 6.70. |

EXAMPLE 33

Synthesis of 4-{[2-((1S)-2-Imidazolyl-1-phenylethoxy)-5-oxo-6,7,8-trihydronaphthyl]methyl}benzenecarbonitrile (Compound 33)

1. 5-[(4-Bromophenyl)methyl]-6-methoxy-2,3,4-trihydronaphthalen-1-one

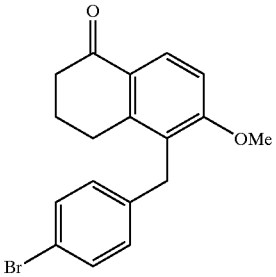

To cut zinc foil, 0.5 mm thick, (11.0 g, 0.16 mol) is added tetrahydrofuran (15.0 mL) and 1,2-dibromoethane (0.300 mL) and the mixture is heated twice to reflux with a hot air gun. After 5 minutes, the mixture is cooled to 0° C. A solution of p-bromobenzylbromide (15.7.0 g, 0.08 mol) in tetrahydrofuran (40 mL) is added dropwise to the zinc under nitrogen over 45 minutes. After 1 hour, the reaction is stopped, and the zinc reagent is used in the following reaction.

Palladium bis(dibenzylideneacetone) (0.58 g, 1 mol %) and 1,1'-bis(diphenyl-phospino)ferrocene (0.55 g, 2 mol %) are dissolved in tetrahydrofuran under nitrogen. After stirring for 10 minutes, 5-bromo-6-methoxytetralone (12.8 g, 0.050 mol) is added at 0° C. followed by the zinc reagent (50 mL of 1.6 M solution, 0.08 mol). The reaction is heated to 70° C. for 48 hours. The reaction is cooled and poured into sat. NH$_4$Cl (500 mL) and extracted with ethyl acetate (2×100 mL). The organic layers are washed with water (2×150 mL) and then brine (1×150 mL), dried over MgSO$_4$, filtered, and concentrated to give a dark brown oil. Chromatography is carried out on silica gel, using 15% ethyl acetate in hexane as eluent, to give a pale yellow solid (2.55 g, 18% yield). MS-APCI 292.0 [M+1].

2. 4-[(2-Hydroxy-5-oxo-6,7,8-trihydronaphthyl)methyl]benzene carbonitrile

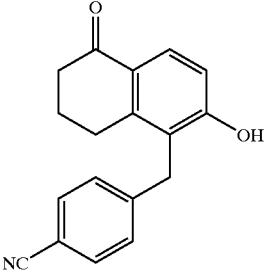

To a solution of the product from step 1 (1.75 g, 6 mmol) in dimethylsulfoxide (25 mL) is added sodium cyanide (1.5 g, 30 mmol) and the mixture is heated to 180° C. After 3 hours, the reaction mixture is poured into ice-water (150 mL) and acidified to a pH of 1 with concentrated hydrochloric acid. The aqueous solution is extracted with ethyl ether (2×50 mL). The organic layers are combined, washed with brine, dried over MgSO$_4$, filtered, and concentrated to give a tan solid. Recrystalization in 1:1 ethyl acetate/hexane gives a tan solid (0.60 g, 36% yield). MS-APCI 278.2 [M+1].

3. 4-{[2-((1S)-2-Imidazolyl-1-phenylethoxy)-5-oxo-6,7,8-trihydronaphthyl]methyl}benzenecarbonitrile To a solution of the product of step 2 (0.50 g, 1.8 mmol) in dry tetrahydrofuran (15 mL) is added (R)-2-imidazol-1-yl-1-phenyl ethanol (0.678 g, 3.6 mmol) and triphenylphosphine (0.932 g, 3.6 mmol). The reaction mixture is cooled to 0° C. and treated with a solution of diethyl azodicarboxylate (0.600 mL, 4.0 mmol) in tetrahydrofuran (5 mL) dropwise. The reaction is warmed to room temperature and stirred overnight. The solution is concentrated, and the residue is taken up in 50 mL ethyl acetate. The organic layer is washed with water (3×25 mL) and brine (2×25 mL). The solvent is removed in vacuo, and 25 mL of ethyl ether is added. The precipitate is filtered and the ether is removed. More ethyl ether is added, and the above procedure is repeated two more times. Fifty milliliters of ethyl acetate is added, and the solution is dried over $MgSO_4$, filtered, and concentrated to give a light tan foam. Chromatography is carried out on silica gel, using 1.0% methanol in methylene chloride as eluent, to give a white foam as the final product (Compound 33) (0.207 g, 26% yield). MS-APCI 448.1 [M+1].

Analysis calculated for $C_{29}H_{25}N_3O_2$ $1.44H_2O$.

| | | | |
|---|---|---|---|
| Theory: | C 73.57, | H 5.94, | N 8.87. |
| Found: | C 73.20, | H 5.90, | N 9.09. |

EXAMPLE 34

Synthesis of 6-((1S)-2-Imidazolyl-1-phenylethoxy)-5-bromo-2,3,4-trihydronaphthalen-1-one (Compound 34)

1. 5-Bromo-6-hydroxy-2,3,4-trihydronapthalen-1-one

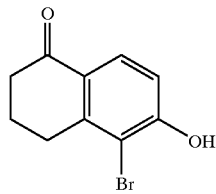

A solution of 2.09 g (8.2 mmol) of 5-bromo-6-methoxy-2,3,4-trihydronapthalen-1-one (Z. Chem. 1970;10:70) in 50 mL $CH_2Cl_2$ is cooled in an ice bath and treated dropwise rapidly with 5.2 mL (55.6 mmol) of $BBr_3$. After stirring at 0° for 0.5 hour, the solution is stirred at room temperature overnight. The solution is poured into ice water and extracted twice with $Et_2O$. The $Et_2O$ is washed twice with 5% NaOH and the NaOH solution back extracted with $Et_2O$. The NaOH solution is acidified with dil. HCl and extracted twice with $Et_2O$. The $Et_2O$ is washed with sat. NaCl and dried over $MgSO_4$. Removal of the $Et_2O$ under reduced pressure gives 1.52 g of the crude product. Two chromatographies on silica gel, eluting with $CH_2Cl_2$ gives 0.33 g (16.8% yield) of the product as a cream solid.

2. 6-((1S)-2-Imidazolyl-1-phenylethoxy)-5-bromo-2,3,4-trihydronaphthalen-1-one

5-Bromo-6-hydroxy-2,3,4-trihydronapthalen-1-one (6.96 g, 0.029 mol), (R)-2-imidazol-1-yl-1-phenyl-ethanol (5.97 g, 0.032 mol) and triphenylphosphine (11.43 g, 0.044 mol) are dissolved in dry THF (100 mL) under a nitrogen atmosphere and cooled in an ice-water bath. DEAD reagent (6.93 mL, 0.044 mol) in dry THF (20 mL) is added over 0.5 hour. The reaction mixture is stirred for an additional 2 hours after the DEAD reagent is added. Solvent is removed in vacuo. The residue is partitioned between diethyl ether and 1N citric acid. The aqueous solution is washed with diethyl ether several times. Then, the aqueous solution is made basic using 50% sodium hydroxide solution and extracted with ethyl acetate (3×). The organic layer is washed with brine, dried over $MgSO_4$ and the solvent is removed in vacuo. The residue is chromatographed using dichloromethane to 97% dichloromethane/3% methanol as eluent. Obtained is a tan solid as the final product (Compound 34) (3.0 g, 25% yield) MS: APCI 412.1 [M+1].

Anal. Calcd. $C_{21}H_{19}N_2Br_1O_2 \cdot 0.06$ mol DCM, MWC=416.40:

| | | | |
|---|---|---|---|
| Theory: | C 60.75, | H 4.63, | N 6.73. |
| Found: | C 60.36, | H 4.42, | N 7.22. |

EXAMPLE 35

Synthesis of 6-((1S)-2-Imidazolyl-1-phenylethoxy)-5-(3-thienyl)-2,3,4-trihydronaphthalen-1-one (Compound 35)

Tetrakistriphenylphosphine palladium (0.083 g, 0.072 mmol) is suspended in dimethoxyethane (15 mL). Compound 34 (1.0 g, 2.4 mmol) is added and stirred at room temperature for 10 minutes. 3-Thiopheneboronic acid (0.47 g, 3.6 mmol) in ethanol (10 mL) is added followed by 2 M solution $Na_2CO_3$ (10 mL), and the reaction mixture is refluxed overnight. The reaction is filtered through a bed of celite, washing with EtOAc. The organic layer is washed with sat. $NaHCO_3$ solution and then brine, dried over $MgSO_4$ and the solvent removed in vacuo. Chromatography using DCM to DCM/MeOH 3% affords a pink foam as the final product (Compound 35) (0.78 g, 79% yield). MS: APCI 415.2 [M+1].

Anal. Calcd. $C_{25}H_{22}N_2O_2S_1 \cdot 0.17$ mol DCM, MWC=428.97:

| | | | |
|---|---|---|---|
| Theory: | C 70.48, | H 5.25, | N 6.53. |
| Found: | C 70.32, | H 5.49, | N 6.53. |

EXAMPLE 36

Synthesis of 6-((1S)-2-Imidazolyl-1-phenylethoxy)-5-(3-furyl)-2,3,4-trihydronaphthalen-1-one, 2,2,2-trifluoroacetic acid (Compound 36)

The title compound (Compound 36) is obtained in a manner similar to Example 35, using 2-furanboronic acid. The reaction is purified by prep. HPLC using reverse phase 0–45% MeCN/water (TFA) and product is lyophilyzed to give a white foam (0.06 g, 9% yield). MS: APCI 399 [M+1].

Anal. Calcd. $C_{25}H_{22}N_2O_3$.1.83 mol TFA/0.12 mol $H_2O$ MWC=609.29:

| Theory: | C 56.50, | H 3.98, | N 4.60. |
|---|---|---|---|
| Found: | C 56.49, | H 3.99, | N 4.41. |

EXAMPLE 37

Synthesis of 6-((1S)-2-Indazolyl-1-phenylethoxy)-5-amino-2,3,4-trihydronaphthalen-1-one (Compound 37)

1. 6-((1S)-2-Imidazolyl-1-phenylethoxy)-5-nitro-2,3,4-trihydronaphthalen-1-one

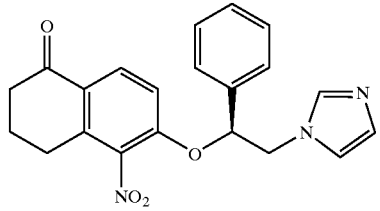

To a solution of 6-hydroxy-5-nitro-1-tetralone (2.09 g, 10.1 mmol) in dry THF (50 mL) is added (R)-2-imidazol-1-yl-1-phenyl-ethanol (2.28 g, 12.1 mmol) followed by triphenylphospine (3.18 g, 12.1 mmol). After approximately 10 minutes, diethylazodicarboxylate (1.9 mL, 12.1 mmol) is added slowly. The reaction becomes homogenous within 2 minutes. The reaction is allowed to stir at room temperature (RT) overnight. The reaction mixture is concentrated under reduced pressure, and the residue is triturated with $Et_2O$ to remove some of the phospine by-products. The residue is dissolved in EtOAc and washed with $H_2O$, saturated aqueous $NaHCO_3$ and brine, dried over $MgSO_4$, and concentrated to give a foam/oil. Purification by chromatography ($SiO_2$, 10% to 20% acetone/$CH_2Cl_2$ then 5% MeOH/$CH_2Cl_2$) affords the title compound as a light brown foam (3.06 g, 8.1 mmol, 80%). The structure is confirmed by NMR and mass spectrometry. MS: m/z 378 [M$^+$+H].

2. 6-((1S)-24-Imidazolyl-1-phenylethoxy)-5-amino-2,3,4-trihydronaphthalen-1-one

A mixture of the product from step 1(2.05 g, 5.43 mmol), MeOH (135 mL), $H_2O$ (30 mL) and glacial acetic acid (3.1 mL, 54 mmol) is treated at reflux with iron powder (3.01 g, 54 mmol). The reaction is monitored by mass spectrometry and is complete in 5 hours. The volume of solvent is reduced under reduced pressure. EtOAc and dilute aqueous $NaHCO_3$ are added. A brownish-green emulsion forms which is filtered through Celite. The mixture is extracted with EtOAc. The combined organic layer is washed with dilute aqueous $NaHCO_3$ and brine, dried over $Na_2SO_4$, and concentrated under reduced pressure to give a brown solid. Purification by chromatography (EtOAc then 6% MeOH/$CH_2Cl_2$) gives the product (Compound 37) as a tan solid (1.43 g, 4.12 mmol, 76%). MS: m/z 348 [M$^+$+H].

EXAMPLE 37a

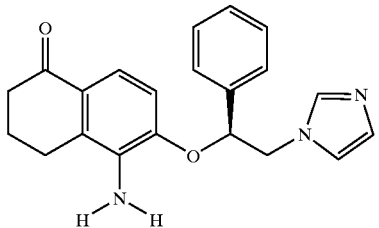

Synthesis of 5-Amino-6-((S)-2-imidazol-1-yl-1-phenyl-ethoxy)-3,4-dihydro-2H-naphthalen-1-one (Compound 37a)

1. 5-Nitro-6-((S)-2-imidazol-1-yl-1-phenyl-ethoxy)-3,4-dihydro-2H-naphthalen-1-one

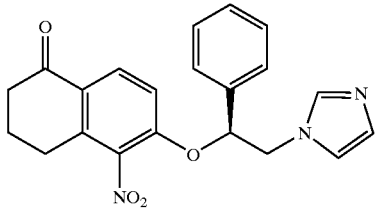

To a solution of 6-hydroxy-5-nitro-1-tetralone (2.09 g, 10.1 mmol) in dry THF (50 mL) was added (R)-2-imidazol-1-yl-1-phenyl-ethanol (2.28 g, 12.1 mmol) followed by triphenylphosphine (3.18 g, 12.1 mmol). After approximately 10 min, diethylazodicarboxylate (1.9 mL, 12.1 mmol) was added slowly. The reaction became homogenous within 2 min. The reaction was allowed to stir at RT overnight. The reaction mixture was concentrated under reduced pressure and the residue was triturated with $Et_2O$ to remove some of the phospine by-products. The residue was dissolved in EtOAc and washed with $H_2O$, saturated aqueous $NaHCO_3$ and brine, dried over $MgSO_4$, and concentrated to give a foam/oil. Purification by chromatography ($SiO_2$, 10 to 20% acetone/$Cl_2Cl_2$ then 5% MeOH/$CH_2Cl_2$) afforded the title compound as a light brown foam (3.06 g, 8.1 mmol, 80%). The structure was confirmed by NMR and mass spectrometry. MS m/z 378 (M$^+$+H).

2. 5-Amino-6-((S)-2-imidazol-1-yl-1-phenyl-ethoxy)-3,4-dihydro-2H-naphthalen-1-one A mixture of 5-nitro-6-((S)-2-imidazol-1-yl-1-phenyl-ethoxy)-3,4-dihydro-2H-naphthalen-1-one (2.05 g, 5.43 mmol), MeOH (135 mL), $H_2O$ (30 mL) and glacial acetic acid (3.1 mL, 54 mmol) was treated at reflux with iron powder (3.01 g, 54 mmol). The reaction was monitored by mass spectrometry and was complete in 5 h. The volume of solvent was reduced under reduced pressure. EtOAc and dilute aqueous $NaHCO_3$ were added. A brownish-green emulsion formed which was filtered through Celite. The mixture was extracted with EtOAc. The combined organic layer was washed with dilute aqueous $NaHCO_3$ and brine, dried over $Na_2SO_4$, and concentrated under reduced pressure to give a brown solid. Purification by chromatography (EtOAc then 6% MeOH/$CH_2Cl_2$) gave the product as a tan solid (1.43 g, 4.12 mmol, 76%). The structure was confirmed by NMR and mass spectrometry. MS m/z 348 (M$^+$+H).

EXAMPLE 38

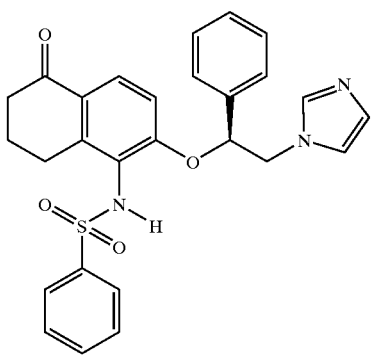

Synthesis of N-[2-((S)-2-Imidazol-1-yl-1-phenyl-ethoxy)-5-oxo-5,6,7,8-tetrahydro-naphthalen-1-yl]-benzenesulfonamide (Compound 38)

To a solution of 5-amino-6-((S)-2-imidazol-1-yl-1-phenyl-ethoxy)-3,4-dihydro-2H-naphthalen-1-one (100 mg, 0.288 mmol) in CH$_2$Cl$_2$ (2 mL) was added pyridine (47 mL, 0.576 mmol, 2 equiv) followed by benzenesulfonyl chloride (44 μL, 0.345 mmol, 1.2 equiv). The reaction was allowed to stir overnight at RT. The reaction was diluted with CH$_2$Cl$_2$, washed with saturated aqueous NH$_4$Cl and brine, dried over MgSO$_4$ to give an oil. Purification by chromatography (4% MeOH/CH$_2$Cl$_2$) gave the title compound as a white foam (114 mg, 0.234 mmol, 81%). The structure was confirmed by NMR and mass spectrometry. MS m/z 488 (M$^+$+H).

EXAMPLE 39

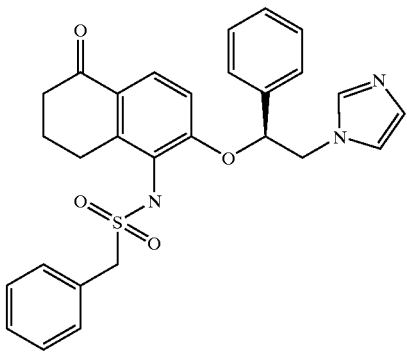

Synthesis of N-[2-((S)-2-Imidazol-1-yl-1-phenyl-ethoxy)-5-oxo-5,6,7,8-tetrahydro-naphthalen-1-yl]-1-phenyl-methanesulfonamide (Compound 39)

The procedure in Example 38 was followed, except α-toluenesulfonyl chloride (83 mg, 0.432 mmol, 1.5 equiv) was used. After stirring overnight, the reaction was diluted with CH$_2$Cl$_2$ and 1N HCl was added. The mixture was extracted with CH$_2$Cl$_2$. The organic layer was washed with brine, dried over MgSO$_4$, and concentrated to give a foam. Purification by chromatography (5% MeOH/CH$_2$Cl$_2$ with 1% NH$_4$OH) afforded the title compound as an off-white foam (108 mg, 0.215 mmol, 75%). The structure was confirmed by NMR and mass spectrometry. MS m/z 502 (M$^+$+H).

EXAMPLE 39a

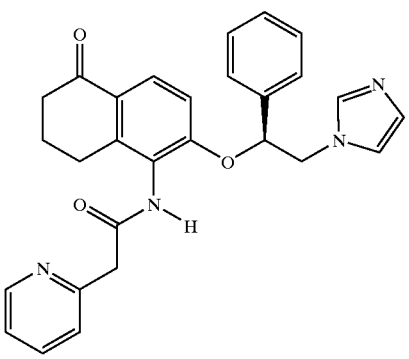

Synthesis of N-[2-((S)-2-Imidazol-1-yl-1-phenyl-ethoxy)-5-oxo-5,6,7,8-tetrahydro-naphthalen-1-yl]-2-pyridin-2-yl-acetamide (Compound 39a)

To a solution of 5-amino-6-((S)-2-imidazol-1-yl-1-phenyl-ethoxy)-3,4-dihydro-2H-naphthalen-1-one (100 mg, 0.288 mmol) and 2-pyridylacetic acid HCl (67 mg, 0.386 mmol) in DMF (3 mL) was added EDCI HCl (111 mg, 0.576 mmol, 2 equiv). The yellow solution turned orange overnight. Some of the DMF was removed under reduced pressure. The residue was dissolved in H$_2$O and 1 M NaOH was added until the solution was basic (pH 10). The mixture was extracted thoroughly with CH$_2$Cl$_2$. The organic layer was washed with brine, dried over Na$_2$SO$_4$ and concentrated to give a bright yellow oil. Purification by chromatography (7% MeOH/CH$_2$Cl$_2$) afforded the title compound as a pale yellow foam (107 mg, 0.229 mmol, 80%). The structure was confirmed by NMR and mass spectrometry. MS m/z 467 (M$^+$+H).

EXAMPLE 40

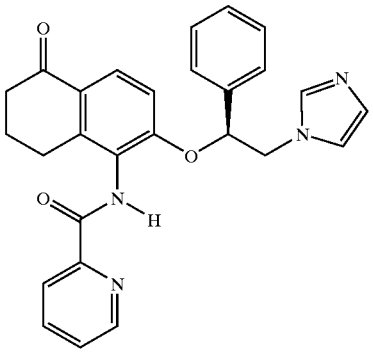

Synthesis of Pyridine-2-carboxylic acid [2-((S)-2-imidazol-1-yl-1-phenyl-ethoxy)-5-oxo-5,6,7,8-tetrahydro-naphthalen-1-yl]-amide (Compound 40)

To a solution of 5-amino-6-((S)-2-imidazol-1-yl-1-phenyl-ethoxy)-3,4-dihydro-2H-naphthalen-1-one (150 mg, 0.432 mmol), picolinic acid (64 mg, 0.518 mmol) and HOBT (73 mg, 0.540 mmol) in DMF (4 mL) was added N-methylmorpholine (62 μL, 0.562 mmol) followed by EDCI HCl (108 mg, 0.562 mmol). After 2 days, the DMF was removed under reduced pressure. The residue was partitioned between EtOAc and H$_2$O. The organic layer was washed with H$_2$O and brine, dried over Na$_2$SO$_4$ and concentrated to give a brown oil. Purification by chromatography (3–5% MeOH/CH$_2$Cl$_2$) afforded the title compound as a tan foam (160 mg, 0.354 mmol, 82%). The structure was confirmed by NMR and mass spectrometry. MS m/z 453 (M$^+$+H).

EXAMPLE 40a

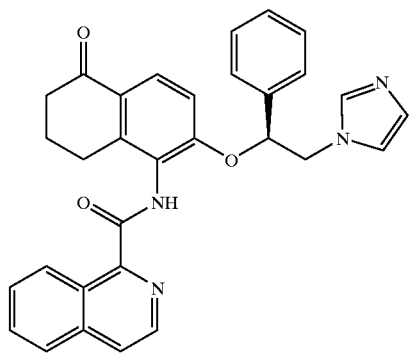

Synthesis of Isoquinoline-1-carboxylic acid [2-((S)-2-imidazol-1-yl-1-phenyl-ethoxy)-5-oxo-5,6,7,8-tetrahydro-naphthalen-1-yl]-amide (Compound 40a)

The procedure in Example 40 was followed using 1-isoquinolinecarboxylic acid. Purification by chromatography (5% MeOH/$CH_2Cl_2$) afforded the title compound as a white foam (135 mg, 0.269 mmol, 93%). The structure was confirmed by NMR and mass spectrometry. MS m/z 503 ($M^+$+H).

EXAMPLE 40b

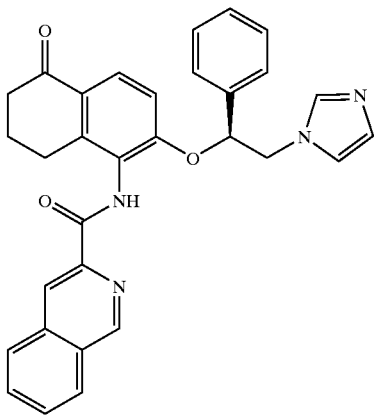

Synthesis of Isoquinioline-3-carboxylic acid [2-((S)-2-imidazol-1-yl-1-phenyl-ethoxy)-5-oxo-5,6,7,8-tetrahydro-naphthalen-1-yl]-amide (Compound 40b)

The procedure in Example 40 was followed using 3-isoquinolinecarboxylic acid hydrate. Purification by chromatography (5% MeOH/$CH_2Cl_2$) afforded the title compound as a tan foam (63 mg, 0.125 mmol, 44%). The structure was confirmed by NMR and mass spectrometry. MS m/z 503 ($M^+$+H).

EXAMPLE 40c

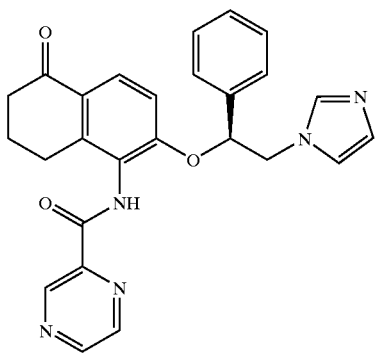

Synthesis of Pyrazine-2-carboxylic acid [2-((S)-2-imidazol-1-yl-4-phenyl-ethoxy)-5-oxo-5,6,7,8-tetrahydro-naphthalen-1-yl]-amide (Compound 40c)

To a mixture of 5-amino-6-((S)-2-imidazol-1-yl-1-phenyl-ethoxy)-3,4-dihydro-2H-naphthalen-1-one (100 mg, 0.288 mmol), 2-pyrazinecarboxylic acid (43 mg, 0.346 mmol), and HATU (132 mg, 0.346 mmol) was added $CH_2Cl_2$ (2.5 mL) and $Et_3N$ (48 µL, 0.346 mmol). The suspension became homogenous after 1 h. The reaction was stirred overnight at RT. The mixture was diluted with $CH_2Cl_2$ and washed with $H_2O$, saturated aqueous $NaHCO_3$ and brine, dried over $Na_2SO_4$, and concentrated to give a foam/oil. Purification by chromatography ($SiO_2$, 6% MeOH/$CH_2Cl_2$ with 1% $NH_4OH$) afforded the title compound as a foam (120 mg, 0.265 mmol, 92%). The structure was confirmed by NMR and mass spectrometry. MS m/z 454 ($M^+$+H).

EXAMPLE 40d

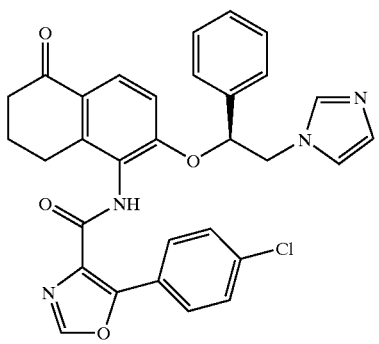

Synthesis of 5-(4-Chloro-phenyl)-oxazole-4-carboxylic acid [2-((S)-2-imidazol-1-yl-1-phenyl-ethoxy)-5-oxo-5,6,7,8-tetrahydro-naphthalen-1-yl]-amide (Compound 40d)

The procedure in Example 40c was followed using 5-(4-chloro-phenyl)-oxazole-4-carboxylic acid. Purification by chromatography ($SiO_2$, 60% EtOAc/$CH_2Cl_2$ then 5% MeOH/$CH_2Cl_2$) afforded the title compound as a foam (120 mg, 0.217 mmol, 75%). The structure was confirmed by NMR and mass spectrometry. MS m/z 553 ($M^+$+H).

EXAMPLE 40e

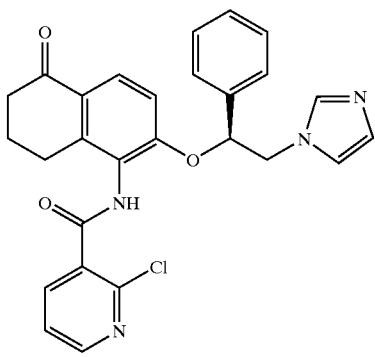

Synthesis of N-[2-((S)-2-Imidazol-1-yl-1-phenyl-ethoxy)-5-oxo-5,6,7,8-tetrahydro-naphthalen-1-yl]-2-chloro-nicotinamide (Compound 40e)

The procedure in Example 40c was followed using 2-chloronicotinic acid. The reaction was heated to reflux (40° C.) for 2 days. Purification by chromatography (SiO$_2$, 2–5% MeOH/CH$_2$Cl$_2$) afforded the title compound as a foam (10 mg, 0.021 mmol, 7%). The structure was confirmed by NMR and mass spectrometry. MS m/z 487 (M$^+$+H).

EXAMPLE 40f

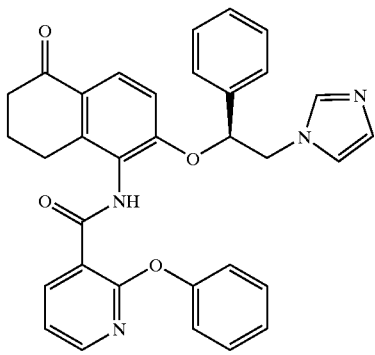

Synthesis of N-[2-((S)-2-Imidazol-1-yl-1-phenyl-ethoxy)-5-oxo-5,6,7,8-tetrahydro-naphthalen-4-1-yl]-2-phenoxy-nicotinamide (Compound 40f)

The procedure in Example 40c was followed using 2-phenoxynicotinic acid. The reaction was heated to reflux (40° C.) for 2 days. Purification by chromatography (SiO$_2$, 2–5% MeOH/CH$_2$Cl$_2$) afforded the title compound as a foam (140 mg, 0.257 mmol, 89%). The structure was confirmed by NMR and mass spectrometry. MS m/z 545 (M$^+$+H).

EXAMPLE 40g

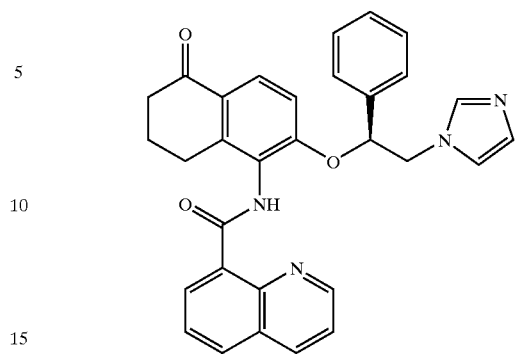

Synthesis of Quinoline-8-carboxylic acid [2-((S)-2-imidazol-1-yl-1-phenyl-ethoxy)-5-oxo-5,6,7,8-tetrahydro-naphthalen-1-yl]-amide (Compound 40g)

The procedure in Example 40c was followed using 2-phenoxynicotinic acid. The reaction was heated to reflux (40° C.) for 1 day. Purification by chromatography (SiO$_2$, 2–5% MeOH/CH$_2$Cl$_2$) afforded the title compound as a foam (135 mg, 0.269 mmol, 93%). The structure was confirmed by NMR and mass spectrometry. MS m/z 503 (M$^+$+H).

EXAMPLE 41

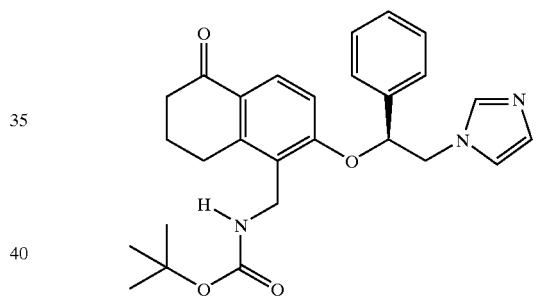

Synthesis of [2-((S)-2-Imidazol-1-yl-1-phenyl-ethoxy)-5-oxo-5,6,7,8-tetrahydro-naphthalen-1-ylmethyl]-carbamic acid tert-butyl ester (Compound 41)

1. 2-Chloro-N-(2-hydroxy-5-oxo-5,6,7,8-tetrahydro-naphthalen-1-ylmethyl)acetamide.

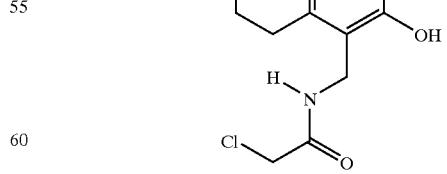

6-Hydroxytetralone (4.87 g, 30.0 mmol) was added to a mixture of glacial acetic acid (20 mL) and concentrated H$_2$SO$_4$ (20 mL) cooled to 0° C. N-Hydroxymethyl-2-chloroacetamide (3.71 g, 30.0 mmol) was added and the mixture was allowed to warm to RT. After stirring overnight, the reaction was poured into ice. An orange sludge formed and the mixture was extracted thoroughly with EtOAc. The organic layer was washed with $H_2O$ and brine, dried over $MgSO_4$ and concentrated to give an orange foam (5.6 g). Recrystalization (EtOH/$H_2O$) afforded the title compound as orange needles (2.46 g, 9.2 mmol, 31%). MS m/z 268/270 ($M^++H$).

2. (2-Hydroxy-5-oxo-5,6,7,8-tetrahydro-naphthalen-1-ylmethyl)-carbamic acid tert-butyl ester.

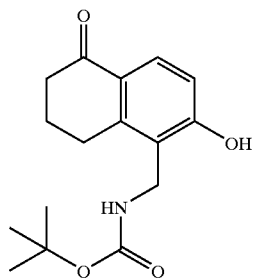

To a slurry of 2-Chloro-N-(2-hydroxy-5-oxo-5,6,7,8-tetrahydro-naphthalen-1-ylmethyl)-acetamide (1.85 g, 6.92 mmol) in THF (25 mL) was added di-tert-butyl dicarbonate (6.04 g, 27.7 mmol, 4 equiv) followed by dimethylaminopyridine (338 mg, 2.77 mmol, 0.4 equiv). The reaction became homogenous and turned red. The reaction was stirred at RT for 2 days at which time it was an orange slurry. The reaction was concentrated and chromatographed (20–30% EtOAc/Hexanes) to give the bis-Boc chloroacetamide as a white foam (2.19 g, 4.69 mmol, 68%). MS m/z 468/470 ($M^++H$).

To a solution of the bis-Boc compound (2.19 g) in THF (30 mL) and MeOH (10 mL) was added 2 N LiOH (10 mL). The mixture was stirred overnight at RT. Some of the solvent was removed under reduced pressure. The residue was neutralized with 1 N HCl and extracted with $CH_2Cl_2$ several times. The organic layer was washed with brine, dried over $MgSO_4$ and concentrated to give a mixture of the mono- and bis-Boc amines. This mixture was treated with $Mg(ClO_4)_2$ in $CH_3CN$ (30 mL) at 50° C. for 4 h. The solvent was removed under reduced pressure and the residue was dissolved in EtOAc. The organics were washed with dilute HCl and brine, dried over $Na_2SO_4$ and concentrated under reduced pressure to give a white solid. Purification by chromatography (30–40% EtOAc/Hexanes) gave the title compound as a white solid (0.964 g, 3.31 mmol, 71%). MS m/z 292 ($M^++H$).

3. [2-((S)-2-Imidazol-1-yl-1-phenyl-ethoxy)-5-oxo-5,6,7,8-tetrahydro-naphthalen-1-ylmethyl]-carbamic acid tert-butyl ester A round bottom flask was charged with (2-Hydroxy-5-oxo-5,6,7,8-tetrahydro-naphthalen-1-ylmethyl)-carbamic acid tert-butyl ester (700 mg, 2.40 mmol), (R)-2-imidazol-1-yl-1-phenyl-ethanol (544 mg, 2.89 mmol), triphenylphospine (759 mg, 2.89 mmol) and dry THF (14 mL). After approximately 15 nm, diethylazodicarboxylate (0.46 mL, 2.89 mmol) was added slowly. The reaction was stirred overnight and concentrated to give a yellow oil. Purification by chromatography (10–20% acetone/$CH_2Cl_2$ then 5% MeOH/$CH_2Cl_2$) afforded the title compound as a white foam (0.850 g, 1.84 mmol, 77%). The structure was confirmed by NMR and mass spectrometry. MS m/z 462 ($M^++H$).

EXAMPLE 42

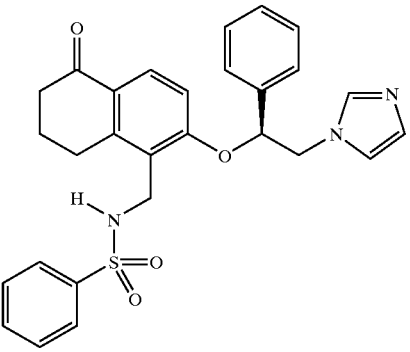

Synthesis of N-[2-((S)-2-Imidazol-1-y-1-phenyl-71-ethoxy)-5-oxo-5,6,7,8-tetrahydro-naphthalen-1-ylmethyl]-benzenesulfonamide (Compound 42)

1. 5-Aminomethyl-6-((S)-2-imidazol-1-yl-1-phenyl-ethoxy)-3,4-dihydro-2H-naphthalen-1-one Bis-Hydrochloride

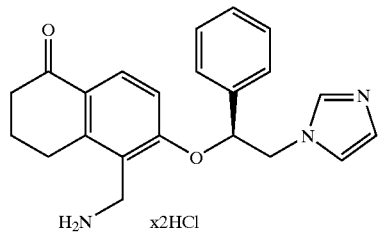

[2-((S)-2-Imidazol-1-yl-1-phenyl-ethoxy)-5-oxo-5,6,7,8-tetrahydro-naphthalen-1-ylmethyl]-carbamic acid tert-butyl ester (0.830 g, 1.80 mmol) was dissolved in dioxane (10 mL) and 4M HCl in dioxane (4 mL) was added. After 15 minutes, a white precipitate formed. The precipitate was collected by filtration, washed with $Et_2O$ and dried in a vacuum oven to give the title compound as a white fluffy solid (0.761 g, 1.75 mmol, 97%). The structure was confirmed by NMR, mass spectrometry and elemental analysis. MS m/z 362 ($M^++H$).

2. N-[2-((S)-2-Imidazol-1-yl-1-phenyl-ethoxy)-5-oxo-5,6,7,8-tetrahydro-naphthalen-1-ylmethyl]-benzenesulfonamide 5-Aminomethyl-6-((S)-2-imidazol-1-yl-1-phenyl-ethoxy)-3,4-dihydro-2H-naphthalen-1-one bis-hydrochloride (74 mg, 0.171 mmol) was dissolved in pyridine (1 mL) and catalytic DMAP (2 mg) was added followed by benzenesulfonyl chloride (26 µL, 0.205 mmol, 1.2 equiv). The reaction was stirred overnight at RT. The mixture was concentrated and the residue was dissolved in $CH_2Cl_2$. The organics were washed with $H_2O$ and brine, dried over $MgSO_4$ and concentrated to give a tan foam. Purification by chromatography (5% MeOH/EtOAc with 1% $NH_4OH$) afforded the title compound as a white foam (57 mg, 0.114 mmol, 67%). The structure was confirmed by NMR and mass spectrometry. MS m/z 502 ($M^++H$).

EXAMPLE 42a

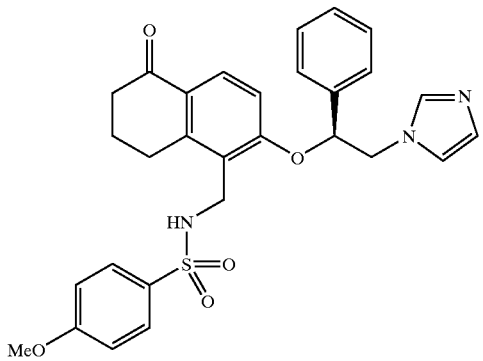

Synthesis of N-[2-((S)-2-Imidazol-1-yl-1-phenyl-ethoxy)-5-oxo-5,6,7,8-tetrahydro-naphthalen-1-ylmethyl]-4-methoxy-benzenesulfonamide (Compound 42a)

To a solution of 5-aminomethyl-6-((S)-2-imidazol-1-yl-1-phenyl-ethoxy)-3,4-dihydro-2H-naphthalen-1-one bis-hydrochloride (40 mg, 0.092 mmole) in CH$_2$Cl$_2$ (1 mL) and pyridine (1 mL) was added 4-methoxybenzenesulfonyl chloride (0.75 mL, 0.4 M solution in trifluorotoluene, 3 equiv). The reaction was shaken overnight. A polyamine resin was added to quench the excess sulfonyl chloride. The mixture was filtered and concentrated. The residue was dissolved in EtOAc and washed with 1 M NaOH and brine, dried over Na$_2$SO$_4$ and concentrated to give a light brown oil. Purification by chromatography (5% MeOH/CH$_2$Cl$_2$ with 1% NH$_4$OH) gave the title compound as an off-white foam (32 mg, 0.060 mmol, 66%). The structure was confirmed by NMR and mass spectrometry. MS m/z 532 (M$^+$+H).

EXAMPLE 42b

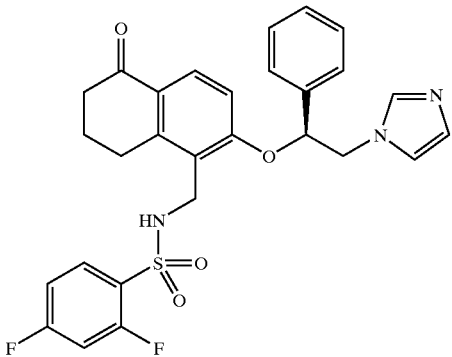

Synthesis of 2,4-Difluoro-N-[2-((S)-2-imidazol-1-yl-1-phenyl-ethoxy)-5-oxo-5,6,7,8-tetrahydro-naphthalen-1-ylmethyl]-benzenesulfonamide; compound with trifluoro-acetic acid (Compound 42b)

The procedure in Example 42a was followed using 2,4-difluorobenzenesulfonyl chloride. Purification by HPLC (10–100% CH$_3$CN/H$_2$O with 0.05% TFA) afforded the title compound as the TFA salt (46 mg, 0.071 mmol). The structure was confirmed by NMR and mass spectrometry. MS m/z 538 (M$^+$+H).

EXAMPLE 42c

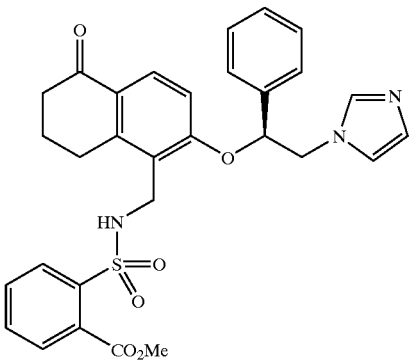

Synthesis of 2-{[2-((S)-2-Imidazol-1-yl-1-phenyl-ethoxy)-5-oxo-5,6,7,8-tetrahydro-naphthalen-1-ylmethyl]-sulfonyl}-benzoic acid methyl ester; compound with trifluoro-acetic acid (Compound 42c)

The procedure in Example 42a was followed using 2-carbomethoxybenzenesulfonyl chloride. Purification by HPLC (10–100% CH$_3$CN/H$_2$O with 0.05% TFA) afforded the title compound as the TFA salt (27 mg, 0.040 mmol). The structure was confirmed by NMR and mass spectrometry. MS m/z 560 (M$^+$+H).

EXAMPLE 42d

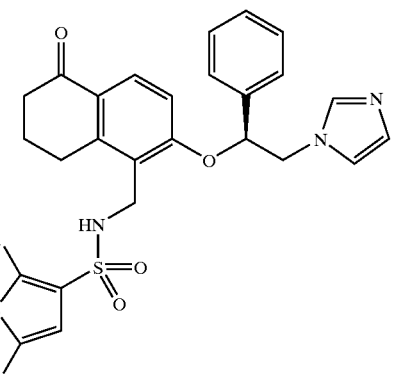

Synthesis of 2,5-Dichloro-thiophene-3-sulfonic acid [2-((S)-2-imidazol-1-yl-1-phenyl-ethoxy)-5-oxo-5,6,7,8-tetrahydro-naphthalen-1-ylmethyl]-amide; compound with trifluoro-acetic acid (Compound 42d)

The procedure in Example 42a was followed using 2,5-dichloro-thiophene-3-sulfonyl chloride. Purification by HPLC (10–100% CH$_3$CN/H$_2$O with 0.05% TFA) afforded the title compound as the TFA salt (54 mg, 0.078 mmol). The structure was confirmed by NMR and mass spectrometry. MS m/z 577 (M$^+$+H).

EXAMPLE 42e

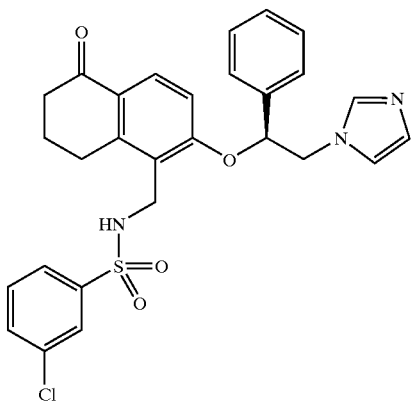

Synthesis of 3-Chloro-N-[2-((S)-2-imidazol-1-yl-1-phenyl-ethoxy)-5-oxo-5,6,7,8-tetrahydro-naphthalen-1-ylmethyl]-benzenesulfonamide; compound with trifluoro-acetic acid (Compound 42e)

The procedure in Example 42a was followed using 3-chlorobenzenesulfonyl chloride. Purification by HPLC (10–100% $CH_3CN/H_2O$ with 0.05% TFA) afforded the title compound as the TFA salt (48 mg, 0.074 mmol). The structure was confirmed by NMR and mass spectrometry. MS m/z 536 ($M^+$+H).

EXAMPLE 42f

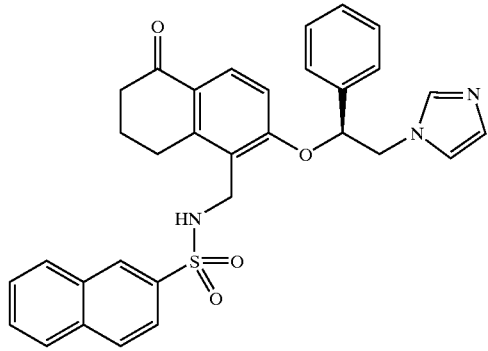

Synthesis of Naphthalene-2-sulfonic acid [2-((S)-2-imidazol-1-yl-1-phenyl-ethoxy)-5-oxo-5,6,7,8-tetrahydro-naphthalen-1-ylmethyl]-amide; compound with trifluoro-acetic acid (Compound 42f)

The procedure in Example 42a was followed using 2-naphthalenesulfonyl chloride. Purification by HPLC (10–100% $CH_3CN/H_2O$ with 0.05% TFA) afforded the title compound as the TFA salt (10 mg, 0.015 mmol). The structure was confirmed by NMR and mass spectrometry. MS m/z 552 ($M^+$+H).

EXAMPLE 42g

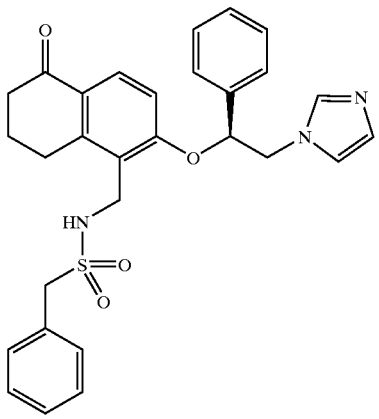

Synthesis of N-[2-((S)-2-Imidazol-1-yl-1-phenyl-ethoxy)-5-oxo-5,6,7,8-tetrahydro-naphthalen-4-ylmethyl]-C-phenyl-methanesulfonamide (Compound 42g)

The procedure in Example 42a was followed using α-toluenesulfonyl chloride. Purification by chromatography (3% $MeOH/CH_2Cl_2$ with 1% $NH_4OH$) afforded the title compound (20 mg, 0.039 mmol). The structure was confirmed by NMR and mass spectrometry. MS m/z 516 ($M^+$+H).

EXAMPLE 42h

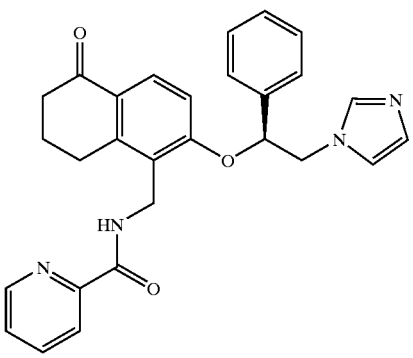

Synthesis of Pyridine-2-carboxylic acid [2-((S)-2-imidazol-1-yl-1-phenyl-ethoxy)-5-oxo-5,6,7,8-tetrahydro-naphthalen-1-ylmethyl]-amide (Compound 42h)

To a solution of 5-aminomethyl-6-((S)-2-imidazol-1-yl-1-phenyl-ethoxy)-3,4-dihydro-2H-naphthalen-1-one bis-hydrochloride (69 mg, 0.159 mmol), picolinic acid (24 mg, 0.191 mmol) and HOBT (27 mg, 0.199 mmol) in DMF (1.6 mL) was added N-methylmorpholine (56 µL, 0.51 mmol) followed by EDCI (40 mg, 0.207 mmol).

The reaction was stirred for 7 h at RT. The reaction was poured into dilute aqueous $NaHCO_3$ and the mixture was extracted with EtOAc. The organic layer was washed with brine, dried over $Na_2SO_4$ and concentrated. Purification by chromatography (5% $MeOH/CH_2Cl_2$) gave the title compound as a white foam (53 mg, 0.114 mmol, 71%). The structure was confirmed by NMR and mass spectrometry. MS m/z 467 ($M^+$+H).

EXAMPLE 42i

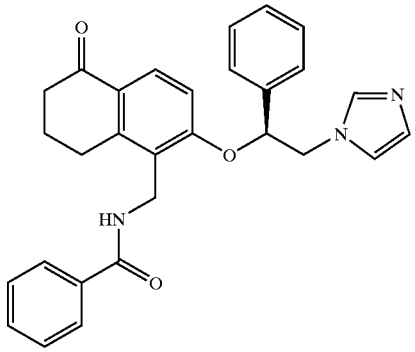

Synthesis of N-[2-((S)-2-Imidazol-1-yl-1-phenyl-ethoxy)-5-oxo-5,6,7,8-tetrahydro-naphthalen-1-ylmethyl]-benzamide (Compound 42i)

The procedure in Example 42h was followed using benzoic acid. Purification by chromatography (5% MeOH/CH$_2$Cl$_2$) gave the title compound as a tan foam (137 mg, 0.295 mmol). The structure was confirmed by NMR and mass spectrometry. MS m/z 466 (M$^+$+H).

EXAMPLE 42j

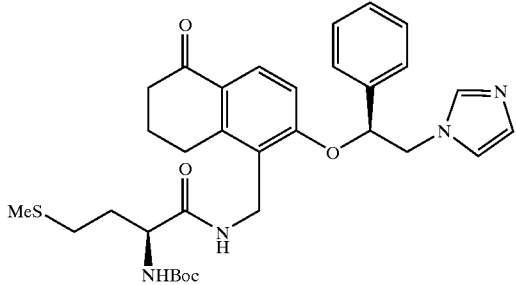

Synthesis of ((S)-1-{[2-((S)-2-Imidazol-1-yl-1-phenyl-ethoxy)-5-oxo-5,6,7,8-tetrahydro-napthalen-1-ylmethyl]-carbamoyl}-3-methylsulfanyl-propyl)-carbamic acid tert-butyl ester (Compound 42j)

The procedure in Example 42h was followed using N-Boc-L-Methionine. Purification by chromatography (5% MeOH/CH$_2$Cl$_2$) gave the title compound as a white foam (183 mg, 0.309 mmol, 67%). The structure was confirmed by NMR and mass spectrometry. MS m/z 593 (M$^+$+H).

EXAMPLE 42k

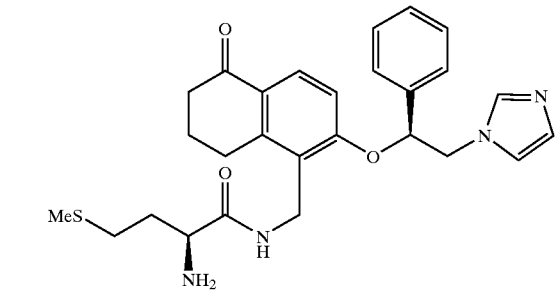

Synthesis of (S)-2-Amino-N-[2-((S)-2-imidazol-1-yl-1-phenyl-ethoxy)-5-oxo-5,6,7,8-tetrahydro-naphthalen-1-ylmethyl]-4-methylsulfanyl-butyramide (Compound 42k)

To a solution of ((S)-1-{[2-((S)-2-Imidazol-1-yl-1-phenyl-ethoxy)-5-oxo-5,6,7,8-tetrahydro-naphthalen-1-ylmethyl]-carbamoyl}-3-methylsulfanyl-propyl)-carbamic acid tert-butyl ester (153 mg, 0.258 mmol) in MeOH (1 mL) was added 4 M HCl in dioxane (3 mL). The mixture was concentrated after 3 h. The residue was neutralized with aqueous NaHCO$_3$ and the mixture was extracted with EtOAc. The organic layer was washed with brine, dried over Na$_2$SO$_4$ and concentrated to give a pale yellow oil. Purification by chromatography (5% MeOH/CH$_2$Cl$_2$ with 1% NH$_4$OH) afforded the title compound as a white foam (76 mg, 0.154 mmol, 60%).

The structure was confirmed by NMR and mass spectrometry. MS m/z 493 (M$^+$+H).

EXAMPLE 43

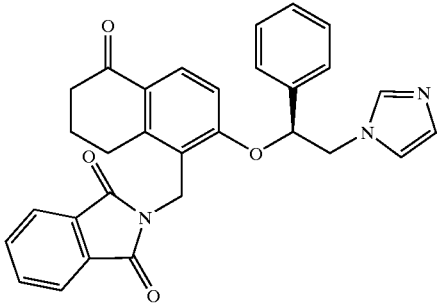

Synthesis of 2-[2-((S)-2-Imidazol-1-yl-1-phenyl-ethoxy)-5-oxo-5,6,7,8-tetrahydro-naphthalen-1-ylmethyl]-isoindole-1,3-dione (Compound 43)

1. 2-(2-Hydroxy-5-oxo-5,6,7,8-tetrahydro-naphthalen-1-ylmethyl)-isoindole-1,3-dione.

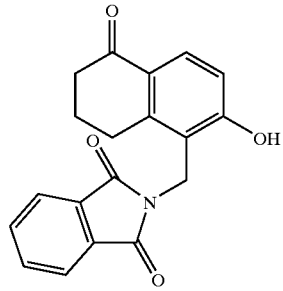

To a solution of 6-hydroxy-1-tetralone (4.87 g, 30.0 mmol) in concentrated H$_2$SO$_4$ (50 mL) was added N-(hydroxymethyl)phthalimide (5.32 g, 30.0 mmol) at RT. The reaction was exothermic. The mixture was stirred overnight and poured into ice. A precipitate formed and the mixture was filtered to give a brown solid. Several recrystalizations (EtOH and EtOAc) were attempted and 1.38 g of the title compound was obtained. The structure was confirmed by NMR and mass spectrometry. MS m/z 322 (M$^+$+H).

2. 2-[2-((S)-2-Imidazol-1-yl-1-phenyl-ethoxy)-5-oxo-5,6,7,8-tetrahydro-naphthalen-1-ylmethyl]-isoindole-1,3-dione To a slurry of 2-(2-Hydroxy-5-oxo-5,6,7,8-tetrahydro-naphthalen-1-ylmethyl)-isoindole-1,3-dione (862 mg, 2.68 mmol) in THF (17 mL) was added ®-2-imidazol-1-yl-1-phenyl-ethanol (606 mg, 3.22 mmol) and triphenylphospine (846 mg, 3.22 mmol). After 15 min, diethylazodicarboxylate (0.51 mL, 3.22 mmol) was added and the reaction became homogenous. The reaction was stirred for 2 days and concentrated to give a reddish-brown foam. Purification by chromatography (10–20% acetone/$CH_2Cl_2$ then 5% MeOH/$CH_2Cl_2$) afforded the title compound as a light brown foam (1.15 g, 2.35 mmol, 87%). The structure was confirmed by NMR and mass spectrometry. MS m/z 492 (M$^+$+H).

EXAMPLE 44

Synthesis of 6-((1S)-2-Imidazolyl-1-phenylethoxy)-5-(2-phenylpropyl)-2,3,4-trihydronaphthalen-1-one (Compound 44)

1. 3-(4,4-Dimethyl(1,3-oxazolin-2-yl))-1-methoxy-2-(2-phenylpropyl)benzene

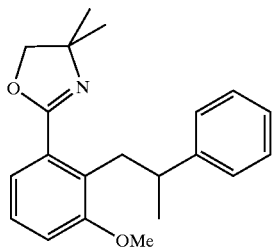

Under nitrogen, a solution of 12.0 g (0.051 mol) of 2-(2,3-dimethoxy-phenyl)-4,4-dimethyl-2-oxazoline (*J. Org. Chem.* 1978;43:1372) in 100 mL THF is treated dropwise with a Grignard solution prepared from 13.2 g (0.066 mol) of 1-bromo-2-phenylpropane and 1.6 g (0.066 g-atom) of magnesium in 50 mL THF. After the addition is complete, the solution is stirred at room temperature overnight. Saturated $NH_4Cl$ solution is added and the mixture extracted twice with $Et_2O$. The $Et_2O$ is washed with sat. NaCl, dried over $MgSO_4$, and the solvent removed under reduced pressure leaving the crude product. Chromatography on silica gel, eluting with $CHCl_3$, gives 9.86 g of impure product. This is taken up in $Et_2O$ and washed with 5% NaOH solution, then sat. NaCl. Drying over $MgSO_4$ and removal of the solvent under reduced pressure leaves 8.0 g (48.5% yield) of the pure product. The structure is confirmed by NMR and mass spectroscopy.

2. 3-Methoxy-2-(2-phenylpropyl)benzoic acid

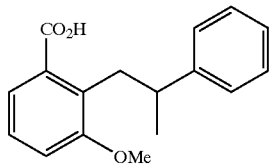

A mixture of 8.0 g (24.7 mmol) of the oxazoline in 500 mL of 18% HCl is heated at reflux for 3 days. The slightly hazy solution is extracted with $Et_2O$ and the $Et_2O$ washed with 5% NaOH. The NaOH solution is washed with $Et_2O$ and acidified to the Congo red end point with conc. HCl. The mixture is extracted with $Et_2O$ and the $Et_2O$ washed with sat. NaCl. Drying over $MgSO_4$ and removal of the solvent under reduced pressure gives 5.92 g (88.6% yield) of the product as an oil. The structure is confirmed by NMR and mass spectroscopy.

3. [3-Methoxy-2-(2-phenylpropyl)phenyl]methan-1-ol

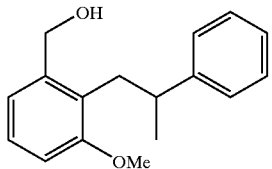

To a suspension of 1.7 g (43.8 mmol) of LAH in 50 mL THF is added dropwise a solution of 5.92 g (21.9 mmol) of the acid of step 2 in 50 mL THF. After stirring at room temperature for 0.5 hour, the solution is heated at reflux overnight. The mixture is decomposed with 1N $H_2SO_4$ and extracted with EtOAc. The EtOAc is washed with 1N $H_2SO_4$, $H_2O$, sat. $NaHCO_3$, and sat. NaCl. Drying over $MgSO_4$ and removal of the solvent under reduced pressure left 5.11 g (91% yield) of the product as an oil. The structure is confirmed by NMR and mass spectroscopy.

4. 3-(Chloromethyl)-1-methoxy-2-(2-phenylpropyl)benzene

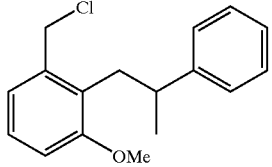

A solution of 5.11 g (19.9 mmol) of the alcohol of step 3 in 50 mL $CH_2Cl_2$ is treated with 5.9 g (29.9 mmol) of $BaCO_3$ and cooled in ice. This is then treated dropwise with 2.2 mL (29.9 mmol) of $SOCl_2$. After stirring at 0° for 15 minutes, the mixture is stirred at room temperature overnight. The mixture is diluted with $CH_2Cl_2$, filtered, washed with sat. $NaHCO_3$, and then with sat. NaCl. Drying over $MgSO_4$ and removal of the solvent under reduced pressure leaves 4.85 g (88.7% yield) of the product as an oil. The structure is confirmed by NMR and mass spectroscopy.

5. Ethyl (2Z)-3-[3-methoxy-2-(2-phenylpropyl)phenyl]prop-2-enoate

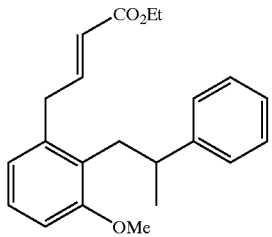

Under nitrogen, a solution of 4.85 g (17.7 mmol) of the chloromethyl compound of step 4, 8.5 mL (35.3 mmol) of tributylamine, and 2.9 mL (26.5 mmol) of ethyl acrylate is treated with 80 mg (0.4 mmol) of $Pd(Oac)_2$ and heated at 100° C. overnight. An additional 2.0 mL of ethyl acrylate and 80 mg $Pd(Oac)_2$ is added and the mixture heated at 100° C. for an additional night. The mixture is diluted with $Et_2O$ and washed twice with 1N HCl, then with $H_2O$, sat.

NaHCO₃, and sat. NaCl. Drying over MgSO₄ and removal of the solvent under reduced pressure gives the crude product. Chromatography on silica gel, eluting with hexane/EtOAc (95:5) gives 2.73 g (45.7% yield) of the product as an oil. The structure is confirmed by NMR and mass spectroscopy. MS: m/z 339 [M+H]⁺.

6. Ethyl 3-[3-methoxy-2-(2-phenylpropyl)phenyl]propanoate

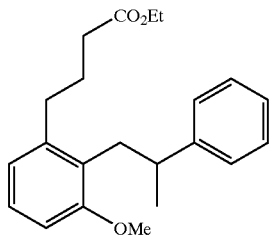

A solution of 2.67 g (7.9 mmol) of the unsaturated ester of step 5 in 50 mL EtOH is treated with 0.5 g of 10% Pd/C and reduced with hydrogen at 25° C. and 50 psi. The mixture is filtered and the solvent removed under reduced pressure giving 2.63 g (96% yield) of the product as a clear oil. The structure is confirmed by NMR and mass spectroscopy.

7. 3-[3-Methoxy-2-(2-phenylpropyl)phenyl]propanoic acid

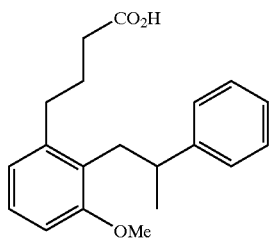

A solution of 2.63 g (7.7 mmol) of the ester of step 6 in 30 mL MeOH is treated with a solution of 1.0 g (23.2 mmol) of NaOH in 10 mL H₂O and the reaction mixture is heated at reflux for 1 hour. The solvent is removed under reduced pressure and the residue taken up in H₂O, and acidified to the Congo red end point with dil. HCl. The mixture is extracted with EtOAc and the EtOAc washed with sat. NaCl. Drying over MgSO₄ and removal of the solvent under reduced pressure gives 2.41 g (100% yield) of the product as an oil. The structure is confirmed by NMR and mass spectroscopy.

8. 6-Methoxy-5-(2-phenylpropyl)-2,3,4-trihydronaphthalen-1-one

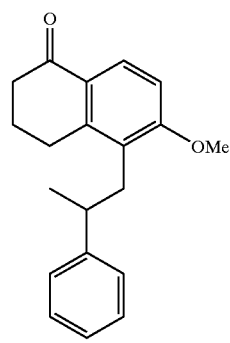

A solution of 2.41 g (7.9 mmol) of the acid of step 7 in 30 mL CH₂Cl₂ is cooled in an ice bath and treated dropwise with 7.0 mL of trifluoracetic anhydride. The solution is kept at 0° C. for 1 hour, then at room temperature for 1 hour. The solution is diluted with Et₂O and 5% NaOH is added cautiously until the mixture is basic. The layers are separated and the organic phase washed with 5% NaOH, then sat. NaCl. Drying over MgSO₄ and removal of the solvent under reduced pressure leaves 2.75 g of the crude product. This is taken up in 20 mL MeOH and 10 mL dioxane and treated with 6 mL of 2N NaOH. After stirring for 1 hour at room temperature, the mixture is diluted with Et₂O and the layers separated. The Et₂O is washed with sat. NaCl, dried over MgSO₄, and the solvent removed under reduced pressure leaving 2.27 g (100% yield) of the product as an oil which crystallizes on standing. The structure is confirmed by NMR and mass spectroscopy.

9. 6-Hydroxy-5-(2-phenylpropyl)-2,3,4-trihydronaphthalen-1-one

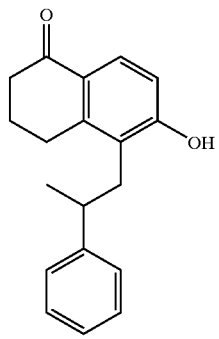

Under nitrogen, a solution of 2.27 g (7.7 mmol) of the methoxy compound of step 8 in 18 mL DMSO is treated with 1.9 g (38.6 mmol) of crushed NaCN and the solution is heated at 180° C. overnight. The mixture is poured into H₂O and acidified to the Congo red end point with dil. HCl. The brown solid that forms is collected and washed with H₂O. This is taken up in Et₂O with a small quantity of acetone and extracted with 5% NaOH. The NaOH solution is washed with Et₂O and the NaOH solution acidified with dil. HCl. The mixture is extracted with EtOAc and the EtOAc washed with sat. NaCl. Drying over MgSO₄ and removal of the solvent under reduced pressure left 1.7 g (78.7% yield) of the product as a brown oil. The structure is confirmed by NMR and mass spectrometry.

10. 6-((1S)-2-Imidazolyl-1-phenylethoxy)-5-(2-phenylpropyl)-2,3,4-trihydronaphthalen-1-one Under nitrogen, a solution of 1.7 g (6.1 mmol) of the phenol, 1.3 g (6.7 mmol) of ®-1-phenyl-2-(1-imidazoyl)ethanol, and 1.91 g (7.3 mmol) of triphenylphosphine in 30 mL THF is treated dropwise over 15 minutes with a solution of 1.2 mL (7.3 mmol) of diethyl azodicarboxylate in 10 mL THF. After stirring at room temperature for 3 days, the mixture is diluted with CH₂Cl₂ and washed with H₂O, then sat. NaCl. Drying over MgSO₄ and removal of the solvent under reduced pressure leaves 3.51 g of the crude product. Two chromatographies on silica gel, eluting with CH₂Cl₂/acetone (80:20) gives 0.75 g (27.5% yield) of final product (Compound 44) as a white foam.

Calcd for C₃₀H₃₀N₂O·0.2 acetone (MW 462.17):

| Theory: | C, 79.52 | H, 6.80 | N, 6.06. |
|---|---|---|---|
| Found: | C, 79.17 | H, 6.70 | N, 6.36. |

EXAMPLE 44a

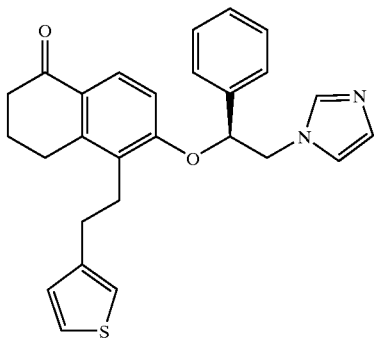

Synthesis of 6-((S)-2-Imidazol-1-yl-1-phenyl-ethoxy)-5-(2-thiophen-3-yl-ethyl)-3,4-dihydro-2H-naphthalen-1-one (Compound 44a)

1-3. [3-Methoxy-2-(2-thiophen-3-yl-ethyl)-phenyl]-methanol

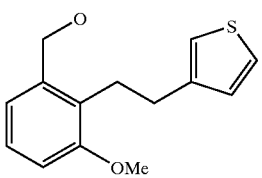

Using the method of example 44, steps 1–3, with 2-(2,3-dimethoxyphenyl)-4,4-dimethyl-2-oxazoline (J. Org. Chem. 43, 1372 (1978) and the Grignard reagent prepared from 1-bromo-2-(3-thiophenyl)ethane and magnesium the title compound was prepared and the structure confirmed by NMR spectroscopy.

4. 3-[2-(2-Bromomethyl-6-methoxy-phenyl)-ethyl]-thiophene

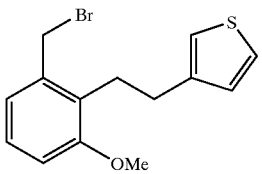

A solution of 20.8 g (83.8 mmol) of [3-methoxy-2-(2-thiophen-3-yl-ethyl)phenyl]-methanol in 200 mL THF was treated with 16.6 g (83.8 mmol) of $BaCO_3$ and cooled in ice. This was then treated dropwise rapidly with 6.0 mL (62.8 mmol) of $PBr_3$. After stirring at 0° for 15 min., the mixture was stirred at room temperature overnight. The mixture was diluted with EtOAc, separated and the aqueuos layer washed with EtOAc. The combined organic layers were washed with water, sat. $NaHCO_3$, and then with sat. NaCl. Drying over $MgSO_4$ and removal of the solvent under reduced pressure left 27.2 g (99% yield) of the product as an oil. The structure was confirmed by NMR and mass spectroscopy.

5. 2-[3-Methoxy-2-(2-thiophen-3-yl-ethyl)-phenyl]-malonic acid dimethyl ester

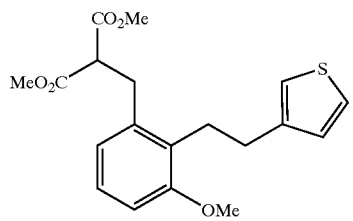

To a solution of 75 mL MeOH was added 2.0 g (83.6 mmol) of sodium pellets, when all the sodium was consumed, 9.6 mL (83.6 mmol) of dimethyl malonate was added. After stirring at room temperature for 0.5 h, a solution of 26.0 g (83.6 mmol) of 3-[2-(2-Bromomethyl-6-methoxy-phenyl)-ethyl]-thiophene in 100 mL MeOH was added dropwise. After stirring for 15 min. at room temperature the mixture was refluxed overnight. The mixture diluted with EtOAc and washed with 1N HCl, $H_2O$, sat. $NaHCO_3$, and sat. NaCl. Drying over $MgSO_4$ and removal of the solvent under reduced pressure left 27.9 g (92% yield) of a golden oil. The structure was confirmed by NMR and mass spectroscopy.

6. [3-Methoxy-2-(2-thiophen-3-yl-ethyl]-phenyl-acetic acid

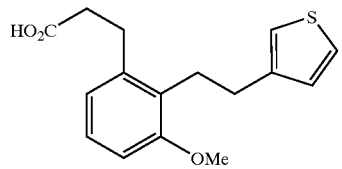

A solution of 27.9 g (7.7 mmol) of 2-[3-Methoxy-2-(2-thiophen-3-yl-ethyl)-phenyl]-malonic acid dimethyl ester in 150 mL MeOH and 150 mL dioxane was treated with a solution of 15 g (0.385 mol) of NaOH in 200 mL $H_2O$ and heated at reflux overnight. The solvent was reduced to half volume, diluted with $H_2O$ and extracted twice with $Et_2O$. The aqueous layer acidified to the Congo red point with dil. HCl. The mixture was extracted with EtOAc and the EtOAc washed with sat. NaCl. Drying over $MgSO_4$ and removal of the solvent under reduced pressure gave 25.95 g of a yellow oil. The oil was taken up in 200 mL dioxane and heated at reflux overnight. Removal of solvent then afforded a 21.4 g (96% yield) of a brown oil. The structure was confirmed by NMR and mass spectroscopy.

7. 2-[3-Methoxy-2-(2-thiophen-3-yl-ethyl)-phenyl]-ethanol

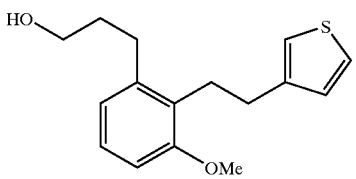

Lithium aluminum hydride (5.5 g, 0.147 mol) was suspended in 80 mL of THF. To the suspension was added dropwise a solution of [3-Methoxy-2-(2-thiophen-3-yl-ethyl)-phenyl]-acetic acid (21.4 g, 0.074 mol) in THF. The mixture was stirred at room temperature for 15 min. then refluxed for 5 h. The mixture was then adjusted to pH 8 by the addition of 1N sulfuric acid and diluted with EtOAc. The organic phase was washed with $1NH_2SO_4$, $H_2O$, saturated sodium bicarbonate, brine and dried over anhydrous magnesium sulfate. The solution was concentrated to yield a golden oil (18.18 g, 89% yield) which crystallized on standing. The structure was confirmed with MS and NMR spectroscopy.

8. 3-{2-[2-(2-Bromo-ethyl)-6-methoxy-phenyl]-ethyl}-thiophene

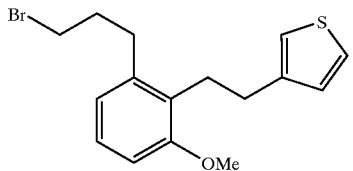

A solution of 18.18 g (0.0658 mol) of 2-[3-Methoxy-2-(2-thiophen-3-yl-ethyl)-phenyl]-ethanol in 300 mL $CH_2Cl_2$ was treated with 17.43 g (0.0658 mol) of triphenylphosphine followed by 11.95 g (0.0658 mol) of recrystallized N-bromosuccinimide which was added in portions. After stirring at room temperature overnight, the solution was filtered through a plug of flash silica gel. The filtrate was concentrated to a golden oil and taken up in $Et_2O$/hexane. The solid triphenylphosphine oxide was filtered and the solution concentrated and $Et_2O$/hexanne treatment repeated to afford a golden oil (20.58 g, 92% yield). The structure was confirmed by NMR and mass spectroscopy.

9. 3-[3-Methoxy-2-(2-thiophen-3-yl-ethyl)-phenyl]-propionitrile

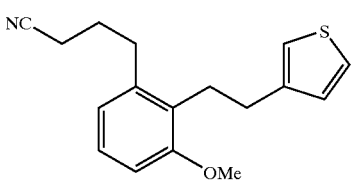

A solution of 20.58 g (0.0607 mol) of 3-{2-[2-(2-Bromo-ethyl)-6-methoxyphenyl]-ethyl}-thiophene in 100 mL acetone and 100 mL EtOH was treated with a solution of 4.7 g (0.0728 mol) of KCN in 50 mL $H_2O$ and heated at reflux overnight. The mixture was concentrated and diluted with EtOAc; washed 2 times with $H_2O$, then sat. NaCl. Drying over $MgSO_4$ and removal of the solvent under reduced pressure left 18.2 g (100% yield) of the product as a golden oil. The structure was confirmed by NMR and mass spectroscopy.

10. 3-[3-Methoxy-2-(2-thiophen-3-yl-ethyl)-phenyl]-propionic acid

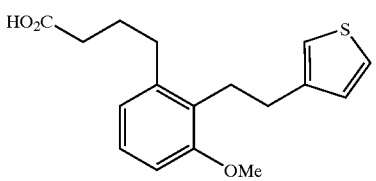

A solution of 17.3 g (0.0606 mol) of 3-[3-Methoxy-2-(2-thiophen-3-yl-ethyl)-phenyl]-propionitrile in 200 mL EtOH was treated with a solution of 13.0 g (0.324 mol) of NaOH in 70 mL $H_2O$ and heated at reflux overnight. The solvent was removed under reduced pressure and the residue taken up in $H_2O$ and washed with $CH_2Cl_2$ then $Et_2O$. The mixture was acidified with dil. HCl to congo red point and extracted 2 times with $CH_2Cl_2$. The organic layer was washed with sat. NaCl. Drying over $MgSO_4$ and removal of the solvent under reduced pressure left 14.34 g (78% yield) of the product as a golden oil. The structure was confirmed by NMR and mass spectroscopy.

11–13. (S)-6-(2-Imidazol-1-yl-1S-phenyl-ethoxy)-5-[2-(3-thiophenyl)-ethyl]-3,4-dihydro-2H-naphthalen-1-one Using the procedures of example 44 steps 8–10 the title compound was prepared from 3-[3-Methoxy-2-(2-thiophen-3-yl-ethyl)-phenyl]-propionic acid. The product was isolated as a white fluffy powder 1.21 g (20% yield 3 steps).

Calcd for $C_{27}H_{26}N_2O_2S.HCl.0.6H_2O$ (MW 489.77) C, 66.21; H, 5.80; N, 5.72. Found C, 66.16; H, 5.73; N, 5.41.

EXAMPLE 44b

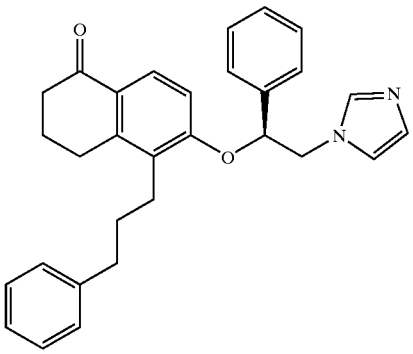

Synthesis of 6-((S)-2-Imidazol-1-yl-1-phenyl-ethoxy)-5-(3-phenyl-propyl)-3,4-dihydro-2H-naphthalen-1-one (Compound 44b)

The title compound was prepared according to the procedure for example 44a steps 1–13, with 2-(2,3-dimethoxyphenyl)-4,4-dimethyl-2-oxazoline (J. Org. Chem. 43, 1372 (1978) and the Grignard reagent prepared from 1-bromo-3-phenyl-propane and magnesium. The title compound was obtained as a tan foam and the structure confirmed by NMR spectroscopy. Calcd for $C_{30}H_{30}N_2O_2.0.1CH_2Cl_2$ (MW 459.05) C, 78.75; H, 6.63 N, 6.10. Found C, 78.72; H, 6.65 N, 5.95.

EXAMPLE 45

Synthesis of 6-((1S)-2-imidazolyl-1-phenylethoxy)-5-benzyl-2,3,4-trihydro-naphthalen-one (Compound 45)

1. N-(2-Hydroxy-1,1-dimethylethyl)-3-methoxybenzamide

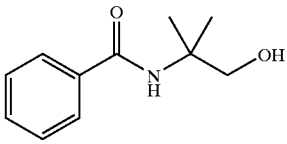

2-Amino-2-methyl-1-propanol (80.23 g, 0.9 mol) is dissolved in dichloromethane (180 mL) and cooled to 5° C., followed by the addition of 3-methoxybenzyl chloride (76.8 g, 0.45 mol) in dichloromethane (150 mL) over 1 hour at 5° C. The mixture is warmed to 25° C. over 3 hours, filtered, and the filtrate is evaporated to an oil. The oil is taken up into ethyl ether, washed with 1N citric acid and then brine, and dried over anhydrous magnesium sulfate. The suspension is filtered and evaporated to an oil which solidifies (93.0 g, 93% yield). NMR spectrum is consistent with structure.

MS: APCI: M+1, 224.1 (M: 223.3).

2. 2-(3-Methoxyphenyl)-4,4-dimethyloxazolidine

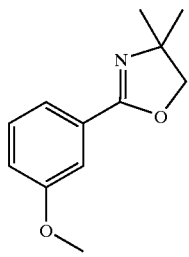

To N-(2-Hydroxy-1,1-dimethylethyl)-3-methoxybenzamide (93 g, 0.42 mol) is added thionyl chloride (98 g, 1.25 mol) in portions over 1 hour. After stirring for 30 minutes, the excess thionyl chloride is evaporated in vacuo giving a solid. With cooling, the solid is dissolved in a mixture of ethyl ether (1 L) and 20% NaOH solution. The mixture is agitated and the phases separated. The aqueous phase is extracted with ethyl ether, which is combined with the preceding ether phase. This is washed with brine, dried over anhydrous magnesium sulfate, filtered and evaporated to an oil (82 g, 96% yield). NMR spectrum is consistent with structure.

3. 6-(4,4-Dimethyl(1,3-oxazolin-2-yl))-2-methoxyphenyl phenyl ketone

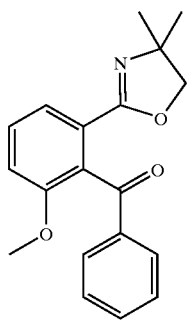

2-(3-Methoxyphenyl)-4,4-dimethyloxazolidine (30.79 g, 0.15 mol) is dissolved in dry tetrahydrofuran (600 mL) followed by cooling to −60° C. To the mixture is added n-butyllithium, (1.6 M in hexane, 100 mL) over 10 minutes. The mixture is stirred at −50° C. for 2 hours, followed by cooling to −60° C. and the addition of a solution of benzoyl chloride (22 g, 0.15 mol) in tetrahydrofuran (100 mL) over 10 minutes. After stirring for 3 hours at −50° C., the mixture is evaporated to a solid and dissolved in a mixture of ethyl acetate and water. The phases are separated, and the organic phase is washed with brine, dried over anhydrous magnesium sulfate, filtered and the filtrate reduced in volume in vacuo. Addition of ethyl ether gives a crystalline precipitate that is filtered and dried to a white solid (34 g, 73% yield). NMR spectrum is consistent with structure.

MS: APCI: M+1, 310.3 (M: 309.4).

4. 2-Benzoyl-3-methoxybenzoic acid

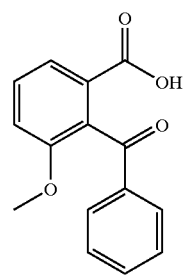

6-(4,4-Dimethyl(1,3-oxazolin-2-yl))-2-methoxyphenyl phenyl ketone (34 g, 0.11 mol) is dissolved in 18% HCl (700 mL) and heated to 110° C. for 18 hours. A suspended solid is filtered off. The filtrate is extracted with ethyl acetate, and the previously filtered solid is dissolved in the ethyl acetate extract. The organic phase is washed with 1N citric acid and then brine, and dried over anhydrous magnesium sulfate. The suspension is filtered and evaporated to a solid (22.1 g, 78% yield). NMR spectrum is consistent with structure. MS: APCI: M+1, 257.1 (M: 256.3).

5. 2-Benzyl-3-methoxy-benzoic acid

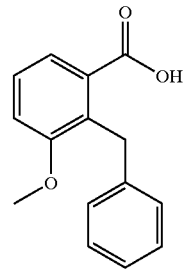

To methanol (500 mL) is added 2-benzoyl-3-methoxybenzoic acid (21.9 g, 0.085 mol) and 20% palladium on carbon catalyst (2.0 g), followed by pressurization of the mixture to 47 psi with hydrogen gas. After 23 hours, the mixture is filtered and the filtrate is evaporated to 100 mL in volume in vacuo. Addition of ethyl ether gives a crystalline solid which is filtered and dried (13 and 14 g, 63% yield). NMR spectrum is consistent with structure. MS: APCI: M−1, 241.0 (M: 242.3).

6. (2-Benzyl-3-methoxyphenyl)methanol

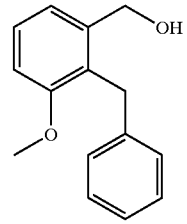

A solution of 6-((S)-2-imidazol-1-yl-1-phenylethoxy)-5-phenethyl-2,3,4-trihydronaphthalen-1-one (13.5 g, 0.056 mol) in tetrahydrofuran (100 mL) is added to a solution of lithium aluminum hydride (4.27 g, 0.112 mol) in tetrahydrofuran (250 mL) over 30 minutes. The mixture is stirred for 2 hours followed by heating to 70° C. for 3 hours and stirring at 25° C. for 18 hours. The mixture is then cooled to −40° C., and the pH is adjusted to 8 by the addition of 6N sulfuric acid. The resulting solid is filtered, washed with ethyl acetate and the filtrates combined. The organic phase is evaporated to an oil, dissolved in ethyl ether, washed with saturated sodium bicarbonate and then brine, and dried over anhydrous magnesium sulfate. The suspension is filtered and evaporated to a solid (12.5 g, 98% yield). NMR spectrum is consistent with structure. MS: APCI: M+1, 516.1 (dimer) (M: 228.3).

7. 3-(Chloromethyl)-1-methoxy-2-benzylbenzene

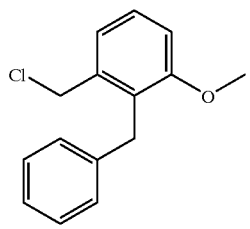

(2-Benzyl-3-methoxyphenyl)methanol (12.5 g, 0.055 mol) and barium carbonate (14.5 g, 0.073 g) are suspended in dichloromethane (120 mL) followed by cooling to 2° C. A solution of thionyl chloride (5.4 mL, 0.073 mol) in dichloromethane (100 mL) is added. The mixture is stirred at 25° C. overnight, filtered, and evaporated to an oil. Addition of ethyl ether and hexane gives a solid (11.74 g, 86.5% yield). NMR spectrum is consistent with structure. MS: APCI: M+1, 246.1 (M: 246.7).

8. Ethyl (2E)-4-[3-methoxy-2-benzylphenyl]but-2-enoate

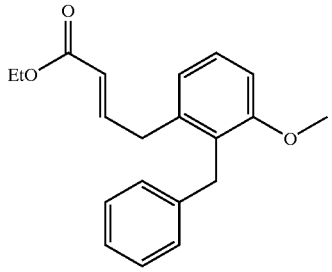

1-(Chloromethyl)-3-methoxy-2-(phenylmethyl) benzene (13.5 g, 0.055 mol), tri-n-butylamine (36 mL), ethyl acrylate (18 mL) and palladium acetate (0.247 g, 1.23 mmol) are mixed and sparged with nitrogen gas, followed by heating to 100° C. for 18 hours. To the mixture is then added palladium acetate (0.5 g, 2.5 mmol) and ethyl acrylate (9 mL) followed by additional heating at 100° C. for 18 hours. The mixture is then filtered at 45[2 to remove catalyst and the filtrate is taken up into ethyl ether. The solution is washed with 1N HCl and then brine before being dried over anhydrous magnesium sulfate. The filtrate is evaporated to an oil that is purified by silica gel chromatography, eluted with a mixture of ethyl acetate/hexane (15:85). The product is recovered as a syrup (6.8 g, 40% yield). NMR spectrum is consistent with structure. MS: APCI: M+1, 311.1 (M: 310.4).

9. Ethyl 4-(2-benzyl-3-methoxyphenyl)butanoate

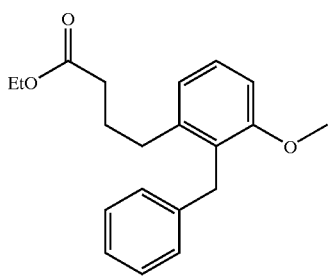

Ethyl (2E)-4-[3-methoxy-2-benzylphenyl]but-2-enoate (6.8 g, 0.022 mol), and 10% palladium on carbon catalyst (1.0 g) are added to absolute ethanol (100 mL) and pressurized to 51 psi with hydrogen gas for 22 hours. The mixture is filtered and evaporated to a crude oil (6.8 g) which is used in the following synthesis without further purification.

10. 4-(2-Benzyl-3-methoxyphenyl)butanoic acid

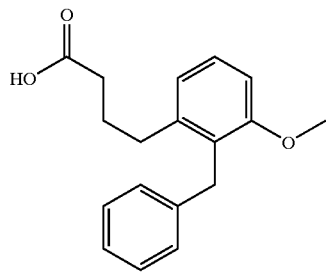

Ethyl 4-(2-benzyl-3-methoxyphenyl)butanoate (6.58 g, 0.021 mol) and sodium hydroxide (4.9 g, 0.122 mol) are added to a mixture of water (20 mL) and dioxane (30 mL) followed by heating at 80° C. for 1 hour. The mixture is evaporated to a solid, upon which water is added, followed by evaporation in vacuo to a suspension. The solid is filtered, and the filtrate is washed with ethyl ether. The aqueous phase is acidified to pH 1 with conc. HCl and extracted with ethyl ether. The ether is washed with brine, dried over anhydrous magnesium sulfate, and filtered.

The filtrate is evaporated to a crystalline solid (4.83 g, 81% yield). NMR spectrum is consistent with structure. MS: APCI: M−1, 281.3 (M: 284.4).

11. 5-Benzyl-6-methoxy-2,3,4-trihydronaphthalen-1-one

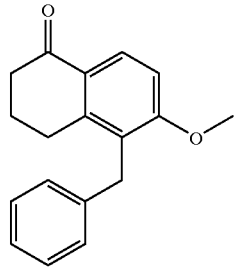

4-(2-Benzyl-3-methoxyphenyl)butanoic acid (4.39 g, 0.015 mol) is dissolved in ethanol-free chloroform (30 mL) and polyphosphate ester (prepared as described in *J. Organic Chemistry*, 1969;34(9):2666) (8 g) is added. The flask is sealed and kept in the dark for 18 hours at 25° C. The mixture is extracted with water, and the chloroform phase is washed with brine, dried over anhydrous magnesium sulfate, filtered, and evaporated to a solid. The solid is recrystallized from an ethyl ether/hexane mixture giving a solid (3.92 g, 95% yield). NMR spectrum is consistent with structure. MS: APCI: M+1, 267.1 (M: 266.3).

12. 5-Benzyl-6-hydroxy-2,3,4-trihydronaphthalen-1-one

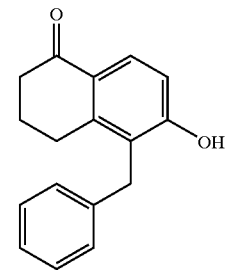

5-Benzyl-6-methoxy-2,3,4-trihydronaphthalen-1-one (3.86 g, 0.014 mol) and sodium cyanide (3.55 g, 0.072 mol) is dissolved dimethylsulfoxide (25 mL), followed by heating at 180° C. for 5 hours. The mixture is cooled to 100° C., poured into 150 g of ice and acidified to pH 1 with conc. HCl. The mixture is repeatedly extracted with ethyl ether, washed with brine, dried over anhydrous magnesium sulfate and filtered. The filtrate is concentrated in vacuo giving a solid upon addition of hexane (1.85 g, 51% yield). NMR spectrum is consistent with structure. MS: APCI: M+1, 253.1 (M: 252.3).

13. 6-((1S)-2-Imidazolyl-1-phenylethoxy)-5-benzyl-2,3,4-trihydro-naphthalen-1-one To tetrahydrofuran (35 mL) is added 5-benzyl-6-hydroxy-2,3,4-trihydronaphthalen-1-one (1.82 g, 7.2 mmol), (R)-2-imidazol-1-yl-1-phenylethanol (1.49 g, 7.9 mmol) and triphenylphosphine (2.55 g, 9.7 mmol). A solution of diethylazodicarboxylate (1.69 g, 9.7 mmol) in tetrahydrofuran (15 mL) is added over 30 minutes. After stirring for 18 hours at 25° C., the mixture is evaporated in vacuo and the residue is suspended in ethyl ether and 1N citric acid, washed exhaustively with ethyl ether and the pH adjusted to 5.5 with 6N NaOH. The aqueous phase is extracted with ethyl ether, separated, washed with brine, dried over anhydrous magnesium sulfate and filtered. The filtrate is evaporated to a solid which is purified by silica gel chromatography eluted with chloroform giving a solid (Compound 45) (1.32 g, 43% yield). NMR spectrum is consistent with structure.

MS: APCI: M+1, 423.1 (M: 422.5). Calcd. For $C_{28}H_{26}N_2O_2$:

| | | | | |
|---|---|---|---|---|
| Theory: | C 76.76, | H 5.98, | N 6.36, | Cl 3.62. |
| Found: | C 76.71, | H 6.25, | N 6.40, | Cl 3.39. |

EXAMPLE 46

Synthesis of 6-((1S)-2-Imidazolyl-1-phenylethoxy)-5-phenoxy-2,3,4-trihydronaphthalen-1-one (Compound 46)

1. 1-(Chloromethyl)-2,3-dimethoxybenzene

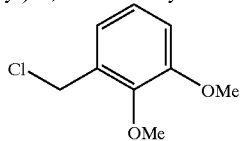

2,3-Dimethoxybenzyl alcohol (112.5 g, 0.677 mol) is dissolved in ethyl ether (390 mL) and purged with anhydrous HCl gas. Upon cooling to 20° C., thionyl chloride (60 mL, 0.68 mol) is added with vigorous stirring over 30 minutes. The solution is washed with cold brine, saturated sodium bicarbonate solution, and brine. The organic phase is dried over anhydrous magnesium sulfate, filtered, and concentrated in vacuo to an oil (125 g). The oil is distilled at 3 mm Hg, Bp. 105–112° C. (99 g, 79% yield). NMR spectrum is consistent with structure.

2. Ethyl (2E)-4-(2,3-dimethoxyphenyl)but-2-enoate

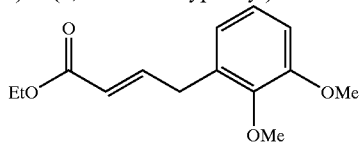

1-(Chloromethyl)-2,3-dimethoxybenzene (87.3 g, 0.47 mol), ethyl acrylate (77 mL, 0.709 mol), and palladium acetate (2.27 g, 9.4 mmol) are added to tri-n-butylamine (175 g, 0.946 mol) and heated to 100° C. for 18 hours. The mixture is filtered through celite, and the filtrate is partitioned between ethyl ether and 1N citric acid. The ether phase is separated and washed with 1N citric acid to remove the amine, washed with brine, dried over anhydrous magnesium sulfate, and filtered. The filtrate is evaporated to an oil (109.2 g, 92% yield). NMR spectrum is consistent with structure.

3. Ethyl 4-(2,3-dimethoxyphenyl)butenoate

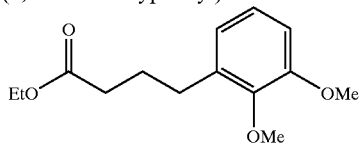

Ethyl (2E)-4-(2,3-dimethoxyphenyl)but-2-enoate (109.2 g, 0.436 mol) and 10% palladium on carbon catalyst (10 g) are added to absolute ethanol (1 L) and pressurized to 47 psi for 18 hours. The mixture is filtered, and the filtrate is evaporated to an oil (106.4 g, 96% yield). NMR spectrum is consistent with structure. MS: APCI: M+1, 253.2 (M: 252.3).

4. 4-(2,3-Dimethoxyphenyl)butanoic acid

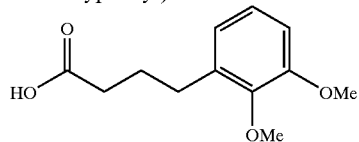

Ethyl 4-(2,3-dimethoxyphenyl)butenoate (106.4 g, 0.42 mol) and 1N sodium hydroxide (800 mL) are added to methanol (400 mL) followed by heating at reflux for 2 hours. The mixture is evaporated to an oil, which is washed with ethyl ether and acidified to pH 1 with conc. HCl. The mixture is then extracted with ethyl ether, washed with brine, dried over anhydrous magnesium sulfate, and filtered. The filtrate is evaporated to a crystalline solid (90.36 g, 96% yield). NMR spectrum is consistent with structure. MS: APCI: M+1, 225.2 (M: 224.3).

5. 5,6-Dimethoxy-3,4-dihydro-2H-naphthalen-1-one

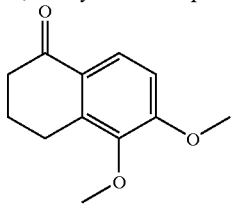

4-(2,3-Dimethoxyphenyl)butanoic acid (90.1 g, 0.40 mol) is dissolved in ethanol-free chloroform (400 mL) and polyphosphate ester (*J. Organic Chemistry*, 1969;34(9):2666) (225 g) is added. The flask is sealed and kept in the dark for 42 hours at 25° C. The mixture is extracted with water, and the chloroform phase is washed with brine, dried over anhydrous magnesium sulfate, filtered, and evaporated to a solid (70.5 g, 85% yield). NMR spectrum is consistent with structure. MS: APCI: M+1, 207 (M: 206.2).

6. 5-Hydroxy-6-methoxy-2,3,4-trihydronaphthalen-1-one 5,6-Dimethoxy-2,3,4-trihydronaphthalen-1-one (73.3 g, 0.36 mol) and methionine (116.6 g, 0.8 mol) are added to 98% methanesulfonic acid (920 mL) followed by stirring at 25° C. for 66 hours. The mixture is poured into ice water (4 L) with rapid stirring, giving a solid that is filtered, washed with water, and allowed to air dry. The solid is dissolved in warm ethyl acetate, washed with brine, dried over anhydrous magnesium sulfate, and filtered. The filtrate is evaporated to give a solid upon addition of ethyl ether (45.23 g, 66% yield). NMR spectrum is consistent with structure. MS: APCI: M+1, 193.1 (M: 192.2).

7. 5-Phenoxy-6-methoxy-2,3,4-trihydronaphthalen-1-one

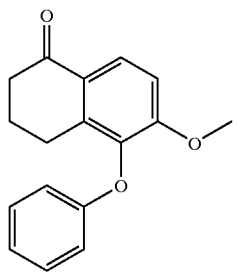

5-Hydroxy-6-methoxy-2,3,4-trihydronaphthalen-1-one (6.96 g, 0.038 mol), copper acetate (10.54 g, 0.058 mol), triphenylbismuth (18.3 g, 0.042 mol), and triethylamine (5.78 mL, 0.042 mol) are added to tetrahydrofuran (75 mL) followed by heating to 50° C. for 10 hours and stirring at 25° C. for 48 hours. The mixture is filtered, and the filtrate is evaporated to an oil which is taken up into a mixture of ethyl ether and water. The organic phase is washed with 1N sodium hydroxide, brine, 1N HCl, and brine again. The organic phase is dried over anhydrous magnesium sulfate, filtered, and evaporated to an oil which is crystallized from a mixture of ethyl acetate and ethyl ether (6.0 g, 59% yield). NMR spectrum is consistent with structure. MS: APCI: M+1,269.1 (M: 268.3).

8. 5-Phenoxy-6-hydroxy-2,3,4-trihydronaphthalen-1-one

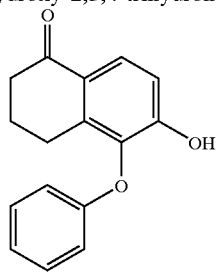

5-Phenoxy-6-methoxy-2,3,4-trihydronaphthalen-1-one (6.0 g, 0.022 mol) and sodium cyanide (5.48 g, 0.11 mol) is dissolved in dimethylsulfoxide (25 mL), followed by heating at 180° C. for 4 hours. The mixture is poured into ice and acidified to pH 1 with conc. HCl. The mixture is repeatedly extracted with ethyl ether, which is washed with brine, dried over anhydrous magnesium sulfate, and filtered. The filtrate is concentrated in vacuo giving a solid (3.53 g, 62% yield). NMR spectrum is consistent with structure. MS: APCI: M+1, 255.1 (M: 254.3).

9. (S)-6-(2-Imidazol-1-yl-1-phenyl-ethoxy)-5-phenoxy-3,4-dihydro-2H-naphthalen-1-one To tetrahydrofuran (35 mL) is added 5-phenoxy-6-hydroxy-2,3,4-trihydronaphthalen-1-one (1.8 g, 7.1 mmol), (R)-2-imidazol-1-yl-19 -phenylethanol (1.48 g, 7.9 mmol) and triphenylphosphine (2.59 g, 10 mmol). A solution of diethylazodicarboxylate (1.66 g, 9.6 mmol) in tetrahydrofuran (15 mL) is added over 30 minutes. After stirring for 3 hours at 25° C., the mixture is evaporated in vacuo, and the residue is suspended in ethyl ether and 1N citric acid, washed exhaustively with ethyl ether, and the pH adjusted to 6 with 4N NaOH. The aqueous phase is extracted with ethyl acetate, which is separated, washed with brine, dried over anhydrous magnesium sulfate, and filtered. The filtrate is evaporated to a solid which is purified by silica gel chromatography eluted with chloroform giving a solid (Compound 46) (1.38 g, 46% yield). NMR spectrum is consistent with structure.

MS: APCI: M+1, 425.1 (M: 424.5). Calcd. for $C_{27}H_{24}N_2O_3$:

| | | | | |
|---|---|---|---|---|
| Theory: | C 73.71, | H 5.50, | N 6.33, | Cl 3.60. |
| Found: | C 76.57, | H 5.85, | N 6.65, | Cl 2.37. |

EXAMPLE 47

Synthesis of 6-((1S)-2-Imidazolyl-1-phenylethoxy)-4-(3-chlorophenyl)-2,3,4-trihydronaphthalen-1-one (Compound 47)

1. 1-(3-Chlorophenyl)-7-methoxy-1,2,3,4-tetrahydronaphthol

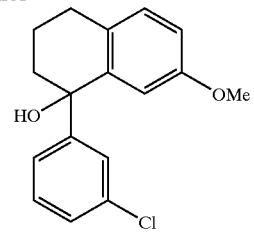

Milligram shavings (1.65 g, 0.68 mol) are suspended in diethyl ether (60 mL). A small quantity of 12 crystals and 3-bromochlorobenzene are added. The reaction mixture is refluxed for 2 hours before the addition of 7-methoxy-1-tetralone (10 g, 0.057 mol). The reaction is refluxed for an additional 2 hours. 1N HCl is poured into the flask and the layers two resulting layers are separated. The organic layer is washed with 1N HCl and then brine, dried over $MgSO_4$, and the solvent removed in vacuo. Chromatography using 20% hexane/DCM to 10% hexane/DCM affords a clear colorless oil (8.5 g, 52% yield). NMR (CDCl₃); MS: APCI 271 [M−17].

2. 4-(3-Chlorophenyl)-6-methoxy-1,2-dihydronaphthalene

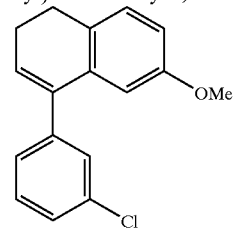

1-(3-Chlorophenyl)-7-methoxy-1,2,3,4-tetrahydronaphthol (8.5 g, 0.03 mol) is dissolved in benzene. p-Toluenesulfonic acid (0.04 g, 0.2 mmol) is added before a Dean-Stark trap is attached, and the reaction is refluxed 2 hours. The reaction mixture is washed with sat. $NaHCO_3$ solution and then brine, dried over $MgSO_4$, and the solvent removed in vacuo (7.37 g, 91% yield). NMR (CDCl₃); MS: APCI 271 [M+1].

3. 1-(3-Chlorophenyl)-7-methoxy-1,2,3,4-tetrahydronaphthalene

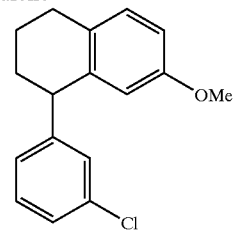

4-(3-Chlorophenyl)-6-methoxy-1,2-dihydronaphthalene (7.3 g, 0.027 mol) is dissolved in ethanol (100 mL) and placed in a Parr shaker. 10% Pd/C (0.5 g) and 5 drops concentrated HCl are added. The reaction is placed under a hydrogen atmosphere with $\Delta P_{calc.}$=24.8#, and $\Delta P_{obs.}$=24.3#. Solvent is removed in vacuo to afford a yellow oil (7.34 g, 100% yield). NMR (CDCl$_3$); MS: APCI 273 [M+1].

4. 4-(3-Chlorophenyl)-6-methoxy-1-tetralone

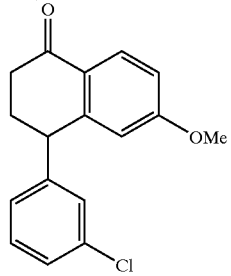

1-(3-Chlorophenyl)-7-methoxy-1,2,3,4-tetrahydronaphthalene (1.2 g, 4.4 mmol) is dissolved in glacial acetic acid (20 mL) and heated to 80° C. Chromium trioxide (0.57 g, 5.7 mmol) in acetic acid (2.5 mL)/water (1 mL) is added to the hot mixture. The reaction mixture is heated for 2 hours at 80° C. Solvent is removed in vacuo. The residue is partitioned between EtOAc and water. Organic layer is washed with saturated NaHCO$_3$ solution, brine, dried over MgSO$_4$ and solvent removed in vacuo. Chromatographed the oil using EtOAc 30%/Hexane giving an amber oil (0.85 g, 70%). NMR (CDCl$_3$); MS: APCI 287.1 [M+1].

5. 4-(3-Chlorophenyl)-6-hydroxy-1-tetralone

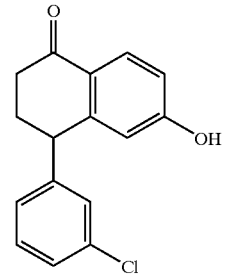

4-(3-Chlorophenyl)-6-methoxy-1-tetralone (0.85 g, 3 mmol) is dissolved in DMSO (10 mL). Crushed NaCN (0.73 g, 15 mmol) is added, and the reaction is heated at 180° C. overnight. The reaction is then poured into water (70 mL) and acidified to pH 2 using concentrated HCl. The resulting brown solid (0.8 g, 100% yield) is filtered and dried in a vacuum oven at 50° C. for 2 hours.

NMR (CDCl$_3$); MS: APCI 273.1 [M+1].

6. 6-((1S)-2-Imidazolyl-1-phenylethoxy)-4-(3-chlorophenyl)-2,3,4-trihydronaphthalen-1-one 4-(3-Chlorophenyl)-6-hydroxy-1-tetralone (0.8 g, 3.0 mmol), [1-R-phenyl-2-(1-imidazole)ethanol] (0.62 g, 3.5 mmol), and triphenylphosphine (1.16 g, 4.4 mmol) are dissolved in dry THF (20 mL). DEAD reagent (0.68 mL, 4.4 mmol) is added, and the reaction is stirred overnight. Solvent is removed in vacuo. 1N HCl is added, and the reaction mixture is washed several times with diethylether. The aqueous layer is neutralized by adding 1N NaOH and extracting with EtOAc. The organic layer is washed with sat. NaHCO$_3$ solution and then brine, dried over MgSO$_4$, and the solvent removed in vacuo. Chromatography using DCM to DCM/MeOH 2% yields a yellow/orange foam (Compound 47) (0.62 g, 50% yield). NMR (CDCl$_3$); MS: APCI 443.1 [M+1].

Anal. Calcd. C$_{27}$H$_{23}$N$_2$Cl$_1$O$_2$.0.13 mol DCM, MWC= 453.99:

| Theory: | C 71.78, | H 5.16, | N 6.17. |
|---|---|---|---|
| Found: | C 71.75, | H 5.11, | N 6.92. |

EXAMPLE 48

Synthesis of (±)-6-(2-imidazolyl-O-phenylethoxy)-4-phenyl-2,3,4-trihydronaphthalen-1-one (Compound 48)

1. Methyl 3-(3-methoxyphenyl)-3-phenylprop-2-enoate

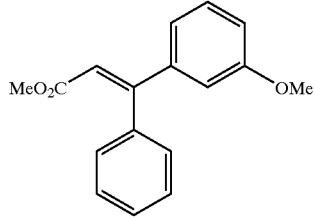

To a solution of 21.73 g (0.1024 mol) of 3-methoxybenzophenone and 10.7 mL (0.1126 mol) of methyl bromoacetate in 200 mL benzene is added 8.4 g (0.128 g—atom of acid washed granular Zn. A crystal of I$_2$ is added and the mixture heated. The mixture is heated at reflux for an additional hour, then decomposed with 12% HCl. The layers are separated and the benzene layer washed 4 times with H$_2$O, then sat. NaHCO$_3$, and finally sat NaCl. Drying over MgSO$_4$ and removal of the solvent under reduced pressure leaves 30.12 g of a yellow oil.

This yellow oil is taken up in 100 mL Ac$_2$O and heated at reflux for 1 hour. The Ac$_2$O is removed under reduced pressure and the residue taken up in Et$_2$O and washed 3 times with sat. NaHCO$_3$ and then sat. NaCl. Drying over MgSO$_4$ and removal of the solvent under reduced pressure affords 28.1 g of a brown oil. Distillation under reduced pressure gives 25.06 g (91.2% yield) of the product or a 1:1 mixture of double bound isomers. The structure is confirmed by NMR and mass spectroscopy.

2. Methyl 3-(3-methoxyphenyl)-3-phenylpropanoate

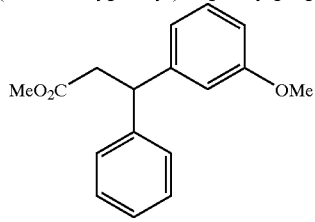

A solution of 25.0 g (0.0932 mol) of the unsaturated ester of step 1 in 600 mL MeOH is treated with 2 g of 20% Pd/C and reduced at 27° C./50 psi of H$_2$. Removal of the solvent under reduced pressure leaves 24.1 g (95.8% yield) of the product as a golden oil. The structure is confirmed by NMR spectroscopy.

3. 3-(3-Methoxyphenyl)-3-phenylpropan-1-ol

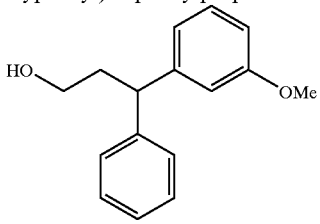

To a suspension of 5.1 g (0.134 mol) of LAH in 100 mL THF is added dropwise a solution of 24.12 g (0.0892 mol) of the ester from step 2 in 200 mL THF. The mixture is stirred at room temperature for 0.5 hour, then heated at reflux for 2 hours. The mixture is decomposed with 1N $H_2SO_4$, diluted with EtOAc, and the layers separated. The organic phase is washed with 1N $H_2SO_4$, $H_2O$, sat. $NaHCO_3$, and sat. NaCl. Drying over $MgSO_4$ and removal of the solvent under reduced pressure leaves 21.46 g (99.4% yield) of the product as a pale yellow oil. The structure is confirmed by NMR and mass spectroscopy.

4. 3-(3-Bromo-1-phenylpropyl)-1-methoxybenzene

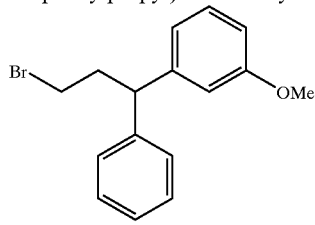

A solution of 21.46 g (0.0886 mol) of the alcohol from step 3 in 350 mL $CH_2Cl_2$ is treated with 23.23 g (0.0886 mol) of triphenylphosphine followed by 15.77 g (0.0886 mol) of recrystallized N-bromosuccinimide which is added in portions. After stirring at room temperature for 2 hours, the solution is filtered through a plug of flash silica gel. The filtrate is passed through silica gel again and the solvent then removed under reduced pressure leaving 27.0 g (100% yield) of the product as a pale yellow oil. The structure is confirmed by NMR spectroscopy.

5. 4-(3-Methoxyphenyl)-4-phenylbutanenitrile

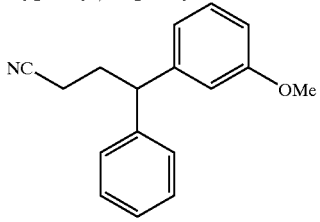

A solution of 27.0 g (0.0885 mol) of the bromo compound from step 4 in 100 mL acetone and 100 mL EtOH is treated with a solution of 6.9 g (0.106 mol) of KCN in 100 mL $H_2O$, and the reaction is heated at reflux overnight. The solvent is removed under reduced pressure and the residue taken up in EtOH and washed 3 times with $H_2O$ and then sat. NaCl. Drying over $MgSO_4$ and removal of the solvent under reduced pressure leaves 22.23 g (100% yield) of the product as a yellow oil. The structure is confirmed by NMR and mass spectroscopy.

6. 4-(3-Methoxyphenyl)-4-phenylbutanoic acid

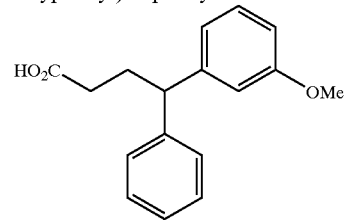

A solution of 22.23 g (0.0885 mol) of the nitrile from step 5 in 175 mL EtOH is treated with a solution of 17.7 g (0.442 mol) of NaOH in 100 mL $H_2O$ and heated at reflux overnight. The solvent is removed under reduced pressure and the residue taken up in $H_2O$ and washed 2 times with $Et_2O$. acidification with dil. HCl causes an oil to separate. This is taken up in EtOAc and washed with sat. NaCl. Drying over $MgSO_4$ and removal of the solvent under reduced pressure leaves 21.46 g (89.8% yield) of the product as a pale yellow oil. The structure is confirmed by NMR and mass spectroscopy.

7. (±)-6-Methoxy-4-phenyl-2,3,4-trihydronaphthalen-1-one

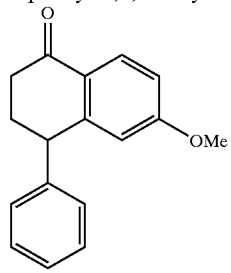

A solution of 10.59 g (0.0392 mol) of the acid from step 6 in 150 mL $CH_2Cl_2$ is cooled in ice and treated dropwise with 35 mL of trifluoroacetic anhydride. After stirring at 0° for 0.5 hour, the solution is stirred at room temperature for 1.5 hours. The solution is diluted with $Et_2O$, and $H_2O$ is added cautiously, followed by 5% NaOH. The layers are separated and the organic phase washed with 5% NaOH until basic, then washed with sat. NaCl. Drying over $MgSO_4$ and removal of the solvent under reduced pressure gives 10.4 g of a yellow oil.

The oil is taken up in 100 mL MeOH and 25 mL of 2N NaOH added and the solution stirred at room temperature for 0.5 hour. The solution is diluted with $Et_2O$ and the layers separated. The $Et_2O$ extract is washed with sat. NaCl. Drying over $MgSO_4$ and removal of the solvent under reduced pressure gives 8.65 g (87.5% yield) of the product.

This is combined with material from another run and chromatographed on silica gel, eluting with $CHCl_3$ to afford 11.4 g of product as an oil. The structure is confirmed by NMR and mass spectroscopy.

8. (±)-6-Hydroxy-4-phenyl-2,3,4-trihydronaphthalen-1-one

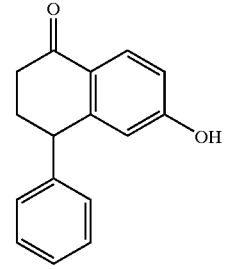

A solution of 11.39 g (0.0451 mol) of the methoxy tetralone from step 7 in 250 mL $CH_2Cl_2$ is cooled in ice and treated dropwise with 29 mL of BBr$_3$. The purple solution is kept at 0° for 0.5 hour, then at room temperature overnight. The solution is poured into H$_2$O and extracted twice with Et$_2$O. The Et$_2$O is washed twice with 5% NaOH and the NaOH back extracted with Et$_2$O. The NaOH extract is acidified with dil. HCl and extracted twice with Et$_2$O. The Et$_2$O is washed with sat. NaCl, dried over Mg SO$_4$, and the solvent removed leaving 10.82 g of a brown foam. Chromatography on silica gel, eluting with CHCl$_3$/MeOH (98:2) gives 2.05 g (19.1% yield) of the product as a pink solid. The structure is confirmed by NMR and mass spectroscopy.

9. 6-(2-Imidazolyl-1-phenylethoxy)-4-phenyl-2,3,4-trihydronaphthalen-1-one

Under nitrogen, a solution of 2.05 g (8.6 mmol) of the phenol from step 8 in 25 mL THF is treated with 1.78 g (9.5 mmol) of (R,S)-1-phenyl-2-(1-imidazoyl)ethanol and 2.26 g (8.6 mmol) of triphenylphosphine. To this is added dropwise over 15 minutes a solution of 1.4 mL (8.6 mmol) of diethyl azodicarboxylate in 5 mL THF. After stirring at room temperature overnight, the solution is diluted with EtOAc and washed 2 times with H$_2$O, then sat. NaHCO$_3$ and finally sat. NaCl. Drying over MgSO$_4$ and removal of the solvent under reduced pressure leaves 8.89 g of a brown oil. Two chromatographies on silica gel, eluting with CHCl$_3$/MeOH (98:2) gives 1.49 g (42.5% yield) of final product (Compound 48) as a tan foam.

Calcd for C$_{27}$H$_{24}$N$_2$O$_2$·0.5 CHCl$_3$ (MW 468.17):

| Theory: | C, 70.55 | H, 5.27 | N, 5.98. |
| Found: | C, 70.74, | H, 5.49, | N, 6.55. |

EXAMPLE 49

Synthesis of (±)-6-(2-imidazolyl-1-phenylethoxy)-5-prop-2-ethyl-2,3,4-trihydronaphthalen-1-one (Compound 49)

1. 2-Imidazolyl-1-phenylethan-1-ol

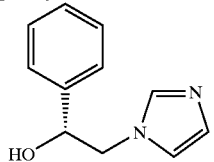

Imidazole (17.6 g, 0.26 mol) is dissolved in absolute ethanol (100 mL). Pyridine (0.6 mL, 4 mmol) is added, and the mixture is heated to reflux for 25 minutes. A solution of styrene oxide (31.1 g, 0.26 mol) in ethanol (40 mL) is added dropwise, followed by heating at reflux for 18 hours. The mixture is evaporated in vacuo to a syrup and suspended between ethyl ether (250 mL) and water (100 mL) giving a solid precipitate. The suspension is filtered and then washed with water and ethyl ether. The solid is dissolved in 500 mL of a mixture of hot chloroform/ethyl acetate, 70:30. The mixture is filtered, washed with brine, dried over anhydrous magnesium sulfate, refiltered, and evaporated in vacuo to a small volume, resulting in a solid precipitate. The solid is filtered, washed with ethyl ether and dried in vacuo (17.1 g, 35% yield). MS: APCI: M+1, 189.2 (M: 188.2). NMR spectrum is consistent with structure.

2. 6-Hydroxy-2,3,4-trihydronaphthalen-1-one

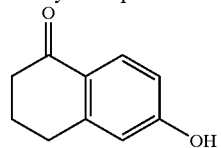

6-Methoxytetralone (167 g, 0.95 mol, Aldrich Chem. Co.) is dissolved in 48% hydrobromic acid and heated to reflux for 5 hours. After stirring for 18 hours at 25° C., an orange solid precipitates. The solid is filtered, partitioned between water and ethyl ether, and filtered off. The solid is exhaustively extracted into ethyl ether which is evaporated to a pink solid (114 g, 74% yield). MS: APCI: M+1, 163.1 (M: 162.2).

3. 6-Prop-2-enyloxy-2,3,4-trihydronaphthalen-1-one

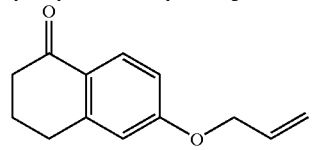

6-Hydroxy-2,3,4-trihydronaphthalen-1-one, (32.44 g, 0.2 mol), anhydrous cesium carbonate (48.87 g, 0.15 mol) and allyl bromide (19 mL, 0.22 mol) are added to dimethylformamide (100 mL). The mixture is heated at 80° C. for 5 hours, followed by stirring at 25° C. for 18 hours. The suspension is filtered, and the filtrate is evaporated in vacuo to remove the dimethylformamide. The residue is taken up into ethyl ether and extracted with saturated sodium bicarbonate, brine, 1N citric acid, and brine, respectively. The organic phase is dried over anhydrous magnesium sulfate, filtered through charcoal, and evaporated to an oil which solidifies upon standing (38 g, 95% yield). NMR spectrum is consistent with structure. MS: APCI: M+1, 203.1 (M: 202.26).

4. 6-Hydroxy-5-prop-2-enyl-2,3,4-trihydronaphthalen-1-one

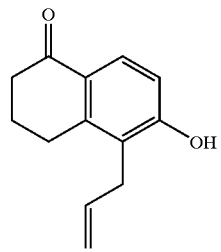

6-Prop-2-enyloxy-2,3,4-trihydronaphthalen-1-one (37.5 g, 0.185 mol) is added to diethylaniline (100 mL) and heated to 210° C. for 18 hours. The solvent is removed in vacuo giving a solid which is recrystallized from ethyl acetate, filtered, and washed with ether giving a solid (21.83 g, 58% yield). NMR spectrum is consistent with structure. MS: APCI: M+1, 203.1 (M: 202.3).

5. (±)-6-(2-Imidazolyl-1-phenylethoxy)-5-prop-2-enyl-2,3,4-trihydro-naphthalen-1-one To tetrahydrofuran (185 mL) is added 6-hydroxy-5-prop-2-enyl-2,3,4-trihydronaphthalen-1-one (1.5 g, 7.42 mmol), (±)-2-imidazolyl-1-phenylethan-1-ol (1.54 g, 8.16 mmol) and triphenylphosphine (2.14 g, 8.16 mmol). A solution of diethylazodicarboxylate (1.42 g, 7.4 mmol) in tetrahydrofuran (25 mL) is added over 1 hour. After stirring for 18 hours at 25° C., the mixture is evaporated in vacuo, and the residue is suspended in ethyl ether and 1N citric acid, washed exhaustively with ethyl ether, and the pH adjusted to 9 with 6N NaOH. The aqueous phase is extracted with ethyl acetate which is separated, washed with brine, dried over anhydrous magnesium sulfate, and filtered. The filtrate is evaporated to an oil which is purified by chromatography on 150 g silica gel eluted with a gradient of chloroform to 1% methanol in chloroform. The product (Compound 49) is recovered as a foam (1.79 g, 64.6% yield). MS: APCI: M+1, 371.1 (M: 372.4). NMR spectrum is consistent with structure.

Calcd. for $C_{24}H_{24}N_2O_2$, $1.0H_2O$:

| Theory: | C 75.92, | H 6.37, | N 7.38, | Cl 0.00, | $H_2O$ 1.89. |
|---|---|---|---|---|---|
| Found: | C 75.44, | H 6.65, | N 7.17, | Cl 0.11, | $H_2O$ 2.55. |

EXAMPLE 50

Synthesis of 6-(2-Imidazolyl-1-phenylethoxy)-5-propyl-2,3,4-trihydro-naphthalen-1-one (Compound 50)

1. 6-Hydroxy-5-propyl-2,3,4-trihydronaphthalen-1-one

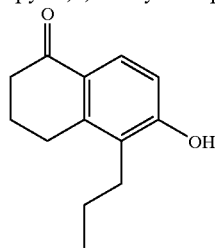

To tetrahydrofuran (100 mL) is added 6-hydroxy-5-prop-2-enyl-2,3,4-trihydronaphthalen-1-one (Example 49, step 1 2.59 g, 12.8 mol) followed by tris(triphenylphosphine) rhodium chloride (0.5 g). The mixture is pressurized to 49 psi with $H_2$ gas for 15 hours, with an observed uptake of $H_2$ gas. The mixture is filtered and then evaporated in vacuo to a small volume after which pentane is added, resulting in a solid precipitate. The solid is filtered and dried in vacuo (1.23 g, 47% yield). MS: APCI: M+1, 205.2 (M: 204.3). NMR spectrum is consistent with structure.

2. 6-(2-Imidazolyl-1-phenylethoxy)-5-propyl-2,3,4-trihydronaphthalen-1-one

To tetrahydrofuran (25 mL) is added the product from step 1 (1.1 g, 5.38 mmol), (±) 2-imidazolyl-1-phenylethan-1-ol (1.11 g, 5.92 mmol), and triphenylphosphine (2.12 g, 8.08 mmol). A solution of diethylazodicarboxylate (1.41 g, 8.08 mmol) in tetrahydrofuran (20 mL) is added over 2 hours. After stirring for 3 hours at 25° C., the mixture is refrigerated overnight and evaporated in vacuo to an oil. The oil is suspended in ethyl ether and 1N citric acid, washed exhaustively with ethyl ether, and the pH adjusted to 13 with 6N NaOH. The aqueous phase is extracted with ethyl ether, which is separated, washed with brine, dried over anhydrous magnesium sulfate, and filtered. The filtrate is evaporated to an oil which is purified by chromatography on 100 g silica gel eluted with a mixture of chloroform/ethyl acetate (50:50). The product (Compound 50) is recovered as a gum (1.1 g, 55% yield). MS: APCI: M+1, 375.2 (M: 374.5). NMR spectrum is consistent with structure.

Calcd. for $C_{24}H_{26}N_2O_2$, 0.08 $CHCl_3$, 0.02$H_2O$:

| Theory: | C 74.61, | H 6.89, | N 7.23, | Cl 2.19, | $H_2O$ 0.93. |
|---|---|---|---|---|---|
| Found: | C 74.77, | H 6.95, | N 7.37, | Cl 2.15, | $H_2O$ 0.78. |

EXAMPLE 51

Synthesis of 6-((1S)-2-Imidazolyl-1-phenylethoxy)-5-prop-2-enyl-2,3,4-trihydronaphthalen-1-one (Compound 51)

1. (1R)-2-Imidazolyl-1-phenylethan-1-ol

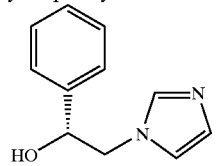

In a manner similar to that of Example 49, step 1, imidazole (2.83 g, 41.6 mmol) is dissolved in absolute ethanol (45 mL). Pyridine (0.11 mL) is added followed by addition of (R)-(+) styrene oxide (5.0 g, 41.6 mol, Aldrich Chemical Co.), followed by heating at reflux for 18 hours. The mixture is evaporated in vacuo to a syrup and suspended between ethyl ether (250 mL) and water (100 mL) to give a solid precipitate. The suspension is filtered and washed with ethyl ether. The solid is recrystallized from hot ethyl acetate and dried in vacuo (2.52 g, 32% yield). MS: APCI: M+1, 189.1 (M: 188.2). NMR spectrum is consistent with structure.

2. 6-((1S)-2-Imidazolyl-1-phenylethoxy)-5-prop-2-enyl-2,3,4-trihydro-naphthalen-1-one To tetrahydrofuran (25 mL) is added the compound of Example 49, step 4 (0.79 g, 3.91 mmol), (1R)-2-imidazolyl-1-phenylethan-1-ol (0.81 g, 4.3 mmol) and triphenylphosphine (1.54 g, 5.87 mmol). A solution of diethylazodicarboxylate (1.02 g, 5.87 mmol) in tetrahydrofuran (20 mL) is added over 1 hour. After stirring for 2 hours at 25° C., the mixture is evaporated in vacuo, and the residue is suspended in ethyl ether and 1N citric acid, washed exhaustively with ethyl ether, and the pH adjusted to 13 with 6N NaOH. The aqueous phase is extracted with ethyl ether, which is separated, washed with brine, dried over anhydrous magnesium sulfate, and filtered. The filtrate is evaporated to a solid that is purified by chromatography on 100 g silica gel eluted with a mixture of chloroform/ethyl acetate (50:50). The product (Compound 51) is recovered as a foam (0.82 g, 56% yield). MS: APCI: M+1, 373.1, (M: 371.5). NMR spectrum is consistent with structure.

Calcd. for $C_{24}H_{24}N_2O_2$, 0.2$H_2O$:

| Theory: | C 76.58, | H 6.61, | N 7.47, | $H_2O$ 0.98. |
|---|---|---|---|---|
| Found: | C 76.65, | H 6.54, | N 7.45, | $H_2O$ 0.96. |

EXAMPLE 52

Synthesis of (±)-6-(2-Imidazolyl-1-phenylethoxy)-5-(2-methylprop-2-enyl)-2,3,4-trihydronaphthalen-1-one (Compound 52)

1. 6-Hydroxy-5-(2-methylprop-2-enyl)-2,3,4-trihydronaphthalen-1-one

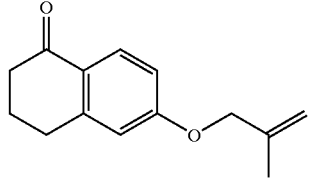

In a manner similar to that of Example 49, step 3, the title compound is prepared from 6-hydroxy-2,3,4-trihydronaphthalen-1-one (32.49 g, 0.2 mol), anhydrous cesium carbonate (65.16 g, 0.2 mol), and methyl bromide (37.5 g, 0.29 mol) (35.9 g, 83% yield). NMR spectrum is consistent with structure.

MS: APCI: M+1, 217.2 (M: 216.3).

2. 6-Hydroxy-5-(2-methylprop-2-enyl)-2,3,4-trihydronaphthalen-1-one

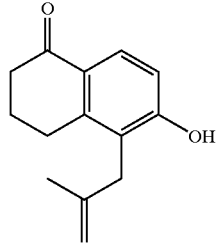

In a manner similar to that of Example 49, step 4, the title compound is prepared from 6-hydroxy-5-(2-methylprop-2-enyl)-2,3,4-trihydronaphthalen-1-one (35.3 g, 0.163 mol) is added to diethylaniline (100 mL) and heated to 210° C. for 18 hours. The solvent is removed in vacuo, and the residue is taken up in ethyl ether, washed with 1N HCl and then brine, and dried over anhydrous magnesium sulfate. The mixture is filtered and evaporated to a solid that is recrystallized from a mixture of tetrahydrofuran and ethyl ether, filtered, and dried in vacuo giving the product as a solid (4.81 g, 14% yield). NMR spectrum is consistent with structure. MS: APCI: M+1, 217.2 (M: 216.3).

3. (±)-6-(2-Imidazolyl-1-phenylethoxy)-5-(2-methylprop-2-enyl)-2,3,4-trihydronaphthalen-1-one To tetrahydrofuran (35 mL) is added 6-hydroxy-5-(2-methyl-allyl)-3,4-dihydro-2H-naphthalen-1-one (1.16 g, 5.38 mmol), (±) 2-imidazol-1-yl-1-phenyl-ethanol (1.11 g, 5.92 mmol), and triphenylphosphine (2.12 g, 8.08 mmol). A solution of diethylazodicarboxylate (1.4 g, 8.08 mmol) in tetrahydrofuran (20 mL) is added over 1 hour. After stirring for 2 hours at 25° C., the mixture is evaporated in vacuo, and the residue is suspended in ethyl ether and 1N citric acid, washed exhaustively with ethyl ether, and the pH adjusted to 14 with 6N NaOH. The aqueous phase is extracted with ethyl ether, which is separated, washed with brine, dried over anhydrous magnesium sulfate, and filtered. The filtrate is evaporated to a solid that is purified by chromatography on 100 g silica gel eluted with a mixture of chloroform/ethyl acetate (80:20). The product (Compound 52) is recovered as a foam (0.80 g, 38% yield).

Calcd. for $C_{25}H_{26}N_2O_2$, 0.025 $CHCl_3$, 0.2$H_2O$:

| | | | | | |
|---|---|---|---|---|---|
| Theory: | C 76.46, | H 6.78, | N 7.13, | $CHCl_3$ 0.81, | $H_2O$ 0.92. |
| Found: | C 76.30, | H 6.93, | N 7.11, | $CHCl_3$ 0.57, | $H_2O$ 0.99. |

EXAMPLE 53

Synthesis of (6-((1S)-2-Imidazolyl-1-phenylethoxy)-5-propyl-2,3,4-trihydronaphthalen-1-one (Compound 53)

To tetrahydrofuran (50 mL, degassed) is added Wilkinsons's catalyst (0.145 g, unreduced, Lancaster Synthesis, Inc.) followed by compound 51 (0.4 g, 1.07 mmol). The mixture is pressurized to 49 psi with hydrogen gas for 16 hours, after which the theoretical uptake of hydrogen gas is observed. The mixture is filtered, evaporated in vacuo, and the residue is purified by chromatography on silica gel eluted with chloroform/1% methanol. The product (Compound 53) is obtained as a glass from ethyl ether (0.187 g, 46% yield). MS: APCI: M+1, 375.2 (M: 374.5).

EXAMPLE 54

Synthesis of 6-((1S)-2-Imidazolyl-1-phenylethoxy)-5-(2-methylprop-2-enyl)-2,3,4-trihydronaphthalen-1-one (Compound 54)

To tetrahydrofuran (35 mL) is added the product from Example 52, step 2 (0.81 g, 3.74 mmol), (R)-2-imidazol-1-yl-1-phenylethanol (0.77 g, 4.11 mmol) and triphenylphosphine (1.47 g, 5.61 mmol). A solution of diethylazodicarboxylate (0.98 g, 5.61 mmol) in tetrahydrofuran (15 mL) is added over 1 hour. After stirring for 18 hours at 25° C., the mixture is evaporated in vacuo, and the residue is suspended in ethyl ether and 1N citric acid, washed exhaustively with ethyl ether and the pH adjusted to 12 with 2N NaOH. The aqueous phase is extracted with a mixture of ethyl acetate and ethyl ether, which is separated, washed with brine, dried over anhydrous magnesium sulfate, and filtered. The filtrate is evaporated to a glass that is purified by chromatography on 50 g silica gel eluted with a mixture of chloroform/3% methanol. The product (Compound 54) is recovered as a foam (0.41 g, 29% yield). NMR spectrum is consistent with structure.

Calcd. for $C_{25}H_{26}N_2O_2$, 0.03 $CHCl_3$, 0.025$H_2O$:

| | | | | | |
|---|---|---|---|---|---|
| Theory: | C 76.98, | H 6.73, | N 7.17, | $CHCl_3$ 0.82, | $H_2O$ 1.16. |
| Found: | C 76.58, | H 6.84, | N 7.13, | $CHCl_3$ 0.89, | $H_2O$ 0.89. |

EXAMPLE 55

Synthesis of 6-((1S)-2-Imidazolyl-1-phenylethoxy)-5-(2-methylpropyl)-2,3,4-trihydronaphthalen-1-one (Compound 55)

1. 6-Hydroxy-5-(2-methylpropyl)-2,3,4-trihydronaphthalen-1-one

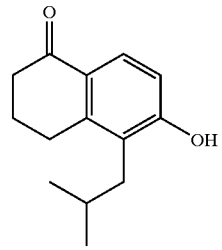

To tetrahydrofuran (100 mL) is added 5% palladium/$BaSO_4$ catalyst (0.2 g) followed by the product from Example 52, step 2 (2.13 g, 9.83 mmol). The mixture is pressurized to 49 psi with hydrogen gas for 5 hours, after which the theoretical uptake of hydrogen gas had been achieved. The mixture is filtered, evaporated in vacuo to a solid, and the residue is purified by recrystallization from a mixture of dichloromethane and pentane. The product is obtained as a solid (1.95 g, 91% yield). MS: APCI: M+1, 219.3 (M: 218.3). NMR spectrum is consistent with structure.

2. 6-((1S)-2-Imidazolyl-1-phenylethoxy)-5-(2-methylpropyl)-2,3,4-trihydronaphthalen-1-one To tetrahydrofuran (50 mL) is added the product from step 1 (1.8 g, 8.25 mmol), (R)-2-imidazol-1-yl-1-phenylethanol (1.78 g, 9.46 mmol), and triphenylphosphine (4.4 g, 16.8 mmol). A solution of diethylazodicarboxylate (2.15 g, 12.3 mmol) in tetrahydrofuran (25 mL) is added over 3 hours. After stirring for 18 hours at 25° C., the mixture is evaporated in vacuo, and the residue is suspended in ethyl ether and 1N citric acid, washed exhaustively with ethyl ether, and the pH adjusted to 13 with 2N NaOH. The aqueous phase is extracted with ethyl ether, which is separated, washed with brine, dried over anhydrous magnesium sulfate, and filtered. The filtrate is evaporated to a glass that is purified by chromatography on 150 g silica gel eluted with a gradient of chloroform to 2% methanol. The product (Compound 55) is recovered as a foam (1.52 g, 48% yield). NMR spectrum is consistent with structure. MS: APCI: M+1, 389.2 (M: 388.5).

Calcd. for $C_{25}H_{28}N_2O_2$, 0.1 $CHCl_3$, 0.25$H_2O$:

| | | | | | |
|---|---|---|---|---|---|
| Theory: | C 74.45, | H 7.12, | N 6.92, | CHCl₃ 2.63, | H₂O 1.11. |
| Found: | C 74.24, | H 7.06, | N 6.87, | CHCl₃ 2.70, | H₂O 1.04. |

EXAMPLE 56

Synthesis of 5-((1S)-2-imidazolyl-1-phenylethoxy)-4-prop-2-enylindan-1-one (Compound 56)

1. 5-Allyloxy-indan-1-one

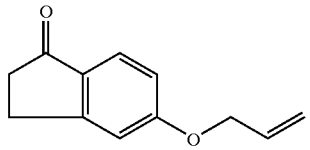

5-Hydroxy-indan-1-one, prepared per R. W. Hartmann, et. al., *J. Med. Chem.*, 1994;37:1275, (14.6 g, 0.099 mol) and cesium carbonate (24.1 g, 0.074 mol) are added to dimethylformamide (55 mL). Allyl bromide (9.39 mL, 0.108 mol) is added dropwise over 10 minutes, and the mixture is heated to 80° C. for 2 hours. After stirring for 18 hours at 25° C., the mixture is filtered, and the solvent is removed in vacuo. The residue is taken up into ethyl ether, washed with saturated sodium bicarbonate solution, brine, 1N citric acid, and finally brine again. The solution is concentrated in vacuo, and a crystalline solid is obtained upon addition of hexane (14.33 g, 77% yield). NMR spectrum is consistent with structure.

2. 4-Allyl-5-hydroxy-indan-1-one

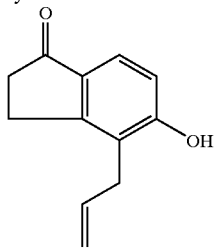

5-Allyloxy-indan-1-one (12 g, 0.064 mol) is dissolved in 1,2,4-trichlorobenzene (64 mL) and heated to 210° C. for 18 hours. The solvent is removed in vacuo, and the residue is purified by silica gel chromatography, eluted with a mixture of hexane/ethyl acetate, followed by recrystallization. A solid is recovered (1.75 g, 14.5% yield). NMR spectrum is consistent with structure.

3. 5-((1S)-2-Imidazolyl-1-phenylethoxy)-4-prop-2-enylindan-1-one

To tetrahydrofuran (65 mL) is added 4-allyl-5-hydroxy-indan-1-one (0.8 g, 4.25 mmol), (R)-2-imidazol-1-yl-1-phenylethanol (0.88 g, 4.25 mmol), and triphenylphosphine (1.67 g, 6.4 mmol). A solution of diethylazodicarboxylate (1.11 g, 6.4 mmol) in tetrahydrofuran (16 mL) is added over 30 minutes. After stirring for 18 hours at 25° C., the mixture is evaporated in vacuo, and the residue is suspended in ethyl ether and 1N citric acid, washed exhaustively with ethyl ether, and the pH adjusted to 13 with 6N NaOH. The aqueous phase is extracted with ethyl ether, which is separated, washed with brine, dried over anhydrous magnesium sulfate, and filtered. The filtrate is evaporated to a solid that is purified by recrystallization and obtained as a solid (440 mg, 29% yield). NMR spectrum is consistent with structure. MS: APCI: M+1, 359.2 (M: 358.4).

Calcd. for C₂₃H₂₂N₂O₂:

| | | | |
|---|---|---|---|
| Theory: | C 77.07, | H 6.19, | N 7.82. |
| Found: | C 76.86, | H 6.24, | N 7.80. |

EXAMPLE 57

Synthesis of (±)-6-(2-imidazolyl-1-(2-pyridyl)ethoxy)-5-(2-phenylethyl)-2,3,4-trihydronaphthalen-1-one (Compound 57)

1. O-(Tetrahydro-2H-pyran-2-yl)-glycolic acid, ethyl ester

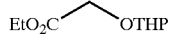

To a stirred solution of glycolic acid, ethyl ester (62.3 g, 0.598 mol) and 3,4-dihydro-2H-pyran (50.30 g, 0.598 mol) in dichloromethane (250 mL) at 4° C. under nitrogen is added p-toluenesulfonic acid monohydrate (0.20 g, 0.0011 mol), and the mixture is stirred. The temperature rises exothermically to 20° C. and is then recooled to 5° C. over 0.5 hour. The reaction mixture is washed with water, dilute aqueous sodium bicarbonate, and water (2x). The organic layer is dried (Na₂SO₄) and rotary evaporated to give 109.8 g of O-(tetrahydro-2H-pyran-2-yl)-glycolic acid, ethyl ester as a pale yellow oil; ¹H-NMR (CDCl₃): 1.26 (t, 3H), 1.48–1.62 (m, 3H), 1.67–1.87 (m, 3H), 3.50 (m, 1H), 3.84 (m, 1H), 4.19 (M, 4H), 4.72 (t, 1H) ppm.

2. 2-Oxo-2-pyridin-2-yl-O-(tetrahydro-2H-pyran-2-yl)ethanol

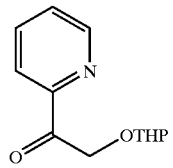

To a stirred solution of 2-bromopyridine (3.70 mL, 0.039 mol) in anhydrous THF (60 mL) at −78° C. under nitrogen is added dropwise a 1.6 M solution of n-butyl lithium in hexanes (22 mL, 0.035 mol) over 5 minutes, and the mixture is stirred for 20 minutes. To the stirred mixture is added a solution of O-(tetrahydro-2H-pyran-2-yl)-glycolic acid, ethyl ester (7.5435 g, 0.04008 mol) in THF (20 mL) over 20 minutes, and the mixture is stirred for 2 hours. The reaction is quenched by rapid dropwise addition of a saturated aqueous solution of ammonium chloride (50 mL). Ethyl ether is added and the mixture allowed to warm to 0° C. The layers are separated and the aqueous layer is extracted with ethyl ether (2x). The organics are combined, washed with brine (3x), dried (Na₂SO₄), and rotary evaporated. The residue is dissolved in hexanes and purified by chromatography on silica gel (300 g, 230–400 mesh), eluting with hexanes-ethyl acetate (4:1, 7×250 mL; 3: 1, 7×250 mL) to give 4.21 g of 2-oxo-2-pyridin-2-yl-O-(tetrahydro-2H-pyran-2-yl)-ethanol as a yellow oil that solidifies upon standing. Mp 63–65° C.

3. (±)-1-Pyridin-2-yl-2-(tetrahydro-2H-pyran-2-yloxy)ethanol

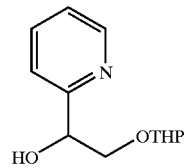

To a stirred solution of 2-oxo-2-pyridin-2-yl-O-(tetrahydro-2H-pyran-2-yl)ethanol (1.15 g, 0.00520 mol) in methanol at 0° C. is added sodium borohydride (0.195 g, 0.00515 mol) in portions. The reaction is stirred for 2.5 hours and rotary evaporated to dryness. The residue is dissolved in ethyl ether, washed with brine (3×), dried (Na$_2$SO$_4$), and rotary evaporated. The residue is purified by chromatography on silica gel (50 g, 230–400 mesh), eluting with hexanes-ethyl acetate (1:1) to give 0.84 g of (±)-1-pyridin-2-yl-2-(tetrahydro-2H-pyran-2-yloxy)-ethanol as a pale yellow oil. MS-APCI m/z 224 [M–H]$^+$.

4. (±)-6-(2-Tetrahydro-2H-1-pyran-2-yloxy-1-(2-pyridyl)ethoxy)-5-(2-phenylethyl)-2,3,4-trihydronaphthalen-1-one

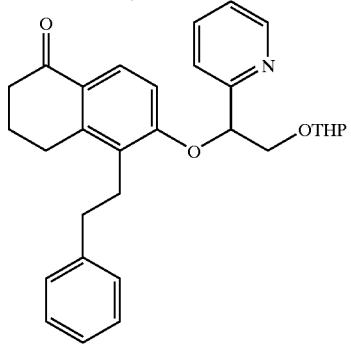

To a stirred solution of 6-hydroxy-5-phenethyl-2,3,4-trihydronaphthalen-1-one (0.960 g, 0.00360 mmol), (±)-1-pyridin-2-yl-2-(tetrahydro-2H-pyran-2-yloxy)-ethanol (0.80 g, 0.0036 mol), and triphenylphosphine (0.946 g, 0.00361 mol) in THF (10 mL) at 0° C. under nitrogen is added dropwise over 6 minutes DEAD (0.57 mL, 0.0036 mol). The reaction is stirred for 1.6 hours and allowed to warm to room temperature overnight. The solution is rotary evaporated to reduced volume (~3 mL), whereupon a white crystalline solid forms. The suspension is nearly dissolved in dichloromethane, and the mixture is subjected to chromatography on silica gel (149 g, 230–400 mesh), eluting with hexanes-ethyl acetate (2:1). The product is rechromatographed on silica gel (109 g), eluting with hexanes acetone (5:2) to give 0.73 g of the title product as an off-white foam. CHN Calc.: C, 76.41; H, 7.05; N, 2.97. Found: C, 76.36; H, 7.21; N, 3.02.

5. 6-(2-Hydroxy-1-(2-pyridyl)ethoxy)-5-(2-phenylethyl)-2,3,4-trihydronaphthalen-1-one

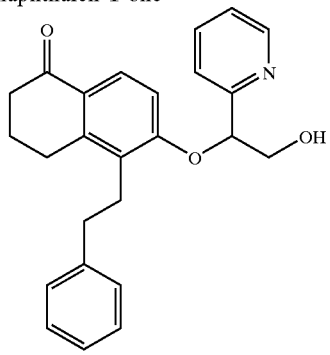

To a stirred solution of the product from step 4 (0.69 g, 0.0015 mol) in THF (3 mL) at room temperature is added acetic acid (9 mL) and water (3 mL), and the solution is stirred for 3 days. The mixture is rotary evaporated in vacuo, and the residue is dissolved in toluene and rotary evaporated to reduced volume until there is no odor of acetic acid. The solution is purified by chromatography on silica gel (52 g, 230–400 mesh), eluting with hexanes acetone (3:2) to give 0.4126 g of the title compound as an off-white foam. $^1$H-NMR (DMSO-d$_6$): 1.91 (m, 2H), 2.43 (t, 2H), 2.77–3.04 (m, 6H), 3.90 (m, 2H), 5.15 (t, 1H), 5.43 (t, 1H), 6.75 (d, 1H), 7.19 (m, 1H), 7.27 (m, 5H), 7.35 (d, 1H), 7.64 (d, 1H), 7.75 (dt, 1H), 8.57 (dd, 1H) ppm.

6. (±)-6-(2-Imidazolyl-1-(2-pyridyl)ethoxy)-5-(2-phenylethyl)-2,3,4-trihydronaphthalen-1-one To a stirred solution of the product from step 5 (0.3428 g, 0.0008846 mol) and pyridine (0.080 mL, 0.00099 mol) in dichloromethane (10 mL) at room temperature under nitrogen is added imidazole (0.075 g, 0.00110 mol), and the resulting suspension is cooled to −78° C. To this mixture is added dropwise trifluoromethanesulfonic anhydride (0.170 mL, 0.00101 mol) over 1 minute, and the mixture is stirred 30 minutes before allowing it to warm overnight to room temperature. The suspension is rotary evaporated, and the residue dissolved in THF. In a separate flask, a 60% dispersion of sodium hydride in mineral oil (0.0499 g, 0.0013 mol) is added to a solution of imidazole (0.0893 g, 0.00131 mol) in THF (3 mL) at 15° C., and the mixture is stirred 10 minutes and added to the reaction mixture in THF. After 17 hours, the reaction is heated at 60° C. for 1 hour, cooled, and rotary evaporated. The residue is purified by chromatography on silica gel (41 g, 230–400 mesh), eluting with dichloromethane-methanol (19:1) to give 0.2390 g of a mixture of recovered starting material and a small amount of desired final product.

To a stirred solution of the mixture of this starting material and final product (0.2000 g, 0.000516 mol), imidazole (0.0350 g, 0.000514 mol), triphenylphosphine (0.1366 g, 0.000521 mol) in THF at 5° C. under nitrogen is added DEAD (0.081 mL, 0.00051 mol) dropwise over 1 minute, and after 10 minutes the mixture is allowed to warm to room temperature. After 18 hours, trifluoroacetic acid (0.15 ML, 0.0019 mol) is added, and the mixture is stirred for 4 days for convenience. Additional triphenylphosphine (0.1350 g, 0.000515 mol), imidazole (0.1480 g, 0.00217 mol) and THF (1.5 mL) are added followed by DEAD (0.085 mL, 0.00054 mol), and the mixture stirred overnight. By TLC on silica gel, eluting with dichloromethane-methanol (10:1), no significant reaction had taken place. Therefore, the mixture is rotary evaporated, and the residue is partitioned between ethyl acetate and water. The organics are washed with brine, dried (Na$_2$SO$_4$), and rotary evaporated. The residue is purified by chromatography on silica gel (28 g, 230–400 mesh), eluting with dichloromethane-methanol (25:1) to give 0.0070 g of final product (Compound 57) as an off-white glass; $^1$H-NMR (CDCl$_3$): 2.00 (m, 2H), 2.53 (m, 2H), 2.76 (m, 2H), 2.90 (m, 2H), 3.11 (m, 2H), 4.53 (m, 2H), 5.60 (t, 1H), 6.52 (d, 1H), 6.82 (s, 1H), 6.88 (d, 1H), 6.96 (s, 1H), 7.18 (d, 2H), 7.22–7.33 (m, 5H), 7.55 (m, 1H), 7.80 (d, 1H), 8.66 (d, 1H) ppm.

EXAMPLE 58

Synthesis of (±)-6-(2-Imidazolyl-1-(3-pyridyl)ethoxy)-5-(2-phenylethyl)-2,3,4-trihydronaphthalen-1-one (Compound 58)

A procedure is employed similar to that described for Example 57, steps 2–6, using 3-bromopyridine (3.70 mL, 0.038 mol). The final product is rotary evaporated, and the residue is purified by chromatography on silica gel (15 g), eluting with CH$_2$Cl$_2$-MeOH (25:1, 20×15 mL; 20:1, 15×15 mL) to give a glaze. The glaze is stirred in Et$_2$O until white solids formed, and the mixture is rotary evaporated and dried in vacuo to give 0.0107 g of the final product (Compound 58); $^1$H-(DMSO-d$_6$): 1.89 (m, 2H), 2.41 (m, 2H), 2.71–2.79 (m, 4H), 2.94 (m, 2H), 4.54 (dd, 1H), 4.67 (dd, 1H), 5.98 (m 1H), 6.80 (d, 1H), 6.83 (s, 1H), 7.16–7.39 (m, 7H), 7.57–7.72 (m, 3H), 8.50 (d, 1H), 8.62 (s, 1H) ppm.

EXAMPLE 58a

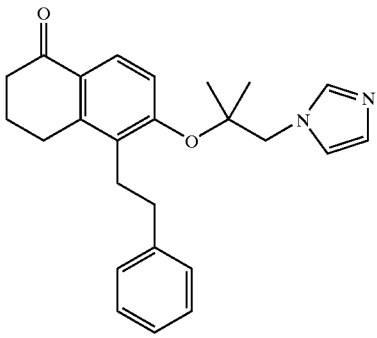

Synthesis of 6-[2-(1H-Imidazol-1-yl)-1,1-dimethylethoxy]-5-(2-phenylethyl)-3,4-dihydro-1 (2H)-naphthalenone (Compound 58a)

1. Ethyl 2-methyl-2-{[5-oxo-1-(2-phenylethyl)-5,6,7,8-tetrahydro-2-naphthalenyl]oxy}propanoate

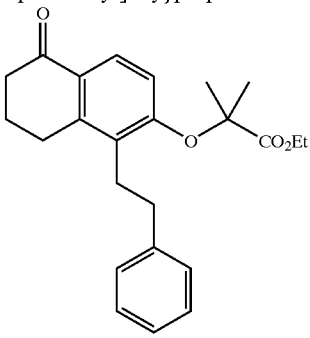

A mixture of 6-hydroxy-5-(2-phenylethyl)-3,4-dihydro-1 (2H)-naphthalenone (2.00 g, 7.5 mmol), potassium carbonate (2.08 g, 15.0 mmol), and acetonitrile (15 mL) was heated to reflux, whereupon ethyl 2-bromo-2-methylpropanoate (1.2 mL, 8.3 mmol) was added. The mixture was stirred at reflux for 2.5 h, whereupon further potassium carbonate (1.04 g, 7.5 mmol) and ethyl 2-bromo-2-methylpropanoate (1.2 mL, 8.3 mmol) were added. The mixture was stirred at reflux for a further 22 h and was then filtered and concentrated. The residue was purified by dry-flash column chromatography (SiO$_2$, 5–30% ethyl acetate-hexane) to give ethyl 2-methyl-2-{[5-oxo-1-(2-phenylethyl)-5,6,7,8-tetrahydro-2-naphthalenyl]oxy}propanoate as a pale yellow oil, 2.75 g, 96% yield. NMR spectrum was consistent with structure. MS EI: M$^{+*}$ 380.1985 (M$^{+*}$ 380.1988).

2. 6-(2-Hydroxy-1,1-dimethylethoxy)-5-(2-phenylethyl)-1,2,3,4-tetrahydro-1-naphthalenol

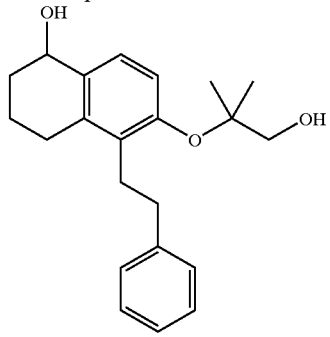

A solution of ethyl 2-methyl-2-{[5-oxo-1-(2-phenylethyl)-5,6,7,8-tetrahydro-2-naphthalenyl]oxy}propanoate (1.00 g, 2.62 mmol) in tetrahydrofuran (4 mL) was added to an ice-cooled suspension of lithium aluminum hydride (150 mg, 3.94 mmol) in tetrahydrofuran (1 mL) the mixture was stirred at room temperature for 1 h, and was then cooled in ice and treated sequentially with water (0.15 mL), 15% aqueous sodium hydroxide (0.15 mL) and water (0.45 mL). The mixture was stirred at room temperature for 10 min, and was then diluted with ether (5 mL) and filtered. The filtrate was concentrated to give 6-(2-hydroxy-1,1-dimethylethoxy)-5-(2-phenylethyl)-1,2,3,4-tetrahydro-1-naphthalenol as a white solid, 0.856 g, 95% yield. NMR spectrum was consistent with structure. Calcd. for C$_{22}$H$_{28}$O$_3$: Theory: C, 77.61; H, 8.29. Found: C, 77.42; H, 8.34.

3. 6-(2-Hydroxy-1,1-dimethylethoxy)-5-(2-phenylethyl)-3,4-dihydro-1(2H)-naphthalenone

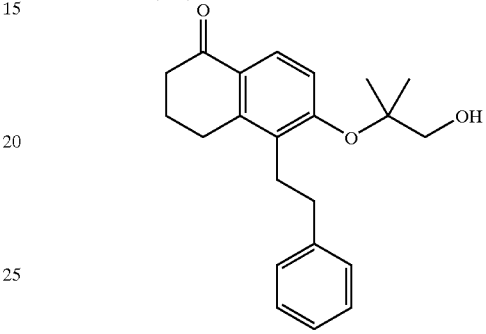

A mixture of 6-(2-hydroxy-1,1-dimethylethoxy)-5-(2-phenylethyl)-1,2,3,4-tetrahydro-1-naphthalenol (0.756 g, 2.22 mmol), tetrahydrofuran (5 mL), and manganese dioxide (4.6 g) was stirred for 4 h. The mixture was filtered through Celite and the filter cake was washed thoroughly with dichloromethane. The combined filtrates were concentrated to give 6-(2-hydroxy-1,1-dimethylethoxy)-5-(2-phenylethyl)-3,4-dihydro-1(2H)-naphthalenone as a pale yellow solid, 0.656 g, 87% yield. NMR spectrum was consistent with structure. Calcd. for C$_{22}$H$_{26}$O$_3$: Theory: C, 78.08; H, 7.74. Found: C, 77.90; H, 7.75.

4. 2-Methyl-2-{[5-oxo-1-(2-phenylethyl)-5,6,7,8-tetrahydro-2-naphthalenyl]oxy}propyl trifluoromethanesulfonate

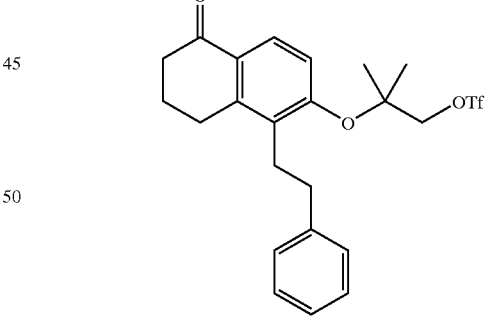

Trifluoromethanesulfonic anhydride (0.12 mL, 0.74 mmol) was added to a solution of pyridine (0.14 mL, 1.77 mmol) in dichloromethane (0.5 mL). The resulting mixture was added over 15 min to an ice-cooled solution of 6-(2-hydroxy-1,1-dimethylethoxy)-5-(2-phenylethyl)-3,4-dihydro-1(2H)-naphthalenone (100 mg, 0.30 mmol) in dichloromethane (0.5 mL). The resulting mixture was stirred for 15 min and was then quenched by the addition of water (2 mL). The mixture was diluted with 1 M aqueous hydrochloric acid (10 mL) and extracted with ethyl acetate (3×5 mL). The combined extracts were washed with 1 M aqueous hydrochloric acid (10 mL), saturated aqueous copper sulfate (3×5 mL), and was then dried (brine, Na$_2$SO$_4$) and concentrated. The residue was purified by dry-flash column chromatography (SiO$_2$, 5–40% ethyl acetate-hexane) to give 2-methyl-2-{[5-oxo-1-(2-phenylethyl)-5,6,7,8-tetrahydro-2-naphthalenyl]oxy}propyl trifluoromethanesulfonate as a colorless oil, 125 mg, 90% yield. NMR spectrum was consistent with structure. MS EI: M$^{+*}$ 470.1376 (M$^{+*}$ 470.1375).

5. 6-[2-(1H-Imidazol-1-yl)-1,1-dimethylethoxy]-5-(2-phenylethyl)-3,4-dihydro-1-(2H)-naphthalenone A mixture of sodium hydride (60% dispersion in oil, 32 mg, 0.81 mmol), acetonitrile (0.4 mL), and imidazole (275 mg, 4.0 mmol) was stirred at room temperature for 10 min, whereupon a solution of 2-methyl-2-{[5-oxo-1-(2-phenylethyl)-5,6,7,8-tetrahydro-2-naphthalenyl]oxy}propyl trifluoromethane-sulfonate (190 mg, 0.40 mmol) in acetonitrile (0.8 mL) was added. The resulting mixture was stirred at reflux for 20 min and was then concentrated. The residue was purified by dry-flash column chromatography (SiO$_2$, 1–10% 2-propanol-dichloromethane) to give 6-[2-(1H-imidazol-1-yl)-1,1-dimethylethoxy]-5-(2-phenylethyl)-3,4-dihydro-1(2H)-naphthalenone as a colorless oil, 126 mg, 92% yield. NMR spectrum was consistent with structure. MS EI: M$^{+*}$ 388.2149 (M$^{+*}$ 388.2151).

EXAMPLE 59

Synthesis of (±)-6-[1-(2-Chlorophenyl)-2-imidazolylethoxy]-5-prop-2-enyl-2,3,4-trihydronaphthalen-1-one (Compound 59)

1. 2-Bromo-1-(2-chlorophenyl)ethan-1-one

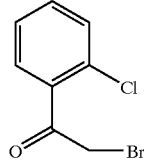

To a stirred solution of o-chloroacetophenone (6.44 mL, 50 mmol) in benzene (100 mL) is added dropwise bromine (2.55 mL, 50 mmol). The reaction is stirred under nitrogen, at room temperature, overnight. The reaction mixture is washed three times with 2 M NaCO$_3$, dried over MgSO$_4$, and concentrated to give a clear oil (9.79 g, 84% yield). MS-APCI: M+1=234.5.

2. 2-Bromo-1-(2-chlorophenyl)ethan-1-ol

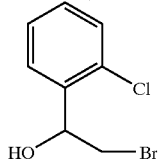

To a solution of the product from step 1 (9.79 g, 41.9 mmol) in methanol (100 mL) is added NaBH$_4$ (1.59 g, 43 mmol) in four equal portions over 15 minutes. The reaction is stirred overnight under nitrogen. The solution is concentrated and the residue taken up in ethyl ether. The organics are washed once with 1N acetic acid and then brine, dried over MgSO$_4$, filtered, and concentrated to give a clear oil (7.31 g, 74% yield). MS-APCI: M+1=235.4.

3. 1-(2-Chlorophenyl)-2-imidazolylethan-1-ol

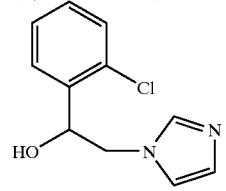

To a suspension of NaH (60% in mineral oil) (1.36 g, 35 mmol) in tetrahydrofuran (100 mL) is added a solution of imidazole (2.32 g, 34 mmol) in tetrahydrofuran (10 mL). The suspension is stirred at 45° C. for 1 hour. The reaction mixture is allowed to cool to room temperature and a solution of the compound from step 2 (7.31 g, 31 mmol) in tetrahydrofuran (20 mL) is added. After the reaction mixture is refluxed overnight, the solvent is concentrated in vacuo and 100 mL of 1N citric acid is added. The aqueous layer is extracted with ethyl ether (3×50 mL) and the pH is adjusted to 10 with 25% NaOH. The aqueous layer is extracted with ethyl acetate (3×50 mL). The organic layers are combined, washed with brine, dried over MgSO$_4$, filtered, and concentrated to give a golden foam. Recrystalization with hot chloroform/methanol (70:30) gives the product as a golden foam (2.6 g, 38% yield). MS-APCI: M+1=223.1.

4. (±)-6-[1-(2-Chlorophenyl)-2-imidazolylethoxy]-5-prop-2-enyl-2,3,4-trihydronaphthalen-1-one To a solution of 6-hydroxy-5-prop-2-enyl-2,3,4-trihydronaphthalen-1-one (Example 49, step 4) (0.9 g, 4.45 mmol) in dry tetrahydrofuran (25 mL) is added the compound from step 3 (1.1 g, 4.9 mmol) and triphenylphosphine (1.28 g, 4.9 mmol). The reaction mixture is cooled to 0° C. and treated with a solution of diethyl azodicarboxylate (1 mL, 6.9 mmol) in tetrahydrofuran (5 mL) dropwise. The reaction is warmed to room temperature and stirred overnight. The solution is concentrated and the residue is taken up in 100 mL ethyl acetate. The organic layer is washed with water (3×50 mL) and brine (2×50 mL). The solvent is removed in vacuo and 50 mL of ethyl ether is added. The precipitate is filtered and the ether is removed. More ethyl ether is added and the above procedure is repeated two more times. One hundred milliliters of ethyl acetate is added, and the solution is dried over MgSO$_4$, filtered, and concentrated to give a light tan foam. Purification is carried out via reversed-phase HPLC (0.1% trifluoroacetic acid in acetonitrile and 0.1% aqueous trifluoroacetic acid as eluent; C-18 column) to give a white solid as the final product (Compound 59); 0.348 g (15% yield). MS-APCI: M+1= 407.2.

Analysis calculated for $C_{24}H_{23}N_2O_2Cl_1.1.32$ $C_2H_{12}F_3.0.75H_2O$:

| Theory: | C, 56.49; | H, 4.51; | N, 4.95. |
| Found: | C, 56.50; | H, 4.50; | N, 4.90. |

EXAMPLE 60

Synthesis of (±)-6-[0-(2,6-Dichlorophenyl)-2-imidazolylethoxy]-5-prop-2-enyl-2,3,4-trihydronaphthalen-1-one, Trifluoroacetic Acid (Compound 60)

The compound is prepared according to the procedure outlined for Example 59, steps 14, using 2,6-dichloroacetophenone. Purification is carried out via reversed-phase HPLC (0.1% trifluoroacetic acid in acetonitrile and 0.1% aqueous trifluoroacetic acid as eluent; C-18 column) to give a white solid (Compound 60) (0.012 g, 1.5% yield). MS-APCI: M+1=441.1.

EXAMPLE 61

Synthesis of (±)-6-(2-imidazolyl-1-(2-thienyl)ethoxy)-5-prop-2-ethyl-2,3,4-trihydronaphthalen-1-one (Compound 61)

1. 2-Bromo-1-(2-thienyl)ethan-1-one

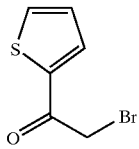

To a stirred solution of 2-acetylthiophene (5.38 mL, 50 mmol) in benzene (100 mL) is added dropwise bromine (2.55 mL, 50 mmol). The reaction is stirred under nitrogen at room temperature overnight. The reaction mixture is washed three times with 2 M $Na_2CO_3$, dried over $MgSO_4$, and concentrated to give a brown oil (8.0 g, 78% yield). MS-APCI: M+1=206.0.

2. 2-Bromo-1-(2-thienyl)ethan-1-ol

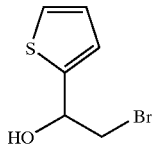

To a solution of the product from step 1 (7.7 g, 37.5 mmol) in methanol (100 mL) is added $NaBH_4$ (1.59 g, 43 mmol) in four equal portions over 15 minutes. The reaction is stirred overnight under nitrogen. The solution is concentrated and the residue taken up in ethyl ether. The organics are washed once with 1N acetic acid and then brine, dried over $MgSO_4$, filtered, and concentrated to give a clear oil (4.9 g, 64% yield). MS-APCI: M+1=207.0.

3. 2-Imidazolyl-1-(2-thienyl)ethan-1-ol

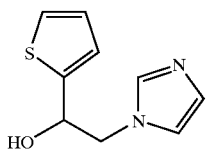

To a suspension of NaH (60% in mineral oil) (1.15 g, 48 mmol) in tetrahydrofuran (100 mL) is added a solution of imidazole (1.64 g, 24 mmol) in tetrahydrofuran (10 mL). The suspension is stirred at 45° C. for 1 hour. The reaction mixture is allowed to cool to room temperature and a solution of the compound from step 2 (4.9 g, 24 mmol) in tetrahydrofuran (20 mL) is added. After the reaction mixture is refluxed overnight, the solvent is concentrated in vacuo, and 100 mL of 1N citric acid is added. The aqueous layer is extracted with ethyl ether (3×50 mL) and the pH is adjusted to 10 with 25% NaOH. The aqueous layer is extracted with ethyl acetate (3×50 mL). The organic layers are combined, washed with brine, dried over $MgSO_4$, filtered, and concentrated to give a golden foam. Recrystalization with hot chloroform/methanol (70:30) gives the product as a golden foam (1.0 g, 21% yield). MS-APCI: M+1=195.0.

4. 6-(2-Imidazolyl-1-(2-thienyl)ethoxy)-5-prop-2-enyl-2,3,4-trihydronaphthalen-1-one To a solution of 6-hydroxy-5-prop-2-enyl-2,3,4-trihydronaphthalen-1-one (Example 49, step 4) (0.285 g, 1.4 mmol) in dry tetrahydrofuran (15 mL) is added the compound from step 3 (0.300 g, 1.55 mmol) and triphenylphosphine (0.259 g, 1.55 mmol). The reaction mixture is cooled to 0° C. and treated with a solution of diethyl azodicarboxylate (0.25 mL, 1.7 mmol) in tetrahydrofuran (5 mL) dropwise. The reaction is warmed to room temperature and stirred overnight. The solution is concentrated, and the residue is taken up in 50 mL ethyl acetate. The organic layer is washed with water (3×25 mL) and brine (2×25 mL). The solvent is removed in vacuo, and 25 mL of ethyl ether is added. The precipitate is filtered, and the ether is removed. More ethyl ether is added and the above procedure is repeated two more times. Fifty milliliters of ethyl acetate is added and the solution is dried over $MgSO_4$, filtered and concentrated to give a light tan foam. Purification is carried out via reversed-phase HPLC (0.1% trifluoroacetic acid in acetonitrile and 0.1% aqueous trifluoroacetic acid as eluent; C-18 column) to give a golden solid as the final product (Compound 61) (0.039 g, 7.5% yield). MS-APCI: M+1= 379.0.

Analysis calculated for $C_{22}H_{22}N_2O_2S_1 \cdot 1.14H_2O$:

| | | | |
|---|---|---|---|
| Theory: | C, 63.50; | H, 5.61; | N, 6.73. |
| Found: | C, 63.40; | H, 5.50; | N, 7.50. |

EXAMPLE 62

Synthesis of 6-((1S)-2-imidazolyl-1-phenylethylthio)-5-propyl-2,3,4-trihydronaphthalen-1-one (Compound 62)

1. 6-Hydroxy-5-propyl-2,3,4-trihydronaphthalen-1-one

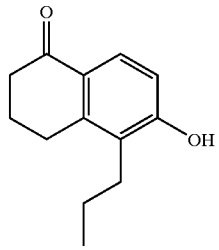

A solution of 4.41 g (21.8 mmol) of 5-allyl-6-hydroxy-1-tetralone in 100 mL THF is treated with 0.4 g 20% Pd/$BaSO_4$ and reduced at 25° C./50 psi $H_2$. The mixture is filtered and the solvent removed under reduced pressure to give 4.45 g (100% yield) of the product as a white solid. The structure is confirmed by NMR and mass spectroscopy.

2. 6-[(Dimethylamino)thioxomethoxy]-5-propyl-2,3,4-trihydronaphthalen-1-one

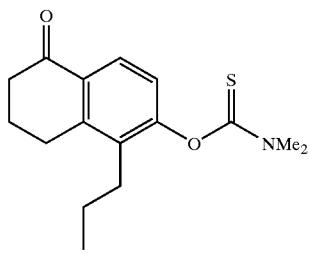

A solution of 5.14 g (25.2 mmol) of the product from step 1 in 50 mL DMF is treated with 8.2 g (25.2 mmol) of $CsCO_3$ and warmed to 85° C. for 0.5 hour. The mixture is then treated dropwise rapidly with a solution of 3.9 g (31 mmol) of N,N-dimethylthiocarbamoyl chloride in 10 mL DMF.

---

Analysis calculated for $C_{24}H_{22}N_2O_2Cl_2 \cdot 1.37 C_2H_1O_2F_3 \cdot 0.88H_2O$:

| | | | |
|---|---|---|---|
| Theory: | C, 52.68; | H, 4.30; | N, 6.10. |
| Found: | C, 52.70; | H, 4.30; | N, 6.10. |

After stirring at room temperature for 0.5 hour, the mixture is heated at 85° C. for 0.5 hour. The mixture is poured into H₂O and extracted twice with EtOAc. The EtOAc layer is washed twice with 5% NaOH, then H₂O, and sat. NaCl. Drying over MgSO₄ and removal of the solvent under reduced pressure leaves the crude product. Chromatography on silica gel, eluting with $CH_2Cl_2$ affords 3.68 g (50.2% yield) of the product as an oil. The structure is confirmed by NMR and mass spectroscopy.

3. N,N-Dimethyl(5-oxo-1-propyl(2-6,7,8-trihydronaphthylthio))-carboxamide

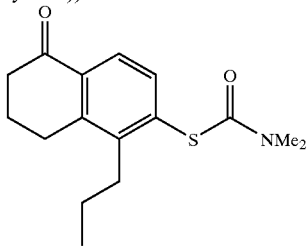

A flask containing 3.56 g (12.2 mmol) of the thiocarbamate from step 2 is heated at 240° C. for 1 hour. The material is taken up in CHCl₃ and washed with sat. NaCl. Drying over MgSO₄ and removal of the solvent under reduced pressure leaves the crude product. Chromatography on silica gel, eluting with CHCl₃/EtOAc (96:4) gives 2.07 g (58.2% yield) of the product as a golden solid. Mp 124–126° C. The structure is confirmed by NMR and mass spectroscopy.

4. 5-Propyl-6-sulfanyl-2,3,4-trihydronaphthalen-1-one

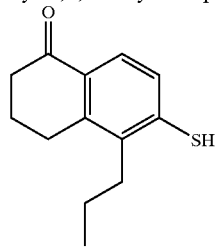

A solution of 2.07 g (7.1 mmol) of the rearranged product from step 3 in 10 mL MeOH is treated with a solution of 1.0 g (25 mmol) of NaOH in 35 mL MeOH and heated at reflux for 1.5 hour. The solution is acidified with conc. HCl, diluted with H₂O, and extracted twice with CHCl₃. The CHCl₃ is washed with sat. NaCl, dried over MgSO₄, and the solvent removed under reduced pressure leaving 1.56 g (100% yield) of the product as an oil which crystallizes on standing. The structure is confirmed by NMR and mass spectroscopy.

5. 6-((1S)-2-Imidazolyl-1-phenylethylthio)-5-propyl-2,3,4-trihydro-naphthalen-1-one Under nitrogen, a solution of 2.24 g (8.5 mmol) of triphenylphosphine in 20 mL THF is cooled in ice and 1.4 mL (8.5 mmol) of diethyl azodicarboxylate added slowly. After stirring at 0° C. for 0.5 hour, 1.5 g (7.8 mmol) of (R)-1-phenyl-2-(1-imidazoyl)ethanol in 10 mL THF is added followed by a solution of 1.56 g (7.1 mmol) of the product from step 4 in 5 mL THF. The reaction is allowed to stir at room temperature for 4 days. The mixture is diluted with Et₂O and extracted twice with 1N HCl. The acid portion is made basic with 50% NaOH and extracted twice with CH₂Cl₂. The CH₂Cl₂ is washed with sat. NaCl, dried over MgSO₄, and the solvent removed under reduced pressure leaving the crude product. Two chromatographies on silica gel, eluting with CH₂Cl₂/acetone (80:20) gives 0.72 g (26% yield) of the final product (Compound 62) as a white hygroscopic foam. The structure is confirmed by NMR and mass spectroscopy. Calcd for $C_{24}H_{26}N_2OS \cdot 0.1CH_2Cl_2$ (MW 398.96):

| Theory: | C, 72.55 | H, 6.62 | N, 7.02. |
| Found: | C, 72.30 | H, 6.53 | N, 6.75. |

EXAMPLE 63

Synthesis of 6-((1S)-2-Imidazolyl-1-phenylethylthio)-5-(2-phenylethyl)-2,3,4-trihydronaphthalen-1-one (Compound 63)

The procedures of Example 62 steps 2–5 are followed using 4.0 g (15 mmol) of 5-phenethyl-6-hydroxy-1-tetralone to give the crude product. Chromatography on silica gel, eluting with CH₂Cl₂/acetone (80:20) gives 0.26 g of the final product (Compound 63) as a tan foam.

Calcd $C_{29}H_{28}N_2OS \cdot 0.05CH_2Cl_2$ (MW 456.78):

| Theory: | C, 76.38 | H, 6.20 | N, 6.13. |
| Found: | C, 76.16 | H, 6.27 | N, 6.26. |

EXAMPLE 63a

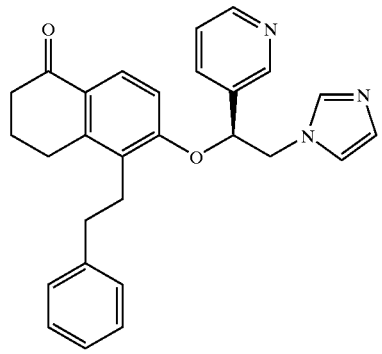

Synthesis of 6-((S)-2-Imidazol-1-yl-1-pyridin-3-yl-ethoxy)-5-phenethyl-3,4-dihydro-2H-naphthalen-1-one (Compound 63a)

1. 2-Bromo-1-pyridin-3-yl-ethanone

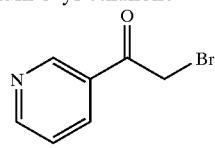

To a stirred solution of 48% hydrobromic acid was added 3-acetylpyridine (24 g, 0.198 mol) with cooling to 0° C. Bromine (34.4 g, 0.215 mol) was added at a dropwise rate followed by stirring at 25° C. for 1.5 hours and heating to 70° C. for 1 hour. The mixture was cooled to 0° C. and ethyl ether, 800 ml was added, giving a solid precipitate. The solid was washed with ether and dried in vacuo giving a white solid as the hydrobromide salt, 48.3 g, 87% yield, mp165–175° C. MS: APCI: M+1: 201.9 (M: 200.04).

2. 2-Bromo-1-pyridin-3-yl-ethanol

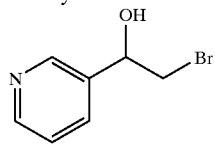

To a stirred suspension of sodium borohydride (5.29 g, 0.14 mol) in methanol (300 ml) was added a suspension of 2-Bromo-1-pyridin-3-yl-ethanone (10 g, 0.035 mol) in methanol (200 mL) at −40° C. over 30 minutes, allowing temperature to reach −35° C. The mixture was warmed to 5° C. over 30 minutes followed by cooling to −60° C. for 1 hour. The methanol was stripped from the mixture in vacuo while cold, followed by trituration with ethyl acetate. The ethyl acetate was decanted and washed with a minimal amount of saturated sodium bicarbonate solution, washed with brine, dried over anhydrous magnesium sulfate and filtered. The filtrate was evaporated to a red oil, 6.92 g, 98% yield, MS: APCI: M+1: 203.9 (M: 202.06). Material appeared to be unstable at 25° C. and was used immediately in the following step.

3. 3-Oxiranyl-pyridine

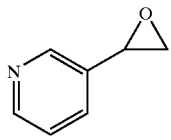

To a stirred suspension of sodium hydride (2.3 g, 0.035 mol) in tetrahydrofuran (100 ml) was added a solution of 2-Bromo-1-pyridin-3-yl-ethanol (7 g, 0.035 mol) over 15 minutes while maintaining temperature at 5° C. for 1 hour. The mixture was cooled to −40° C. and allowed to warm to 25° C. over 16 hours. Solids were removed by filtration and the filtrate was evaporated to an oil. The oil was triturated with pentane leaving behind a dark orange gum. Th decantate was evaporated to an oil, 2.62 g, 62% yield, MS: APCI: M+1: 121.9 (M: 221.14).

4. 2-Imidazol-1-yl-1-pyridin-3-yl-ethanol

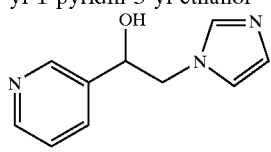

Imidazole (1.84 g, 0.027 mol) in dimethylformamide (8 ml) was added to 3-Oxiranyl-pyridine (2.62 g, 0.022 mol) followed by heating to 100° C. for 3 hours. The solvent was removed in vacuo and the residue was chromatographed on a Biotage 40S silica gel column eluted with a gradient of 100% chloroform to 90:10 chloroform/methanol, giving a solid, 1.62 g, 38% yield, mp. 119–121° C. NMR spectroscopy confirmed the identity of the product.

4. 6-((S)-2-Imidazol-1-yl-1-pyridin-3-yl-ethoxy)-5-phenethyl-3,4-dihydro-2H-naphthalen-1-one In a manner similar to that of Example 20 Step 4, 6-Hydroxy-5-phenethyl-3,4-dihydro-2H-naphthalen-1-one (0.86 g, 3.23 mmol), and 2-imidazol-1-yl-pyridinyl-ethanol gave a solid mixture of r and s isomers, 0.82 g, 58% yield. MS: APCI: M+1, 438.3 (M: 437.6).

The rs isomer mixture thus obtained was separated by chiral chromatography using a 5μ Chiralpak AS column (Daicel Chemical Industries) 25×4.5 cm eluted at 11.0 ml/min with a mixture of hexanes and isopropanol. The fractions observed at 275 nm corresponding to the second eluted isomer at 17.06 minutes retention time were collected and evaporated to a solid, 0.354 g, 12.8% yield, MS: APCI: M+1: 438.2 (M: 437.55).

Calcd. For C28H27N3O2, 0.75H2O: Theory: C, 74.56; H, 6.37; N, 9.36 Found: C, 74.29; H, 6.52; N, 9.14.

EXAMPLE 63b

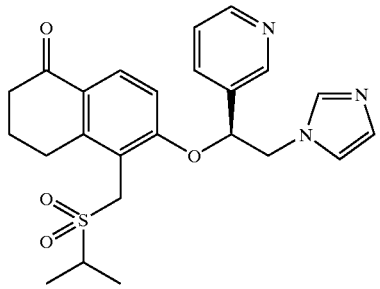

Synthesis of 6-((S)-2-Imidazol-1-yl-1-pyridin-3-yl-ethoxy)-5-(propane-2-sulfonylmethyl)-3,4-dihydro-2H-napthalen-1-one (Compound 63b)

1. (R)-2-Imidazol-1-yl-1-pyridin-3-yl-ethanol

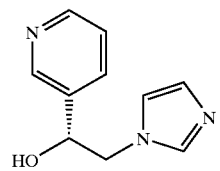

The racemic mixture of 2-imidazol-1-yl-1-pyridin-3-yl-ethanol prepared per (example 63a step 4) was separated by chiral chromatography using a 5μ Chiralpak AS column (Daicel Chemical Industries) 25×4.5 cm eluted at 1.0 ml/min with a mixture of hexanes and isopropanol. The fractions observed at 275 nm corresponding to the second eluted isomer at 14.6 minutes retention time were collected and evaporated to a solid, and used as is in the following reaction.

2. 6-((S)-2-Imidazol-1-yl-1-pyridin-3-yl-ethoxy)-5-(propane-2-sulfonylmethyl)-3,4-dihydro-2H-napthalen-1-one In a manner similar to that of Example 7, step 2, 6-Hydroxy-5-isopropylsulfonylmethyl-3,4-dihydro-2H-naphthalen-1-one (0.19 g, 0.67 mmol) and (R)-2-Imidazol-1-yl-1-pyridin-3-yl-ethanol (0.16 g, 0.80 mmol) gave 0.30 g, 100% yield of a solid foam. MS: APCI: M+1: 454.1 (M: 453.6). Calcd. For C24H27N3O4S, 0.125 CHCl3: Theory: C, 61.85; H, 5.84; N, 8.97; Cl, 2.84. Found: C 61.65; H, 5.78; N, 10.04; Cl, 2.49.

EXAMPLE 63ba

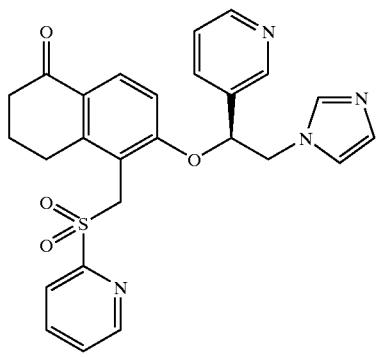

Synthesis of 6-((S)-2-Imidazol-1-yl-1-pyridin-3-yl-ethoxy)-5-(pyridin-2-ylsulfonylmethyl)-3,4-dihydro-2H-napthalen-1-one (Compound 63ba)

In a manner similar to that of Example 10, (R)-2-Imidazol-1-yl-1-pyridin-3-yl-ethanol (0.389 g, 2.02 mmol)

and 6-Hydroxy-5-(pyridine-2-sulfonylmethyl)-,3,4-trihydro-2H-naphthalen-1-one (0.564 g, 1.78 mmol) gave 0.174 g, 18% yield of solid.

MS: APCI: M+1: 489.1 (M: 488.57). Calcd. For C26H24N4O4S, 1.1H$_2$O Theory: C, 61.42; H, 5.19; N, 11.02, H$_2$O 3.89. Found: C, 61.21; H, 5.21; N, 10.89, H$_2$O 3.09.

EXAMPLE 63c

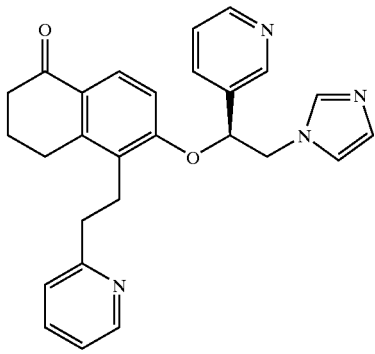

Synthesis of 6-(S)-2-Imidazol-1-yl-1-pyridin-3-ethoxy)-5-(2-pyridin-2-yl-ethyl)-3,4-dihydro-2H-naphthalen-1-one (Compound 63c)

In a manner similar to that of Example 24, 6-Hydroxy-5-(2-pyridin-2-yl-ethyl-2,3,4-trihydronaphthalen-1-one (0.15 g, 0.56 mmol), and ((R)-2-Imidazol-1-yl-1-pyridin-3-yl-ethanol (0.134 g, 0.627 mmol) gave a solid, 0.106 g, 43% yield. MS: APCI: M+1, 439.3 (M: 438.5). Calcd. For C27H26N4O2, 0.5H2O: Theory: C, 73.20; H, 6.03; N, 12.70; H$_2$O 2.00. Found: C, 73.13; H, 5.94; N, 12.65; H$_2$O 0.27.

EXAMPLE 63d

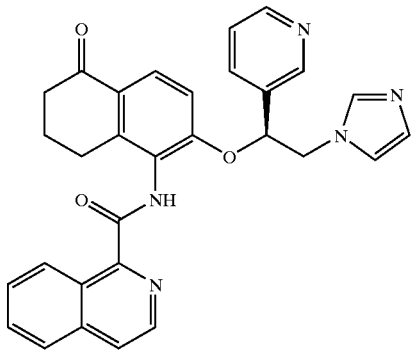

Synthesis of Isoquinoline-1-carboxylic acid [2-((S)-2-imidazol-1-yl-1-pyridin-3-yl-ethoxy)-5-oxo-5,6,7,8-tetrahydro-naphthalen-1-yl]-amide (Compound 63d)

1. 6-((S)-2-Imidazol-1-yl-1-pyridin-3-yl-ethoxy)-5-nitro-3,4-dihydro-2H-naphthalen-1-one To a solution of 6-hydroxy-5-nitro-1-tetralone (0.957 g, 4.62 mmol) in dry THF (20 mL) was added (R)-2-imidazol-1-yl-1-pyridin-3-yl-ethanol (0.875 g, 4.62 mmol) followed by triphenylphospine (1.33 g, 5.08 mmol). After approximately 10 min, diethylazodicarboxylate (0.80 mL, 5.08 mmol) was added slowly. The reaction became homogenous. The reaction was allowed to stir at RT overnight. The reaction mixture was concentrated under reduced pressure and the residue was triturated with Et$_2$O to remove some of the phospine by-products. The residue was dissolved in EtOAc and washed with H$_2$O, saturated aqueous NaHCO$_3$ and brine, dried over Na$_2$SO$_4$, and concentrated to give a foam/oil. Purification by chromatography (SiO$_2$, 4–10% MeOH/CH$_2$Cl$_2$) afforded the title compound as a tan foam (1.66 g, 4.39 mmol, 95%). The structure was confirmed by NMR and mass spectrometry. MS m/z 379 (M$^+$+H).

2. 5-Amino-6-((S)-2-imidazol-1-yl-1-pyridin-3-yl-ethoxy)-3,4-dihydro-2H-naphthalen-1-one A mixture of 6-((S)-2-Imidazol-1-yl-1-pyridin-3-yl-ethoxy)-5-nitro-3,4-dihydro-2H-naphthalen-1-one (1.60 g, 4.23 mmol), MeOH (85 mL), H$_2$O (19 mL) and glacial acetic acid (2.4 mL, 42 mmol) was treated at reflux with iron powder (2.34 g, 42 mmol). The reaction was monitored by mass spectrometry and was complete in 4 h. The volume of solvent was reduced under reduced pressure. EtOAc and dilute aqueous NaHCO$_3$ were added. A brownish-green emulsion formed which was filtered through Celite. The mixture was extracted with EtOAc. The combined organic layer was washed with dilute aqueous NaHCO$_3$ and brine, dried over Na$_2$SO$_4$, and concentrated under reduced pressure to give an off-white foam (0.685 g, 1.97 mmol, 46%). The structure was confirmed by NMR and mass spectrometry. MS m/z 349 (M$^+$+H).

3. Isoquinoline-1-carboxylic acid [2-((S)-2-imidazol-1-yl-1-pyridin-3-yl-ethoxy)-5-oxo-5,6,7,8-tetrahydro-naphthalen-1-yl]-amide To a mixture of 5-amino-6-((S)-2-imidazol-1-yl-1-phenyl-ethoxy)-3,4-dihydro-2H-naphthalen-1-one (100 mg, 0.287 mmol), 1-isoquinoline carboxylic acid (60 mg, 0.344 mmol), and HATU (131 mg, 0.344 mmol) was added CH$_2$Cl$_2$ (3 mL) and Et$_3$N (48 μL, 0.344 mmol). The reaction was stirred at RT for 5 h. The mixture was diluted with CH$_2$Cl$_2$ and washed with H$_2$O, saturated aqueous NaHCO$_3$ and brine, dried over Na$_2$SO$_4$, and concentrated to give a foam/oil. Purification by chromatography (SiO$_2$, 5–8% MeOH/CH$_2$Cl$_2$) afforded the title compound as a foam (114 mg, 0.226 mmol, 79%). The structure was confirmed by NMR and mass spectrometry. MS m/z 504 (M$^+$+H).

EXAMPLE 63e

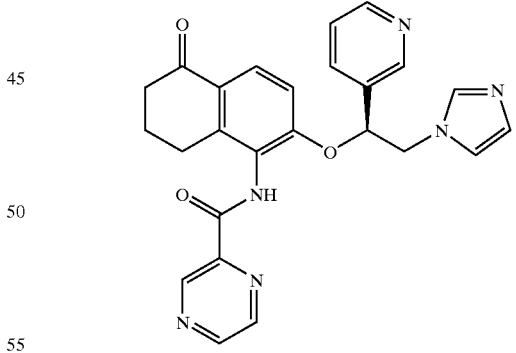

Synthesis of Pyrazine-2-carboxylic acid [2-((S)-2-imidazol-1-yl-1-pyridin-3-yl-ethoxy)-5-oxo-5,6,7,8-tetrahydro-naphthalen-1-yl]-amide (Compound 63e)

The procedure in Example 63d step 3 was followed using 2-pyrazinecarboxylic acid. The reaction was stirred at RT for 4 h. Purification by chromatography (SiO$_2$, 5–10% MeOH/CH$_2$Cl$_2$) afforded the title compound as a foam (55 mg, 0.121 mmol, 42%). The structure was confirmed by NMR and mass spectrometry. MS m/z 455 (M$^+$+H).

EXAMPLE 63f

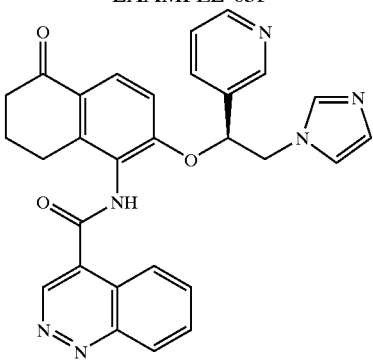

Synthesis of Cinnoline-4-carboxylic acid [2-((S)-2-imidazol-1-yl-1-pyridin-3-yl-ethoxy)-5-oxo-5,6,7,8-tetrahydro-naphthalen-1-yl]-amide (Compound 63f)

The procedure in Example 63d step 3 was followed using cinnoline-4-carboxylic acid. The reaction was stirred at RT for 1 day and at reflux for 1 day. Purification by chromatography ($SiO_2$, 5–8% $MeOH/CH_2Cl_2$ with 1% $NH_4OH$) afforded the title compound as a foam (63 mg, 0.125 mmol, 44%). The structure was confirmed by NMR and mass spectrometry. MS m/z 505 ($M^+$+H).

EXAMPLE 63g

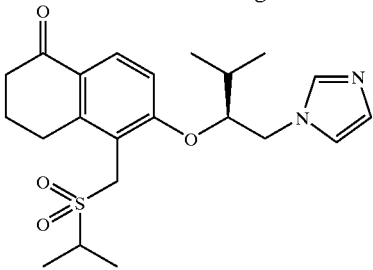

Synthesis of 6-((S)-1-Imidazol-1-ylmethyl-2-methyl-propoxy)-5-(propane-2-sulfonylmethyl)-3,4-dihydro-2H-napthalen-1-one (Compound 63g)

1. (R)-1-Imidazol-1-yl-3-methyl-butan-2-ol

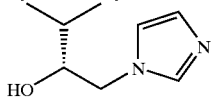

To a solution of (R)-1,2-epoxy-3-methylbutane (6.08 g, 60 mmol, Chirex Chemical Corp.) in acetonitrile (50 ml) was added imidazole (3.41 g, 50 mmol) followed by heating to 80° C. for 15 hours. The mixture was concentrated in vacuo and the purified by silica gel chromatography eluted with 10% methanol: dichloromethane with 1% ammonium hydroxide, giving a waxy solid, 5.0 g, 65% yield.

2. 6-((S)-1-Imidazol-1-ylmethyl-2-methyl-propoxy)-5-(propane-2-sulfonylmethyl)-3,4-dihydro-2H-napthalen-1-one In a manner similar to that of Example 7, step 2, 6-Hydroxy-5-isopropylsulfonylmethyl-3,4-dihydro-2H-naphthalen-1-one (1.02 g, 3.60 mmol) and (R)-1-Imidazol-1-yl-3-methyl-butan-2-ol (0.73 g, 4.7 mmol) gave 0.5 g, 33% yield of a solid foam. MS: APCI: M+1: 419.2 (M: 418.6). Calcd. For C22H30N2O4S, 0.15 $CHCl_3$: Theory: C, 60.95; H, 6.96; N, 6.42; Cl, 3.65. Found: C, 60.51; H, 7.02; N, 6.39; Cl, 3.32.

EXAMPLE 63h

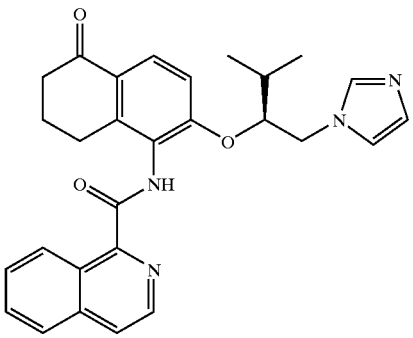

Synthesis of Isoquinoline-1-carboxylic acid [2-((S)-1-imidazol-1-ylmethyl-2-methyl-propoxy)-5-oxo-5,6,7,8-tetrahydro-naphthalen-1-yl]-amide (Compound 63h)

1. 6-((S)-1-imidazol-1-ylmethyl-2-methyl-propoxy)-5-nitro-3,4-dihydro-2H-naphthalen-1-one To a solution of 6-hydroxy-5-nitro-1-tetralone (0.888 g, 4.29 mmol) in dry THF (10 mL) was added (R)-1-imidazol-1-ylmethyl-2-methyl-propanol (0.737 g, 4.78 mmol) followed by triphenylphospine (1.26 g, 4.78 mmol). After approximately 10 min, diethylazodicarboxylate (0.75 mL, 4.78 mmol) was added slowly. The reaction was allowed to stir at RT for 2 days. The reaction mixture was concentrated under reduced pressure and the residue was purified by chromatography ($SiO_2$, 20% $acetone/CH_2Cl_2$ then 5% $MeOH/CH_2Cl_2$) afforded the title compound as a foam (1.02 g, 2.97 mmol, 69%). The structure was confirmed by NMR and mass spectrometry. MS m/z 344 ($M^+$+H).

2. 5-Amino-6-((S)-1-imidazol-1-ylmethyl-2-methyl-propoxy)-3,4-dihydro-2H-naphthalen-1-one

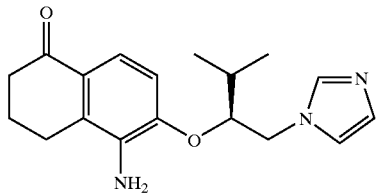

A mixture of 6-((S)-1-imidazol-1-ylmethyl-2-methyl-propoxy)-5-nitro-3,4-dihydro-2H-naphthalen-1-one (1.02 g, 2.97 mmol), MeOH (60 ML), $H_2O$ (15 mL) and glacial acetic acid (1.7 mL, 29 mmol) was treated at reflux with iron powder (1.62 g, 29 mmol). The reaction was monitored by mass spectrometry and was complete in 5 h. The volume of solvent was reduced under reduced pressure. EtOAc and dilute aqueous $NaHCO_3$ were added. A brownish-green emulsion formed which was filtered through Celite. The mixture was extracted with EtOAc. The combined organic layer was washed with dilute aqueous $NaHCO_3$ and brine, dried over $Na_2SO_4$, and concentrated under reduced pres sure. Purification by chromatography (4% MeOH/EtOAc with 1% NH$_4$OH) afforded the title compound as a white foam (0.750 g, 2.39 mmol, 81%). The structure was confirmed by NMR and mass spectrometry. MS m/z 314 (M$^+$+H).

3. Isoquinoline-1-carboxylic acid [2-((S)-1-imidazol-1-ylmethyl-2-methyl-propoxy)-5-oxo-5,6,7,8-tetrahydro-naphthalen-1-yl]-amide To a solution of 5-amino-6-((S)-1-imidazol-1-ylmethyl-2-methyl-propoxy)-3,4-dihydro-2H-naphthalen-1-one (105 mg, 0.335 mmol) and 1-isoquinoline carboxylic acid (70 mg, 0.402 mmol) in DMF (3 mL) was added Et$_3$N (56 µL, 0.402 mmol) followed by HATU (153 mg, 0.402 mmol). The reaction was stirred at RT overnight. The DMF was removed under reduced pressure. The residue was diluted with EtOAc and washed with H$_2$O, saturated aqueous NaHCO$_3$ and brine, dried over Na$_2$SO$_4$, and concentrated. Purification by chromatography (5% MeOH/EtOAc with 1% NH$_4$OH) afforded the title compound as a foam (66 mg, 0.141 mmol, 42%). The structure was confirmed by NMR and mass spectrometry. MS m/z 469 (M$^+$+H).

EXAMPLE 63i

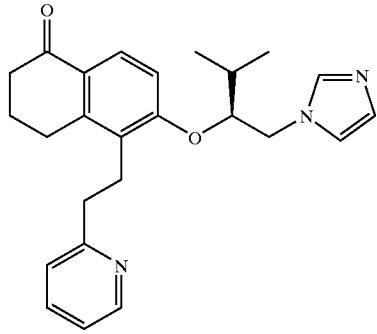

Synthesis of (S)-6-(1-imidazol-1-ylmethyl-2-methyl-propoxy)-5-(2-pyridin-4-yl-ethyl)-3,4-dihydro-2H-naphthalen-1-one (Compound 63i)

The title compound was prepared using the procedure of Example 24, step 4 using 6-hydroxy-5-(2-pyridine-2-yl-ethyl)-3,4-dihydro-2H-naphthalen-1-one and (R)-1-Imidazol-1-ylmethyl-2-methyl-propanol.

The product was obtained as a white foam (0.13 g, 17% yield). MS APCI 404 [M+H]$^+$; anal. calcd. for C$_{25}$H$_{29}$N$_3$O$_2$.2HCL/2.61H$_2$O MWC=523.47; C, 57.36%; H, 6.97%; N, 8.03% found C, 57.37%; H, 6.81%; N, 8.35%.

EXAMPLE 63j

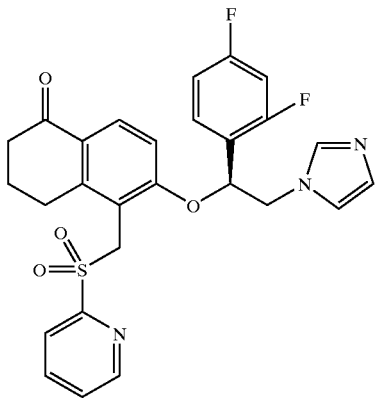

Synthesis of (S)-6-[-1-(2,4-Difluoro-phenyl)-2-imidazol-1-yl-1-ethoxy]-5-(pyridin-2-ylsulfonylmethyl)-3,4-dihydro-2H-naphthalen-1-one (Compound 63j)

1. (R)-1-(2,4-Difluoro-phenyl)-2-Imidazol-1-yl-ethanol

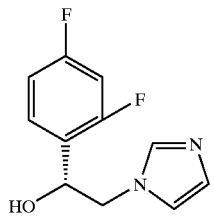

Imidazole (3.27 g, 0.048 mol) was dissolved in DMF (15 mL) and heated to 100° C. Then the 2,4-difluorophenylstyrene oxide (Chirex, 5 g, 0.032 mol) in 15 mL DMF was added dropwise over ½ hour. Reaction was heated at 100° C. over the weekend. Solvent removed in vacuo and EtOAc was added. The organic layer was washed with water (2×), sat. NaHCO$_3$ soln. (2×), and brine. Dried over MgSO$_4$ and solvent removed in vacuo. Recrystallized using EtOAc (20 mL) giving an off-white solid (3.4 g, 47% yield). NMR (DMSO); MS 225 [M+H]$^+$; mp 117–120° C.; anal calcd. for C$_{11}$H$_{10}$F$_2$N$_2$O$_1$ C, 58.93%; H, 4.50%; N, 12.49% found C, 58.96%; H, 4.37%; N, 12.38%.

2. (S)-6-[-1-(2,4-Difluoro-phenyl)-2-imidazol-1-yl-1-ethoxy]-5-(pyridin-2-ylsulfonylmethyl)-3,4-dihydro-2H-naphthalen-1-one The title compound was prepared using the procedure of Example 10, step (b) using 6-Hydroxy-5-(pyridine-2-sulfonylmethyl)-3,4-dihydro-2H-naphthalen-1-one and (R)-1-(2,4-difluoro-phenyl)-2-Imidazol-1-yl-ethanol.

Obtained white foam (0.34 g, 94% yield). NMR (DMSO); MS APCI 524 [M+H]+; HPLC RT=14.04 min. 93.4% pure 254 nm; anal. calcd. for $C_{27}H_{23}F_2N_3O_4S_1 \cdot 1.48HCl/0.96H_2O$ MWC=594.82 C, 54.52%; H, 4.47%; N, 7.06% found C, 54.52%; H, 4.47%; N, 6.84%.

EXAMPLE 63k

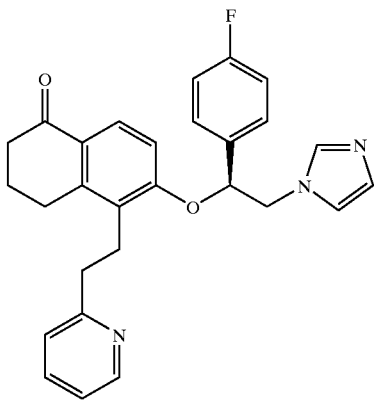

Synthesis of (S)-6-[-1-(4-Fluoro-phenyl)-2-imidazol-1-yl-1-ethoxy]-5-(2-pyridin-4-yl-ethyl)-3,4-dihydro-2H-naphthalen-1-one (Compound 63k)

1. (R)-1-(4-Fluoro-phenyl)-2-Imidazol-1-yl-ethanol

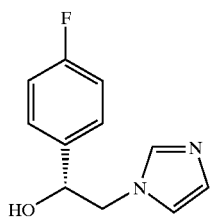

Imidazole (7.34 g, 0.11 mol) was dissolved in DMF (25 mL) and heated to 100° C. Then the 4-fluorophenylstyrene oxide (Chirex, 10 g, 0.072 mol) in DMF (25 mL) was added dropwise over ½ hour. Reaction was heated at 100° C. for 4 hours then stirred at room temperature overnight. Filtered white solid (7.27 g, 31% yield). NMR (DMSO); MS APCI 207 [M+H]+; mp 162–164° C.; anal. calcd. for $C_{11}H_{11}F_1N_2O_1$ C, 64.07%; H, 5.38%; N, 13.58% found C, 63.99%; H, 5.33%; N, 13.70%.

2. (S)-6-[-1-(4-Fluoro-phenyl)-2-imidazol-1-yl-1-ethoxy]-5-(2-pyridin-4-yl-ethyl)-3,4-dihydro-2H-naphthalen-1-one The title compound was prepared using the procedure of Example 24, step 4 using 6-hydroxy-5-(2-pyridine-2-yl-ethyl)-3,4-dihydro-2H-naphthalen-1-one and (R)-1-(4-fluoro-phenyl)-2-Imidazol-1-yl-ethanol. HPLC 100% 254 nm RT=14.5 min.; MS APCI 456 [M+H]+, anal calcd. for $C_{28}H_{26}F_1N_3O_2 \cdot 2HCl/2.19H_2O$ MWC=567.91 C, 59.22%; H, 5.75%; N, 7.40% found C, 59.22%; H, 5.48%; N, 7.57%.

EXAMPLE 631

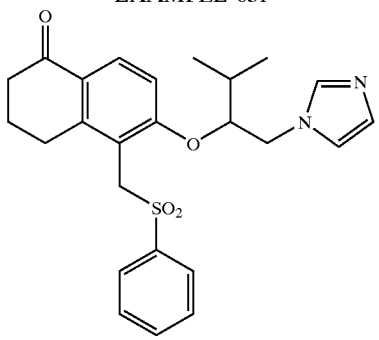

Synthesis of 6-[1-(1H-Imidazol-1-ylmethyl)-2-methylpropoxy]-5-[(phenylsulfonyl)methyl]-3,4-dihydro-1(2H)-naphthalenone (Compound 631)

1. 2-Isopropyloxirane

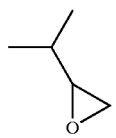

3-Methyl-1-butene (6.25 g, 89 mmol) was passed into an ice-cooled suspension of m-chloroperoxybenzoic acid (15.0 g, 70%, 61 mmol) in o-dichlorobenzene (45 mL). The mixture was stirred at room temperature for 17 h, and was then filtered. The filtrate was washed with saturated aqueous $Na_2S_2O_5$ (2×10 mL), saturated aqueous $NaHCO_3$. (2×10 mL), and dried (brine, $Na_2SO_4$, KOH). The mixture was distilled to give 2-isopropyloxirane (2.38 g, 46%) as a colorless liquid. NMR spectrum was consistent with structure.

2. 1-(1H-Imidazol-1-yl)-3-methyl-2-butanol

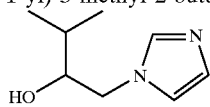

A solution of 2-isopropyloxirane (2.28 g, 26 mmol) and imidazole (1.80 g, 26 mmol) in acetonitrile (25 mL) was stirred at reflux for 16 h. The mixture was concentrated, and the residue was purified by flash column chromatography ($SiO_2$, $CH_2Cl_2$-methanol-ammonium hydroxide 80:20:1) to give 1-(1H-imidazol-1-yl)-3-methyl-2-butanol as a yellow oil, 1.88 g, 46% yield. NMR spectrum was consistent with structure. MS EI: M+• 154.1103 (M+• –154.1106).

4. 6-hydroxy-5-[(phenylsulfonyl)methyl]-3,4-dihydro-1(2H)-naphthalenone

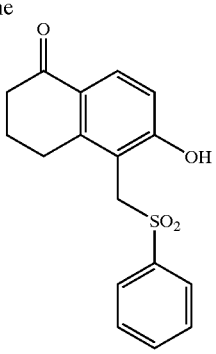

A mixture of 5-(chloromethyl)-6-hydroxy-3,4-dihydro-1(2H)-naphthalenone (10.0 g, 48 mmol), sodium phenylsulfinate (23.4 g, 142 mmol) and acetonitrile (100 mL) was stirred at reflux under nitrogen overnight. The mixture was poured onto ice. The precipitate was isolated by filtration, air dried, and crystallized from methanol-dichloromethane-ethyl acetate to give 6-hydroxy-5-[(phenylsulfonyl)methyl]-3,4-dihydro-1(2H)-naphthalenone as a cream solid, 12.16 g, 84% yield. NMR spectrum was consistent with structure.

5. 6-[1-(1H-Imidazol-1-ylmethyl)-2-methylpropoxy]-5-[(phenylsulfonyl)methyl]-3,4-dihydro-1(2H)-naphthalenone Diethyl azodicarboxylate (0.16 mL, 0.99 mmol) was added over 10 min to a mixture of 6-Hydroxy-5-[(phenylsulfonyl)methyl]-3,4-dihydro-1(2H)-naphthalenone (300 mg, 0.99 mmol), 1-(1H-imidazol-1-yl)-3-methyl-2-butanol (167 mg, 1.08 mmol), triphenylphosphine (259 mg, 0.99 mmol) and tetrahydrofuran (2 mL) under nitrogen. The resulting mixture was stirred for 3 d, whereupon it was concentrated and the residue was purified by dry-flash column chromatography (SiO$_2$, 1–9% 2-propanol-dichloromethane) to give 6-[1-(1H-imidazol-1-ylmethyl)-2-methylpropoxy]-5-[(phenylsulfonyl)methyl]-3,4-dihydro-1 (2H)-naphthalenone as a colorless solid, 46 mg, 10% yield. NMR spectrum was consistent with structure. Calcd. for C$_{25}$H$_{28}$N$_2$O$_4$S.¼H$_2$O: Theory: C, 65.69; H, 6.28; N, 6.13. Found: C, 65.77; H, 6.67; N, 6.11.

EXAMPLE 63m

Synthesis of 6-{[1-(1H-Imidazol-ylmethyl)pentyl]oxy}-5-[(phenylsulfonyl)methyl]-3,4-dihydro-1(2H)-naphthalenone (Compound 63m)

1. 1-(1H-Imidazol-1-yl)-2-hexanol

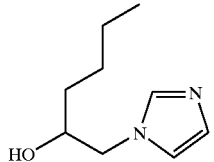

A solution of 1,2-epoxyhexane (2.0 mL, 17 mmol) and imidazole (1.08 g, 16 mmol) in acetonitrile (14 mL) was stirred at reflux for 19 h. The mixture was concentrated, taken up in 2.5 M aqueous hydrochloric acid (15 mL), washed with ethyl acetate (3×6 mL), basified with sodium carbonate and extracted with ethyl acetate (3×6 mL). The combined extracts were dried (Na$_2$SO$_4$) and concentrated. The residue was purified by flash column chromatography (SiO$_2$, CH$_2$Cl$_2$-methanol-ammonium hydroxide 80:20:1) to give 1-(1H-imidazol-1-yl)-2-hexanol as a colorless oil, 1.68 g, 63% yield. NMR spectrum was consistent with structure. MS EI: M$^{+\cdot}$ 168.1259 (M$^{+\cdot}$ 168.1263).

2. 6-{[1-(1H-Imidazol-1-ylmethyl)pentyl]oxy}-5-[(phenylsulfonyl)methyl]-3,4-dihydro-1(2H)-naphthalenone Diethyl azodicarboxylate (0.16 mL, 0.99 mmol) was added over 10 min to a mixture of 6-Hydroxy-5-[(phenylsulfonyl)methyl]-3,4-dihydro-1(2H)-naphthalenone (300 mg, 0.99 mmol), 1-(1H-imidazol-1-yl)-2-hexanol (166 mg, 1.08 mmol), triphenylphosphine (259 mg, 0.99 mmol) and tetrahydrofuran (2 mL) under nitrogen. The resulting mixture was stirred for 5 d, whereupon it was concentrated and the residue was purified by dry-flash column chromatography (SiO$_2$, 1–9% 2-propanol-dichloromethane) to give 6-{[1-(1H-imidazol-1-ylmethyl)pentyl]oxy}-5-[(phenylsulfonyl)methyl]-3,4-dihydro-1 (2H)-naphthalenone as a colorless foam, 283 mg, 62% yield. NMR spectrum was consistent with structure. MS EI: M$^{+\cdot}$ 466.1919 (M$^{+\cdot}$ 466.1926).

EXAMPLE 63n

Synthesis of 6-[1-(1H-Imidazol-1-ylmethyl) propoxy]-5-[(phenylsulfonyl)methyl]-3,4-dihydro-1 (2H)-naphthalenone (Compound 63n)

1. 1-(1H-Imidazol-1-yl)-2-butanol

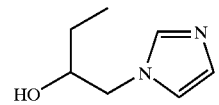

A solution of 1,2-epoxybutane (2.0 mL, 23 mmol) and imidazole (2.37 g, 35 mmol) in acetonitrile (20 mL) was stirred at reflux for 24 h. The mixture was concentrated, taken up in water (30 mL) and extracted with ethyl acetate (9×10 mL). The combined extracts were dried (Na$_2$SO$_4$) and concentrated. The residue was purified by flash column chromatography (SiO$_2$, CH$_2$Cl$_2$-methanol-ammonium hydroxide 80:20:1) to give 1-(1H-imidazol-1-yl)-2-butanol (1.57 g, 48%) as a colorless oil. NMR spectrum was consistent with structure. MS EI: M$^{+\cdot}$ 140.0948 (M$^{+\cdot}$ 140.0950).

2. 6-[1-(1H-Imidazol-1-ylmethyl)propoxy]-5-[(phenylsulfonyl)methyl]-3,4-dihydro-1(2H)-naphthalenone Diethyl azodicarboxylate (0.16 mL, 0.99 mmol) was added over 10 min to a mixture of 6-hydroxy-5-[(phenylsulfonyl)methyl]-3,4-dihydro-1(2H)-naphthalenone (300 mg, 0.99 mmol), 1-(1H-imidazol-1-yl)-2-butanol (165 mg, 1.08 mmol), triphenylphosphine (260 mg, 0.99 mmol) and tetrahydrofuran (2 mL) under nitrogen. The resulting mixture was stirred for 6 d, whereupon it was concentrated. The residue was purified by dry-flash column chromatography (SiO$_2$, 1–9% 2-propanol-dichloromethane) to give 6-[1-(1H-imidazol-1-ylmethyl)propoxy]-5-[(phenylsulfonyl)methyl]-3,4-dihydro-1(2H)-naphthalenone as a foam, 125 mg, 29% yield. NMR spectrum was consistent with structure. MS EI: M$^{+\cdot}$ 438.1608 (M$^{+\cdot}$ 438.1613).

EXAMPLE 63o

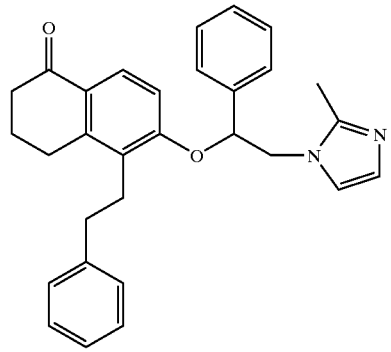

Synthesis of (±)-6-[2-(2-Methyl-imidazol-yl)-1-phenyl-ethoxy]-5-phenethyl-3,4-dihydro-2H-naphthalen-1-one (Compound 63o)

The title compound was prepared using the procedure of Example 20, step 4 using 6-hydroxy-5-(2-phenyl-ethyl)-3,4-dihydro-2H-naphthalen-1-one and 2-methylimidazole.

The product was obtained as a white foam (0.34 g, 52% yield). MS APCI 451 [M+H]$^+$.

EXAMPLE 63p

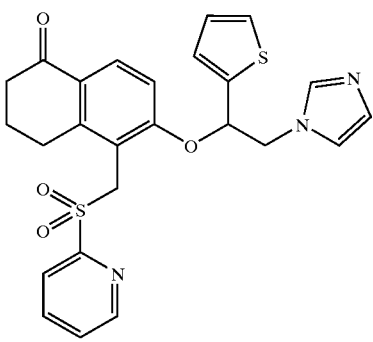

Synthesis of 6-(2-Imidazol-yl-1-thiophen-2-yl-ethoxy)-5-(pyridine-2-sulfonylmethyl)-3,4-dihydro-2H-naphthalen-1-one (Compound 63p)

1. 2-Imidazol-1-yl-N-methoxy-N-methyl-acetamide

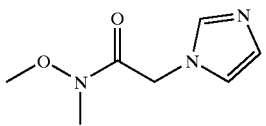

60% sodium hydride in oil (0.296 g, 7.4 mol) was washed with tetrahydrofuran and suspended in additional tetrahydrofuran (10 ml). To this was added imidazole (0.506 g, 7.43 mol) followed by stirring at 25° C. for 1 hour. To the mixture was added a solution of 2-chloro-N-methoxy-N-methyl-acetamide (1.02 g, 7.4 mmol, prepared per *Tetrahedron Letters Vol.* 30, No. 29, pp3779–80, 1989.) followed by stirring at 25° C. for 15. The mixture was filtered, and the filtrate was evaporated to an oil in vacuo and purifide by chromatography on silica gel eluted with a gradient of chloroform to 10% methanol:chloroform giving a solid 0.46 g, 37% yield.

2. 2-Imidazol-1-yl-1-thiophen-2-yl-ethanone

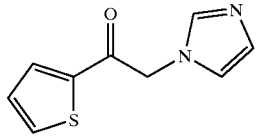

To magnesium turnings (0.16 g, 24 mmol) was added 2-bromothiophene. To the mixture was added tetrahydrofuran (4 ml), a catalytic amount of iodine and additional tetrahydrofuran (6 ml). The mixture was heated to 50° C. giving solution of the magnesium metal. The solution was cooled and added to a mixture of 2-Imidazol-1-yl-N-methoxy-N-methyl-acetamide in tetrahydrofuran (5 ml) at 0° C. This mixture was stirred for 16 hours and was poured into 20% ammonium chloride solution (20 ml), partitioned and extracted with tetrahydrofuran. The organic phase was diluted with ethyl ether and washed with brine, dried over anhydrous magnesium sulfate and concentrated in vacuo to a brown solid, 0.57 g, 58% yield. MS: APCI: M+1: 192.9 (M: 192.24).

3. 2-Imidazol-1-yl-1-thiophen-2-yl-ethanol

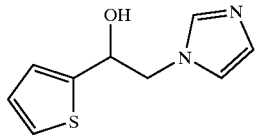

2-Imidazol-1-yl-1-thiophen-2-yl-ethanone (0.53 g, 2.76 mol) was added to a solution of sodium borohydride (0.11 g, 2.9 mol) in methanol (30 ml) at 0° C. The temperature was allowed to reach 25° C. for 1 hour followed by dilution with ethyl ether. The ethyl ether was washed with a minimal amount of saturated sodium bicarbonate solution, washed with brine, dried over anhydrous magnesium sulfate and filtered. The filtrate was evaporated to a solid, 0.41 g, 77% yield, MS: APCI: M+1: 194.9 (M: 194.26).

4. 6-(2-Imidazol-1-yl-1-thiophen-2-yl-ethoxy)-5-(pyridine-2-sulfonylmethyl)-3,4-dihydro-2H-naphthalen-1-one In a manner similar to that of Example 10, 6-Hydroxy-5-(pyridine-2-sulfonylmethyl-3,4-dihydro-2H-naphthalen-1-one (0.53 g, 1.7 mmol), and 2-Imidazol-1-yl-1-thiophen-2-yl-ethanol (0.37 g, 1.9 mmol) gave a solid, 0.06 g, 7.3% yield. MS: APCI: M+1, 494.0 (M: 493.6). Calcd. For C25H23N3O4S2, 0.1H2O, 0.06 CHCl3: Theory: C, 59.89; H, 4.66; N, 8.36; Cl, 1.27; H$_2$O 0.36. Found: C, 59.55; H, 4.65; N, 8.50; Cl, 1.29, H$_2$O 0.76.

EXAMPLE 63q

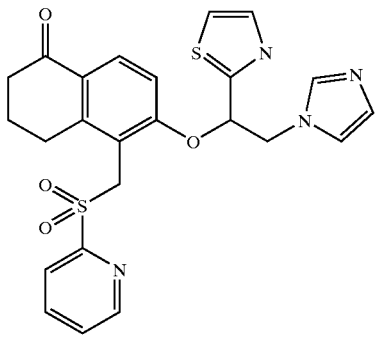

Synthesis of 6-(2-Imidazol-1-yl-1-thiazol-2-yl-ethoxy)-5-(pyridine-2-sulfonylmethyl)-3,4-dihydro-2H-naphthalen-1-one (Compound 63q)

1. 2-Imidazol-1-yl-1-thiazol-2-yl-ethanone

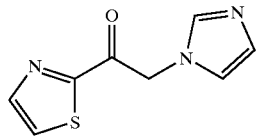

To tetrahydrofuran (20 ml) was added tetramethylethylenediamine (1.16 g, 10 mmol) followed by 4 ml of a solution of n-butyllithium in hexanes, 2.5M. The mixture was cooled to −75° C. and 2-bromothiazole (1.64 g, 10 mmol) was added over 5 minutes. After stirring for 2 hours at −75° C. a solution of 2-Imidazol-1-yl-N-methoxy-N-methyl-acetamide (1.4 g, 8.26 mmol) in tetrahydrofuran (20 ml) was added over 15 minutes. After stirring at −78° C. for 2 hours, the temperature was increased to −10° C. This mixture was poured into 1N citric acid solution, agitated and extracted with ethyl ether. The pH of the aqueous phase was adjusted to 14 with 50% NaOH and extracted with dichloromethane. The dichloromethane was dried over anhydrous magnesium sulfate and concentrated in vacuo to a brown oil containing a solid. The oil was decanted and the solid was purified on a short plug of silica gel eluted with dichloromethane, giving a solid, 0.92 g. Further chromatography on a Biotage 12s column eluted with a gradient of hexane to 20% chloroform gate the product as a solid, 0.528 g, 33% yield. MS: APCI: M+1: 193.3 (M: 193.3).

2. 2-Imidazol-1-yl-1-thiazol-2-yl-ethanol

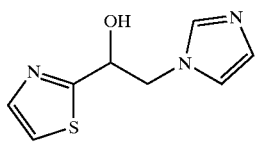

2-Imidazol-1-yl-1-thiazol-2-yl-ethanone (0.50 g, 2.6 mol) was added to a solution of sodium borohydride (0.099 g, 2.63 mol) in methanol (30 ml) at 0° C. The temperature was allowed to reach 25° C. for 1 hour followed by evaporation in vacuo. To the residue was added sodium bicarbonate solution and ethyl acetate, followed by agitation and separation of the organic phase The aqueous phase was exhaustively washed with dichloromethane and the organic extracts were combined, dried over anhydrous magnesium sulfate and filtered. The filtrate was evaporated to a solid and purified by chromatography on silica gel eluted with chloroform. 0.23 g, 45% yield.

3. 6-(2-Imidazol-1-yl-1-thiazol-2-yl-ethoxy)-5-(pyridine-2-sulfonylmethyl)-3,4-dihydro-2H-naphthalen-1-one In a manner similar to that of Example 10, 6-Hydroxy-5-(pyridine-2-sulfonylmethyl-3,4-dihydro-2H-naphthalen-1-one (0.326 g, 1.03 mmol), and 2-Imidazol-1-yl-1-thiazol-2-yl-ethanol (0.230 g, 1.18 mmol) gave a solid, 0.138 g, 27% yield. MS: APCI: M+1, 495.0 (M: 494.6). Calcd. For C24H22N4O4S2, 0.3H2O, 0.05 CHCl3: Theory: C, 57.09; H, 4.39; N, 11.07; Cl, 1.05 H2O 1.07. Found: C, 56.69; H, 4.81; N, 11.19; Cl, 1.11; H2O 1.46.

EXAMPLE 63r

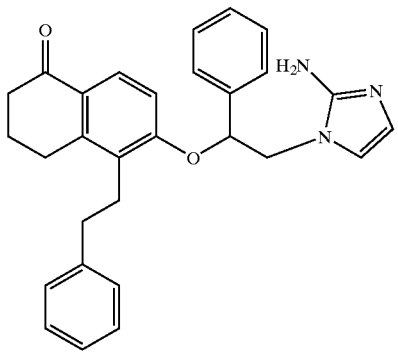

Synthesis of 6-[2-(2-Amino-imidazol-1-yl)-1-phenyl-ethoxy]-5-phenethyl-3,4-dihydro-2H-naphthalen-1-one (Compound 63r)

1. 2-(2-Nitro-imidazol-1-yl)-1-pyridin-3-yl-ethanone

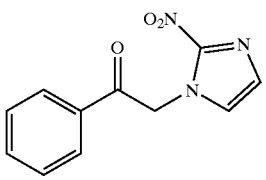

Sodium metal (0.41 g, 0.0177 mol) was dissolved in methanol (8 ml) and added to a solution of 2-nitroimidazole (2 g, 0.0177 mol) in 20 ml dimethylformamide. The mixture was stirred for 30 minutes, followed by addition of phenacyl bromide (3.58 g, 18 mmol) The mixture was heated to 130° C. for 1 hour, giving a solid precipitate. The solvents were removed in vacuo and the residue was taken up into ethyl acetate. The solution was washed with water and brine, dried over anhydrous magnesium sulfate, filtered and evaporated to give a solid precipitate. The paste was diluted with ethyl ether, filtered, washed with ether and dried in vacuo giving a yellow solid 2.7 g, 66% yield, mp125–127° C. MS: APCI: M+1: 232.0 (M: 231.4).

2. 2-(2-Nitro-imidazol-1-yl)-1-pyridin-3-yl-ethanol

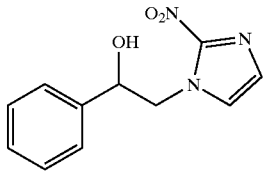

To methanol at −35° C. was added sodium borohydride (0.43 g, 11.3 mmol) followed by 2-(2-Nitro-imidazol-1-yl)-1-pyridin-3-yl-ethanone (2.63 g, 11.3 mmol) suspended in methanol (25 ml). The mixture was warmed gradually to 25° C. over 1 hour, followed by evaporation in vacuo to a solid. The solid was resuspended in ethyl aceatate, washed with water, brine, dried over anhydrous magnesium sulfate and filtered. The filtrate was concentrated in vacuo and ethyl ether was added, giving a solid precipitate. The solid was dried in vacuo, 2.0 g, 76% yield.

3. 6-[2-(2-Nitro-imidazol-1-yl)-1-phenyl-ethoxy]-5-phenethyl-3,4-dihydro-2H-naphthalen-1-one

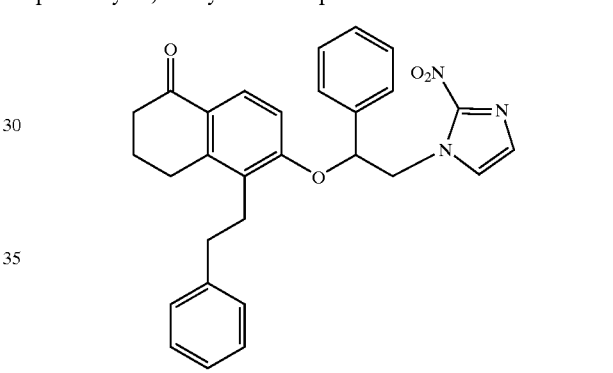

In a manner similar to that of Example 20 Step 4, 6-Hydroxy-5-phenethyl-3,4-dihydro-2H-naphthalen-1-one (0.86 g, 3.23 mmol), and): 2-(2-Nitro-imidazol-1-yl)-1-pyridin-3-yl-ethanol gave a solid, 0.92 g, 51% yield, mp 185–188° C. MS: APCI: M+1, 482.2 (M: 481.6). Calcd. For C29H27N3O4, 0.03H2O: Theory: C, 71.87; H, 5.62; N, 8.66; Cl, 0.66. Found: C, 71.87; H, 5.79; N, 8.62; Cl, 0.64.

4. 6-[2-(2-Amino-imidazol-1-yl)-1-phenyl-ethoxy]-5-phenethyl-3,4-dihydro-2H-naphthalen-1-one To a mixture of methanol (25 ml) and acetic acid (2 ml) was added 6-[2-(2-Nitro-imidazol-1-yl)-1-phenyl-ethoxy]-5-phenethyl-3,4-dihydro-2H-naphthalen-1-one (0.57 g, 1.18 mmol) followed by heating to 80° C. to give solution. To the mixture was added iron powder, (0.66 g, 11.9 mmol, Aldrich 99.99%, 10 micron) followed by heating at reflux for 3 hours. The mixture was evaporated in vacuo to a gummy solid. The residue was suspended in ethyl acetate, filtered, and washed with saturated sodium bicarbonate. The organic phase was washed with brine, dried over anhydrous magnesium sulfate, filtered and evaporated to a solid. The solid was purified by chromatography on a Biotage 12s silica gel column eluted with a gradient of chloroform to 10% methanol:chloroform. The product was recovered as a yellow foam, 0.148 g, 28% yield, MS: APCI: M+1, 452.3 (M: 451.6).

Calcd. For C29H29N3O2, 0.15H2O, 0.05CHCl3: Theory: C, 75.81; H, 6.43; N, 9.13; Cl, 1.16; H2O 0.58. Found: C, 75.71; H, 6.46; N, 8.91; Cl, 1.24, H2O 0.59.

EXAMPLE 64

Synthesis of 6-((1S)-2-Imidazolyl-1-phenylethoxy)-5-(methoxymethyl)-2,3,4-trihydronaphthalen-1-one (Compound 64)

1. 6-Hydroxy-5-(methoxymethyl)-2,3,4-trihydronaphthalen-1-one

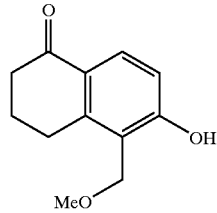

To a heated solution (64° C.) of 5-chloromethyl-6-hydroxy-2,3,4-trihydronaphthalen-1-one (8.1 g, 38.5 mmol) in methanol (250 mL) under $N_2$ is slowly added diisopropylethylamine (8.05 mL, 46.2 mmol) in 2 mL methanol via an addition funnel. The reaction is stirred at 64° C. for 1 hour, cooled and concentrated in vacuo to a pink syrup. The residue is dissolved in chloroform (100 mL) and washed with 1 M citric acid (2×30 mL) and then brine (1×30 mL), and dried over anhydrous sodium sulfate. The solution is evaporated to dryness in vacuo and subsequently in a vacuum oven to yield 7.6 g of pink crystals. Low resolution mass spectrum (APCI) m/z 207 [M+H]+ (H. Sugihara, K. Ukawa, H. Kuriki, M. Nishikawa, and Y. Sanno, *Chem. Pharm. Bull.* (Tokyo) 1977; 25:2988).

2. 6-((1S)-2-Imidazolyl-1-phenylethoxy)-5-(methoxymethyl)-2,3,4-trihydronaphthalen-1-one 6-Hydroxy-5-(methoxymethyl)-2,3,4-trihydronaphthalen-1-one (9.2 g, 44.7 mmol), (R)-2-imidazol-1-yl-1-phenylethanol (8.4 g, 44.7 mmol) and polystyrene triphenylphosphine resin (40.5 g, loading 1.65 mmol/g, Argonaut Technologies) are combined in a 75×300 mm peptide reaction vessel with dichloromethane (800 mL). To this heterogeneous mixture is carefully added diethylazodicarboxylate (10.5 mL, 67 mmol) in 3 portions via syringe. After mixing by inversion at RT (12 hours), the spent triphenyphosphine resin is removed by gravity filtration and washed with tetrahydrofuran (1×400 mL) and dichloromethane (2×400 mL). The combined filtrate and washes are concentrated in vacuo to yield a yellow-brown oil which is dissolved in methanol (200 mL) and treated with macroporous sulfonic acid resin (60 g, loading 1.45 mmol/g, Argonaut Technologies Inc.). After mixing by inversion (1 hour), the sulfonic acid resin is collected by gravity filtration and washed with methanol (4×50 mL), tetrahydrofuran (2×50 mL), and methanol (2×50 mL). Elution of product from the resin with 2.0 M ammonia in methanol (150 mL) and concentration in vacuo yields a yellow oil that is purified by flash silica gel chromatography (ethyl acetate/hexanes/triethylamine 18:1:1) to give 15.4 g of the desired product (Compound 64) as a colorless glass. Low resolution mass spectrum (APCI) m/z 377 [M+H]+.

EXAMPLE 65

Synthesis of 6-((1S)-2-Imidazolyl-1-phenylethoxy)-5-[(4-methoxphenoxy)methyl]-2,3,4-trihydronaphthalen-1-one (Compound 65)

1. 6-((1S)-2-Imidazolyl-1-phenylethoxy)-5-(bromomethyl)-2,3,4-trihydronaphthalen-1-one hydrobromide

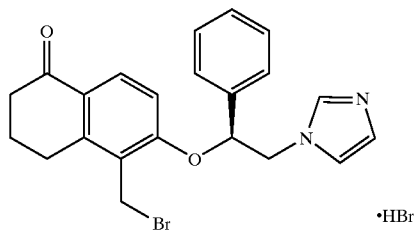

An argon flushed 1 L round bottomed flask equipped with a reflux condenser and a gas inlet adapter is charged with 6-((1S)-2-imidazolyl-1-phenylethoxy)-5-(methoxymethyl)-2,3,4-trihydronaphthalen-1-one (14.3 g, 38.1 mmol) and glacial acetic acid (300 mL). The reaction flask is placed in a 50° C. oil bath and 30% hydrogen bromide in acetic acid (20.6 mL, 76.3 mmol) is carefully introduced via syringe. The resulting mixture is allowed to stir at 50° C. (4 hours), then cooled to RT and concentrated in vacuo to give an orange foam. Re-crystallization (2×) from chloroform diethyl ether yields 21.3 g of off-white fluffy crystals. Low resolution mass spectrum (APCI) m/z 426 [M+H]+.

2. 6-((1S)-2-Imidazolyl-1-phenylethoxy)-5-[(4-methoxyphenoxy)methyl]-2,3,4-trihydronaphthalen-1-one Sodium hydride 60% in oil (19.2 mg, 0.48 mmol, Aldrich), freshly distilled tetrahydrofuran (2 mL), and 4-methoxyphenol in 1 mL THF (60 mg, 0.48 mmol, Aldrich) are introduced into an argon purged 15 mL round bottom flask. The reaction mixture is stirred until the slurry is homogeneous. The product from step 1 (100 mg, 0.19 mmol) in THF (4.0 mL) is added via syringe to a stirring phenoxide solution. The mixture is heated to reflux with a heat gun (1 minute), cooled, and concentrated in vacuo to yield a pinkish residue. The resulting residue is dissolved in ethyl acetate (4.0 mL) and washed with a 2 M NaOH solution (4×2.0 mL). The organic layer is concentrated to an oil, diluted with methanol (8.0 mL), and stirred with macroporous polystyrene sulfonic acid resin (330 mg, loading 1.45 mmol/g, Argonaut Technologies, Inc.) for 1 hour. The resin is collected by gravity filtration and washed with methanol and then THF (3.0 mL each). Elution of the product from the resin with 2.0 M ammonia in methanol (3.0 mL) and concentration in vacuo yields 52 mg of product (Compound 65) as a glass. Low resolution mass spectrum (APCI) m/z 469 [M+H]+.

EXAMPLE 66

Synthesis of 6-((1S)-2-Imidazolyl-1-phenylethoxy)-5-(phenoxymethyl)-2,3,4-trihydronaphthalen-1-one (Compound 66)

Phenol (94 mg, 1.0 mmol, 1.0 M in THF) and excess sodium hydride (60% in oil) (30 mg) are combined in a septum capped, argon purged 2-dram vial. After bubbling ceases (15.0 minutes), the heterogeneous solution was removed by syringe, and filtered by negative pressure through a 0.45 $\mu$M disk syringe filter (Whatman PTFE) into an evacuated 2-dram vial containing the product from Example 65, step 1 (100 mg, 0.19 mmol, 0.19 M in THF/acetonitrile (1:1)). The vial is capped with a Teflon lined cap and placed in a heater-shaker at 60° C. for 45 minutes. The reaction mixture is cooled to room temperature, concentrated in vacuo, diluted with chloroform (4.0 mL), and washed with 2.0 M NaOH (2×4.0 mL). The organic layer is dried over anhydrous sodium sulfate, concentrated under a stream of $N_2$ gas, diluted in methanol (4.0 mL), and treated with macroporous sulfonic acid resin (300 mg, Loading 1.45 mmol/g, Argonaut Technologies, Inc.) for 1 hour by gentle magnetic stirring. The resin is collected using gravity filtration, washed serially with methanol, ethyl acetate, and methanol, respectively (3.0 mL each). Elution of the product from the resin with 2.0 M ammonia in methanol and evaporation of the solvent via a $N_2$ gas stream produces 58 mg of desired product (Compound 66) as a glass. Low resolution mass spectrum (APCI) m/z 439 [M+H]+.

EXAMPLE 67

Synthesis of 6-((1S)-2-Imidazolyl-1-phenylethoxy)-5-{[3-(tert-butyl)phenoxy]methyl}-2,3,4-trihydronaphthalen-1-one (Compound 67)

According to the method in Example 66, 3-tert-butylphenol (150 mg, 1.0 mmol, 1.0 M in THF) is combined with the product from Example 65, step 1 (100 mg, 0.19 mmol, 0.19 M in THF/acetonitrile (1:1)) to produce 62 mg of the desired product (Compound 67) as a glass. Low resolution mass spectrum (APCI) m/z 495 [M+H]$^+$.

EXAMPLE 68

Synthesis of 6-((1S)-2-Imidazolyl-1-phenylethoxy)-5-{[2-(methylethyl)phenoxy]methyl}-2,3,4-trihydronaphthalen-1-one (Compound 68)

According to the method in Example 66, 2-isopropylphenol (136 mg, 1.0 mmol, 1.0 M in THF) is combined with product from Example 65, step 1 (100 mg, 0.19 mmol, 0.19 M in THF/acetonitrile (1:1)) to produce 60 mg of the desired product (Compound 68) as a glass. Low resolution mass spectrum (APCI) m/z 481 [M+H]$^+$.

EXAMPLE 69

Synthesis of 6-((1S)-2-imidazolyl-1-phenylethoxy)-5-[(3-chlorophenoxy)methyl]-2,3,4-trihydronaphthalen-1-one (Compound 69)

According to the method in Example 66, 3-chlorophenol (129 mg, 1.0 mmol, 1.0 M in THF) is combined with the product from Example 65, step 1 (100 mg, 0.19 mmol, 0.19 M in THF/acetonitrile (1:1)) to produce 45 mg of the desired product (Compound 69) as a glass. Low resolution mass spectrum (APCI) m/z 473 [M+H]$^+$.

EXAMPLE 70

Synthesis of 6-((1S)-2-Imidazolyl-1-phenylethoxy)-5-{[2-methyl-5-(methylethyl)phenoxy]methyl}-2,3,4-trihydronaphthalen-1-one (Compound 70)

According to the method in Example 66, 5-isoproyl-2-methyl-phenol (150 mg, 1.0 mmol, 1.0 M in THF) is combined with the product from Example 65, step 1 (100 mg, 0.19 mmol, 0.19 M in THF/acetonitrile (1:1)) to produce 59 mg of the desired product (Compound 70) as a glass. Low resolution mass spectrum (APCI) m/z 495 [M+H]$^+$.

EXAMPLE 71

Synthesis of 6-((1S)-2-imidazolyl-1-phenylethoxy)-5-[(3,5-dimethoxyphenoxy)methyl]-2,3,4-trihydronaphthalen-1-one (Compound 71)

According to the method in Example 66, 3,5-dimethoxyphenol (154 mg, 1.0 mmol, 1.0 M in THF) is combined with the product from Example 65, step 1 (100 mg, 0.19 mmol, 0.19 M in THF/acetonitrile (1:1)) to produce 68 mg of the desired product (Compound 71) as a glass. Low resolution mass spectrum (APCI) m/z 499 [M+H]$^+$.

EXAMPLE 72

Synthesis of 6-((1S)-2-Imidazolyl-1-phenylethoxy)-5-{[4-(methylethyl)phenoxy]methyl}-2,3,4-trihydronaphthalen-1-one (Compound 72)

According to the method in Example 66, 4-isopropyl-phenol (136 mg, 1.0 mmol, 1.0 M in THF) is combined with the product from Example 65, step 1 (100 mg, 0.19 mmol, 0.19 M in THF/acetonitrile (1:1)) to produce 63 mg of the desired product (Compound 72) as a glass. Low resolution mass spectrum (APCI) m/z 481 [M+H]$^+$.

EXAMPLE 73

Synthesis of 6-((1S)-2-Imidazolyl-1-phenylethoxy)-5-(2-5,6,7,8-tetrahydro-naphthyloxymethyl)-2,3,4-trihydronaphthalen-1-one (Compound 73)

According to the method in Example 66, 5,6,7,8-tetrahydro-naphthalen-2-ol (148 mg, 1.0 mmol, 1.0 M in THF) is combined with the product from Example 65, step 1 (100 mg, 0.19 mmol, 0.19 M in THF/acetonitrile (1:1)) to produce 69 mg of the desired product (Compound 73) as a glass. Low resolution mass spectrum (APCI) m/z 493 [M+H]$^+$.

EXAMPLE 74

Synthesis of 6-((1S)-2-Imidazolyl-1-phenylethoxy)-5-{[3-(methylethyl)phenoxy]methyl}-2,3,4-trihydronaphthalen-1-one (Compound 74)

According to the method in Example 66, 3-isopropyl-phenol (136 mg, 1.0 mmol, 1.0 M in THF) is combined with the product from Example 65, step 1 (100 mg, 0.19 mmol, 0.19 M in THF/acetonitrile (1:1)) to produce 65 mg of the desired product (Compound 74) as a glass. Low resolution mass spectrum (APCI) m/z 481 [M+H]$^+$.

EXAMPLE 75

Synthesis of 6-((1S)-2-Imidazolyl-1-phenylethoxy)-5-[(4-pyrrolylphenoxy)methyl]-2,3,4-trihydronaphthalen-1-one (Compound 75)

According to the method in Example 66, 4-pyrrol-1-yl-phenol (159 mg, 1.0 mmol, 1.0 M in THF) is combined with the product from Example 65, step 1 (100 mg, 0.19 mmol, 0.19 M in THF/acetonitrile (1:1)) to produce 64 mg of the desired product (Compound 75) as a glass. Low resolution mass spectrum (APCI) m/z 504 [M+H]$^+$.

EXAMPLE 76

Synthesis of 6-((1S)-2-Imidazolyl-1-phenylethoxy)-5-(indol-4-yloxymethyl)-2,3,4-trihydronaphthalen-1-one (Compound 76)

According to the method in Example 66, 1H-indol-4-ol (133 mg, 1.0 mmol, 1.0 M in THF) is combined with the product from Example 65, step 1 (100 mg, 0.19 mmol, 0.19 M in THF/acetonitrile (1:1)) to produce 67 mg of the desired product (Compound 76) as a glass. Low resolution mass spectrum (APCI) m/z 478 [M+H]$^+$.

EXAMPLE 77

Synthesis of 6-((1S)-2-Imidazolyl-1-phenylethoxy)-5-{[2-(methylethoxy)phenyl]methyl}-2,3,4-trihydronaphthalen-4-1-one (Compound 77)

According to the method in Example 66, 2-isopropoxy-phenol (152 mg, 1.0 mmol, 1.0 M in THF) is combined with the product from Example 65, step 1 (100 mg, 0.19 mmol, 0.19 M in THF/acetonitrile (1:1)) to produce 64 mg of the desired product (Compound 77) as a glass. Low resolution mass spectrum (APCI) m/z 497 [M+H]$^+$.

EXAMPLE 78

Synthesis of 6-((1S)-2-Imidazolyl-4-phenylethoxy)-5-[(2-ethoxyphenoxy)methyl]-2,3,4-trihydronaphthalen-1-one (Compound 78)

According to the method in Example 66, 2-ethoxyphenol (138 mg, 1.0 mmol, 1.0 M in THF) is combined with the product from Example 65, step 1 (100 mg, 0.19 mmol, 0.19 M in THF/acetonitrile (1:1)) to produce 55 mg of the desired product (Compound 78) as a glass. Low resolution mass spectrum (APCI) m/z 483 [M+H]$^+$.

EXAMPLE 79

Synthesis of 6-((1S)-2-Imidazolyl-1-phenylethoxy)-5-[(4-ethoxyphenoxy)methyl]-2,3,4-trihydronaphthalen-1-one (Compound 79)

According to the method in Example 66, 4-ethoxyphenol (138 mg, 1.0 mmol, 1.0 M in THF) is combined with the product from Example 65, step 1 (100 mg, 0.19 mmol, 0.19 M in THF/acetonitrile (1:1)) to produce 64 mg of the desired product (Compound 79) as a glass. Low resolution mass spectrum (APCI) m/z 483 [M+H]$^+$.

EXAMPLE 80

Synthesis of 6-(1S)-2-Imidazolyl-1-phenylethoxy)-5-[(3-ethylphenoxy)methyl]-2,3,4-trihydronaphthalen-1-one (Compound 80)

According to the method in Example 66, 3-ethylphenol (122 mg, 1.0 mmol, 1.0 M in THF) is combined with the product from Example 65, step 1 (100 mg, 0.19 mmol, 0.19 M in THF/acetonitrile (1:1)) to produce 64 mg of the desired product (Compound 80) as a glass. Low resolution mass spectrum (APCI) m/z 467 [M+H]$^+$.

EXAMPLE 81

Synthesis of Methyl 2-{[2-((1S)-2-imidazolyl-1-phenylethoxy)-5-oxo-6,7,8-trihydronaphthyl]methoxy}benzoate (Compound 81)

According to the method in Example 66, methyl 2-hydroxybenzoate (152 mg, 1.0 mmol, 1.0 M in THF) is combined with the product from Example 65, step 1 (100 mg, 0.19 mmol, 0.19 M in THF/acetonitrile (1:1)) to produce 14 mg of the desired product (Compound 81) as a glass. Low resolution mass spectrum (LC-MS, APCI) m/z 497 [M+H]$^+$.

EXAMPLE 82

Synthesis of 6-((1S)-2-Imidazolyl-1-phenylethoxy)-5-[(6-methyl(3-pyridyloxy))methyl]-2,3,4-trihydronaphthalen-1-one (Compound 82)

According to the method in Example 66, 6-methylpyridin-3-ol (109 mg, 1.0 mmol, 1.0 M in THF) is combined with the product from Example 65, step 1 (100 mg, 0.19 mmol, 0.19 M in THF/acetonitrile (1:1)) to produce 27 mg of the desired product (Compound 82) as a glass. Low resolution mass spectrum (LC-MS, APCI) m/z 454 [M+H]$^+$.

EXAMPLE 83

Synthesis of 6-((1S)-2-imidazolyl-1-phenylethoxy)-5-[(6-methyl(3-pyridyloxy))methyl]-2,3,4-trihydronaphthalen-1-one (Compound 83)

According to the method in Example 66, 5-chloropyridin-3-ol (129 mg, 1.0 mmol, 1.0 M in THF) is combined with the product from Example 65, step 1 (100 mg, 0.19 mmol, 0.19 M in THF/acetonitrile (1:1)) to produce 38 mg of the desired product (Compound 83) as a glass. Low resolution mass spectrum (LC-MS, APCI) m/z 474 [M+H]$^+$.

EXAMPLE 84

Synthesis of 6-((1S)-2-Imidazolyl-1-phenylethoxy)-5-[(4-ethylphenoxy)methyl]-2,3,4-trihydronaphthalen-1-one (Compound 84)

According to the method in Example 66, 4-ethylphenol (122 mg, 1.0 mmol, 1.0 M in THF) is combined with the product from Example 65, step 1 (100 mg, 0.19 mmol, 0.19 M in THF/acetonitrile (1:1)) to produce 26 mg of the desired product (Compound 84) as a glass. Low resolution mass spectrum (LC-MS, APCI) m/z 467 [M+H]$^+$.

EXAMPLE 85

Synthesis of 6-(1S)-2-Imidazolyl-1-phenylethoxy)-5-(2-naphthyloxymethyl)-2,3,4-trihydronaphthalen-1-one (Compound 85)

According to the method in Example 66, naphthalen-2-ol (144 mg, 1.0 mmol, 1.0 M in THF) is combined with the product from Example 65, step 1 (100 mg, 0.19 mmol, 0.19 M in THF/acetonitrile (1:1)) to produce 30 mg of the desired product (Compound 85) as a glass. Low resolution mass spectrum (LC-MS, APCI) m/z 489 [M+H]$^+$.

EXAMPLE 86

Synthesis of 6-((1S)-2-Imidazolyl-1-phenylethoxy)-5-[(2-chloro-5-methylphenoxy)methyl]-2,3,4-trihydronaphthalen-1-one (Compound 86)

According to the method in Example 66, 2-chloro-5-methylphenol (142 mg, 1.0 mmol, 1.0 M in THF) is combined with the product from Example 65, step 1 (100 mg, 0.19 mmol, 0.19 M in THF/acetonitrile (1:1)) to produce 27 mg of the desired product (Compound 86) as a glass. Low resolution mass spectrum (LC-MS, APCI) m/z 487 [M+H]$^+$.

EXAMPLE 87

Synthesis of 6-((1S)-2-Imidazolyl-1-phenylethoxy)-5-{[2-(methylpropyl)phenoxy]methyl}-2,3,4-trihydronaphthalen-1-one (Compound 87)

According to the method in Example 66, 2-sec-butylphenol (150 mg, 1.0 mmol, 1.0 M in THF) is combined with the product from Example 65, step 1 (100 mg, 0.19 mmol, 0.19 M in THF/acetonitrile (1:1)) to produce 20 mg of the desired product (Compound 87) as a glass. Low resolution mass spectrum (LC-MS, APCI) m/z 495 [M+H]$^+$.

EXAMPLE 88

Synthesis of Methyl 3-{[2-((1S)-2-imidazolyl-1-phenylethoxy)-5-oxo-6,7,8-trihydronaphthyl]methoxy}benzoate (Compound 88)

According to the method in Example 66, methyl 3-hydroxybenzoate (152 mg, 1.0 mmol, 1.0 M in THF) is combined with the product from Example 65, step 1 (100 mg, 0.19 mmol, 0.19 M in THF/acetonitrile (1:1)) to produce 14 mg of the desired product (Compound 88) as a glass. Low resolution mass spectrum (LC-MS, APCI) m/z 497 [M+H]$^+$.

EXAMPLE 89

Synthesis of 6-((1S)-2-Imidazolyl-1-phenylethoxy)-5-[(2,4,6-trimethylphenoxy)methyl]-2,3,4-trihydronaphthalen-1-one (Compound 89)

According to the method in Example 66, 2,4,6-trimethylphenol (136 mg, 1.0 mmol, 1.0 M in THF) is combined with the product from Example 65, step 1 (100 mg, 0.19 mmol, 0.19 M in THF/acetonitrile (1:1)) to produce 35 mg of the desired product (Compound 89) as a glass. Low resolution mass spectrum (LC-MS, APCI) m/z 481 [M+H]$^+$.

EXAMPLE 90

Synthesis of 6-((1S)-2-Imidazolyl-1-phenylethoxy)-5-{[4-(methylpropyl)phenoxy]methyl}-2,3,4-trihydronaphthalen-1-one (Compound 90)

According to the method in Example 66, 4-sec-butylphenol (150 mg, 1.0 mmol, 1.0 M in THF) is combined with the product from Example 65, step 1 (100 mg, 0.19 mmol, 0.19 M in THF/acetonitrile (1:1)) to produce 16 mg of the desired product (Compound 90) as a glass. Low resolution mass spectrum (LC-MS, APCI) m/z 495 [M+H]+.

EXAMPLE 91

Synthesis of 6-((1S)-2-imidazolyl-1-phenylethoxy)-5-{[4-(trifluoroethyl)phenoxy]methyl}-2,3,4-trihydronaphthalen-1-one (Compound 91)

According to the method in Example 66, 4-trifluoromethylphenol (162 mg, 1.0 mmol, 1.0 M in THF) is combined with the product from Example 65, step 1 (100 mg, 0.19 mmol, 0.19 M in THF/acetonitrile (1:1)) to produce 27 mg of the desired product (Compound 91) as a glass. Low resolution mass spectrum (LC-MS, APCI) m/z 507 [M+H]+.

EXAMPLE 92

Synthesis of 6-((1S)-2-imidazolyl-1-phenylethoxy)-5-(2H-benzo[d]1,3-dioxolan-5-yloxymethyl)-2,3,4-trihydronaphthalen-1-one (Compound 92)

According to the method in Example 66, benzo[1,3]dioxol-5-ol (138 mg, 1.0 mmol, 1.0 M in THF) is combined with the product from Example 65, step 1 (100 mg, 0.19 mmol, 0.19 M in THF/acetonitrile (1:1)) to produce 23 mg of the desired product (Compound 92) as a glass. Low resolution mass spectrum (LC-MS, APCI) m/z 483 [M+H]+.

EXAMPLE 93

Synthesis of 6-((1S)-2-Imidazolyl-1-phenylethoxy)-5-(2H-benzo[d]1,3-dioxolan-5-yloxymethyl)-2,3,4-trihydronaphthalen-1-one (Compound 93)

According to the method in Example 66, 4-chloro-3-methyl-phenol (142 mg, 1.0 mmol, 1.0 M in THF) is combined with the product from Example 65, step 1 (100 mg, 0.19 mmol, 0.19 M in THF/acetonitrile (1:1)) to produce 32 mg of the desired product (Compound 93) as a glass. Low resolution mass spectrum (LC-MS, APCI) m/z 487 [M+H]+.

EXAMPLE 94

Synthesis of 6-((1S)-2-Imidazolyl-1-phenylethoxy))-5-(8-quinolyloxymethyl)-2,3,4-trihydronaphthalen-1-one (Compound 94)

According to the method in Example 66, quinolin-8-ol (145 mg, 1.0 mmol, 1.0 M in THF) is combined with the product from Example 65, step 1 (100 mg, 0.19 mmol, 0.19 M in THF/acetonitrile (1:1)) to produce 40 mg of the desired product (Compound 94) as a glass. Low resolution mass spectrum (LC-MS, APCI) m/z 490 [M+H]+.

EXAMPLE 95

Synthesis of 6-((1S)-2-Imidazolyl-1-phenylethoxy)-5-(8-quinolyloxymethyl)-2,3,4-trihydronaphthalen-1-one (Compound 95)

According to the method in Example 66, 3-dimethylaminophenol (137 mg, 1.0 mmol, 1.0 M in THF) is combined with the product from Example 65, step 1 (100 mg, 0.19 mmol, 0.19 M in THF/acetonitrile (1:1)) to produce 32 mg of the desired product (Compound 95) as a glass. Low resolution mass spectrum (LC-MS, APCI) m/z 482 [M+H]+.

EXAMPLE 96

Synthesis of 6-((1S)-2-Imidazolyl-1-phenylethoxy)-5-{[4-(trifluoromethoxy)phenoxy]methyl}-2,3,4-trihydronaphthalen-1-one (Compound 96)

According to the method in Example 66, 4-trifluoromethoxy-phenol (178 mg, 1.0 mmol, 1.0 M in THF) is combined with the product from Example 65, step 1 (100 mg, 0.19 mmol, 0.19 M in THF/acetonitrile (1:1)) to produce 29 mg of the desired product (Compound 96) as a glass. Low resolution mass spectrum (LC-MS, APCI) m/z 523 [M+H]+.

EXAMPLE 97

Synthesis of 6-((1S)-2-Imidazolyl-1-phenylethoxy)-5-{[4-(phenoxy)phenoxy]methyl}-2,3,4-trihydronaphthalen-1-one (Compound 97)

According to the method in Example 66, 4-phenoxyphenol (186 mg, 1.0 mmol, 1.0 M in THF) is combined with the product from Example 65, step 1 (100 mg, 0.19 mmol, 0.19 M in THF/acetonitrile (1:1)) to produce 32 mg of the desired product (Compound 97) as a glass. Low resolution mass spectrum (LC-MS, APCI) m/z 531 [M+H]+.

EXAMPLE 98

Synthesis of 6-((1S)-2-Imidazolyl-1-phenylethoxy)-5-[(4-chlorophenoxy)methyl]-2,3,4-trihydronaphthalen-1-one (Compound 98)

According to the method in Example 66, 4-chlorophenol (128 mg, 1.0 mmol, 1.0 M in THF) is combined with the product from Example 65, step 1 (100 mg, 0.19 mmol, 0.19 M in THF/acetonitrile (1:1)) to produce 34 mg of the desired product (Compound 98) as a glass. Low resolution mass spectrum (LC-MS, APCI) m/z 473 [M+H]+.

EXAMPLE 99

Synthesis of 6-((1S)-2-Imidazolyl-1-phenylethoxy)-5-[(3-methylphenoxy)methyl]-2,3,4-trihydronaphthalen-1-one (Compound 99)

According to the method in Example 66, 3-methylphenol (108 mg, 1.0 mmol, 1.0 M in THF) is combined with the product from Example 65, step 1 (100 mg, 0.19 mmol, 0.19 M in THF/acetonitrile (1:1)) to produce 36 mg of the desired product (Compound 99) as a glass. Low resolution mass spectrum (LC-MS, APCI) m/z 453 [M+H]+.

EXAMPLE 100

Synthesis of 6-((1S)-2-Imidazolyl-1-phenylethoxy)-5-[(4-methylphenoxy)methyl]-2,3,4-trihydronaphthalen-1-one (Compound 100)

According to the method in Example 66, 4-methylphenol (108 mg, 1.0 mmol, 1.0 M in THF) is combined with the product from Example 65, step 1 (100 mg, 0.19 mmol, 0.19 M in THF/acetonitrile (1:1)) to produce 37 mg of the desired product (Compound 100) as a glass. Low resolution mass spectrum (LC-MS, APCI) m/z 453 [M+H]+.

EXAMPLE 101

Synthesis of 6-((1S)-2-Imidazolyl-1-phenylethoxy)-5-[(2-fluorophenoxy)methyl]-2,3,4-trihydronaphthalen-1-one (Compound 101)

According to the method in Example 66, 2-fluorophenol (112 mg, 1.0 mmol, 1.0 M in THF) is combined with the product from Example 65, step 1 (100 mg, 0.19 mmol, 0.19 M in THF/acetonitrile (1:1)) to produce 38 mg of the desired product (Compound 101) as a glass. Low resolution mass spectrum (LC-MS, APCI) m/z 457 [M+H]+.

EXAMPLE 102

Synthesis of 6-(1S)-2-Imidazolyl-1-phenylethoxy)-5-[(3-fluorophenoxy)methyl]-2,3,4-trihydronaphthalen-1-one (Compound 102)

According to the method in Example 66, 3-fluorophenol (112 mg, 1.0 mmol, 1.0 M in THF) is combined with the product from Example 65, step 1 (100 mg, 0.19 mmol, 0.19 M in THF/acetonitrile (1:1)) to produce 33 mg of the desired product (Compound 102) as a glass. Low resolution mass spectrum (LC-MS, APCI) m/z 457 [M+H]$^+$.

EXAMPLE 103

Synthesis of 6-((1S)-2-Imidazolyl-1-phenylethoxy)-5-[(4-fluorophenoxy)methyl]-2,3,4-trihydronaphthalen-1-one (Compound 103)

According to the method in Example 66, 4-fluorophenol (112 mg, 1.0 mmol, 1.0 M in THF) is combined with the product from Example 65, step 1 (100 mg, 0.19 mmol, 0.19 M in THF/acetonitrile (1:1)) to produce 5 mg of the desired product (Compound 103) as a glass. Low resolution mass spectrum (LC-MS, APCI) m/z 457 [M+H]$^+$.

EXAMPLE 104

Synthesis of 6-((1S)-2-Imidazolyl-1-phenylethoxy)-5-(naphenyloxymethyl)-2,3,4-trihydronaphthalen-1-one (Compound 104)

According to the method in Example 66, naphthalen-1-ol (144 mg, 1.0 mmol, 1.0 M in THF) is combined with the product from Example 65, step 1 (100 mg, 0.19 mmol, 0.19 M in THF/acetonitrile (1:1)) to produce 41 mg of the desired product (Compound 104) as a glass. Low resolution mass spectrum (LC-MS, APCI) m/z 489 [M+H]$^+$.

EXAMPLE 105

Synthesis of 6-((1S)-2-Imidazolyl-1-phenylethoxy)-5-[(3-methoxyphenoxy)methyl]-2,3,4-trihydronaphthalen-1-one (Compound 105)

According to the method in Example 66, 3-methoxyphenol (124 mg, 1.0 mmol, 1.0 M in THF) is combined with the product from Example 65, step 1 (100 mg, 0.19 mmol, 0.19 M in THF/acetonitrile (1:1)) to produce 32 mg of the desired product (Compound 105) as a glass. Low resolution mass spectrum (LC-MS, APCI) m/z 469 [M+H]$^+$.

EXAMPLE 106

Synthesis of 6-((1S)-2-Imidazolyl-1-phenylethoxy)-5-[(2-chlorophenoxy)methyl]-2,3,4-trihydronaphthalen-1-one (Compound 106)

According to the method in Example 66, 2-chlorophenol (128 mg, 1.0 mmol, 1.0 M in THF) is combined with the product from Example 65, step 1 (100 mg, 0.19 mmol, 0.19 M in THF/acetonitrile (1:1)) to produce 32 mg of the desired product (Compound 106) as a glass. Low resolution mass spectrum (LC-MS, APCI) m/z 473 [M+H]$^+$.

EXAMPLE 107

Synthesis of 6-((1S)-2-Imidazolyl-1-phenylethoxy)-5-(6-quinolyloxymethyl)-2,3,4-trihydronaphthalen-1-one (Compound 107)

According to the method in Example 66, quinolin-5-ol (145 mg, 1.0 mmol, 1.0 M in THF) is combined with the product from Example 65, step 1 (100 mg, 0.19 mmol, 0.19 M in THF/acetonitrile (1:1)) to produce 48 mg of the desired product (Compound 107) as a glass. Low resolution mass spectrum (LC-MS, APCI) m/z 490 [M+H]$^+$.

EXAMPLE 108

Synthesis of 6-((1S)-2-Imidazolyl-1-phenylethoxy)-5-(6-quinolyloxymethyl)-2,3,4-trihydronaphthalen-1-one (Compound 108))

3-Chlorobenzenethiol (144 mg, 1.0 mmol, 1.0 M in THF) and 6-((1S)-2-imidazolyl-1-phenylethoxy)-5-(bromomethyl)-2,3,4-trihydronaphthalen-1-one hydrobromide (Example 65, step 1) (100 mg, 0.198 mmol, 0.10 M in THF/acetonitrile (1:1)) are combined in a 2-dram Teflon capped vial and placed in a heater-shaker at 60° C. (295 rpm, 1 hour). The reaction mixture is cooled to RT, diluted with ethyl acetate (3 mL), and washed with 2 M NaOH (2×2.0 mL) and then brine (1×2.0 mL). The organic layer is concentrated to approximately 1.0 mL total volume, diluted with methanol (3.0 mL), treated with macroporous polystyrene sulfonic acid resin (200 mg, loading 1.45 mmol/g, Argonaut Technologies, Inc.). The resulting heterogeneous mixture is placed on a short stroke shaker at 450 rpm for 1 hour. The sulfonic acid resin is collected by gravity filtration and washed sequentially with methanol, ethyl acetate, and methanol (4.0 mL each). Elution of product from the sulfonic acid resin with 2.0 M ammonia in methanol and evaporation of the solvent provides 9 mg of the desired sulfide (Compound 108) as a tan glass. Low resolution mass spectrum (LC-MS, APCI) m/z 489 [M+H]$^+$.

EXAMPLE 109

Synthesis of 6-((1S)-2-Imidazolyl-1-phenylethoxy)-5-[(4-biomophenylthio)methyl]-2,3,4-trihydronaphthalen-1-one (Compound 109)

According to the method of Example 108, 4-bromobenzenethiol (189 mg, 1.0 mmol, 1.0 M in THF) is combined with the product from Example 65, step 1 (100 mg, 0.198 mmol, 0.10 M in THF/acetonitrile (1:1)) to afford 7 mg of the desired sulfide (Compound 109) as a tan glass. Low resolution mass spectrum (LC-MS, APCI) m/z 533 [M+H]$^+$.

EXAMPLE 110

Synthesis of 6-((1S)-2-Imidazolyl-1-phenylethoxy)-5-[(4-fluorophenylthio)methyl]-2,3,4-trihydronaphthalen-1-one (Compound 110)

According to the method of Example 108, 4-fluorobenzenethiol (128 mg, 1.0 mmol, 1.0 M in THF) is combined with the product from Example 65, step 1 (100 mg, 0.198 mmol, 0.10 M in THF/acetonitrile (1:1)) to afford 36 mg of the desired sulfide (Compound 110) as a tan glass. Low resolution mass spectrum (LC-MS, APCI) m/z 472 [M+H]$^+$.

EXAMPLE 111

Synthesis of N-(4-{[2-((1S)-2-Imidazolyl-1-phenylethoxy)-5-oxo-6,7,8-trihydronaphthyl]methylthio}phenyl)acetamide (Compound 111)

According to the method of Example 108, N-(4-mercapto-phenyl)acetamide (167 mg, 1.0 mmol, 1.0 M in THF) is combined with the product from Example 65, step 1 (100 mg, 0.198 mmol, 0.10 M in THF/acetonitrile (1:1)) to afford 56 mg of the desired sulfide (Compound 111) as a tan glass. Low resolution mass spectrum (LC-MS, APCI) m/z 511 [M+H]$^+$.

EXAMPLE 112

Synthesis of 6-((1S)-2-Imidazolyl-1-phenylethoxy)-5-[(4-hydroxyphenylthio)methyl]-2,3,4-trihydronaphthalen-1-one (Compound 112)

According to the method of Example 108, 4-mercaptophenol (126 mg, 1.0 mmol, 1.0 M in THF) is combined with the product from Example 65, step 1 (100 mg, 0.198 mmol, 0.10 M in THF/acetonitrile (1:1)) to afford 23 mg of the desired sulfide (Compound 112) as a tan glass. Low resolution mass spectrum (LC-MS, APCI) m/z 470 [M+H]+.

EXAMPLE 113

Synthesis of 6-((1S)-2-Imidazolyl-1-phenylethoxy)-5-[(4-methylphenylthio)methyl]-2,3,4-trihydronaphthalen-4-1-one (Compound 113)

According to the method of Example 108, 4-methylbenzenethiol (124 mg, 1.0 mmol, 1.0 M in THF) is combined with the product from Example 65, step 1 (100 mg, 0.198 mmol, 0.10 M in THF/acetonitrile (1:1)) to afford 34 mg of the desired sulfide (Compound 113) as a tan glass. Low resolution mass spectrum (LC-MS, APCI) m/z 468 [M+H]+.

EXAMPLE 114

Synthesis of 6-((1S)-2-Imidazolyl-1-phenylethoxy)-5-[(2-methylpropylthio) methyl]-2,3,4-trihydronaphthalen-1-one (Compound 114)

According to the method of Example 108, 2-methylpropane-1]-thiol (90 mg, 1.0 mmol, 1.0 M in THF) is combined with the product from Example 65, step 1 (100 mg, 0.198 mmol, 0.10 M in THF/acetonitrile (1:1)) to afford 36 mg of the desired sulfide (Compound 114) as a tan glass. Low resolution mass spectrum (LC-MS, APCI) m/z 434 [M+H]+.

EXAMPLE 115

Synthesis of 6-((1S)-2-Imidazolyl-1-phenylethoxy)-5-[(2-hydroxyethylthio) methyl]-2,3,4-trihydronaphthalen-1-one (Compound 115)

According to the method of Example 108, 2-mercaptoethanol (78 mg, 1.0 mmol, 1.0 M in THF) is combined with the product from Example 65, step 1 (100 mg, 0.198 mmol, 0.10 M in THF/acetonitrile (1:1)) to afford 40 mg of the desired sulfide (Compound 115) as a tan glass. Low resolution mass spectrum (LC-MS, APCI) m/z 422 [M+H]+.

EXAMPLE 116

Synthesis of 6-((1S)-2-Imidazolyl-1-phenylethoxy)-5-[(2-phenylethylthio) methyl]-2,3,4-trihydronaphthalen-1-one (Compound 116)

According to the method of Example 108, 2-phenylethanethiol (1138 mg, 1.0 mmol, 1.0 M in THF) is combined with the product from Example 65, step 1 (100 mg, 0.198 mmol, 0.10 M in THF/acetonitrile (1:1)) to afford 40 mg of the desired sulfide (Compound 116) as a tan glass. Low resolution mass spectrum (LC-MS, APCI) m/z 482 [M+H]+.

EXAMPLE 117

Synthesis of 6-((1S)-2-Imidazolyl-1-phenylethoxy)-5-(cyclohexylthiomethyl)-2,3,4-trihydronaphthalen-1-one (Compound 117)

According to the method of Example 108, cyclohexanethiol (116 mg, 1.0 mmol, 1.0 M in THF) is combined with the product from Example 65, step 1 (100 mg, 0.198 mmol, 0.10 M in THF/acetonitrile (1:1)) to afford 39 mg of the desired sulfide (Compound 117) as a tan glass. Low resolution mass spectrum (LC-MS, APCI) m/z 460 [M+H]+.

EXAMPLE 118

Synthesis of Methyl 3-{[2-((1S)-2-Imidazolyl-1-phenylethoxy)-5-oxo-6,7,8-trihydronaphthyl] methylthio}propanoate (Compound 118)

According to the method of Example 108, 3-mercaptopropionic acid methyl ester (120 mg, 1.0 mmol, 1.0 M in THF) is combined with the product from Example 65, step 1 (100 mg, 0.198 mmol, 0.10 M in THF/acetonitrile (1:1)) to afford 39 mg of the desired sulfide (Compound 118) as a tan glass. Low resolution mass spectrum (LC-MS, APCI) m/z 464 [M+H]+.

EXAMPLE 119

Synthesis of 6-((1S)-2-Imidazolyl-1-phenylethoxy)-5-(imidazol-2-ylthiomethyl)-2,3,4-trihydronaphthalen-1-one (Compound 119)

According to the method of Example 108, 1H-imidazole-2-thiol (100 mg, 1.0 mmol, 1.0 M in THF) is combined with the product from Example 65, step 1 (100 mg, 0.198 mmol, 0.10 M in THF/acetonitrile (1:1)) to afford 46 mg of the desired sulfide (Compound 119) as a tan glass. Low resolution mass spectrum (LC-MS, APCI) m/z 444 [M+H]+.

EXAMPLE 120

Synthesis of 6-((1S)-2-Imidazolyl-1-phenylethoxy)-5-(1H-1,2,4-triazol-3-ylthiomethyl)-2,3,4-trihydronaphthalen-1-one (Compound 120)

According to the method of Example 108, 1H-[1,2,4] triazole-3-thiol (101 mg, 1.0 mmol, 1.0 M in THF) is combined with the product from Example 65, step 1 (100 mg, 0.198 mmol, 0.10 M in THF/acetonitrile (1:1)) to afford 20 mg of the desired sulfide (Compound 120) as a tan glass. Low resolution mass spectrum (LC-MS, APCI) m/z 445 [M+H]+.

EXAMPLE 121

Synthesis of 6-((1S)-2-Imidazolyl-1-phenylethoxy)-5-[(1-methylimidazol-2-ylthio)methyl]-2,3,4-trihydronaphthalen-1-one (Compound 121)

According to the method of Example 108, 1-methyl-1H-imidazole-2-thiol (114 mg, 1.0 mmol, 1.0 M in THF) is combined with the product from Example 65, step 1 (100 mg, 0.198 mmol, 0.10 M in THF/acetonitrile (1:1)) to afford 51 mg of the desired sulfide (Compound 121) as a tan glass. Low resolution mass spectrum (LC-MS, APCI) m/z 458 [M+H]+.

EXAMPLE 122

Synthesis of 6-((1S)-2-Imidazolyl-1-phenylethoxy)-5-(benzothiazol-2-ylthiomethyl)-2,3,4-trihydronaphthalen-1-one (Compound 122)

According to the method of Example 108, 1H-benzoimidazole-2-thiol (150 mg, 1.0 mmol, 1.0 M in THF) is combined with the product from Example 65, step 1 (100 mg, 0.198 mmol, 0.10 M in THF/acetonitrile (1:1)) to afford 45 mg of the desired sulfide (Compound 122) as a tan glass. Low resolution mass spectrum (LC-MS, APCI) m/z 494 [M+H]+.

EXAMPLE 123

Synthesis of 6-((1S)-2-Imidazolyl-1-phenylethoxy)-5-[(5-chlorobenzothiazol-2-ylthio)methyl]-2,3,4-trihydronaphthalen-1-one (Compound 123)

According to the method of Example 108, 5-chlorobenzothiazole-2-thiol (201 mg, 1.0 mmol, 1.0 M in THF) is combined with the product from Example 65, step 1 (100 mg, 0.198 mmol, 0.10 M in THF/acetonitrile (1:1)) to afford 5 mg of the desired sulfide (Compound 123) as a tan glass. Low resolution mass spectrum (LC-MS, APCI) m/z 545 [M+H]+.

EXAMPLE 124

Synthesis of 6-((1S)-2-Imidazolyl-1-phenylethoxy)-5-(2-furylthiomethyl)-2,3,4-trihydronaphthalen-1-one (Compound 124)

According to the method of Example 108, furan-2-ylmethanethiol (114 mg, 1.0 mmol, 1.0 M in THF) is combined with the product from Example 65, step 1 (100 mg, 0.198 mmol, 0.10 M in THF/acetonitrile (1:1)) to afford 39 mg of the desired sulfide (Compound 124) as a tan glass. Low resolution mass spectrum (LC-MS, APCI) m/z 458 [M+H]$^+$.

EXAMPLE 125

Synthesis of 6-((1S)-2-Imidazolyl-1-phenylethoxy)-5-[(5-nitrobenzimidazol-2-ylthio)methyl]-2,3,4-trihydronaphthalen-1-one (Compound 125)

According to the method of 5108, 5-nitro-1H-benzoimidazole-2-thiol (195 mg, 1.0 mmol, 1.0 M in THF) is combined with the product from Example 65, step 1 (100 mg, 0.198 mmol, 0.10 M in THF/acetonitrile (1:1)) to afford 4 mg of the desired sulfide (Compound 125) as a tan glass. Low resolution mass spectrum (LC-MS, APCI) m/z 539 [M+H]$^+$.

EXAMPLE 126

Synthesis of 2-{[2-((1S)-2-Imidazolyl-1-phenylethoxy)-5-oxo-6,7,8-trihydronaphthyl]methylthio}pyridine-3-carboxylic acid (Compound 126)

According to the method of Example 108, 2-mercaptonicotinic acid (155 mg, 1.0 mmol, 1.0 M in THF) is combined with the product from Example 65, step 1 (100 mg, 0.198 mmol, 0.10 M in THF/acetonitrile (1:1)) to afford 38 mg of the desired sulfide (Compound 126) as a tan glass. Low resolution mass spectrum (LC-MS, APCI) m/z 499 [M+H]$^+$.

EXAMPLE 127

Synthesis of 6-((1S)-2-Imidazolyl-phenylethoxy)-5-[(1-methyl(1,2,3,4-tetraazol-5-ylthio))methyl]-2,3,4-trihydronaphthalen-1-one (Compound 127)

According to the method of Example 108, 1-methyl-1H-tetrazole-5-thiol (116 mg, 1.0 mmol, 1.0 M in THF) is combined with the product from Example 65, step 1 (100 mg, 0.198 mmol, 0.10 M in THF/acetonitrile (1:1)) to afford 49 mg of the desired sulfide (Compound 127) as a tan glass. Low resolution mass spectrum (LC-MS, APCI) m/z 460 [M+H]$^+$.

EXAMPLE 128

Synthesis of 6-((1S)-2-Imidazol-1-phenylethoxy)-5-[(2,2,2-trifluoroethylthio) methyl]-2,3,4-trihydronaphthalen-1-one (Compound 128)

According to the method of Example 108, 2,2,2-trifluoroethanethiol (116 mg, 1.0 mmol, 1.0 M in THF) is combined with the product from Example 65, step 1 (100 mg, 0.198 mmol, 0.10 M in THF/acetonitrile (1:1)) to afford 24 mg of the desired sulfide (Compound 128) as a tan glass. Low resolution mass spectrum (LC-MS, APCI) m/z 460 [M+H]$^+$.

EXAMPLE 129

Synthesis of 6-((1S)-2-Imidazolyl-1-phenylethoxy)-5-(2-naphthylthiomethyl)-2,3,4-trihydronaphthalen-1-one (Compound 129)

According to the method of Example 108, naphthalen-2-thiol (160 mg, 1.0 mmol, 1.0 M in THF) is combined with the product from Example 65, step 1 (100 mg, 0.198 mmol, 0.10 M in THF/acetonitrile (1:1)) to afford 9 mg of the desired sulfide (Compound 129) as a tan glass. Low resolution mass spectrum (LC-MS, APCI) m/z 504 [M+H]$^+$.

EXAMPLE 130

Synthesis of 6-((1S)-2-Imidazolyl-1-phenylethoxy)-5-[(2-bromophenylthio) methyl]-2,3,4-trihydronaphthalen-1-one (Compound 130)

According to the method of Example 108, 2-bromobenzenethiol (189 mg, 1.0 mmol, 1.0 M in THF) is combined with the product from Example 65, step 1 (100 mg, 0.198 mmol, 0.10 M in THF/acetonitrile (1:1)) to afford 36 mg of the desired sulfide (Compound 130) as a tan glass. Low resolution mass spectrum (LC-MS, APCI) m/z 532 [M+H]$^+$.

EXAMPLE 131

Synthesis of 6-((1S)-2-Imidazolyl-1-phenylethoxy)-5-[(2-chlorophenylthio) methyl]-2,3,4-trihydronaphthalen-1-one (Compound 131)

According to the method of Example 108, 2-chlorobenzenethiol (144 mg, 1.0 mmol, 1.0 M in THF) is combined with the product from Example 65, step 1 (100 mg, 0.198 mmol, 0.10 M in THF/acetonitrile (1:1)) to afford 40 mg of the desired sulfide (Compound 131) as a tan glass. Low resolution mass spectrum (LC-MS, APCI) m/z 488 [M+H]$^+$.

EXAMPLE 132

Synthesis of 6-((1S)-2-Imidazolyl-1-phenylethoxy)-5-[(2,6-dichlorophenylthio) methyl]-2,3,4-trihydronaphthalen-1-one (Compound 132)

According to the method of Example 108, 2,6-dichlorobenzenethiol (179 mg, 1.0 mmol, 1.0 M in THF) is combined with the product from Example 65, step 1 (100 mg, 0.198 mmol, 0.10 M in THF/acetonitrile (1:1)) to afford 30 mg of the desired sulfide (Compound 132) as a tan glass. Low resolution mass spectrum (LC-MS, APCI) m/z 522 [M+H]$^+$.

EXAMPLE 133

Synthesis of 6-((1S)-2-Imidazolyl-1-phenylethoxy)-5-[(2-methoxyphenylthio) methyl]-2,3,4-trihydronaphthalen-1-one (Compound 133)

According to the method of Example 108, 2-methoxybenzenethiol (140 mg, 1.0 mmol, 1.0 M in THF) is combined with the product from Example 65, step 1 (100 mg, 0.198 mmol, 0.10 M in THF/acetonitrile (1:1)) to afford 37 mg of the desired sulfide (Compound 133) as a tan glass. Low resolution mass spectrum (LC-MS, APCI) m/z 484 [M+H]$^+$.

EXAMPLE 134

Synthesis of 6-((1S)-2-Imidazolyl-1-phenylethoxy)-5-[(2-methylphenylthio) methyl]-2,3,4-trihydronaphthalen-1-one (Compound 134)

According to the method of Example 108, 2-methylbenzenethiol (124 mg, 1.0 mmol, 1.0 M in THF) is combined with the product from Example 65, step 1 (100 mg, 0.198 mmol, 0.10 M in THF/acetonitrile (1:1)) to afford 34 mg of the desired sulfide (Compound 134) as a tan glass. Low resolution mass spectrum (LC-MS, APCI) m/z 468 [M+H]$^+$.

EXAMPLE 135

Synthesis of 6-((1S)-2-Imidazolyl-1-phenylethoxy)-5-[(4-methoxyphenylthio) methyl-2,3,4-trihydronaphthalen-1-one (Compound 135)

According to the method of Example 108, 4-methoxybenzenethiol (140 mg, 1.0 mmol, 1.0 M in THF) is combined with the product from Example 65, step 1 (100 mg, 0.198 mmol, 0.10 M in THF/acetonitrile (1:1)) to afford 44 mg of the desired sulfide (Compound 135) as a tan glass. Low resolution mass spectrum (LC-MS, APCI) m/z 484 [M+H]$^+$.

EXAMPLE 136

Synthesis of 6-((1S)-2-Imidazolyl-1-phenylethoxy)-5-[(4-methyl(1,2,4-triazol-3-ylthio))methyl]-2,3,4-trihydronaphthalen-1-one (Compound 136)

According to the method of Example 108, 4-methyl-4H-[1,2,4]triazole-3-thiol (115 mg, 1.0 mmol, 1.0 M in THF) is combined with the product from Example 65, step 1 (100 mg, 0.198 mmol, 0.10 M in THF/acetonitrile (1:1)) to afford 21 mg of the desired sulfide (Compound 136) as a tan glass. Low resolution mass spectrum (LC-MS, APCI) m/z 459 [M+H]$^+$.

EXAMPLE 137

Synthesis of 6-((1S)-2-Imidazolyl-1-phenylethoxy)-5-[(4-nitrophenylthio) methyl]-2,3,4-trihydronaphthalen-1-one (Compound 137)

According to the method of Example 108, 4-nitrobenzenethiol (155 mg, 1.0 mmol, 1.0 M in THF) is combined with the product from Example 65, step 1 (100 mg, 0.198 mmol, 0.10 M in THF/acetonitrile (1:1)) to afford 42 mg of the desired sulfide (Compound 137) as a tan glass. Low resolution mass spectrum (LC-MS, APCI) m/z 499 [M+H]$^+$.

EXAMPLE 138

Synthesis of 6-((1S)-2-Imidazolyl-1-phenylethoxy)-5-[(3-methoxyphenylthio) methyl]-2,3,4-trihydronaphthalen-4-1-one (Compound 138)

According to the method of Example 108, 3-methoxybenzenethiol (140 mg, 1.0 mmol, 1.0 M in THF) is combined with the product from Example 65, step 1 (100 mg, 0.198 mmol, 0.10 M in THF/acetonitrile (1:1)) to afford 48 mg of the desired sulfide (Compound 138) as a tan glass. Low resolution mass spectrum (LC-MS, APCI) m/z 484 [M+H]$^+$.

EXAMPLE 139

Synthesis of 6-((1S)-2-Imidazolyl-1-phenylethoxy)-5-[(4-chlorophenylthio) methyl]-2,3,4-trihydronaphthalen-1-one (Compound 139)

According to the method of Example 108, 4-chlorobenzenethiol (144 mg, 1.0 mmol, 1.0 M in THF) is combined with the product from Example 65, step 1 (100 mg, 0.198 mmol, 0.10 M in THF/acetonitrile (1:1)) to afford 5 mg of the desired sulfide (Compound 139) as a tan glass. Low resolution mass spectrum (LC-MS, APCI) m/z 488 [M+H]$^+$.

EXAMPLE 140

Synthesis of 6-((1S)-2-Imidazolyl-1-phenylethoxy-5-(2-quinolylthiomethyl)-2,3,4-trihydronaphthalen-1-one (Compound 140)

According to the method of Example 108, quinoline-2-thiol (161 mg, 1.0 mmol, 1.0 M in THF) is combined with the product from Example 65, step 1 (100 mg, 0.198 mmol, 0.10 M in THF/acetonitrile (1:1)) to afford 41 mg of the desired sulfide (Compound 140) as a tan glass. Low resolution mass spectrum (LC-MS, APCI) m/z 505 [M+H]$^+$.

EXAMPLE 141

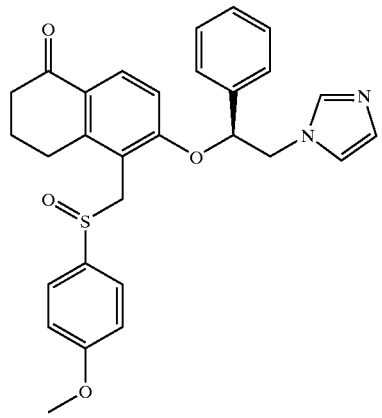

Synthesis of 6-((S)-2-Imidazol-1-yl-1-phenyl-ethoxy)-5-(4-methoxy-benzenesulfinylmethyl)-3,4-dihydro-2H-napthalen-1-one (Compound 141)

1. 6-((S)-2-Imidazol-1-yl-1-phenyl-ethoxy)-5-(4-methoxy-phenylsulfanylmethyl)-3,4-dihydro-2H-napthalen-1-one To a solution of 5-Bromomethyl-6-(2-imidazol-1-yl-1-phenyl-ethoxy)-3,3-dihydro-2H-napthalen-1-one, example 65 step 1 (100 mg, 0.198 mmol) in 1:1 anhydrous tetrahydrofuran/acetonitrile (2 ml) was added the 4-methoxybenzene thiol (140 mg, 1.0 mmol, 1.0M in THF). The mixture was stirred for 18 hours at 60° C. After cooling to room temperature, the solvent was removed and ethyl acetate (3 ml) was added. The mixture was extracted sequentially with 2 $\underline{N}$ NaOH, (2×), and brine, (2×). The organic layer was dried over Na$_2$SO$_4$, and the solvent removed in vacuo to give 18.9 mg of the desired sulfide as a tan glass. 18.9 mg, 20% yield. MS LC-MS, APCI m/z 485 [M+H]$^+$.

2. 6-((S)-2-Imidazol-1-yl-1-phenyl-ethoxy)-5-(4-methoxy-benzenesulfinylmethyl)-3,4-dihydro-2H-napthalen-1-one To the above product was added Davis oxiziridine reagent, which is 2-Benzensulfonyl-3-phenyloxaziridine (26 mg, 0.1 mmole) in chloroform (2 ml). After stirring for 18 hr at room temperature, the solvent was removed in vacuo. The material was purified by reversed-phase HPLC (0.1% trifluoroacetic acid in acetonitrile and 0.1% aqueous trifluoroacetic acid as eluent; C-18 column) to give 3 mg of the desired product (Compound 141) as a colorless solid. LC-MS, APCI m/z 501 [M+H]$^+$.

EXAMPLE 142

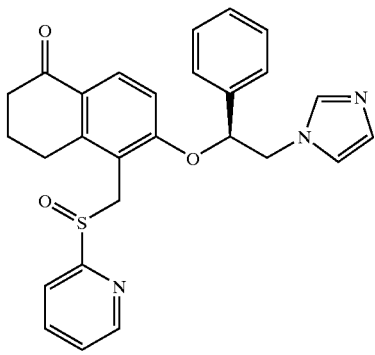

Synthesis of (±)-6-((S)-2-Imidazol-1-yl-1-phenyl-ethoxy)-5-(pyridine-2-sulfinylmethyl)-3,4-dihydro-2H-napthalen-1-one (Compound 142)

The title compound was prepared according to the procedure for example 141 steps 1,2 using 5-Bromomethyl-6-(2-imidazol-1-yl-1-phenyl-ethoxy)-3,3-dihydro-2H-napthalen-1-one example 65 step 1, and pyridine-2-thiol. LC-MS, APCI m/z 472 [M+H]+.

EXAMPLE 143

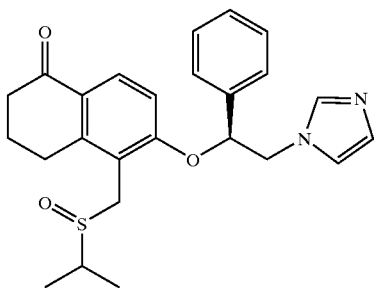

Synthesis of (±)-6-((S)-2-Imidazol-1-yl-1-phenyl-ethoxy)-5-(propane-2-sulfinylmethyl)-3,4-dihydro-2H-napthalen-1-one (Compound 143)

The title compound was prepared according to the procedure for example 141 steps 1,2 using 5-Bromomethyl-6-(2-imidazol-1-yl-1-phenyl-ethoxy)-3,3-dihydro-2H-napthalen-1-one example 65 step 1, and propane-2-thiol. LC-MS, APCI m/z 437 [M+H]+.

EXAMPLE 144

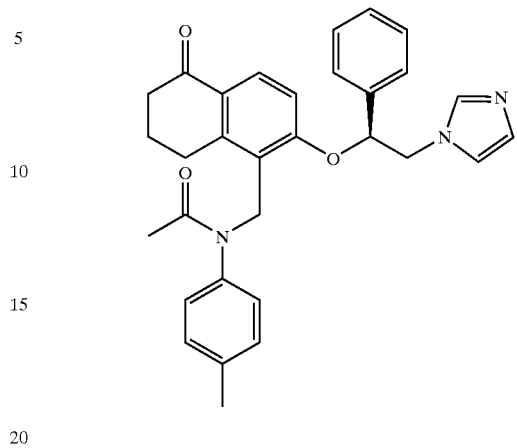

Synthesis of N-[2-((S)-2-Imidazol-1-yl-1-phenyl-ethoxy)-5-oxo-5,6,7,8-tetrahydro-naphthalen-1-ylmethyl]-N-p-tolyl-acetamide (Compound 144)

To a solution of N-p-Tolyl-acetamide (149 mg, 0.1 mmol) in 10:1 anhydrous THF/DMF (15 ml) was added NaH, 95%, (50 mg, 2 mmol) at 0° C. After stirring for 30 min, a solution of 5-Bromomethyl-6-(2-imidazol-1-yl-1-phenyl-ethoxy)-3,3-dihydro-2H-napthalen-1-one, example 65, step 1 (505 mg, 1 mmol) in 1:1 THF/DMF (5 ml) and triethylamine (101 mg, 1 mmol) was added. The mixture was stirred for 18 hr at room temperature. The reaction mixture was diluted up to 25 ml with 2 N NaOH and extracted with ethyl acetate, 3×10 ml. The organics were combined, washed with brine, dried over anhydrous magnesium sulfate and evaporated in vacuo. The material was purified by chromatography on 10 g of MP-TsOH (macroporous polystyrene sulfonic acid) eluted with a methanol. 27 mg, 5.5% Yield. LC-MS, APCI m/z 494 [M+H]+.

EXAMPLE 145

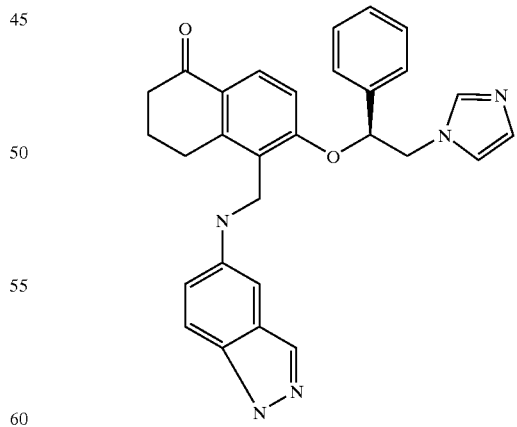

Synthesis of 6-((S)-2-Imidazol-1-yl-1-phenyl-ethoxy)-5-[1H-indazol-5-ylamino)methyl]-3,4-dihydro-2H-napthalen-1-one (Compound 145)

A solution of 5-Bromomethyl-6-(2-imidazol-1-yl-1-phenyl-ethoxy)-3,3-dihydro-2H-napthalen-1-one, example 65, step 1 (100 mg, 0.198 mmol) in 1:1 anhydrous tetrahydrofuran/acetonitrile (2 ml) was dispensed into a 16×20 mm screw cap vial. To this mixture was added 0.75 ml of 0.4 M 1H-indazol-5-ylamine solution in acetonitrile (0.3 mmol). The mixture was shaken for 1 hour at 50° C. After cooling to room temperature, 2 ml of 2 N NaOH was added. The mixture was extracted with ethyl acetate 3×2 ml. The organic layers were combined, washed with brine (2 ml), dried (Na$_2$SO$_4$), and the solvent removed in vacuo. The material was purified by chromatography on 10 g of Zorbax C-18, eluted with a gradient of 20 to 80% water/acetonitrile to afford 18 mg of the desired product LC-MS, APCI m/z 478 [M+H]$^+$.

EXAMPLE 146

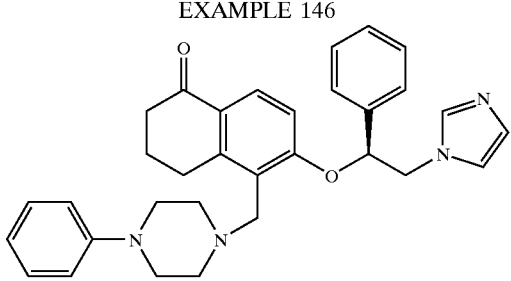

Synthesis of 6-((S)-2-Imidazol-1-yl-1-phenyl-ethoxy)-5-(4-phenyl-piperazin-1-ylmethyl)-3,4-dihydro-2H-napthalen-1-one (Compound 146)

The title compound was prepared according to the procedure for example 145 using 5-bromomethyl-6-(2-imidazol-1-yl-1-phenyl-ethoxy)-3,3-dihydro-2H-napthalen-1-one, example 65 step 1, and 1-phenyl-piperazine to afford 8 mg of the desired product. LC-MS, APCI m/z 507 [M+H]$^+$.

EXAMPLE 147

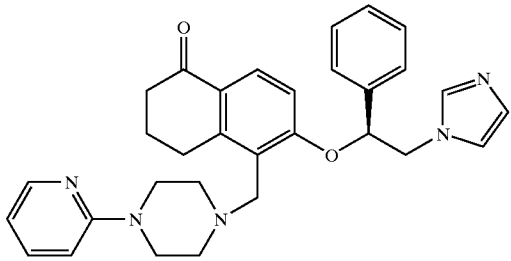

Synthesis of 6-((S)-2-Imidazol-1-yl-1-phenyl-ethoxy)-5-(4-pyridin-2-yl-piperazin-1-ylmethyl)-3,4-dihydro-2H-napthalen-1-one (Compound 147)

The title compound was prepared according to the procedure for example 145 using 5-bromomethyl-6-(2-imidazol-1-yl-1-phenyl-ethoxy)-3,3-dihydro-2H-napthalen-1-one, example 65 step 1 and 1-pyridin-2-yl-piperazine to afford 40 mg of the desired product. LC-MS, APCI m/z 508 [M+H]$^+$.

EXAMPLE 148

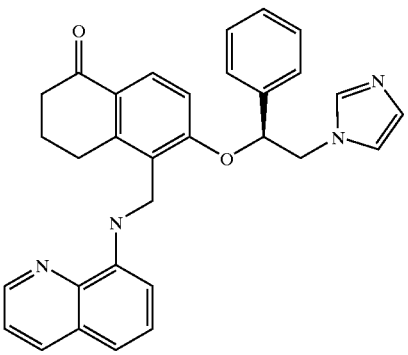

Synthesis of 6-((S)-2-Imidazol-1-yl-1-phenyl-ethoxy)-5-(quinolin-8-ylaminomethyl)-3,4-dihydro-2H-napthalen-1-one (Compound 148)

The title compound was prepared according to the procedure for example 145 using 5-bromomethyl-6-(2-imidazol-1-yl-1-phenyl-ethoxy)-3,3-dihydro-2H-napthalen-1-one, example 65 step 1 and quinolin-8-ylamine to afford 20 mg of the desired product. LC-MS, APCI m/z 489 [M+H]$^+$.

EXAMPLE 149

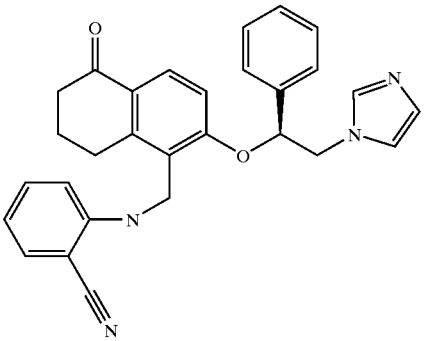

Synthesis of 2-{[2-((S)-2-Imidazol-1-yl-1-phenyl-ethoxy)-5-oxo-5,6,7,8-tetrahydro-napthalen-1-ylmethyl]-amino}-benzonitrile (Compound 149)

The title compound was prepared according to the procedure for example 145 using 5-bromomethyl-6-(2-imidazol-1-yl-1-phenyl-ethoxy)-3,3-dihydro-2H-napthalen-1-one, example 65 step 1 and 2-amino-benzonitrile to afford 22 mg of the desired product LC-MS, APCI m/z 463 [M+H]$^+$.

EXAMPLE 150

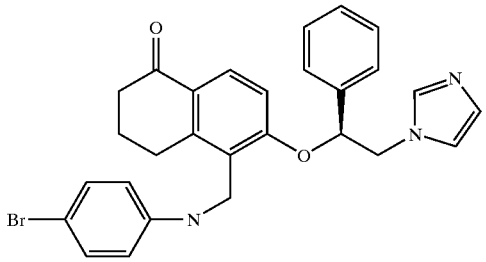

Synthesis of 5-[(4-Fluoro-phenylamino)-methyl]-6-((S)-2-imidazol-1-yl-1-phenyl-ethoxy)-3,4-dihydro-2H-napthalen-1-one (Compound 150)

The title compound was prepared according to the procedure for example 145 using 5-bromomethyl-6-(2- imidazol-1-yl-1-phenyl-ethoxy)-3,3-dihydro-2H-napthalen-1-one, example 65 step 1 and 4-bromo-phenylamine to afford 36 mg of the desired product LC-MS, APCI m/z 516 [M]⁺.

EXAMPLE 151

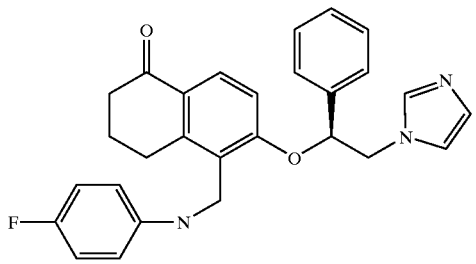

Synthesis of 5-[(4-Fluoro-phenylamino)-methyl]-6-((S)-2-imidazol-1-yl-1-phenyl-ethoxy)-3,4-dihydro-2H-napthalen-1-one (Compound 151)

The title compound was prepared according to the procedure for example 145 using 5-bromomethyl-6-(2-imidazol-1-yl-1-phenyl-ethoxy)-3,3-dihydro-2H-napthalen-1-one, example 65 step 1 and 4-fluoro-phenylamine to afford 25 mg of the desired product LC-MS, APCI m/z 456 [M+H]⁺.

EXAMPLE 152

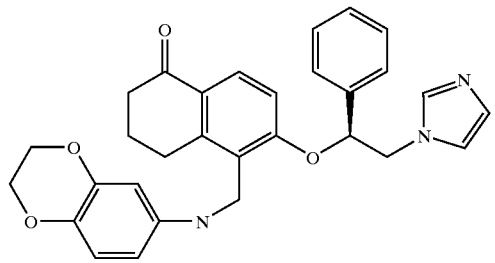

Synthesis of 5-[(2,3-Dihydro-benzo[1,4]dioxin-6-ylamino)-methyl]-6-((S)-2-imidazol-1-yl-1-phenyl-ethoxy)-3,4-dihydro-2H-napthalen-1-one (Compound 152)

The title compound was prepared according to the procedure for example 145 using 5-bromomethyl-6-(2-imidazol-1-yl-1-phenyl-ethoxy)-3,3-dihydro-2H-napthalen-1-one, example 65 step 1 and 2,3-dihydro-benzo[1,4]dioxin-6-ylamine to afford 18 mg of the desired product. LC-MS, APCI m/z 496 [M+H]⁺.

EXAMPLE 153

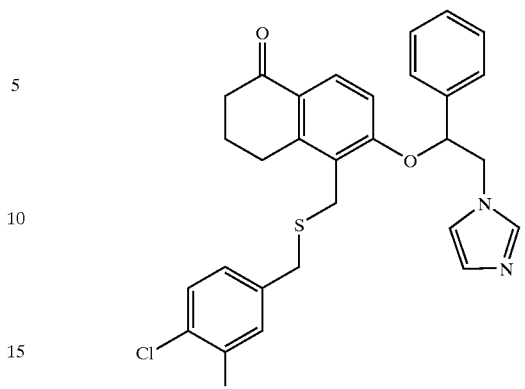

Synthesis of 5-(304-Dichloro-benzylsulfanylmethyl)-6-((1S)-2-imidazol-1-yl-1-phenyl-ethoxy)-3,4-dihydro-2H-naphthalen-1-one (Compound 153)

1. 5-(3,4-Dichloro-benzylsulfanylmethyl)-6-hydroxy-3,4-dihydro-2H-naphthalen-1-one 5-Chloromethyl-6-hydroxy-1-tetralone (315 mg, 1.5 mmol) and (3,4-Dichloro-phenyl)-methanethiol (1.0 mL, 6.0 mmol) were sealed in a 16×120 mm screw capped tube and heated to 40° C. overnight. The excess (3,4-Dichloro-phenyl)methanethiol was removed in vacuo and the residue was purified by silica gel chromatography (hexanes/ethyl acetate/acetic acid, 58:40:2) to give 350 mg (63%) of the desired product as a tan powder: (LC-MS, APCI) m/z 367/369 [M+H]⁺.

2. 5-(3,4-Dichloro-benzylsulfanylmethyl)-6-((1S)-2-imidazol-1-yl-1-phenyl-ethoxy)-3,4-dihydro-2H-naphthalen-1-one 5-(3,4-Dichloro-benzylsulfanylmethyl)-6-hydroxy-3,4-dihydro-2H-naphthalen-1-one (256 mg, 0.69 mmol), (R)-2-imidazol-1-yl-1-phenyl-ethanol (144 mg, 0.75 mmol), and triphenylphosphine resin (1.46 g, loading 1.41 mmol/g) were combined in dry tetrahydrofuran (10 mL) and treated with diisopropyl azodicarboxylate (271 µL, 2.0 mmol). The resulting orange-brown heterogeneous mixture was allowed to stir at ambient temperature overnight. The spent triphenylphosphine resin was removed by filtration, washing sequentially with ethyl acetate, methanol, and chloroform. The filtrate was concentrated in vacuo and the crude material was purified by silica gel chromatography (hexanes/ethyl acetate/triethylamine 28:70:2) to give 280 mg (75%) of the desired product as a colorless solid: (LC-MS, APCI) m/z 553/555 [M+H]⁺.

3. 6-(2-Imidazol-1-yl-1-phenyl-ethoxy)-5-{[2-(pyridin-4-yloxy)-ethylamino]-methyl}-3,4-dihydro-2H-naphthalen-1-one 2-(Pyridin-4-yloxy)-ethylamine (1.0 mL, 0.4 mmol, 0.4 M in $\mu,\mu,\mu$-trifluorotoluene) and 6-((1S)-2-imidazoyl-1-phenylethoxy)-5-(bromomethyl)-2,3,4-trihydronapthalen-1-one (Example 65, step 1)(100 mg, 0.198 mmol) were sealed in a 16×120 mm screw capped tube and heated to 50° C. (45 min). Reaction mixture was cooled to rt and partitioned between 2N sodium hydroxide and ethyl acetate. The organic layer was separated, washed (brine), dried (Na₂SO₄), and concentrated in vacuo. The residue was purified by flash silica gel chromatography (ethyl acetate/ triethylamine/methanol, 17:2:1) to give 31 mg (32%) of the desired product as a colorless glass: (LC-MS, APCI) m/z 483 [M+H]⁺.

EXAMPLE 154

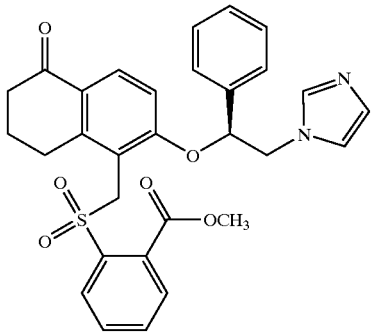

Methyl 2-{[(2-{[(1S)-2-(1H-Imidazol-1-yl)-1-phenylethyl]oxy}-5-oxo-5,6,7,8-tetrahydro-1-naphthalenyl)methyl]sulfonyl}benzoate (Compound 154)

1. Methyl 2-(2-hydroxy-5-oxo-5,6,7,8-tetrahydro-1-naphthalenyl)methylsulfanylbenzoate.

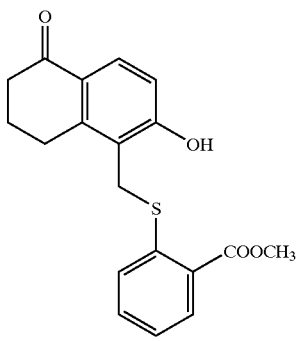

To a stirred mixture of 5-chloromethyl-6-hydroxy-3,4-dihydro-2H-naphthalen-1-one (6.29 g, 29.8 mmol) and methyl thiosalicylate (5.0 g, 29.8 mmol) in dichloromethane (100 ml) was added triethylamine (9.0 ml). The mixture was further stirred at 22° C. under a nitrogen atmosphere and in the dark for 23 h. The volatiles were evaporated under reduced pressure to give a pink solid which was triturated with methanol (30 ml). 0.1N HCl (100 ml) was added and acidified to pH=1 with conc HCl. The mixture was further stirred at room temperature for 3 h. The precipitate was filtered, washed with water and dried to give the desired product as a light pink solid, 10.0 g, 98% yield; mp 203–205° C. (from MeOH). NMR spectrum was consistent with structure. Calcd. For: $C_{19}H_{18}O_6S \cdot 0.5H_2O$:

| Theory: | C, 64.94; | H, 5.45; | S, 9.13. |
|---|---|---|---|
| Found: | C, 65.28; | H, 5.53; | S, 9.52. |

2. Methyl 2-(2-hydroxy-5-oxo-5,6,7,8-tetrahydro-1-naphthalenyl)methylsulfonylbenzoate

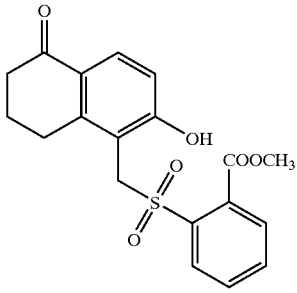

To a mixture of methyl 2-(2-hydroxy-5-oxo-5,6,7,8-tetrahydro-1-naphthalenyl)methylsulfanylbenzoate (5.00 g, 14.6 mmol) in dichloromethane (200 ml) was added solid m-CPBA (8.92 g of a 70% pure sample, 36.6 mmol) portionwise while stirring at 0° C. After 5 h at 0° C., DMSO (10 ml) was added and stirred for 10 min. Volatiles were removed under reduced pressure. The residue was treated with an excess of an aqueous solution of sodium bicarbonate and stirred at 0° C. for 30 min. The precipitate was filtered; washed with water; and dried to give a colorless solid, 4.70 g, 86% yield; mp 194–196° C. (from ethyl acetate). NMR spectrum was consistent with structure. Calcd. For: $C_{19}H_{18}O_6S$:

| Theory: | C, 60.95; | H, 4.85; | S, 8.56. |
|---|---|---|---|
| Found: | C, 60.55; | H, 5.10; | S, 8.35. |

3. Methyl 2-{[(2-{[((S)-2-(1H-imidazol-1-yl)-1-phenylethyl]oxy}-5-oxo-5,6,7,8-tetrahydro-1-naphthalenyl)methyl]sulfonyl}benzoate To a stirred homogeneous mixture of methyl 2-{[(2-{[(1S)-2-(1H-imidazol-1-yl)-1-phenylethyl]oxy}-5-oxo-5,6,7,8-tetrahydro-1-naphthalenyl)methyl]sulfonyl}benzoate (1.98 g, 5.3 mmol), (R)-2-imidazol-1-yl-1 phenylethanol (1.00 g, 5.3 mmol) and triphenylphosphine (2.10 g, 8.0 mmol) in THF (70 ml) under a nitrogen atmosphere was added dropwise (over 25 min) a solution of diethyl azodicarboxylate (1.39 g, 8.0 mmol) in THF (30 ml). The reaction was further stirred at room temperature (22° C.) for 66 h. Brine was added and the product was extracted into ethyl acetate. The ethyl acetate solution was evaporated and the crude product was purified by a silica gel column, using ethyl acetate to remove the non-polar impurities and dichloromethane-methanol (10:1) to elute the required compound as a colorless solid, 2.62 g, 91% yield; mp 212° C. (from ethyl acetate-MeOH). NMR spectrum was consistent with structure. Calcd. For: $C_{30}H_{28}N_2O_6S \cdot 0.5H_2O$:

| Theory: | C, 65.08; | H, 5.28; | N, 5.06. |
|---|---|---|---|
| Found: | C, 65.21; | H, 5.12; | N, 4.90. |

EXAMPLE 155

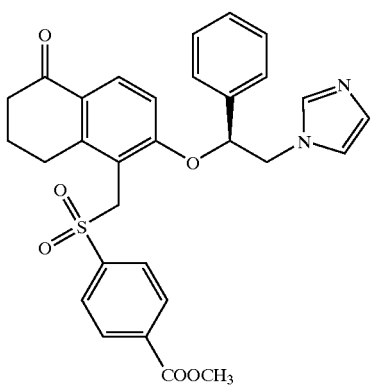

Methyl 4-{[(2-{[(1S)-2-(1H-imidazol-1-yl)-1-phenylethyl]oxy}-5-oxo-5,6,7,8-tetrahydro-1-naphthalenyl)methyl]sulfonyl}benzoate (Compound 155)

1. Methyl 4-(2-hydroxy-5-oxo-5,6,7,8-tetrahydro-1-naphthalenyl)methyl]sulfanyl}benzoate

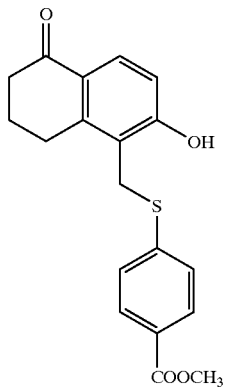

Using the method in Example 154, this compound was prepared from 5-chloromethyl-6-hydroxy-3,4-dihydro-2H-naphthalen-1-one (6.29 g, 29.8 mmol) and methyl 4-mercaptobenzoate (5.00 g, 29.8 mmol) to give the desired compound as a coilorless solid, 9.96 g, 98% yield, mp 191–192° C. (from dicloromethane-MeOH). NMR spectrum was consistent with structure. Calcd. For $C_{19}H_{18}O_4S$:

| Theory: | C, 66.65; | H, 5.30. |
| Found: | C, 66.84; | H, 5.38. |

2. Methyl 4-(2-hydroxy-5-oxo-5,6,7,8-tetrahydro-1-naphthalenyl)methylsulfonylbenzoate

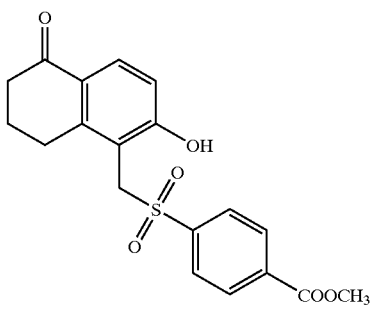

Using the method in Example 154 this compound was prepared from methyl 4-(2-hydroxy-5-oxo-5,6,7,8-tetrahydro-1-naphthalenyl)methylsulfanylbenzoate (5.00 g, 14.6 mmol) and m-CPBA (8.92 g of a 70% pure sample, 36.6 mmol) as a colorless solid, 5.09 g, 93% yield; mp 132–134° C. (from ethyl acetate). NMR spectrum was consistent with structure. Calcd. For $C_{19}H_{18}O_6S.0.5H_2O$:

| Theory: | C, 60.95; | H, 4.85. |
| Found: | C, 59.13; | H, 5.18. |

3. Methyl 4-{[(2-{[(1S)-2-(1H-imidazol-1-yl)-1-phenylethyl]oxy}-5-oxo-5,6,7,8-tetrahydro-1-naphthalenyl)methyl]sulfonyl}benzoate Using the method in Example 154, this compound was prepared from methyl 4-(2-hydroxy-5-oxo-5,6,7,8-tetrahydro-1-naphthalenyl)methylsulfonylbenzoate (1.98 g, 5.3 mmol), (R)-2-imidazol-1-yl-1-phenylethanol (1.00 g, 5.3 mmol), $Ph_3P$ (2.10 g, 8.0 mmol), and diethyl azodicarboxylate (1.39 g, 8.0 mmol) as a solid-foam, 2.78 g, 96% yield; mp 105° C. NMR spectrum was consistent with structure. Calcd. For $C_{30}H_{28}N_2O_6S.H_2O$:

| Theory: | C, 60.04; | H, 5.37; | N, 4.98. |
| Found: | C, 64.33; | H, 5.19; | N, 5.32. |

EXAMPLE 156

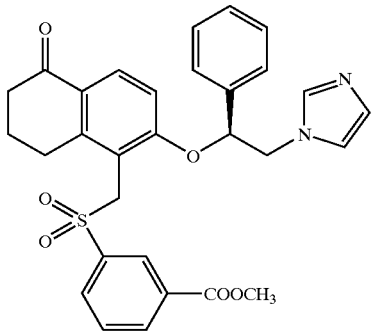

Methyl 4-{[(2-{[(1S)-2-(1H-Imidazol-1-yl)-1-phenylethyl]oxy}-5-oxo-5,6,7,8-tetrahydro-1-naphthalenyl)methyl]sulfonyl}benzoate (Compound 156)

1. Methyl 3-{[(2-{[(1S)-2-(1H-imidazol-1-yl)-1-phenylethyl]oxy}-5-oxo-5,6,7,8-tetrahydro-1-naphthalenyl)methyl]sulfonyl}benzoate

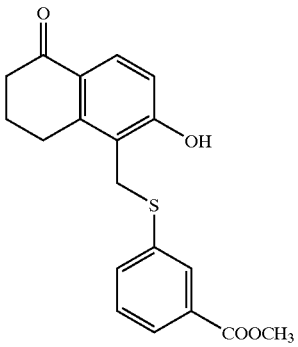

Using the method in Example 154, this compound was prepared from 5-chloromethyl-6-hydroxy-3,4-dihydro-2H-naphthalen-1-one (6.16 g, 29.2 mmol) and methyl 3-mercaptobenzoate (4.90 g, 29.2 mmol) to give the desired compound as a pale pink solid, 9.31 g, 93% yield; mp 93–95° C. (from ethyl acetate). NMR spectrum was consistent with structure. Calcd. For $C_{19}H_{18}O_4S$:

| | | |
|---|---|---|
| Theory: | C, 66.65; | H, 5.30. |
| Found: | C, 66.43; | H, 5.56. |

2. Methyl 3-(2-hydroxy-5-oxo-5,6,7,8-tetrahydro-1-naphthalenyl)methylsulfonylbenzoate

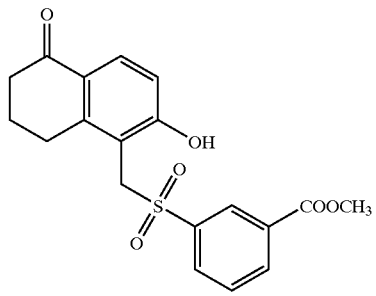

Using the method in Example 154 this compound was prepared from methyl 3-(2-hydroxy-5-oxo-5,6,7,8-tetrahydro-1-naphthalenyl)methylsulfanylbenzoate (5.00 g, 14.6 mmol) and m-CPBA (8.92 g of a 70% pure sample, 36.6 mmol) as a colorless solid, 5.13 g, 94% yield; mp 230–232° C. (from dichloromethane-MeOH). NMR spectrum was consistent with structure. Calcd. For $C_{19}H_{18}O_6S$:

| | | |
|---|---|---|
| Theory: | C, 60.95; | H, 4.85. |
| Found: | C, 61.09; | H, 4.98. |

3. Methyl 3-{[(2-{[(1S)-2-(1H-imidazol-1-yl)-1-phenylethyl]oxy}-5-oxo-5,6,7,8-tetrahydro-1-naphthalenyl)methyl]sulfonyl}benzoate Using the method in Example 154, this compound was prepared from methyl 3-(2-hydroxy-5-oxo-5,6,7,8-tetrahydro-1-naphthalenyl)methylsulfonylbenzoate (1.98 g, 5.3 mmol), (R)-2-imidazol-1-yl-1-phenylethanol (1.00 g, 5.3 mmol), Ph₃P (2.10 g, 8.0 mmol), and diethyl azodicarboxylate (1.39 g, 8.0 mmol) as a solid-foam, 2.80 g, 96% yield; mp 85° C. NMR spectrum was consistent with structure. Calcd. For $C_{30}H_{28}N_2O_6S \cdot 0.5H_2O$:

| | | | |
|---|---|---|---|
| Theory: | C, 65.08; | H, 5.28; | N, 5.06. |
| Found: | C, 65.22; | H, 5.23; | N, 5.17. |

EXAMPLE 157

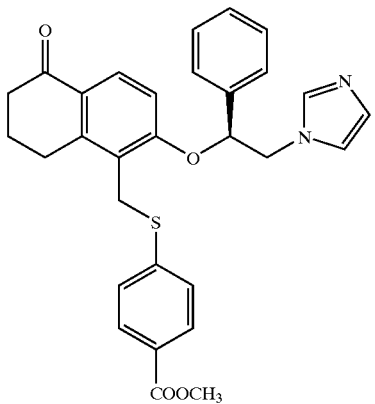

Methyl 4-{[(2-{[(1S)-2-(1H-Imidazol-1-yl)-1-phenylethyl]oxy}-5-oxo-5,6,7,8-tetrahydro-1-naphthalenyl)methyl]sulfanyl}benzoate (Compound 157)

Using method in Example 154, this compound was prepared from methyl 4-(2-hydroxy-5-oxo-5,6,7,8-tetrahydro-1-naphthalenyl)methylsulfanylbenzoate (1.81 g, 5.3 mmol), (R)-2-imidazol-1-yl-1-phenylethanol (1.00 g, 5.3 mmol), Ph₃P (2.10 g, 8.0 mmol), and diethyl azodicarboxylate (1.39 g, 8.0 mmol) and purified by a silica-column (eluting with dichloromethane-MeOH 20:1) as a solid-foam, 2.70 g, 99% yield; mp 75° C. NMR spectrum was consistent with structure. Calcd. For $C_{30}H_{28}N_2O_4S \cdot H_2O$:

| | | | |
|---|---|---|---|
| Theory: | C, 67.90; | H, 5.70; | N, 5.28. |
| Found: | C, 68.31; | H, 5.46; | N, 5.68. |

EXAMPLE 158

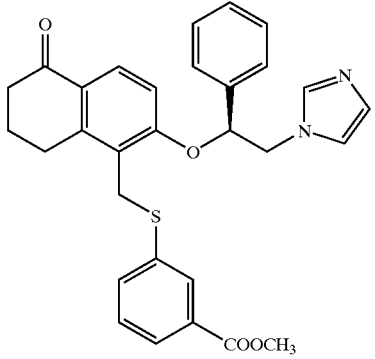

Methyl 3-{[(2-{[(1S)-2-(1H-Imidazol-1-yl)-1-phenylethyl]oxy}-5-oxo-5,6,7,8-tetrahydro-1-naphthalenyl)methyl]sulfanyl}benzoate (Compound 158)

Using the method in Example 154, this compound was prepared from methyl 3-(2-hydroxy-5-oxo-5,6,7,8-tetrahydro-1-naphthalenyl)methylsulfanylbenzoate (1.81 g, 5.3 mmol), (R)-2-imidazol-1-yl-1-phenylethanol (1.00 g, 5.3 mmol), Ph₃P (2.10 g, 8.0 mmol), and diethyl azodicarboxylate (1.39 g, 8.0 mmol) and purified by a silica-column (eluting with dichloromethane-MeOH 20:1) as a solid-foam, 2.56 g, 94% yield; mp 65° C. NMR spectrum was consistent with structure. Calcd. For $C_{30}H_{28}N_2O_4S \cdot 0.5H_2O$:

| | | | |
|---|---|---|---|
| Theory: | C, 69.08; | H, 5.60; | N, 5.37. |
| Found: | C, 69.08; | H, 5.55; | N, 5.67 |

EXAMPLE 159

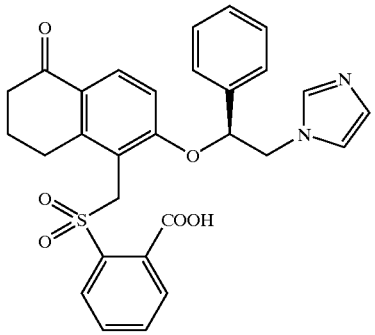

2-{[(2-{[(1S)-2-(1H-Imidazol-1-yl)-1-phenylethyl]oxy}-5-oxo-5,6,7,8-tetrahydro-1-naphthalenyl)methyl]sulfonyl}benzoic Acid (Compound 159)

A mixture of methyl 2-{[(2-{[(1S)-2-(1H-imidazol-1-yl)-1-phenylethyl]oxy}-5-oxo-5,6,7,8-tetrahydro-1-naphthalenyl)methyl]sulfonyl}benzoate (2.47 g, 4.54 mmol), 2N lithium hydroxide (9.1 ml), p-dioxane (45 ml) and water (27 ml) was stirred at room temperature for 2 h. Water (200 ml) was added and acidified with conc HCl to pH 3 at 0° C. Aqueous NaCl (50 ml) was added and further stirred at 0° C. for 1H. The precipitate was filtered, washed with water, and dried, to give a beige solid, 1.88 g, 78% yield; mp 230° C. (from dichloromethane-MeOH). NMR spectrum was consistent with structure. Calcd. For $C_{29}H_{26}N_2O_6S \cdot H_2O$:

| | | | |
|---|---|---|---|
| Theory: | C, 63.49; | H, 5.14; | N, 5.11. |
| Found: | C, 63.53; | H, 5.08; | N, 4.99. |

EXAMPLE 160

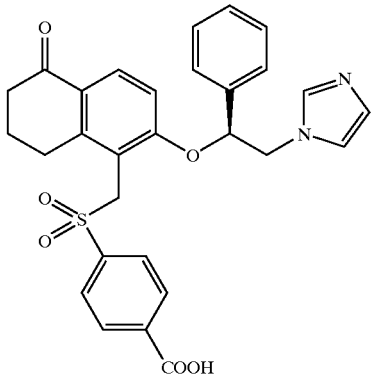

4-{[(2-{[(1S)-2-(1H-Imidazol-1-yl)-1-phenylethyl]oxy}-5-oxo-5,6,7,8-tetrahydro-1-naphthalenyl)methyl]sulfonyl}benzoic Acid (Compound 160)

Using the method for Example 159, this compound was prepared from methyl 4-{[(2-{[(1S)-2-(1H-imidazol-1-yl)-1-phenylethyl]oxy}-5-oxo-5,6,7,8-tetrahydro-1-naphthalenyl)methyl]sulfonyl}benzoate (2.32 g, 4.27 mmol) as a pale yellow solid, 1.82 g, 81% yield, mp 250° C. NMR was consistent with structure.

Calcd. For $C_{29}H_{26}N_2O_6S \cdot 1.5H_2O$:

| | | | |
|---|---|---|---|
| Theory: | C, 62.47; | H, 5.24; | N, 5.02. |
| Found: | C, 62.45; | H, 5.38; | N, 5.16. |

EXAMPLE 161

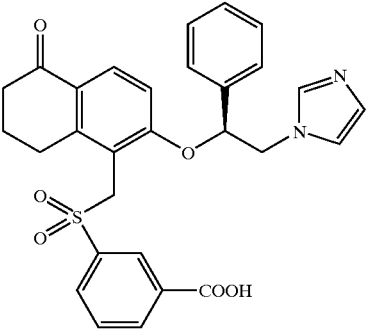

3-{[(2-{[(1S)-2-(1H-Imidazol-1-yl)-1-phenylethyl]oxy}-5-oxo-5,6,7,8-tetrahydro-1-naphthalenyl)methyl]sulfonyl}benzoic Acid (Compound 161)

Using the method for Example 159, this compound was prepared from methyl 3-{[(2-{[(1S)-2-(1H-imidazol-1-yl)-1-phenylethyl]oxy}-5-oxo-5,6,7,8-tetrahydro-1-naphthalenyl)methyl]sulfonyl}benzoate (2.36 g, 4.34 mmol) as a beige solid, 2.18 g, 95% yield, mp 236–238° C. NMR was consistent with structure. Calcd. For $C_{29}H_{26}N_2O_6S \cdot H_2O$:

| | | | |
|---|---|---|---|
| Theory: | C, 63.49; | H, 5.14; | N, 5.11. |
| Found: | C, 69.46; | H, 5.07; | N, 5.16. |

EXAMPLE 162

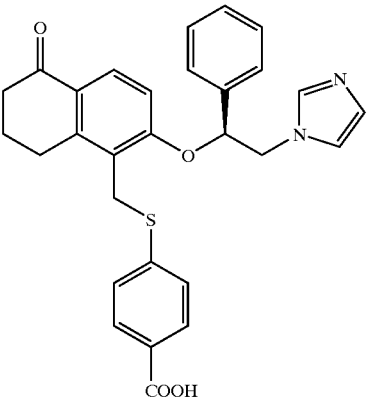

4-{[(2-{[(1S)-2-(1H-Imidazol-1-yl)-1-phenylethyl]oxy}-5-oxo-5,6,7,8-tetrahydro-1-naphthalenyl)methyl]sulfanyl}benzoic Acid (Compound 162)

Using the method for Example 159, this compound was prepared from methyl 4-{[(2-{[(1S)-2-(1H-imidazol-1-yl)-1-phenylethyl]oxy}-5-oxo-5,6,7,8-tetrahydro-1-naphthalenyl)methyl]sulfanyl}benzoate (2.29 g, 4.47 mmol)

as a beige solid, 2.20 g, 98% yield, mp 215° C. NMR was consistent with structure. Calcd. For $C_{29}H_{26}N_2O_4S \cdot 0.5H_2O$:

| Theory: | C, 68.62; | H, 5.36; | N, 5.52. |
| Found: | C, 68.74; | H, 5.52; | N, 5.93. |

EXAMPLE 163

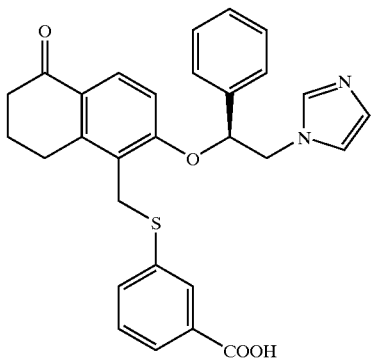

3-{[(2-{[(1S)-2-(1H-Imidazol-1-yl)-1-phenylethyl]oxy}-5-oxo-5,6,7,8-tetrahydro-1-naphthalenyl)methyl]sulfanyl}benzoic Acid (Compound 163)

Using the method for Example 159, this compound was prepared from methyl 3-{[(2-{[(1S)-2-(1H-imidazol-1-yl)-1-phenylethyl]oxy}-5-oxo-5,6,7,8-tetrahydro-1-naphthalenyl)methyl]sulfanyl}benzoate (2.12 g, 4.14 mmol) as a beige solid, 2.04 g, 99% yield, mp 225° C. NMR was consistent with structure. Calcd. For $C_{29}H_{26}N_2O_4S \cdot 0.5H_2O$:

| Theory: | C, 68.62; | H, 5.36; | N, 5.22. |
| Found: | C, 68.88; | H, 5.22; | N, 5.47. |

EXAMPLE 164

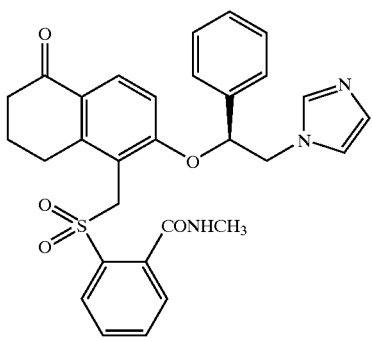

2-{[(2-{[(1S)-2-(1H-Imidazol-1-yl)-1-phenylethyl]oxy}-5-oxo-5,6,7,8-tetrahydro-1-naphthalenyl)methyl]sulfonyl)-N-methylbenzamide (Compound 164)

A mixture of 2-{[(2-{[(1S)-2-(1H-imidazol-1-yl)-1-phenylethyl]oxy}-5-oxo-5,6,7,8-tetrahydro-1-naphthalenyl)methyl]sulfonyl}benzoic acid. (159 mg, 0.30 mmol) and 1,1'-carbonyldiimidazole (73 mg, 0.45 mmol) in DMF (2 ml) was stirred at 50° C.(bath) for 10 min. Triethylamine (0.21 ml, 1.50 mmol) and methylamine hydrochloride (61 mg, 0.90 mmol) were added. The reaction mixture was stirred at room temperature for 24 h. Water (15 ml) was added and stirred at 0° C. for 30 min. The precipitate was filtered, washed with water, and dried to give a crude product which was recrystalized from ethyl acetate-MeOH to afford the required compound as a light brown solid, 85 mg, 52% yield; mp 249–251° C. NMR was consistent with the structure. Calcd. For $C_{30}H_{29}N_3O_5S$:

| Theory: | C, 66.28; | H, 5.38; | N, 7.73. |
| Found:  | C, 65.97; | H, 5.50; | N, 7.57. |

EXAMPLE 165

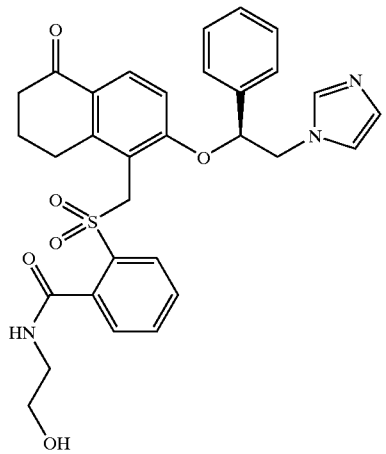

N-(2-Hydroxyethyl)-2-{[(2-{[(1S)-2-(1H-imidazol-1-yl)-1-phenylethyl]oxy}-oxo-5,6,7,8-tetrahydro-1-naphthalenyl)methyl]sulfonyl}benzamide (Compound 165)

Using the method for Example 164, this compound was prepared from 2-{[(2-{[(1S)-2-(1H-imidazol-1-yl)-1-phenylethyl]oxy}-5-oxo-5,6,7,8-tetrahydro-1-naphthalenyl)methyl]sulfonyl}benzoic acid (159 mg, 0.30 mmol) and 2-aminoethanol (92 mg, 1.50 mmol). The reaction product was extracted into ethyl acetate and purified by a silica column (eluted with dichloromethane-MeOH 20:1) to give a pale yellow solid, 100 mg, 58% yield; mp 241–243° C. (from ethyl acetate-MeOH). NMR was consistent with the structure. Calcd. For $C_{31}H_{31}N_3O_6S$

| Theory: | C, 64.91; | H, 5.45; | N, 7.32. |
| Found:  | C, 64.66; | H, 5.56; | N, 7.23. |

EXAMPLE 166

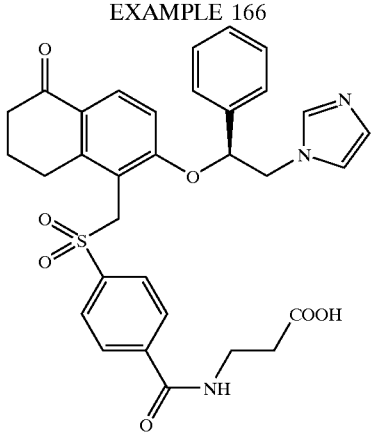

N-4-{[(2-{[(1S)-2-(1H-Imidazol-1-yl)-1-phenylethyl]oxy}-5-oxo-5,6,7,8-tetrahydro-1-naphthalenyl)methyl]sulfonyl}benzoyl-β-alanine
(Compound 166)

To a solution of ethyl 3-[(4-{[(2-{[(1S)-2-(1H-imidazol-1-yl)-1-phenylethyl]oxy}-5-oxo-5,6,7,8-tetrahydro-1-naphthalenyl)methyl]sulfonyl}benzoyl)amino]propanoate (370 mg, 0.588 mmol) in a mixed solvent of water (6 ml) and p-dioxane (6 ml) was added 2N LiOH (1.2 ml, 2.35 mmol). The reaction mixture was stirred at room temperature for 2 h. Brine (30 ml) was added and the pH adjusted to 6 by addition of conc HCl. The resulting mixture was concentrated under pressure at 35° C. (bath). It was stood at 0° C. for several hours. The precipitate was filtered, washed with cold water and dried to give the desired acid as a light brown solid, 220 mg, 62% yield; mp 220° C. NMR spectrum was consistent with the structure. Calcd. For $C_{32}H_{31}N_3O_7S \cdot 2H_2O$:

| Theory: | C, 60.27; | H, 5.53; | N, 6.59. |
|---|---|---|---|
| Found: | C, 60.81; | H, 5.48; | N, 6.74 |

EXAMPLE 167

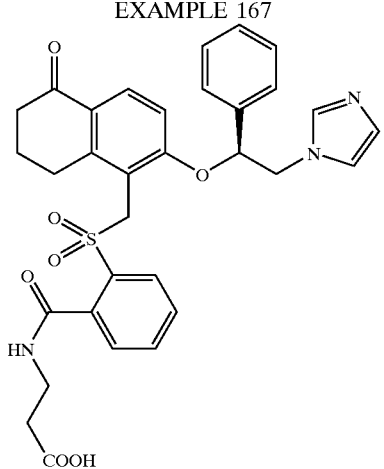

N-2-{[(2-{[(1S)-2-(1H-Imidazol-1-yl)-1-phenylethyl]oxy}-5-oxo-5,6,7,8-tetrahydro-1-naphthalenyl)methyl]sulfonyl}benzoyl-β-alanine
(Compound 167)

Using method for Example 166, this acid was prepared from ethyl 3-[(2-{[(2-{[(1S)-2-(1H-imidazol-1-yl)-1-phenylethyl]oxy}-5-oxo-5,6,7,8-tetrahydro-1-naphthalenyl)methyl]sulfonyl}benzoyl)amino]propanoate (400 mg, 0.636 mmol) as a beige solid, 260 mg, 68% yield; mp 215° C. NMR spectrum was consistent the structure. Calcd. For $C_{32}H_{31}N_3O_7S \cdot 2H_2O$:

| Theory: | C, 60.27; | H, 5.53; | N, 6.59. |
|---|---|---|---|
| Found: | C, 60.41; | H, 5.56; | N, 6.40. |

EXAMPLE 168

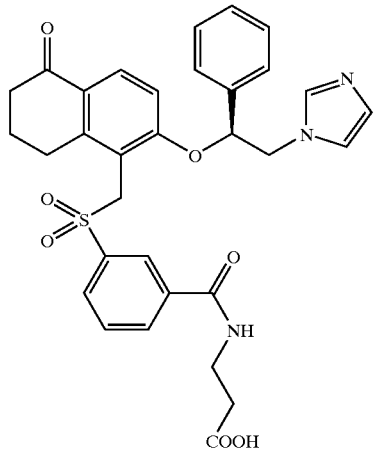

N-3-{[(2-{[(1S)-2-(1H-Imidazol-1-yl)-1-phenylethyl]oxy}-5-oxo-5,6,7,8-tetrahydro-1-naphthalenyl)methyl]sulfonyl}benzoyl-β-alanine
(Compound 168)

Using the method for Example 166, this acid was prepared from ethyl 3-[(3-{[(2-{[(1S)-2-(1H-imidazol-1-yl)-1-phenylethyl]oxy}-5-oxo-5,6,7,8-tetrahydro-1-naphthalenyl)methyl]sulfonyl}benzoyl)amino]propanoate (400 mg, 0.636 mmol) as a colorless solid, 230 mg, 60% yield; mp 220° C. NMR spectrum was consistent the structure. Calcd. For $C_{32}H_{31}N_3O_7S \cdot 2H_2O$:

| Theory: | C, 60.27; | H, 5.53; | N, 6.59. |
|---|---|---|---|
| Found: | C, 59.92; | H, 5.24; | N, 6.43 |

EXAMPLE 169

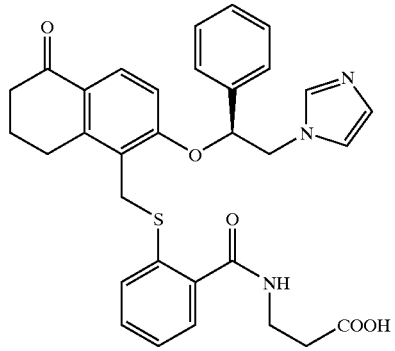

N-2-{[(2-{[(1S)-2-(1H-Imidazol-1-yl)-1-phenylethyl]oxy}-5-oxo-5,6,7,8-tetrahydro-1-naphthalenyl)methyl]sulfanyl}benzoyl-β-alanine
(Compound 169)

Using the method for Example 166, this acid was prepared from ethyl 3-[(3-{[(2-{[(1S)-2-(1H-imidazol-1-yl)-1- phenylethyl]oxy}-5-oxo-5,6,7,8-tetrahydro-1-naphthalenyl)methyl]sulfanyl}benzoyl)amino]propanoate (380 mg, 0.636 mmol) as a colorless solid, 230 mg, 64% yield; mp 230° C. NMR spectrum was consistent the structure. Calcd. For $C_{32}H_{31}N_3O_5S.2.5H_2O$:

| Theory: | C, 62.53; | H, 5.90; | N, 6.84. |
| Found: | C, 62.47; | H, 5.43; | N, 6.92 |

EXAMPLE 170

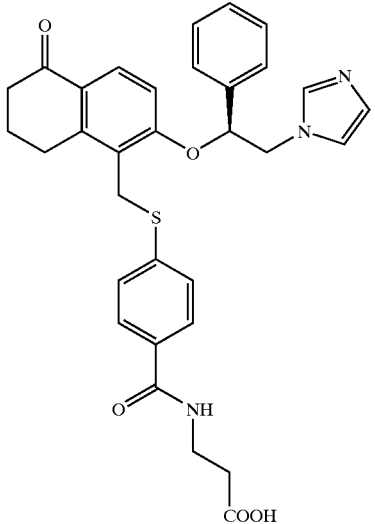

N-4-{[(2-{[(1S)-2-(1H-Imidazol-1-yl)-1-phenylethyl]oxy}-5-oxo-5,6,7,8-tetrahydro-1-naphthalenyl)methyl]sulfanyl}benzoyl-β-alanine (Compound 170)

Using the method for Example 166, this acid was prepared from ethyl 3-[(4-{[(2-{[(1S)-2-(1H-imidazol-1-yl)-1-phenylethyl]oxy}-5-oxo-5,6,7,8-tetrahydro-1-naphthalenyl)methyl]sulfanyl}benzoyl)amino]propanoate (380 mg, 0.636 mmol) as a beige solid, 230 mg, 64% yield; mp 240° C. NMR spectrum was consistent with the structure. Calcd. For $C_{32}H_{31}N_3O_5S.1.5H_2O$:

| Theory: | C, 64.41; | H, 5.74; | N, 7.04. |
| Found: | C, 64.32; | H, 5.62; | N, 5.17. |

EXAMPLE 171

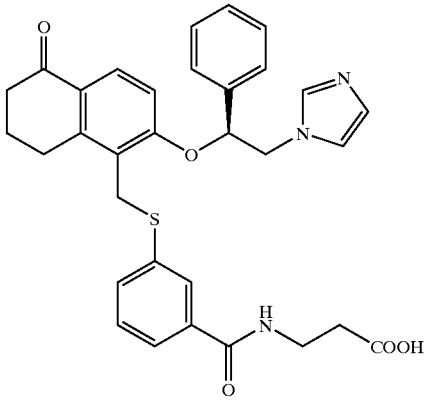

N-3-{[(2-{[(1S)-2-(1H-Imidazol-1-yl)-1-phenylethyl]oxy}-5-oxo-5,6,7,8-tetrahydro-1-naphthalenyl)methyl]sulfanyl}benzoyl-β-alanine (Compound 171)

Using method for Example 166, this acid was prepared from ethyl 3-[(3-{[(2-{[(1S)-2-(1H-imidazol-1-yl)-1-phenylethyl]oxy}-5-oxo-5,6,7,8-tetrahydro-1-naphthalenyl)methyl]sulfanyl}benzoyl)amino]propanoate (380 mg, 0.636 mmol) as a beige solid, 270 mg, 75% yield; mp 235° C. NMR spectrum was with consistent the structure. Calcd. For $C_{32}H_{31}N_3O_5S.1.5H_2O$:

| Theory: | C, 64.41; | H, 5.74; | N, 7.04. |
| Found: | C, 64.34; | H, 5.31; | N, 6.95. |

EXAMPLE 172

N-(2-Hydroxyethyl)-3-{[(2-{[(1S)-2-(1H-imidazol-1-yl)-1-phenylethyl]oxy}-5-oxo-5,6,7,8-tetrahydro-1-naphthalenyl)methyl]sulfanyl}benzamide (Compound 172)

A mixture of 1,1'-carbonyldiimidazole (49 mg, 0.30 mmol, 0.60M in DMF) and 3-{[(2-{[(1S)-2-(1H-imidazol-1-yl)-1-phenylethyl]oxy}-5-oxo-5,6,7,8-tetrahydro-1-naphthalenyl)methyl]sulfanyl}benzoic acid (50 mg, 0.10 mmol, 0.20M in DMF) in a capped vial were placed in a heater-shaker at 55° C. for 20 min. It was removed from the heater-shaker and stood at room temperature. A solution of 2-aminoethanol (31 mg, 0.50 mmol, 1.0M in DMF) was added and the reaction mixture was further shaken at room temperature over-night. Water (6 ml) was added and the mixture was shaken at room temperature for 10 min. before being stored in refrigerator over-night. The precipitate was filtered, washed with cold water (2×0.5 ml) and dried in a vacuum oven at 40° C. until constant weight was obtained. 44 mg of the required benzamide was obtained as a beige solid: Low resolution mass spectrum (LC-MS, APCI) m/z 542 $[M+H]^+$.

EXAMPLE 173

N-(2-Hydroxyethyl)-2-{[(2-{[(1S)-2-(1H-imidazol-1-yl)-1-phenylethyl]oxy}-5-oxo-5,6,7,8-tetrahydro-1-naphthalenyl)methyl]sulfanyl}benzamide (Compound 173)

Using the method in Example 172, 2-{[(2-{[(1S)-2-(1H-imidazol-1-yl)-1-phenylethyl]oxy}-5-oxo-5,6,7,8tetrahydro-1-naphthalenyl)methyl]sulfanyl}benzoic acid (50 mg, 0.10 mmol, 0.20M in DMF) and 2-aminoethanol (31 mg, 0.50 mmol, 1.0M in DMF) were combined to give 30 mg of the desired compound: Low resolution mass spectrum (LC-MS, APCI) m/z 542 $[M+H]^+$.

EXAMPLE 174

N-(2-Hydroxyethyl)-4-{[(2-{[(1S)-2-(1H-imidazol-1-yl)-1-phenylethyl]oxy}-5-oxo-5,6,7,8-tetrahydro-1-naphthalenyl)methyl]sulfanyl}benzamide (Compound 174)

Using the method in Example 172, 4-{[(2-{[(1S)-2-(1H-imidazol-1-yl)-1-phenylethyl]oxy}-5-oxo-5,6,7,8-tetrahydro-1-naphthalenyl)methyl]sulfanyl}benzoic acid (50 mg, 0.10 mmol, 0.20M in DMF) and 2-aminoethanol (31 mg, 0.50 mmol, 1.0M in DMF) were combined to give 45 mg of the desired compound: Low resolution mass spectrum (LC-MS, APCI) m/z 542 $[M+H]^+$. -

EXAMPLE 175

N-(2-Hydroxyethyl)-4-{[(2-{[(1S)-2-(1H-imidazol-1-yl)-1-phenylethyl]oxy}-5-oxo-5,6,7,8-tetrahydro-1-naphthalenyl)methyl]sulfonyl}benzamide (Compound 175)

Using the method in Example 172, 4-{[(2-{[(1S)-2-(1H-imidazol-1-yl)-1-phenylethyl]oxy}-5-oxo-5,6,7,8-tetrahydro-1-naphthalenyl)methyl]sulfonyl}benzoic acid (53 mg, 0.10 mmol, 0.20M in DMF) and 2-aminoethanol (31 mg, 0.50 mmol, 1.0M in DMF) were combined to give 27 mg of the desired compound: Low resolution mass spectrum (LC-MS, APCI) m/z 574 [M+H]$^+$.

EXAMPLE 176

N-(2-Hydroxyethyl)-3-{[(2-{[(1S)-2-(1H-imidazol-1-yl)-1-phenylethyl]oxy}-5-oxo-5,6,7,8-tetrahydro-4-naphthalenyl)methyl]sulfonyl}benzamide (Compound 176)

Using the method in Example 172, 3-{[(2-{[(1S)-2-(1H-imidazol-1-yl)-1-phenylethyl]oxy}-5-oxo-5,6,7,8-tetrahydro-1-naphthalenyl)methyl]sulfonyl}benzoic acid (53 mg, 0.10 mmol, 0.20M in DMF) and 2-aminoethanol (31 mg, 0.50 mmol, 1.0M in DMF) were combined to give 28 mg of the desired compound: Low resolution mass spectrum (LC-MS, APCI) m/z 574 [M+H]$^+$.

EXAMPLE 177

N-[2-(Dimethylamino)ethyl]-4-{[(2-{[(1S)-2-(1H-imidazol-1-yl)-1-phenylethyl]oxy}-5-oxo-5,6,7,8-tetrahydro-1-naphthalenyl)methyl]sulfanyl}benzamide (Compound 177)

Using the method in Example 172, 4-{[(2-{[(1S)-2-(1H-imidazol-1-yl)-1-phenylethyl]oxy}-5-oxo-5,6,7,8-tetrahydro-1-naphthalenyl)methyl]sulfanyl}benzoic acid (50 mg, 0.10 mmol, 0.20M in DMF) and 2-dimethylaminoethylamine (27 mg, 0.30 mmol, 0.60M in DMF) were combined to give 50 mg of the desired compound: Low resolution mass spectrum (LC-MS, APCI) m/z 569 [M+H]$^+$.

EXAMPLE 178

N-[2-(Dimethylamino)ethyl]-3-{[(2-{[(1S)-2-(1H-imidazol-1-yl)-1-phenylethyl]oxy}-5-oxo-5,6,7,8-tetrahydro-1-naphthalenyl)methyl]sulfanyl}benzamide (Compound 178)

Using the method in Example 172, 3-{[(2-{[(1S)-2-(1H-imidazol-1-yl)-1-phenylethyl]oxy}-5-oxo-5,6,7,8-tetrahydro-1-naphthalenyl)methyl]sulfanyl}benzoic acid (50 mg, 0.10 mmol, 0.20M in DMF) and 2-dimethylaminoethylamine (27 mg, 0.30 mmol, 0.60M in DMF) were combined to give 46 mg of the desired compound: Low resolution mass spectrum (LC-MS, APCI) m/z 569 [M+H]$^+$.

EXAMPLE 179

N-[2-(Dimethylamino)ethyl]-2-{[(2-{[(1S)-2-(1H-imidazol-1-yl)-1-phenylethyl]oxy}-5-oxo-5,6,7,8-tetrahydro-1-naphthalenyl)methyl]sulfanyl}benzamide (Compound 179)

Using the method in Example 172, 2-{[(2-{[(1S)-2-(1H-imidazol-1-yl)-1-phenylethyl]oxy}-5-oxo-5,6,7,8-tetrahydro-1-naphthalenyl)methyl]sulfanyl}benzoic acid (50 mg, 0.10 mmol, 0.20M in DMF) and 2-dimethylaminoethylamine (27 mg, 0.30 mmol, 0.60M in DMF) were combined to give 27 mg of the desired compound: Low resolution mass spectrum (LC-MS, APCI) m/z 569 [M+H]$^+$.

EXAMPLE 180

N-[2-(Dimethylamino)ethyl]-2-{[(2-{[(1S)-2-(1H-imidazol-1-yl)-1-phenylethyl]oxy}-5-oxo-5,6,7,8-tetrahydro-1-naphthalenyl)methyl]sulfonyl}benzamide (Compound 180)

Using the method in Example 172, 2-{[(2-{[(1S)-2-(1H-imidazol-1-yl)-1-phenylethyl]oxy}-5-oxo-5,6,7,8-tetrahydro-1-naphthalenyl)methyl]sulfonyl}benzoic acid (53 mg, 0.10 mmol, 0.20M in DMF) and 2-dimethylaminoethylamine (27 mg, 0.30 mmol, 0.60M in DMF) were combined to give 20 mg of the desired compound: Low resolution mass spectrum (LC-MS, APCI) m/z 601 [M+H]$^+$.

EXAMPLE 181

N-[2-(Dimethylamino)ethyl]-4-{[(2-{[(1S)-2-(1H-imidazol-1-yl)-1-phenylethyl]oxy}-5-oxo-5,6,7,8-tetrahydro-1-naphthalenyl)methyl]sulfonyl}benzamide (Compound 181)

Using the method in Example 172, 4-{[(2-{[(1S)-2-(1H-imidazol-1-yl)-1-phenylethyl]oxy}-5-oxo-5,6,7,8-tetrahydro-1-naphthalenyl)methyl]sulfonyl}benzoic acid (53 mg, 0.10 mmol, 0.20M in DMF) and 2-dimethylaminoethylamine (27 mg, 0.30 mmol, 0.60M in DMF) were combined to give 26 mg of the desired compound: Low resolution mass spectrum (LC-MS, APCI) m/z 601 [M+H]$^+$.

EXAMPLE 182

N-[2-(Dimethylamino)ethyl]-3-{[(2-{[(1S)-2-(1H-imidazol-1-yl)-1-phenylethyl]oxy}-5-oxo-5,6,7,8-tetrahydro-1-naphthalenyl)methyl]sulfonyl}benzamide (Compound 182)

Using the method in Example 172, 3-{[(2-{[(1S)-2-(1H-imidazol-1-yl)-1-phenylethyl]oxy}-5-oxo-5,6,7,8-tetrahydro-1-naphthalenyl)methyl]sulfonyl}benzoic acid (53 mg, 0.10 mmol, 0.20M in DMF) and 2-dimethylaminoethylamine (27 mg, 0.30 mmol, 0.60M in DMF) were combined to give 15 mg of the desired compound: Low resolution mass spectrum (LC-MS, APCI) m/z 601 [M+H]$^+$.

EXAMPLE 183

Ethyl 3-[(2-{[(2-{[(1S)-2-(1H-Imidazol1-yl)-1-phenylethyl]oxy}-5-oxo-5,6,7,8-tetrahydro-1-naphthalenyl)methyl]sulfonyl}benzoyl)amino]propanoate. (Compound 183)

Using the method in Example 172, 3-{[(2-{[(1S)-2-(1H-imidazol-1-yl)-1-phenylethyl]oxy}-5-oxo-5,6,7,8-tetrahydro-1-naphthalenyl)methyl]sulfonyl}benzoic acid (53 mg, 0.10 mmol, 0.20M in DMF), B-alanine ethyl ester hydrochloride (77 mg, 0.5 mmol, 1.0M in DMF) and triethylamine (51 mg, 0.5 mmol, 1.0M in DMF) were combined to give 53 mg of the desired compound: Low resolution mass spectrum (LC-MS, APCI) m/z 630 [M+H]$^+$.

EXAMPLE 184

Ethyl 4-[(2-{[(2-{[(1S)-2-(1H-Imidazol-1-yl)-1-phenylethyl]oxy}-5-oxo-5,6,7,8-tetrahydro-1-naphthalenyl)methyl]sulfonyl}benzoyl)amino]propanoate. (Compound 184)

Using the method in Example 172, 4-{[(2-{[(1S)-2-(1H-imidazol-1-yl)-1-phenylethyl]oxy}-5-oxo-5,6,7,8- tetrahydro-1-naphthalenyl)methyl]sulfonyl}benzoic acid (53 mg, 0.10 mmol, 0.20M in DMF), β-alanine ethyl ester hydrochloride (77 mg, 0.5 mmol, 1.0M in DMF) and triethylamine (51 mg, 0.5 mmol, 1.0M in DMF) were combined to give 42 mg of the desired compound: Low resolution mass spectrum (LC-MS, APCI) m/z 630 [M+H]$^+$.

EXAMPLE 185

Ethyl 27-[(2-{[(2-{[(S)-2-(1H-Imidazol-1-yl)-1-phenylethyl]oxy}-5-oxo-5,6,7,8-tetrahydro-1-naphthalenyl)methyl]sulfonyl}benzoyl)amino] propanoate. (Compound 185)

Using the method in Example 172, 2-{[(2-{[(1S)-2-(1H-imidazol-1-yl)-1-phenylethyl]oxy}-5-oxo-5,6,7,8-tetrahydro-1-naphthalenyl)methyl]sulfonyl}benzoic acid (53 mg, 0.10 mmol, 0.20M in DMF), β-alanine ethyl ester hydrochloride (77 mg, 0.5 mmol, 1.0M in DMF) and triethylamine (51 mg, 0.5 mmol, 1.0M in DMF) were combined to give 40 mg of the desired compound: Low resolution mass spectrum (LC-MS, APCI) m/z 630 [M+H]$^+$.

EXAMPLE 186

Ethyl 2-[(2-{[(2-{[(1S)-2-(1H-Imidazol-1-yl)-1-phenylethyl]oxy}-5-oxo-5,6,7,8-tetrahydro-1-naphthalenyl)methyl]sulfanyl}benzoyl)amino] propanoate. (Compound 186)

Using the method in Example 172, 2-{[(2-{[(1S)-2-(1H-imidazol-1-yl)-1-phenylethyl]oxy}-5-oxo-5,6,7,8-tetrahydro-1-naphthalenyl)methyl]sulfanyl}benzoic acid (50 mg, 0.10 mmol, 0.20M in DMF), β-alanine ethyl ester hydrochloride (77 mg, 0.5 mmol, 1.0M in DMF) and triethylamine (51 mg, 0.5 mmol, 1.0M in DMF) were combined to give 42 mg of the desired compound: Low resolution mass spectrum (LC-MS, APCI) m/z 598 [M+H]$^+$.

EXAMPLE 187

Ethyl 3-[(2-{[(2-{[(1S)-2-(1H-Imidazol-1-yl)-1-phenylethyl]oxy}-5-oxo-5,6,7,8-tetrahydro-1-naphthalenyl)methyl]sulfanyl}benzoyl)amino propanoate. (Compound 187)

Using the method in Example 172, 3-{[(2-{[(1S)-2-(1H-imidazol-1-yl)-1-phenylethyl]oxy}-5-oxo-5,6,7,8-tetrahydro-1-naphthalenyl)methyl]sulfanyl}benzoic acid (50 mg, 0.10 mmol, 0.20M in DMF), β-alanine ethyl ester hydrochloride (77 mg, 0.5 mmol, 1.0M in DMF) and triethylamine (51 mg, 0.5 mmol, 1.0M in DMF) were combined to give 53 mg of the desired compound: Low resolution mass spectrum (LC-MS, APCI) m/z 598 [M+H]$^+$.

EXAMPLE 188

Ethyl 4-[(2-{[(2-{[(1S)-2-(1H-Imidazol-1-yl)-1-phenylethyl]oxy}-5-oxo-5,6,7,8-tetrahydro-1-naphthalenyl)methyl]sulfanyl}benzoyl)amino] propanoate. (Compound 188)

Using the method in Example 172, 4-{[(2-{[(1S)-2-(1H-imidazol-1-yl)-1-phenylethyl]oxy}-5-oxo-5,6,7,8-tetrahydro-1-naphthalenyl)methyl]sulfanyl}benzoic acid (50 mg, 0.10 mmol, 0.20M in DMF), β-alanine ethyl ester hydrochloride (77 mg, 0.5 mmol, 1.0M in DMF) and triethylamine (51 mg, 0.5 mmol, 1.0M in DMF) were combined to give 53 mg of the desired compound: Low resolution mass spectrum (LC-MS, APCI) m/z 598 [M+H]$^+$.

EXAMPLE 189

4-{[(2-{[(1S)-2-(1H-Imidazol-1-yl)-1-phenylethoxy]oxy}-5-oxo-5,6,7,8-tetrahydro-1-naphthalenyl)methyl]sulfonyl}-N-methylbenzamide (Compound 189)

Using the method in Example 172, 4-{[(2-{[(1S)-2-(1H-imidazol-1-yl)-1-phenylethyl]oxy}-5-oxo-5,6,7,8-tetrahydro-1-naphthalenyl)methyl]sulfonyl}benzoic acid (53 mg, 0.10 mmol, 0.20M in DMF) and a saturated solution of methylamine (1.0 ml in DMF) were combined to give 15 mg of the desired compound: Low resolution mass spectrum (LC-MS, APCI) m/z 544 [M+H]$^+$.

EXAMPLE 190

3-{[(2-{[(1S)-2-(1H-Imidazol-1-yl)-1-phenylethyl]oxy}-5-oxo-5,6,7,8-tetrahydro-1-naphthalenyl)methyl]sulfonyl}-N-methylbenzamide (Compound 190)

Using the method in Example 172, 3-{[(2-{[(1S)-2-(1H-imidazol-1-yl)-1-phenylethyl]oxy}-5-oxo-5,6,7,8-tetrahydro-1-naphthalenyl)methyl]sulfonyl}benzoic acid (53 mg, 0.10 mmol, 0.20M in DMF) and a saturated solution of methylamine (1.0 ml in DMF) were combined to give 11 mg of the desired compound: Low resolution mass spectrum (LC-MS, APCI) m/z 544 [M+H]$^+$.

EXAMPLE 191

4-{[(2-{[(1S)-2-(1H-Imidazol-1-yl)-1-phenylethyl]oxy}-5-oxo-5,6,7,8-tetrahydro-1-naphthalenyl)methyl]sulfanyl}-N-methylbenzamide (Compound 191)

Using the method in Example 172, 4-{[(2-{[(1S)-2-(1H-imidazol-1-yl)-1-phenylethyl]oxy}-5-oxo-5,6,7,8-tetrahydro-1-naphthalenyl)methyl]sulfanyl}benzoic acid (50 mg, 0.10 mmol, 0.20M in DMF) and a saturated solution of methylamine (1.0 ml in DMF) were combined to give 40 mg of the desired compound: Low resolution mass spectrum (LC-MS, APCI) m/z 512 [M+H]$^+$.

EXAMPLE 192

3-{[(2-{[(1S)-2-(1H-Imidazol-1-yl)-1-phenylethyl]oxy}-5-oxo-5,6,7,8-tetrahydro-naphthalenyl)methyl]sulfanyl}-N-methylbenzamide (Compound 192)

Using the method in Example 172, 3-{[(2-{[(1S)-2-(1H-imidazol-1-yl)-1-phenylethyl]oxy}-5-oxo-5,6,7,8-tetrahydro-1-naphthalenyl)methyl]sulfanyl}benzoic acid (50 mg, 0.10 mmol, 0.20M in DMF) and a saturated solution of methylamine (1.0 ml in DMF) were combined to give 36 mg of the desired compound: Low resolution mass spectrum (LC-MS, APCI) m/z 512 [M+H]$^+$.

EXAMPLE 193

2-{[(2-{[(1S)-2-(1H-Imidazol-1-yl)-1-phenylethyl]oxy}-5-oxo-5,6,7,8-tetrahydro-1-naphthalenyl)methyl]sulfanyl}-N-methylbenzamide (Compound 193)

Using the method in Example 172, 2-{[(2-{[(1S)-2-(1H-imidazol-1-yl)-1-phenylethyl]oxy}-5-oxo-5,6,7,8-tetrahydro-1-naphthalenyl)methyl]sulfanyl}benzoic acid (50 mg, 0.10 mmol, 0.20M in DMF) and a saturated solution of methylamine (1.0 ml in DMF) were combined to give 26 mg of the desired compound: Low resolution mass spectrum (LC-MS, APCI) m/z 512 [M+H]$^+$.

EXAMPLE 194

N-[(2R)-2-Hydroxypropyl]-2-{[(2-{[(1S)-2-(1H-imidazol-1-yl)-1-phenylethyl]oxy}-5-oxo-5,6,7,8-tetrahydro-1-naphthalenyl)methyl]sulfanyl}benzamide (Compound 194)

Using the method in Example 172, 2-{[(2-{[(1S)-2-(1H-imidazol-1-yl)-1-phenylethyl]oxy}-5-oxo-5,6,7,8- tetrahydro-1-naphthalenyl)methyl]sulfanyl}benzoic acid (50 mg, 0.10 mmol, 0.20M in DMF) and (R)-1-amino-2-propanol (23 mg, 0.30 mmol, 0.6M in DMF) were combined to give 32 mg of the desired compound: Low resolution mass spectrum (LC-MS, APCI) m/z 556 [M+H]$^+$.

EXAMPLE 195

N-[(2R)-2-Hydroxypropyl]-4-{[(2-{[(1S)-2-(1H-imidazol-1-yl)-1-phenylethyl]oxy}-5-oxo-5,6,7,8-tetrahydro-1-naphthalenyl)methyl] sulfanyl}benzamide (Compound 195)

Using the method in Example 172, 4-{[(2-{[(1S)-2-(1H-imidazol-1-yl)-1-phenylethyl]oxy}-5-oxo-5,6,7,8-tetrahydro-1-naphthalenyl)methyl]sulfanyl}benzoic acid (50 mg, 0.10 mmol, 0.20M in DMF) and (R)-1-amino-2-propanol (23 mg, 0.30 mmol, 0.6M in DMF) were combined to give 48 mg of the desired compound: Low resolution mass spectrum (LC-MS, APCI) m/z 556 [M+H]$^+$.

EXAMPLE 196

N-[(2S)-2-Hydroxypropyl]-4-{[(2-{[(1S)-2-(1H-imidazol-1-yl)-1-phenylethyl]oxy}-5-oxo-5,6,7,8-tetrahydro-1-naphthalenyl)methyl] sulfanyl}benzamide (Compound 196)

Using the method in Example 172, 4-{[(2-{[(1S)-2-(1H-imidazol-1-yl)-1-phenylethyl]oxy}-5-oxo-5,6,7,8-tetrahydro-1-naphthalenyl)methyl]sulfanyl}benzoic acid (50 mg, 0.10 mmol, 0.20M in DMF) and (S)-1-amino-2-propanol (23 mg, 0.30 mmol, 0.6M in DMF) were combined to give 48 mg of the desired compound: Low resolution mass spectrum (LC-MS, APCI) m/z 556 [M+H]$^+$.

EXAMPLE 197

N-[(2S)-2-Hydroxypropyl]-3-{[(2-{[(1S)-2-(1H-imidazol-1-yl)-1-phenylethyl]oxy}-5-oxo-5,6,7,8-tetrahydro-1-naphthalenyl)methyl] sulfanyl}benzamide (Compound 197)

Using the method in Example 172, 3-{[(2-{[(1S)-2-(1H-imidazol-1-yl)-1-phenylethyl]oxy}-5-oxo-5,6,7,8-tetrahydro-1-naphthalenyl)methyl]sulfanyl}benzoic acid (50 mg, 0.10 mmol, 0.20M in DMF) and (S)-1-amino-2-propanol (23 mg, 0.30 mmol, 0.6M in DMF) were combined to give 52 mg of the desired compound: Low resolution mass spectrum (LC-MS, APCI) m/z 556 [M+H]$^+$.

EXAMPLE 198

N-[(2S)-2-Hydroxypropyl]-2-{[(2-{[(1S)-2-(1H-imidazol-1-yl)-1-phenylethyl]oxy}-5-oxo-5,6,7,8-tetrahydro-1-naphthalenyl)methyl] sulfanyl}benzamide (Compound 198)

Using the method in Example 172, 2-{[(2-{[(1S)-2-(1H-imidazol-1-yl)-1-phenylethyl]oxy}-5-oxo-5,6,7,8-tetrahydro-1-naphthalenyl)methyl]sulfanyl}benzoic acid (50 mg, 0.10 mmol, 0.20M in DMF) and (S)-1-amino-2-propanol (23 mg, 0.30 mmol, 0.6M in DMF) were combined to give 37 mg of the desired compound: Low resolution mass spectrum (LC-MS, APCI) m/z 556 [M+H]$^+$.

EXAMPLE 199

N-[(2S)-2-Hydroxypropyl]-4-{[(2-{[(1S)-2-(1H-imidazol-1-yl)-1-phenylethyl]oxy}-5-oxo-5,6,7,8-tetrahydro-1-naphthalenyl)methyl] sulfonyl}benzamide (Compound 199)

Using the method in Example 172, 4-{[(2-{[(1S)-2-(1H-imidazol-1-yl)-1-phenylethyl]oxy}-5-oxo-5,6,7,8-tetrahydro-1-naphthalenyl)methyl]sulfonyl}benzoic acid (53 mg, 0.10 mmol, 0.20M in DMF) and (S)-1-amino-2-propanol (23 mg, 0.30 mmol, 0.6M in DMF) were combined to give 32 mg of the desired compound: Low resolution mass spectrum (LC-MS, APCI) m/z 588 [M+H]$^+$.

EXAMPLE 200

N-[(2S)-2-Hydroxypropyl]-3-{[(2-{[(1S)-2-(1H-imidazol-1-yl)-1-phenylethyl]oxy}-5-oxo-5,6,7,8-tetrahydro-1-naphthalenyl)methyl] sulfonyl}benzamide (Compound 200)

Using the method in Example 172, 3-{[(2-{[(1S)-2-(1H-imidazol-1-yl)-1-phenylethyl]oxy}-5-oxo-5,6,7,8-tetrahydro-1-naphthalenyl)methyl]sulfonyl}benzoic acid (53 mg, 0.10 mmol, 0.20M in DMF) and (S)-1-amino-2-propanol (23 mg, 0.30 mmol, 0.6M in DMF) were combined to give 34 mg of the desired compound: Low resolution mass spectrum (LC-MS, APCI) m/z 588 [M+H]$^+$.

EXAMPLE 201

N-[(2S)-2-Hydroxypropyl]-2-{[(2-{[(1S)-2-(1H-imidazol-1-yl)-1-phenylethyl]oxy}-5-oxo-5,6,7,8-tetrahydro-6-naphthalenyl)methyl] sulfonyl}benzamide (Compound 201)

Using the method in Example 172, 2-{[(2-{[(1S)-2-(1H-imidazol-1-yl)-1-phenylethyl]oxy}-5-oxo-5,6,7,8-tetrahydro-1-naphthalenyl)methyl]sulfonyl}benzoic acid (53 mg, 0.10 mmol, 0.20M in DMF) and (S)-1-amino-2-propanol (23 mg, 0.30 mmol, 0.6M in DMF) were combined to give 23 mg of the desired compound: Low resolution mass spectrum (LC-MS, APCI) m/z 588 [M+H]$^+$.

EXAMPLE 202

N-[(2R)-2-Hydroxypropyl]-2-{[(2-{[(1S)-2-(1H-imidazol-1-yl)-1-phenylethyl]oxy}-5-oxo-5,6,7,8-tetrahydro-1-naphthalenyl)methyl] sulfonyl}benzamide (Compound 202)

Using the method in Example 172, 2-{[(2-{[(1S)-2-(1H-imidazol-1-yl)-1-phenylethyl]oxy}-5-oxo-5,6,7,8-tetrahydro-1-naphthalenyl)methyl]sulfonyl}benzoic acid (53 mg, 0.10 mmol, 0.20M in DMF) and (R)-1-amino-2-propanol (23 mg, 0.30 mmol, 0.6M in DMF) were combined to give 32 mg of the desired compound: Low resolution mass spectrum (LC-MS, APCI) m/z 588 [M+H]$^+$.

EXAMPLE 203

N-[(2R)-2-Hydroxpropyl]-4-{[(2-{[(1S)-2-(1H-imidazol-1-yl)-1-phenylethyl]oxy}-5-oxo-5,6,7,8-tetrahydro-1-naphthalenyl)methyl] sulfonyl}benzamide (Compound 203)

Using the method in Example 172, 4-{[(2-{[(1S)-2-(1H-imidazol-1-yl)-1-phenylethyl]oxy}-5-oxo-5,6,7,8-tetrahydro-1-naphthalenyl)methyl]sulfonyl}benzoic acid (53 mg, 0.110 mmol, 0.20M in DMF) and (R)-1-amino-2-propanol (23 mg, 0.30 mmol, 0.6M in DMF) were combined to give 22 mg of the desired compound: Low resolution mass spectrum (LC-MS, APCI) m/z 588 [M+H]$^+$.

EXAMPLE 204

N-[(2R)-2-Hydroxypropyl]-3-{[(2-{[(1S)-2-(H-imidazol-1-yl)-1-phenylethyl]oxy}-5-oxo-5,6,7,8-tetrahydro-1-naphthalenyl)methyl] sulfonyl}benzamide (Compound 204)

Using the method in Example 172, 3-{[(2-{[(1S)-2-(1H-imidazol-1-yl)-1-phenylethyl]oxy}-5-oxo-5,6,7,8- tetrahydro-1-naphthalenyl)methyl]sulfonyl}benzoic acid (53 mg, 0.10 mmol, 0.20M in DMF) and (R)-1-amino-2-propanol (23 mg, 0.30 mmol, 0.6M in DMF) were combined to give 27 mg of the desired compound: Low resolution mass spectrum (LC-MS, APCI) m/z 588 [M+H]$^+$.

EXAMPLE 205

N-Ally-6-3-{[(2-{[(1S)-2-(1H-imidazol-1-yl)-1-phenylethyl]oxy}-5-oxo-5,6,7,8-tetrahydro-1-naphthalenyl)methyl]sulfonyl}benzamide
(Compound 205)

Using the method in Example 172, 3-{[(2-{[(1S)-2-(1H-imidazol-1-yl)-1-phenylethyl]oxy}-5-oxo-5,6,7,8-tetrahydro-1-naphthalenyl)methyl]sulfonyl}benzoic acid (53 mg, 0.10 mmol, 0.20M in DMF) and 3-aminopropene (17 mg, 0.30 mmol, 0.6M in DMF were combined to give 44 mg of the desired compound: Low resolution mass spectrum (LC-MS, APCI) m/z 570 [M+H]$^+$.

EXAMPLE 206

N-Allyl-4-{[(2-{[(1S)-2-(1H-imidazol-1-yl)-1-phenylethyl]oxy}-5-oxo-5,6,7-tetrahydro-1-naphthalenyl)methyl]sulfonyl}benzamide
(Compound 206)

Using the method in Example 172, 4-{[(2-{[(1S)-2-(1H-imidazol-1-yl)-1-phenylethyl]oxy}-5-oxo-5,6,7,8-tetrahydro-1-naphthalenyl)methyl]sulfonyl}benzoic acid (53 mg, 0.10 mmol, 0.20M in DMF) and 3-aminopropene (17 mg, 0.30 mmol, 0.6M in DMF) were combined to give 42 mg of the desired compound: Low resolution mass spectrum (LC-MS, APCI) m/z 570 [M+H]$^+$.

EXAMPLE 207

N-Allyl-2-{[(2-{[(1S)-2-(1H-imidazol-1-yl)-1-phenylethyl]oxy}-5-oxo-5,6,7,8-tetrahydro-1-naphthalenyl)methyl]sulfonyl}benzamide
(Compound 207)

Using the method in Example 172, 2-{[(2-{[(1S)-2-(1H-imidazol-1-yl)-1-phenylethyl]oxy}-5-oxo-5,6,7,8-tetrahydro-1-naphthalenyl)methyl]sulfonyl}benzoic acid (53 mg, 0.10 mmol, 0.20M in DMF) and 3-aminopropene (17 mg, 0.30 mmol, 0.6M in DMF) were combined to give 38 mg of the desired compound: Low resolution mass spectrum (LC-MS, APCI) m/z 570 [M+H]$^+$.

EXAMPLE 208

N-Allyl-2-{[(2-{[(1S)-2-(1H-imidazol1-yl)-1-phenylethyl]oxy}-5-oxo-5,6,7-tetrahydro-1-naphthalenyl)methyl]sulfanyl}benzamide
(Compound 208)

Using the method in Example 172, 2-{[(2-{[(1S)-2-(1H-imidazol-1-yl)-1-phenylethyl]oxy}-5-oxo-5,6,7,8-tetrahydro-1-naphthalenyl)methyl]sulfanyl}benzoic acid (50 mg, 0.10 mmol, 0.20M in DMF) and 3-aminopropene (17 mg, 0.30 mmol, 0.6M in DMF) were combined to give 46 mg of the desired compound: Low resolution mass spectrum (LC-MS, APCI) m/z 538 [M+H]$^+$.

EXAMPLE 209

N-Allyl-4-{[(2-{[(1S)-2-(1H-imidazol-1-yl)-1-phenylethyl]oxy}-5-oxo-5,6,7-tetrahydro-1-naphthalenyl)methyl]sulfanyl}benzamide
(Compound 209)

Using the method in Example 172, 4-{[(2-{[(1S)-2-(1H-imidazol-1-yl)-1-phenylethyl]oxy}-5-oxo-5,6,7,8-tetrahydro-1-naphthalenyl)methyl]sulfanyl}benzoic acid (50 mg, 0.10 mmol, 0.20M in DMF) and 3-aminopropene (17 mg, 0.30 mmol, 0.6M in DMF) were combined to give 52 mg of the desired compound: Low resolution mass spectrum (LC-MS, APCI) m/z 538 [M+H]$^+$.

EXAMPLE 210

N-Allyl-3-{[(2-{[(1S)-2-(1H-imidazol-1-yl)-1-phenylethyl]oxy}-5-oxo-5,6,7,8-tetrahydro-1-naphthalenyl)methyl]sulfanyl}benzamide
(Compound 210)

Using the method in Example 172, 3-{[(2-{[(1S)-2-(1H-imidazol-1-yl)-1-phenylethyl]oxy}-5-oxo-5,6,7,8-tetrahydro-1-naphthalenyl)methyl]sulfanyl}benzoic acid (50 mg, 0.10 mmol, 0.20M in DMF) and 3-aminopropene (17 mg, 0.30 mmol, 0.6M in DMF) were combined to give 48 mg of the desired compound: Low resolution mass spectrum (LC-MS, APCI) m/z 538 [M+H]$^+$.

EXAMPLE 211

2-{[(2-{[(1S)-2-(1H-Imidazol-1-yl)-1-phenylethyl]oxy}-5-oxo-5,6,7,8-tetrahydro-1-naphthalenyl)methyl]sulfanyl}-N-(2-propynyl)benzamide
(Compound 211)

Using the method in Example 172, 2-{[(2-{[(1S)-2-(1H-imidazol-1-yl)-1-phenylethyl]oxy}-5-oxo-5,6,7,8-tetrahydro-1-naphthalenyl)methyl]sulfanyl}benzoic acid (50 mg, 0.10 mmol, 0.20M in DMF) and 3-aminopropyne (17 mg, 0.30 mmol, 0.6M in DMF) were combined to give 45 mg of the desired compound: Low resolution mass spectrum (LC-MS, APCI) m/z 536 [M+H]$^+$.

EXAMPLE 212

4-{[(2-{[(1S)-2-(1H-Imidazol-1-yl)-1-phenylethyl]oxy}-5-oxo-5,6,7,8-tetrahydro-1-naphthalenyl)methyl]sulfanyl}-N-(2-propynyl)benzamide
(Compound 212)

Using the method in Example 172, 4-{[(2-{[(1S)-2-(1H-imidazol-1-yl)-1-phenylethyl]oxy}-5-oxo-5,6,7,8-tetrahydro-1-naphthalenyl)methyl]sulfanyl}benzoic acid (50 mg, 0.10 mmol, 0.20M in DMF) and 3-aminopropyne (17 mg, 0.30 mmol, 0.6M in DMF) were combined to give 54 mg of the desired compound: Low resolution mass spectrum (LC-MS, APCI) m/z 536 [M+H]$^+$.

EXAMPLE 213

3-{[(2-{[(1S)-2-(1H-Imidazol-1-yl)-1-phenylethyl]oxy}-5-oxo-5,6,7,8-tetrahydro-1-naphthalenyl)methyl]sulfanyl}-N-(2-propynyl)benzamide
(Compound 213)

Using the method in Example 172, 3-{[(2-{[(1S)-2-(1H-imidazol-1-yl)-1-phenylethyl]oxy}-5-oxo-5,6,7,8-tetrahydro-1-naphthalenyl)methyl]sulfanyl}benzoic acid (50 mg, 0.10 mmol, 0.20M in DMF) and 3-aminopropyne (17 mg, 0.30 mmol, 0.6M in DMF) were combined to give 49 mg of the desired compound: Low resolution mass spectrum (LC-MS, APCI) m/z 536 [M+H]$^+$.

EXAMPLE 214

4-{[(2-{[(1S)-2-(1H-Imidazol-1-yl)-1-phenylethyl]oxy}-5-oxo-5,6,7,8-tetrahydro-1-naphthalenyl)methyl]sulfonyl}-N-(2-propynyl)benzamide
(Compound 214)

Using the method in Example 172, 4-{[(2-{[(1S)-2-(1H-imidazol-1-yl)-1-phenylethyl]oxy}-5-oxo-5,6,7,8- tetrahydro-1-naphthalenyl)methyl]sulfonyl}benzoic acid (53 mg, 0.10 mmol, 0.20M in DMF) and 3-aminopropyne (17 mg, 0.30 mmol, 0.6M in DMF) were combined to give 44 mg of the desired compound: Low resolution mass spectrum (LC-MS, APCI) m/z 568 [M+H]⁺.

EXAMPLE 215

3-{[(2-{[(1S)-2-(1H-Imidazol-1-yl)-1-phenylethyl]oxy}-5-oxo-5,6,7,8-tetrahydro-1-naphthalenyl)methyl]sulfonyl}-N-(2-propynyl)benzamide (Compound 215)

Using the method in Example 172, 3-{[(2-{[(1S)-2-(1H-imidazol-1-yl)-1-phenylethyl]oxy}-5-oxo-5,6,7,8-tetrahydro-1-naphthalenyl)methyl]sulfonyl}benzoic acid (53 mg, 0.10 mmol, 0.20M in DMF) and 3-aminopropyne (17 mg, 0.30 mmol, 0.6M in DMF) were combined to give 40 mg of the desired compound: Low resolution mass spectrum (LC-MS, APCI) m/z 568 [M+H]⁺.

EXAMPLE 216

2-{[(2-{[(1S)-2-(1H-Imidazol-1-yl)-1-phenylethyl]oxy}-5-oxo-5,6,7,8-tetrahydro-1-naphthalenyl)methyl]sulfonyl}-N-(2-propynyl)benzamide (Compound 216)

Using the method in Example 172, 2-{[(2-{[(1S)-2-(1H-imidazol-1-yl)-1-phenylethyl]oxy}-5-oxo-5,6,7,8-tetrahydro-1-naphthalenyl)methyl]sulfonyl}benzoic acid (53 mg, 0.10 mmol, 0.20M in DMF) and 3-aminopropyne (17 mg, 0.30 mmol, 0.6M in DMF) were combined to give 38 mg of the desired compound: Low resolution mass spectrum (LC-MS, APCI) m/z 568 [M+H]⁺.

EXAMPLE 217

N-Cyclopentyl-4-{[(2-{[(1S)-2-(1H-imidazol-1-yl)-1-phenylethyl]oxy}-5-oxo-5,6,7,8-tetrahydro-1-naphthalenyl)methyl]sulfonyl}benzamide (Compound 217)

Using the method in Example 172, 4-{[(2-{[(1S)-2-(1H-imidazol-1-yl)-1-phenylethyl]oxy}-5-oxo-5,6,7,8-tetrahydro-1-naphthalenyl)methyl]sulfonyl}benzoic acid (53 mg, 0.10 mmol, 0.20M in DMF) and cyclopentylamine (26 mg, 0.30 mmol, 0.6M in DMF) were combined to give 57 mg of the desired compound: Low resolution mass spectrum (LC-MS, APCI) m/z 598 [M+H]⁺.

EXAMPLE 218

N-Cyclopentyl-3-{[(2-{[(1S)-2-(1H-imidazol-1-yl)-1-phenylethyl]oxy}-5-oxo-5,6,7,8-tetrahydro-1-naphthalenyl)methyl]sulfonyl}benzamide (Compound 218)

Using the method in Example 172, 3-{[(2-{[(1S)-2-(1H-imidazol-1-yl)-1-phenylethyl]oxy}-5-oxo-5,6,7,8-tetrahydro-1-naphthalenyl)methyl]sulfonyl}benzoic acid (53 mg, 0.10 mmol, 0.20M in DMF) and cyclopentylamine (26 mg, 0.30 mmol, 0.6M in DMF) were combined to give 59 mg of the desired compound: Low resolution mass spectrum (LC-MS, APCI) m/z 598 [M+H]⁺.

EXAMPLE 219

N-Cyclopentyl-2-{[(2-{[(1S)-2-(1H-imidazol-1-yl)-1-phenylethyl]oxy}-5-oxo-5,6,7,8-tetrahydro-1-naphthalenyl)methyl]sulfonyl}benzamide (Compound 219)

Using the method in Example 172, 2-{[(2-{[(1S)-2-(1H-imidazol-1-yl)-1-phenylethyl]oxy}-5-oxo-5,6,7,8-tetrahydro-1-naphthalenyl)methyl]sulfonyl}benzoic acid (53 mg, 0.10 mmol, 0.20M in DMF) and cyclopentylamine (26 mg, 0.30 mmol, 0.6M in DMF) were combined to give 42 mg of the desired compound: Low resolution mass spectrum (LC-MS, APCI) m/z 598 [M+H]⁺.

EXAMPLE 220

N-Cyclopentyl-4-{[(2-{[(S)-2-(1H-imidazol-1-yl)-1-phenylethyl]oxy}-5-oxo-5,6,7,8-tetrahydro-1-naphthalenyl)methyl]sulfanyl}benzamide (Compound 220)

Using the method in Example 172, 4-{[(2-{[(1S)-2-(1H-imidazol-1-yl)-1-phenylethyl]oxy}-5-oxo-5,6,7,8-tetrahydro-1-naphthalenyl)methyl]sulfanyl}benzoic acid (50 mg, 0.10 mmol, 0.20M in DMF) and cyclopentylamine (26 mg, 0.30 mmol, 0.6M in DMF) were combined to give 51 mg of the desired compound: Low resolution mass spectrum (LC-MS, APCI) m/z 566 [M+H]⁺.

EXAMPLE 221

N-Cyclopentyl-71-3-{[(2-{[(1S)-2-(1H-imidazol-1-yl)-1-phenylethyl]oxy}-5-oxo-5,6,7,8-tetrahydro-1-naphthalenyl)methyl]sulfanyl}benzamide (Compound 221)

Using the method in Example 172, 3-{[(2-{[(1S)-2-(1H-imidazol-1-yl)-1-phenylethyl]oxy}-5-oxo-5,6,7,8-tetrahydro-1-naphthalenyl)methyl]sulfanyl}benzoic acid (50 mg, 0.10 mmol, 0.20M in DMF) and cyclopentylamine (26 mg, 0.30 mmol, 0.6M in DMF) were combined to give 48 mg of the desired compound: Low resolution mass spectrum (LC-MS, APCI) m/z 566 [M+H]⁺.

EXAMPLE 222

N-Cyclopentyl-2-{[(2-{[(1S)-2-(1H-imidazol-1-yl)-1-phenylethyl]oxy}-5-oxo-5,6,7,8-tetrahydro-1-naphthalenyl)methyl]sulfanyl}benzamide (Compound 222)

Using the method in Example 172, 2-{[(2-{[(1S)-2-(1H-imidazol-1-yl)-1-phenylethyl]oxy}-5-oxo-5,6,7,8-tetrahydro-1-naphthalenyl)methyl]sulfanyl}benzoic acid (50 mg, 0.10 mmol, 0.20M in DMF) and cyclopentylamine (26 mg, 0.30 mmol, 0.6M in DMF) were combined to give 47 mg of the desired compound: Low resolution mass spectrum (LC-MS, APCI) m/z 566 [M+H]⁺.

EXAMPLE 223

N-Cyclopropyl-4-{[(2-{[(1S)-2-(1H-imidazol-1-yl)-1-phenylethyl]oxy}-5-oxo-5,6,7,8-tetrahydro-1-naphthalenyl)methyl]sulfonyl}benzamide (Compound 223)

Using the method in Example 172, 4-{[(2-{[(1S)-2-(1H-imidazol-1-yl)-1-phenylethyl]oxy}-5-oxo-5,6,7,8-tetrahydro-1-naphthalenyl)methyl]sulfonyl}benzoic acid (53 mg, 0.10 mmol, 0.20M in DMF) and cyclopropylamine (17 mg, 0.30 mmol, 0.6M in DMF) were combined to give 41 mg of the desired compound: Low resolution mass spectrum (LC-MS, APCI) m/z 570 [M+H]⁺.

EXAMPLE 224

N-Cyclopropyl-3-{[(2-{[(1S)-2-(1H-imidazol-1-yl)-1-phenylethyl]oxy}-5-oxo-5,6,7,8-tetrahydro-1-naphthalenyl)methyl]sulfonyl}benzamide (Compound 224)

Using the method in Example 172, 3-{[(2-{[(1S)-2-(1H-imidazol-1-yl)-1-phenylethyl]oxy}-5-oxo-5,6,7,8- tetrahydro-1-naphthalenyl)methyl]sulfonyl}benzoic acid (53 mg, 0.10 mmol, 0.20M in DMF) and cyclopropylamine (17 mg, 0.30 mmol, 0.6M in DMF) were combined to give 44 mg of the desired compound: Low resolution mass spectrum (LC-MS, APCI) m/z 570 [M+H]+.

EXAMPLE 225

N-Cyclopropyl-2-{[(2-{[(1S)-2-(1H-imidazol-1-yl)-1-phenylethyl]oxy}-5-oxo-5,6,7,8-tetrahydro-1-naphthalenyl)methyl]sulfonyl}benzamide (Compound 225)

Using the method in Example 172, 2-{[(2-{[(1S)-2-(1H-imidazol-1-yl)-1-phenylethyl]oxy}-5-oxo-5,6,7,8-tetrahydro-1-naphthalenyl)methyl]sulfonyl}benzoic acid (53 mg, 0.10 mmol, 0.20M in DMF) and cyclopropylamine (17 mg, 0.30 mmol, 0.6M in DMF) were combined to give 42 mg of the desired compound: Low resolution mass spectrum (LC-MS, APCI) m/z 570 [M+H]+.

EXAMPLE 226

N-Cyclopropyl-4-{[(2-{[(1S)-2-(1H-imidazol-1-yl)-1-phenylethyl]oxy}-5-oxo-5,6,7,8-tetrahydro-1-naphthalenyl)methyl]sulfanyl}benzamide (Compound 226)

Using the method in Example 172, 4-{[(2-{[(1S)-2-(1H-imidazol-1-yl)-1-phenylethyl]oxy}-5-oxo-5,6,7,8-tetrahydro-1-naphthalenyl)methyl]sulfanyl}benzoic acid (50 mg, 0.10 mmol, 0.20M in DMF) and cyclopropylamine (17 mg, 0.30 mmol, 0.6M in DMF) were combined to give 47 mg of the desired compound: Low resolution mass spectrum (LC-MS, APCI) m/z 538 [M+H]+.

EXAMPLE 227

N-Cyclopropyl-3-{[(2-{[(1S)-2-(1H-imidazol-1-yl)-1-phenylethyl]oxy}-5-oxo-5,6,7,8-tetrahydro-1-naphthalenyl)methyl]sulfanyl}benzamide (Compound 227)

Using the method in Example 172, 3-{[(2-{[(1S)-2-(1H-imidazol-1-yl)-1-phenylethyl]oxy}-5-oxo-5,6,7,8-tetrahydro-1-naphthalenyl)methyl]sulfanyl}benzoic acid (50 mg, 0.10 mmol, 0.20M in DMF) and cyclopropylamine (17 mg, 0.30 mmol, 0.6M in DMF) were combined to give 52 mg of the desired compound: Low resolution mass spectrum (LC-MS, APCI) m/z 538 [M+H]+.

EXAMPLE 228

N-Cyclopropyl-2-{[(2-{[(1S)-2-(1H-imidazol-1-yl)-1-phenylethyl]oxy}-5-oxo-5,6,7,8-tetrahydro-1-naphthalenyl)methyl]sulfanyl}benzamide (Compound 228)

Using the method in Example 172, 2-{[(2-{[(1S)-2-(1H-imidazol-1-yl)-1-phenylethyl]oxy}-5-oxo-5,6,7,8-tetrahydro-1-naphthalenyl)methyl]sulfanyl}benzoic acid (50 mg, 0.10 mmol, 0.20M in DMF) and cyclopropylamine (17 mg, 0.30 mmol, 0.6M in DMF) were combined to give 43 mg of the desired compound: Low resolution mass spectrum (LC-MS, APCI) m/z 538 [M+H]+.

EXAMPLE 229

N-(2-Furylmethyl)-4-{[(2-{[(1S)-2-(1H-imidazol-1-yl)-1-phenylethyl]oxy}-5-oxo-5,6,7,8-tetrahydro-1-naphthalenyl)methyl]sulfonyl}benzamide (Compound 229)

Using the method in Example 172, 4-{[(2-{[(1S)-2-(1H-imidazol-1-yl)-1-phenylethyl]oxy}-5-oxo-5,6,7,8-tetrahydro-1-naphthalenyl)methyl]sulfonyl}benzoic acid (53 mg, 0.10 mmol, 0.20M in DMF) and furfurylamine (29 mg, 0.30 mmol, 0.6M in DMF) were combined to give 53 mg of the desired compound: Low resolution mass spectrum (LC-MS, APCI) m/z 610 [M+H]+.

EXAMPLE 230

N-(2-Furylmethyl)-3-{[(2-{[(1S)-2-(1H-imidazol-1-yl)-1-phenylethyl]oxy}-5-oxo-5,6,7,8-tetrahydro-1-naphthalenyl)methyl]sulfonyl}benzamide (Compound 230)

Using the method in Example 172, 3-{[(2-{[(1S)-2-(1H-imidazol-1-yl)-1-phenylethyl]oxy}-5-oxo-5,6,7,8-tetrahydro-1-naphthalenyl)methyl]sulfonyl}benzoic acid (53 mg, 0.10 mmol, 0.20M in DMF) and furfurylamine (29 mg, 0.30 mmol, 0.6M in DMF) were combined to give 55 mg of the desired compound: Low resolution mass spectrum (LC-MS, APCI) m/z 610 [M+H]+.

EXAMPLE 231

N-(2-Furylmethyl)-2-{[(2-{[(1S)-2-(1H-imidazol-1-yl)-1-phenylethyl]oxy}-5-oxo-5,6,7,8-tetrahydro-1-naphthalenyl)methyl]sulfonyl}benzamide (Compound 231)

Using the method in Example 172, 2-{[(2-{[(1S)-2-(1H-imidazol-1-yl)-1-phenylethyl]oxy}-5-oxo-5,6,7,8-tetrahydro-1-naphthalenyl)methyl]sulfonyl}benzoic acid (53 mg, 0.10 mmol, 0.20M in DMF) and furfurylamine (29 mg, 0.30 mmol, 0.6M in DMF) were combined to give 51 mg of the desired compound: Low resolution mass spectrum (LC-MS, APCI) m/z 610 [M+H]+.

EXAMPLE 232

N-[2-Hydroxy-1-(hydroxymethyl)ethyl]-2-{[(2-{[(1S)-2-(1H-imidazol-1-yl)-1-phenylethyl]oxy}-5-oxo-5,6,7,8-tetrahydro-1-naphthalenyl)methyl]sulfanyl}benzamide (Compound 232)

Using the method in Example 172, 2-{[(2-{[(1S)-2-(1H-imidazol-1-yl)-1-phenylethyl]oxy}-5-oxo-5,6,7,8-tetrahydro-1-naphthalenyl)methyl]sulfanyl} benzoic acid (50 mg, 0.10 mmol, 0.20M in DMF) and serinol (46 mg, 0.50 mmol, 1.0M in DMF) were combined (reaction time 3 days at room temperature) to give 30 mg of the desired compound: Low resolution mass spectrum (LC-MS, APCI) m/z 572 [M+H]+.

EXAMPLE 233

N-[2-Hydroxy-1-(hydroxymethyl)ethyl]-4-{[(2-{[(1S)-2-(1H-imidazol-1-yl)-1-phenylethyl]oxy}-5-oxo-5,6,7,8-tetrahydro-1-naphthalenyl)methyl]sulfanyl}benzamide (Compound 233)

Using the method in Example 172, 4-{[(2-{[(1S)-2-(1H-imidazol-1-yl)-1-phenylethyl]oxy}-5-oxo-5,6,7,8-tetrahydro-1-naphthalenyl)methyl]sulfanyl}benzoic acid (50 mg, 0.10 mmol, 0.20M in DMF) and serinol (46 mg, 0.50 mmol, 1.0M in DMF) were combined (reaction time 3 days at room temperature) to give 48 mg of the desired compound: Low resolution mass spectrum (LC-MS, APCI) m/z 572 [M+H]+.

EXAMPLE 234

N-[2-Hydroxy-1-(hydroxymethyl)ethyl]-3-{[(2-{[(1S)-2-(1H-imidazol-1-yl)-1-phenylethyl]oxy}-5-oxo-5,6,7,8-tetrahydro-1-naphthalenyl)methyl]sulfanyl}benzamide (Compound 234)

Using the method in Example 172, 3-{[(2-{[(1S)-2-(1H-imidazol-1-yl)-1-phenylethyl]oxy}-5-oxo-5,6,7,8- tetrahydro-1-naphthalenyl)methyl]sulfanyl}benzoic acid (50 mg, 0.10 mmol, 0.20M in DMF) and serinol (46 mg, 0.50 mmol, 1.0M in DMF) were combined (reaction time 3 days at room temperature) to give 46 mg of the desired compound: Low resolution mass spectrum (LC-MS, APCI) m/z 572 [M+H]⁺.

EXAMPLE 235

N-[2-Hydroxy-1-(hydroxymethyl)ethyl]-4-{[(2-{[(1S)-2-(1H-imidazol-1-yl)-1-phenylethyl]oxy}-5-oxo-5,6,7,8-tetrahydro-1-naphthalenyl)methyl]sulfonyl}benzamide (Compound 235)

Using the method in Example 172, 4-{[(2-{[(1S)-2-(1H-imidazol-1-yl)-1-phenylethyl]oxy}-5-oxo-5,6,7,8-tetrahydro-1-naphthalenyl)methyl]sulfonyl}benzoic acid (53 mg, 0.10 mmol, 0.20M in DMF) and serinol (46 mg, 0.50 mmol, 1.0M in DMF) were combined (reaction time 3 days at room temperature) to give 40 mg of the desired compound: Low resolution mass spectrum (LC-MS, APCI) m/z 604 [M+H]⁺.

EXAMPLE 236

N-[2-Hydroxy-1-(hydroxymethyl)ethyl]-3-{[(2-{[(1S)-2-(1H-imidazol-1-yl)-1-phenylethyl]oxy}-5-oxo-5,6,7,8-tetrahydro-1-naphthalenyl)methyl]sulfonyl}benzamide (Compound 236)

Using the method in Example 172, 3-{[(2-{[(1S)-2-(1H-imidazol-1-yl)-1-phenylethyl]oxy}-5-oxo-5,6,7,8-tetrahydro-1-naphthalenyl)methyl]sulfonyl}benzoic acid (53 mg, 0.10 mmol, 0.20M in DMF) and serinol (46 mg, 0.50 mmol, 1.0M in DMF) were combined (reaction time 3 days at room temperature) to give 45 mg of the desired compound: Low resolution mass spectrum (LC-MS, APCI) m/z 604 [M+H]⁺.

EXAMPLE 237

N-[2-Hydroxy-1-(hydroxymethyl)ethyl]-2-{[(2-{[(1S)-2-(1H-imidazol-1-yl)-1-phenylethyl]oxy}-5-oxo-5,6,7,8-tetrahydro-1-naphthalenyl)methyl]sulfonyl}benzamide (Compound 237)

Using the method in Example 172, 2-{[(2-{[(1S)-2-(1H-imidazol-1-yl)-1-phenylethyl]oxy}-5-oxo-5,6,7,8-tetrahydro-1-naphthalenyl)methyl] sulfonyl}benzoic acid (53 mg, 0.10 mmol, 0.20M in DMF) and serinol (46 mg, 0.50 mmol, 1.0M in DMF) were combined (reaction time 3 days at room temperature) to give 23 mg of the desired compound: Low resolution mass spectrum (LC-MS, APCI) m/z 604 [M+H]⁺.

EXAMPLE 238

N-(2-Furylmethyl)-4-{[(2-{[(1S)-2-(1H-imidazol-1-yl)-1-phenylethyl]oxy-}-5-oxo-5,6,7,8-tetrahydro-1-naphthalenyl)methyl]sulfanyl}benzamide (Compound 238)

Using the method in Example 172, 4-{[(2-{[(1S)-2-(1H-imidazol-1-yl)-1-phenylethyl]oxy}-5-oxo-5,6,7,8-tetrahydro-1-naphthalenyl)methyl]sulfanyl}benzoic acid (50 mg, 0.10 mmol, 0.20M in DMF) and furfurylamine (29 mg, 0.30 mmol, 0.6M in DMF) were combined to give 56 mg of the desired compound: Low resolution mass spectrum (LC-MS, APCI) m/z 578 [M+H]⁺.

EXAMPLE 239

N-(2-Furylmethyl)-3-{[(2-{[(1S)-2-(1H-imidazol-1-yl)-1-phenylethyl]oxy}-5-oxo-5,6,7,8-tetrahydro-1-naphthalenyl)methyl]sulfanyl}benzamide (Compound 239)

Using the method in Example 172, 3-{[(2-{[(1S)-2-(1H-imidazol-1-yl)-1-phenylethyl]oxy}-5-oxo-5,6,7,8-tetrahydro-1-naphthalenyl)methyl]sulfanyl}benzoic acid (50 mg, 0.10 mmol, 0.20M in DMF) and furfurylamine (29 mg, 0.30 mmol, 0.6M in DMF) were combined to give 56 mg of the desired compound: Low resolution mass spectrum (LC-MS, APCI) m/z 578 [M+H]⁺.

EXAMPLE 240

N-(2-Furylmethyl)-2-{[(2-{[(1S)-2-(1H-imidazol-1-yl)-1-phenylethyl]oxy}-5-oxo-5,6,7,8-tetrahydro-1-naphthalenyl)methyl]sulfanyl}benzamide (Compound 240)

Using the method in Example 172, 2-{[(2-{[(1S)-2-(1H-imidazol-1-yl)-1-phenylethyl]oxy}-5-oxo-5,6,7,8-tetrahydro-1-naphthalenyl)methyl]sulfanyl}benzoic acid (50 mg, 0.10 mmol, 0.20M in DMF) and furfurylamine (29 mg, 0.30 mmol, 0.6M in DMF) were combined to give 54 mg of the desired compound: Low resolution mass spectrum (LC-MS, APCI) m/z 578 [M+H]⁺.

EXAMPLE 241

N-[(1R)-1-(Hydroxymethyl)propyl]-4-{[(2-{[(1S)-2-(1H-imidazol-1-yl)-1-phenylethyl]oxy}-5-oxo-5,6,7,8-tetrahydro-1-naphthalenyl)methyl]sulfonyl}benzamide (Compound 241)

Using the method in Example 172, 4-{[(2-{[(1S)-2-(1H-imidazol-1-yl)-1-phenylethyl]oxy}-5-oxo-5,6,7,8-tetrahydro-1-naphthalenyl)methyl]sulfonyl}benzoic acid (53 mg, 0.10 mmol, 0.20M in DMF) and (R)-2-amino-1-butanol (45 mg, 0.50 mmol, 1.0M in DMF) were combined to give 35 mg of the desired compound: Low resolution mass spectrum (LC-MS, APCI) m/z 602 [M+H]⁺.

EXAMPLE 242

N-[(1R)-1-(Hydroxymethyl)propyl]-3-{[(2-{[(1S)-2-(1H-imidazol-1-yl)-1-phenylethyl]oxy}-5-oxo-5,6,7,8-tetrahydro-1-naphthalenyl)methyl]sulfonyl}benzamide (Compound 242)

Using the method in Example 172, 3-{[(2-{[(1S)-2-(1H-imidazol-1-yl)-1-phenylethyl]oxy}-5-oxo-5,6,7,8-tetrahydro-1-naphthalenyl)methyl]sulfonyl}benzoic acid (53 mg, 0.10 mmol, 0.20M in DMF) and (R)-2-amino-1-butanol (45 mg, 0.50 mmol, 1.0M in DMF) were combined to give 39 mg of the desired compound: Low resolution mass spectrum (LC-MS, APCI) m/z 602 [M+H]⁺.

EXAMPLE 243

N-[(1R)-1-(Hydroxymethyl)propyl]-2-{[(2-{[(1S)-2-(1H-imidazol-1-yl)-1-phenylethyl]oxy}-5-oxo-5,6,7,8-tetrahydro-1-naphthalenyl)methyl]sulfonyl}benzamide (Compound 243)

Using the method in Example 172, 2-{[(2-{[(1S)-2-(1H-imidazol-1-yl)-1-phenylethyl]oxy}-5-oxo-5,6,7,8-tetrahydro-1-naphthalenyl)methyl]sulfonyl}benzoic acid (53 mg, 0.10 mmol, 0.20M in DMF) and (R)-2-amino-1-butanol (45 mg, 0.50 mmol, 1.0M in DMF) were combined to give 32 mg of the desired compound: Low resolution mass spectrum (LC-MS, APCI) m/z 602 [M+H]⁺.

EXAMPLE 244

N-[(1R)-1-(Hydroxymethyl)propyl]-2-{[(2-{[(1S)-2-(1H-imidazol-1-yl)-1-phenylethyl]oxy}-5-oxo-5,6,7,8-tetrahydro-1-naphthalenyl)methyl]sulfanyl}benzamide (Compound 244)

Using the method in Example 172, 2-{[(2-{[(1S)-2-(1H-imidazol-1-yl)-1-phenylethyl]oxy}-5-oxo-5,6,7,8- tetrahydro-1-naphthalenyl)methyl]sulfanyl}benzoic acid (50 mg, 0.10 mmol, 0.20M in DMF) and (R)-2-amino-1-butanol (45 mg, 0.50 mmol, 1.0M in DMF) were combined to give 51 mg of the desired compound: Low resolution mass spectrum (LC-MS, APCI) m/z 570 [M+H]$^+$.

EXAMPLE 245

N-[(1R)-1-(Hydroxymethyl)propyl]-4-{[(2-{[(1S)-2-(1H-imidazol-1-yl)-1-phenylethyl]oxy}-5-oxo-5,6,7,8-tetrahydro-1-naphthalenyl)methyl]sulfanyl}benzamide (Compound 245)

Using the method in Example 172, 4-{[(2-{[(1S)-2-(1H-imidazol-1-yl)-1-phenylethyl]oxy}-5-oxo-5,6,7,8-tetrahydro-1-naphthalenyl)methyl]sulfanyl}benzoic acid (50 mg, 0.10 mmol, 0.20M in DMF) and (R)-2-amino-1-butanol (45 mg, 0.50 mmol, 1.0M in DMF) were combined to give 53 mg of the desired compound: Low resolution mass spectrum (LC-MS, APCI) m/z 570 [M+H]$^+$.

EXAMPLE 246

N-[(1R)-1-(Hydroxymethyl)propyl]-3-{[(2-{[(1S)-2-(1H-imidazol-1-yl)-1-phenylethyl]oxy}-5-oxo-5,6,7,8-tetrahydro-1-naphthalenyl)methyl]sulfanyl}benzamide (Compound 246)

Using the method in Example 172, 3-{[(2-{[(1S)-2-(1H-imidazol-1-yl)-1-phenylethyl]oxy}-5-oxo-5,6,7,8-tetrahydro-1-naphthalenyl)methyl]sulfanyl}benzoic acid (50 mg, 0.10 mmol, 0.20M in DMF) and (R)-2-amino-1-butanol (45 mg, 0.50 mmol, 1.0M in DMF) were combined to give 50 mg of the desired compound: Low resolution mass spectrum (LC-MS, APCI) m/z 570 [M+H]$^+$.

EXAMPLE 247

4-{[(2-{[(1S)-2-(1H-Imidazol-1-yl)-1-phenylethyl]oxy}-5-oxo-5,6,7,8-tetrahydro-1-naphthalenyl)methyl]sulfonyl}-N-[(2S)-2-methylbutyl]benzamide (Compound 247)

Using the method in Example 172, 4-{[(2-{[(1S)-2-(1H-imidazol-1-yl)-1-phenylethyl]oxy}-5-oxo-5,6,7,8-tetrahydro-1-naphthalenyl)methyl]sulfonyl}benzoic acid (53 mg, 0.10 mmol, 0.20M in DMF) and (S)-2-methylbutylamine (26 mg, 0.30 mmol, 0.6M in DMF) were combined to give 60 mg of the desired compound: Low resolution mass spectrum (LC-MS, APCI) m/z 600 [M+H]$^+$.

EXAMPLE 248

3-{[(2-{[(1S)-2-(1H-Imidazol-1-yl)-1-phenylethyl]oxy}-5-oxo-5,6,7,8-tetrahydro-1-naphthalenyl)methyl]sulfonyl-N-[(2S)-2-1-methylbutyl]benzamide (Compound 248)

Using the method in Example 172, 3-{[(2-{[(1S)-2-(1H-imidazol-1-yl)-1-phenylethyl]oxy}-5-oxo-5,6,7,8-tetrahydro-1-naphthalenyl)methyl]sulfonyl}benzoic acid (53 mg, 0.10 mmol, 0.20M in DMF) and (S)-2-methylbutylamine (26 mg, 0.30 mmol, 0.6M in DMF) were combined to give 58 mg of the desired compound: Low resolution mass spectrum (LC-MS, APCI) m/z 600 [M+H]$^+$.

EXAMPLE 249

2-[(2-{[(1S)-2-(1H-Imidazol-1-yl)-1-phenylethyl]oxy}-5-oxo-5,6,7,8-tetrahydro-1-naphthalenyl)methyl]sulfonyl}-N-[(2S)-2-methylbutyl]benzamide (Compound 249)

Using the method in Example 172, 2-{[(2-{[(1S)-2-(1H-imidazol-1-yl)-1-phenylethyl]oxy}-5-oxo-5,6,7,8-tetrahydro-1-naphthalenyl)methyl]sulfonyl}benzoic acid (53 mg, 0.10 mmol, 0.20M in DMF) and (S)-2-methylbutylamine (26 mg, 0.30 mmol, 0.6M in DMF) were combined to give 60 mg of the desired compound: Low resolution mass spectrum (LC-MS, APCI) m/z 600 [M+H]$^+$.

EXAMPLE 250

2-{[(2-{[(1S)-2-(1H-Imidazol-1-yl)-1-phenylethyl]oxy}-5-oxo-5,6,7,8-tetrahydro-1-naphthalenyl)methyl]sulfanyl}-N-[(2S)-2-1-methylbutyl]benzamide (Compound 250)

Using the method in Example 172, 2-{[(2-{[(1S)-2-(1H-imidazol-1-yl)-1-phenylethyl]oxy}-5-oxo-5,6,7,8-tetrahydro-1-naphthalenyl)methyl]sulfanyl}benzoic acid (50 mg, 0.10 mmol, 0.20M in DMF) and (S)-2-methylbutylamine (26 mg, 0.30 mmol, 0.6M in DMF) were combined to give 57 mg of the desired compound: Low resolution mass spectrum (LC-MS, APCI) m/z 568 [M+H]$^+$.

EXAMPLE 251

4-{[(2-{[(1S)-2-(1H-Imidazol-1-yl)-1-phenylethyl]oxy}-5-oxo-5,6,7,8-tetrahydro-1-naphthalenyl)methyl]sulfanyl}-N-[(2S)-2-methylbutyl]benzamide (Compound 251)

Using the method in Example 172, 4-{[(2-{[(1S)-2-(1H-imidazol-1-yl)-1-phenylethyl]oxy}-5-oxo-5,6,7,8-tetrahydro-1-naphthalenyl)methyl]sulfanyl}benzoic acid (50 mg, 0.10 mmol, 0.20M in DMF) and (S)-2-methylbutylamine (26 mg, 0.30 mmol, 0.6M in DMF) were combined to give 56 mg of the desired compound: Low resolution mass spectrum (LC-MS, APCI) m/z 568 [M+H]$^+$.

EXAMPLE 252

3-{[(2-{[(1S)-2-(1H-Imidazol-1-yl)-1-phenylethyl]oxy}-5-oxo-5,6,7,8-tetrahydro-1-naphthalenyl)methyl]sulfanyl}-N-[(2S)-2-methylbutyl]benzamide (Compound 252)

Using the method in Example 172, 3-{[(2-{[(1S)-2-(1H-imidazol-1-yl)-1-phenylethyl]oxy}-5-oxo-5,6,7,8-tetrahydro-1-naphthalenyl)methyl]ulfanyl}benzoic acid (50 mg, 0.10 mmol, 0.20M in DMF) and (S)-2-methylbutylamine (26 mg, 0.30 mmol, 0.6M in DMF) were combined to give 57 mg of the desired compound: Low resolution mass spectrum (LC-MS, APCI) m/z 568 [M+H]$^+$.

EXAMPLE 253

N-(2-Hydroxypropyl)-4-{[(2-{[(1S)-2-(1H-imidazol-1-yl)-1-phenylethyl]oxy}-5-oxo-5,6,7,8-tetrahydro-1-naphthalenyl)methyl]sulfonyl}benzamide (Compound 253)

Using the method in Example 172, 4-{[(2-{[(1S)-2-(1H-imidazol-1-yl)-1-phenylethyl]oxy}-5-oxo-5,6,7,8-tetrahydro-1-naphthalenyl)methyl]sulfonyl}benzoic acid (53 mg, 0.10 mmol, 0.20M in DMF) and 1-amino-2-propanol (23 mg, 0.30 mmol, 0.6M in DMF) were combined to give 23 mg of the desired compound: Low resolution mass spectrum (LC-MS, APCI) m/z 588 [M+H]$^+$.

EXAMPLE 254

N-(2-Hydroxypropyl)-3-{[(2-{[(1S)-2-(1H-imidazol-1-yl)-1-phenylethyl]oxy}-5-oxo-5,6,7,8-tetrahydro-1-naphthalenyl)methyl]sulfonyl}benzamide (Compound 254)

Using the method in Example 172, 3-{[(2-{[(1S)-2-(1H-imidazol-1-yl)-1-phenylethyl]oxy}-5-oxo-5,6,7,8- tetrahydro-1-naphthalenyl)methyl]sulfonyl}benzoic acid (53 mg, 0.10 mmol, 0.20M in DMF) and 1-amino-2-propanol (23 mg, 0.30 mmol, 0.6M in DMF) were combined to give 27 mg of the desired compound: Low resolution mass spectrum (LC-MS, APCI) m/z 588 [M+H]$^+$.

EXAMPLE 255

N-(2-Hydroxypropyl)-2-{[(2-{[(1S)-2-(1H-imidazol-1-yl)-1-phenylethyl]oxy}-5-oxo-5,6,7,8-tetrahydro-1-naphthalenyl))methyl]sulfonyl}benzamide (Compound 255)

Using the method in Example 172, 2-{[(2-{[(1S)-2-(1H-imidazol-1-yl)-1-phenylethyl]oxy}-5-oxo-5,6,7,8-tetrahydro-1-naphthalenyl)methyl]sulfonyl}benzoic acid (53 mg, 0.10 mmol, 0.20M in DMF) and 1-amino-2-propanol (23 mg, 0.30 mmol, 0.6M in DMF) were combined to give 42 mg of the desired compound: Low resolution mass spectrum (LC-MS, APCI) m/z 588 [M+H]$^+$.

EXAMPLE 256

N-(2-Hydroxypropyl)-4-{[(2-{[(1S)-2-(1H-imidazol-1-yl)-1-phenylethyl]oxy}-5-oxo-5,6,7,8-tetrahydro-1-naphthalenyl)methyl]sulfanyl}benzamide (Compound 256)

Using the method in Example 172, 4-{[(2-{[(1S)-2-(1H-imidazol-1-yl)-1-phenylethyl]oxy}-5-oxo-5,6,7,8-tetrahydro-1-naphthalenyl)methyl]sulfanyl}benzoic acid (50 mg, 0.10 mmol, 0.20M in DMF) and 1-amino-2-propanol (23 mg, 0.30 mmol, 0.6M in DMF) were combined to give 46 mg of the desired compound: Low resolution mass spectrum (LC-MS, APCI) m/z 556 [M+H]$^+$.

EXAMPLE 257

N-(2-Hydroxypropyl)-2-{[(2-{[(1S)-2-(1H-imidazol-1-yl)-1-phenylethyl]oxy}-5-oxo-5,6,7,8-tetrahydro-1-naphthalenyl)methyl]sulfanyl}benzamide (Compound 257)

Using the method in Example 172, 2-{[(2-{[(1S)-2-(1H-imidazol-yl)-1-phenylethyl]oxy}-5-oxo-5,6,7,8-tetrahydro-1-naphthalenyl)methyl]sulfanyl}benzoic acid (50 mg, 0.10 mmol, 0.20M in DMF) and 1-amino-2-propanol (23 mg, 0.30 mmol, 0.6M in DMF) were combined to give 32 mg of the desired compound: Low resolution mass spectrum (LC-MS, APCI) m/z 556 [M+H]$^+$.

EXAMPLE 258

N-(2-Hydroxypropyl)-3-{[(2-{[(1S)-2-(1H-imidazol-1-yl)-1-phenylethyl]oxy}-5-oxo-5,6,7,8-tetrahydro-1-naphthalenyl)methyl]sulfanyl}benzamide (Compound 258)

Using the method in Example 172, 3-{[(2-{[(1S)-2-(1H-imidazol-1-yl)-1-phenylethyl]oxy}-5-oxo-5,6,7,8-tetrahydro-1-naphthalenyl)methyl]sulfanyl}benzoic acid (50 mg, 0.10 mmol, 0.20M in DMF) and 1-amino-2-propanol (23 mg, 0.30 mmol, 0.6M in DMF) were combined to give 46 mg of the desired compound: Low resolution mass spectrum (LC-MS, APCI) m/z 556 [M+H]$^+$.

EXAMPLE 259

3-{[(2-{[(1S)-2-(1H-Imidazol-1-yl)-1-phenylethyl]oxy}-5-oxo-5,6,7,8-tetrahydro-1-naphthalenyl)methyl]sulfonyl}-N-(2-methoxyethyl)benzamide (Compound 259)

Using the method in Example 172, 3-{[(2-{[(1S)-2-(1H-imidazol-1-yl)-1-phenylethyl]oxy}-5-oxo-5,6,7,8-tetrahydro-1-naphthalenyl)methyl]sulfanyl}benzoic acid (50 mg, 0.10 mmol, 0.20M in DMF) and 2-methoxyethylamine (23 mg, 0.30 mmol, 0.6M in DMF) were combined to give 49 mg of the desired compound: Low resolution mass spectrum (LC-MS, APCI) m/z 556 [M+H]$^+$.

EXAMPLE 260

2-{[(2-{[(1S)-2-(1H-Imidazol-1-yl)-1-phenylethyl]oxy}-5-oxo-5,6,7,8-tetrahydro-1-naphthalenyl)methyl]sulfanyl}-N-(2-methoxyethyl)benzamide (Compound 260)

Using the method in Example 172, 2-{[(2-{[(1S)-2-(1H-imidazol-1-yl)-1-phenylethyl]oxy}-5-oxo-5,6,7,8-tetrahydro-1-naphthalenyl)methyl]sulfanyl}benzoic acid (50 mg, 0.10 mmol, 0.20M in DMF) and 2-methoxyethylamine (23 mg, 0.30 mmol, 0.6M in DMF) were combined to give 43 mg of the desired compound: Low resolution mass spectrum (LC-MS, APCI) m/z 556 [M+H]$^+$.

EXAMPLE 261

4-{[(2-{[1S)-2-(1H-Imidazol-1-yl)-1-phenylethyl]oxy}-5-oxo-5,6,7,8-tetrahydro-1-naphthalenyl)methyl]sulfanyl}-N-(2-methoxyethyl)benzamide (Compound 261)

Using the method in Example 172, 4-{[(2-{[(1S)-2-(1H-imidazol-1-yl)-1-phenylethyl]oxy}-5-oxo-5,6,7,8-tetrahydro-1-naphthalenyl)methyl]sulfanyl}benzoic acid (50 mg, 0.10 mmol, 0.20M in DMF) and 2-methoxyethylamine (23 mg, 0.30 mmol, 0.6M in DMF) were combined to give 56 mg of the desired compound: Low resolution mass spectrum (LC-MS, APCI) m/z 556 [M+H]$^+$.

EXAMPLE 262

4-{[(2-{[(1S)-2-(1H-Imidazol-1-yl)-1-phenylethyl]oxy}-5-oxo-5,6,7,8-tetrahydro-1-naphthalenyl)methyl]sulfonyl}-N-(2-methylethyl)benzamide (Compound 262)

Using the method in Example 172, 4-{[(2-{[(1S)-2-(1H-imidazol-1-yl)-1-phenylethyl]oxy}-5-oxo-5,6,7,8-tetrahydro-1-naphthalenyl)methyl]sulfonyl}benzoic acid (53 mg, 0.10 mmol, 0.20M in DMF) and 2-methoxyethylamine (23 mg, 0.30 mmol, 0.6M in DMF) were combined to give 38 mg of the desired compound: Low resolution mass spectrum (LC-MS, APCI) m/z 588 [M+H]$^+$.

EXAMPLE 263

3-{[(2-{[(1S)-2-(1H-In imidazol-1-yl)-1-phenylethyl]oxy}-5-oxo-5,6,7,8-tetrahydro-1-naphthalenyl)methyl]sulfonyl}-N-(2-methoxyethyl)benzamide (Compound 263)

Using the method in Example 172, 3-{[(2-{[(1S)-2-(1H-imidazol-1-yl)-1-phenylethyl]oxy}-5-oxo-5,6,7,8-tetrahydro-1-naphthalenyl)methyl]sulfonyl}benzoic acid (53 mg, 0.10 mmol, 0.20M in DMF) and 2-methoxyethylamine (23 mg, 0.30 mmol, 0.6M in DMF) were combined to give 42 mg of the desired compound: Low resolution mass spectrum (LC-MS, APCI) m/z 588 [M+H]$^+$.

EXAMPLE 264

2-{[(2-{[(1S)-2-(1H-Imidazol-1-yl)-1-phenylethyl]oxy}-5-oxo-5,6,7,8-tetrahydro-1-naphthalenyl)-methyl]sulfonyl}-N-(2-methoxyethyl)benzamide (Compound 264)

Using the method in Example 172, 2-{[(2-{[(1S)-2-(1H-imidazol-1-yl)-1-phenylethyl]oxy}-5-oxo-5,6,7,8- tetrahydro-1-naphthalenyl)methyl]sulfonyl}benzoic acid (53 mg, 0.10 mmol, 0.20M in DMF) and 2-methoxyethylamine (23 mg, 0.30 mmol, 0.6M in DMF) were combined to give 27 mg of the desired compound: Low resolution mass spectrum (LC-MS, APCI) m/z 588 [M+H]+.

EXAMPLE 265

The pharmaceutical utility of compounds of this invention are indicated by the following assay for inhibitors of protein:farnesyl transferease (PFT) or farnesyl protein transferase (FPT).

PFT Inhibitory Activity

The PFT or FPT inhibitory activity of compounds of the present invention were assayed in HEPES buffer (pH 7.4) containing 5 mM potassium phosphate and 20 µM $ZnCl_2$. The solution also contained 5 mM DTT (dithiothreitol), 5 mM $MgCl_2$, and 0.1% PEG 8000. Assays were performed in 96 well plates (Wallec) and employed solutions composed of varying concentrations of a compound of the present invention in 10% DMSO (dimethylsulfoxide). Upon addition of both substrates, radiolabeled farnesyl pyrophosphate ([$^{13}$H], specific activity 15–30 Ci/mmol, final concentration 134 nM) and (biotinyl)-Ahe-Thr-Lys-Cys-Val-Ile-Met ([3aS[3a alpha, 4 beta, 6a alpha]-hexahydro-2-oxo-1H-thieno[3,4-d] imidazole-5-pentanoic acid]-[7-aminoheptanoic acid]-Thr-Lys-Cys-Val-Ile-Met) (Ahe is 7-aminoheptanoic acid, Thr is threonine, Lys is lysine, Cys is cysteine, Val is valine, Ile is isoleucine, and Met is methionine) (final concentration 0.2 µM), the enzyme reaction was started by addition of SF9 affinity purified rat FPT. After incubation at 30° C. for 30 minutes, the reaction was terminated by diluting the reaction 2.5-fold with a stop buffer containing 1.5 M magnesium acetate, 0.2 M $H_3PO_4$, 0.5% BSA (bovine serum albumin), and strepavidin beads (Amersham) at a concentration of 1.3 mg/mL. After allowing the plate to settle for 30 minutes at room temperature, radioactivity was quantitated on a micro-Beta counter (Model 1450, Wallec). The assay was also carried out without 5 mM potassium phosphate.

The compounds of the present invention have inhibitory activities ($IC_{50}$) ranging from 0.1 to about 40 nM in the above assay. The compounds of Formula I, which are a sub-genus of the compounds disclosed in WO98/34921, which is PCT Application No. PCT/US98/03025, have inhibitory activities ($IC_{50}$) ranging from 0.1 to about 30 nM in the above assay. PCT/US98/03025 discloses the compound of Example 80, which is 6-[2-(1H-1-Imidazolyl)-1-phenylethoxy]-1,2,3,4-tetrahydro-1-naphthalenone, and has the following structure:

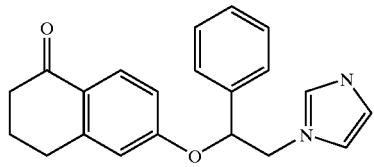

The compound of Example 80 has an $IC_{50}$ of 73 nM. The above data supports the conclusion that the compounds of Formula I have surprising and unexpectedly high inhibitory activities as compared to the compound of Example 80 in PCT/US98/03025.

The data in Table 2 below shows the FPT inhibitory activity of specific compounds of the present invention.

TABLE 2

| Example | FTase $IC_{50}$ nM |
|---|---|
| 1 | 0.3 |
| 2 | 3 |
| 3 | 0.3 |
| 4 | 0.3 |
| 5 | 2 |
| 6 | 0.4 |
| 7 | 6 |
| 8 | 3 |
| 9 | 4 |
| 10 | 0.3 |
| 10a | 30.5 |
| 10b | 2.5 |
| 10c | 5.3 |
| 10d | 5.5 |
| 11 | 0.2 |
| 12 | 4 |
| 13 | 2 |
| 14 | 26 |
| 15 | 0.2 |
| 16 | 0.8 |
| 17 | 0.3 |
| 18 | 8 |
| 19 | 14 |
| 19a | 1.9 |
| 19b | 3.6 |
| 19c | 1.4 |
| 19d | 1.9 |
| 20 | 0.4 |
| 21 | 8 |
| 22 | 26 |
| 23 | 11 |
| 24 | 0.4 |
| 25 | 5 |
| 26 | 2 |
| 26a | 5 |
| 26b | 0.85 |
| 26c | 0.2 |
| 27 | 10 |
| 28 | 13 |
| 29 | 0.1 |
| 30 | 0.2 |
| 31 | 10 |
| 32 | 25 |
| 33 | 4 |
| 34 | 25 |
| 35 | 15 |
| 36 | 7 |
| 37 | 13 |
| 37a | 14 |
| 38 | 31 |
| 39 | 1 |
| 39a | 38 |
| 40 | 7.3 |
| 40a | 0.65 |
| 40b | 6 |
| 40c | 1.2 |
| 40d | 9 |
| 40e | 2.5 |
| 40f | 13 |
| 40g | 0.8 |
| 41 | 14 |
| 42 | 1.5 |
| 42a | 1.1 |
| 42b | 3.5 |
| 42c | 3.5 |
| 42d | 2 |
| 42e | 1.5 |
| 42f | 4 |
| 42g | 1.5 |
| 42h | 8 |
| 42i | 1.5 |
| 42j | 4.4 |
| 42k | 16 |
| 43 | 1.7 |
| 44 | 0.2 |
| 44a | 0.87 |
| 44b | 3.1 |

TABLE 2-continued

| Example | FTase IC$_{50}$ nM |
|---|---|
| 45 | 2 |
| 46 | 37 |
| 47 | 2 |
| 48 | 35 |
| 49 | 17 |
| 50 | 8 |
| 51 | 3 |
| 52 | 8 |
| 53 | 5 |
| 54 | 5 |
| 55 | 1 |
| 56 | 15 |
| 57 | 7 |
| 58 | 0.5 |
| 58a | 1.6 |
| 59 | 12 |
| 60 | 29 |
| 61 | 7 |
| 62 | 10 |
| 63 | 0.2 |
| 63a | 0.4 |
| 63b | 0.94 |
| 63ba | 0.16 |
| 63c | 0.3 |
| 63d | 0.17 |
| 63e | 9.7 |
| 63f | 13 |
| 63g | 9.5 |
| 63h | 2.5 |
| 63i | 1.8 |
| 63j | 1.5 |
| 63k | 2 |
| 63l | 5.5 |
| 63m | 1 |
| 63n | 7 |
| 63o | 4 |
| 63p | 0.55 |
| 63q | 0.5 |
| 63r | 35 |
| 64 | 11 |
| 65 | 0.4 |
| 66 | 12 |
| 67 | 1 |
| 68 | 1 |
| 69 | 0.7 |
| 70 | 7 |
| 71 | 4 |
| 72 | 5 |
| 73 | 2 |
| 74 | 3 |
| 75 | 3 |
| 76 | 1 |
| 77 | 1 |
| 78 | 0.8 |
| 79 | 0.8 |
| 80 | 1 |
| 81 | 4 |
| 82 | 9 |
| 83 | 18 |
| 84 | 4 |
| 85 | 10 |
| 86 | 5 |
| 87 | 7 |
| 88 | 7 |
| 89 | 7 |
| 90 | 5 |
| 91 | 5 |
| 92 | 4 |
| 93 | 3 |
| 94 | 3 |
| 95 | 7 |
| 96 | 5 |
| 97 | 6 |
| 98 | 3 |
| 99 | 5 |
| 100 | 4 |
| 101 | 3 |
| 102 | 5 |
| 103 | 5 |
| 104 | 5 |
| 105 | 5 |
| 106 | 6 |
| 107 | 10 |
| 108 | 3 |
| 109 | 30 |
| 110 | 2 |
| 111 | 3 |
| 112 | 17 |
| 113 | 3 |
| 114 | 2 |
| 115 | 5 |
| 116 | 5 |
| 117 | 1 |
| 118 | 4 |
| 119 | 12 |
| 120 | 13 |
| 121 | 4 |
| 122 | 16 |
| 123 | 30 |
| 124 | 5 |
| 125 | 15 |
| 126 | 19 |
| 127 | 3 |
| 128 | 3 |
| 129 | 8 |
| 130 | 1 |
| 131 | 1 |
| 132 | 1 |
| 133 | 1 |
| 134 | 1 |
| 135 | 4 |
| 136 | 18 |
| 137 | 4 |
| 138 | 4 |
| 139 | 11 |
| 140 | 19 |
| 141 | 0.35 |
| 142 | 0.55 |
| 143 | 1.4 |
| 144 | 35 |
| 145 | 16 |
| 146 | 34 |
| 147 | 19 |
| 148 | 5.3 |
| 149 | 3 |
| 150 | 16 |
| 151 | 19 |
| 152 | 5 |
| 153 | 15 |
| 154 | 2.6 |
| 155 | 20 |
| 156 | 5 |
| 157 | 4 |
| 158 | 4 |
| 159 | 5.5 |
| 160 | 10 |
| 161 | 5 |
| 162 | 8 |
| 163 | 5 |
| 164 | 5.3 |
| 165 | 6.4 |
| 166 | 30 |
| 167 | 7 |
| 168 | 10 |
| 169 | 7 |
| 170 | 7 |
| 171 | 6 |
| 172 | 5 |
| 173 | 4 |
| 174 | 3 |
| 175 | 10 |
| 176 | 7 |
| 177 | 3 |
| 178 | 8 |

TABLE 2-continued

| Example | FTase IC$_{50}$ nM |
|---|---|
| 179 | 6 |
| 180 | 6 |
| 181 | 20 |
| 182 | 10 |
| 183 | 7 |
| 184 | 9 |
| 185 | 4 |
| 186 | 4 |
| 187 | 7 |
| 188 | 4 |
| 189 | 10 |
| 190 | 8 |
| 191 | 2 |
| 192 | 7 |
| 193 | 5 |
| 194 | 0.2 |
| 195 | 0.2 |
| 196 | 0.2 |
| 197 | 0.2 |
| 198 | 0.2 |
| 199 | 0.4 |
| 200 | 0.24 |
| 201 | 0.2 |
| 202 | 0.2 |
| 203 | 1.2 |
| 204 | 0.65 |
| 205 | 0.2 |
| 206 | 0.8 |
| 207 | 0.2 |
| 208 | 0.2 |
| 209 | 0.2 |
| 210 | 0.2 |
| 211 | 0.2 |
| 212 | 0.2 |
| 213 | 0.2 |
| 214 | 0.37 |
| 215 | 0.2 |
| 216 | 0.4 |
| 217 | 0.2 |
| 218 | 0.2 |
| 219 | 0.47 |
| 220 | 0.2 |
| 221 | 0.2 |
| 222 | 0.2 |
| 223 | 0.24 |
| 224 | 0.2 |
| 225 | 0.2 |
| 226 | 0.2 |
| 227 | 0.2 |
| 228 | 0.2 |
| 229 | 0.55 |
| 230 | 0.2 |
| 231 | 0.2 |
| 232 | 0.2 |
| 233 | 0.45 |
| 234 | 0.25 |
| 235 | 15 |
| 236 | 0.2 |
| 237 | 0.28 |
| 238 | 0.2 |
| 239 | 0.3 |
| 240 | 0.2 |
| 241 | 0.26 |
| 242 | 0.2 |
| 243 | 0.2 |
| 244 | 0.2 |
| 245 | 0.2 |
| 246 | 0.2 |
| 247 | 0.2 |
| 248 | 0.2 |
| 249 | 0.25 |
| 250 | 0.2 |
| 251 | 0.2 |
| 252 | 0.2 |
| 253 | 0.7 |
| 254 | 1 |
| 255 | 0.2 |
| 256 | 0.2 |
| 257 | 0.2 |
| 258 | 0.2 |
| 259 | 0.2 |
| 260 | 0.2 |
| 261 | 0.2 |
| 262 | 0.8 |
| 263 | 0.2 |
| 264 | 0.2 |

The enzyme inhibitory activity of the invention compounds, as established in the foregoing assay, demonstrates that the compounds are useful in preventing and treating uncontrolled cellular proliferation, and are thus useful for preventing and treating disease states characterized by such proliferation.

The compounds of the present invention will be used in the form of pharmaceutical formulations, and the following examples illustrate typical dosage forms.

EXAMPLE 266

Tablet Formulation

| Ingredient | Amount |
|---|---|
| Compound No. 12 | 50 mg |
| Lactose | 80 mg |
| Cornstarch (for mix) | 10 mg |
| Cornstarch (for paste) | 8 mg |
| Magnesium Stearate (1%) | 2 mg |
|  | 150 mg |

Compound No. 12 is mixed with the lactose and cornstarch (for mix) and blended to uniformity to a powder. The cornstarch (for paste) is suspended in 6 mL of water and heated with stirring to form a paste. The paste is added to the mixed powder, and the mixture is granulated. The wet granules are passed through a No. 8 hard screen and dried at 50° C. The mixture is lubricated with 1% magnesium stearate and compressed into a tablet. The tablets are administered to a patient at the rate of 1 to 4 each day for prevention and treatment of atherosclerosis.

EXAMPLE 267

Parenteral Solution

In a solution of 700 mL of propylene glycol and 200 mL of water for injection is added 20.0 g of Compound No. 8. The mixture is stirred and the pH is adjusted to 5.5 with hydrochloric acid. The volume is adjusted to 1000 mL with water for injection. The solution is sterilized, filled into 5.0 mL ampoules, each containing 2.0 mL (40 mg of Compound No. 8), and sealed under nitrogen. The solution is administered by injection to a patient suffering from cancer and in need of treatment.

EXAMPLE 268

Patch Formulation

Compound No. 26 (10 mg) is suspended in a mixture of mineral oil, polyisobutylene, and colloidal silicon dioxide (5 mg each). This mixture is applied evenly to a 10 cm$^2$ microporous polypropylene membrane (which has a backing layer of pigmented polyester film) that controls the rate of delivery of active agent to the skin surface of a patient. The membrane is layered onto an adhesive formulation of polyisobutylene, and the mixture is covered with a protective slit release liner of polyester that is removed immediately before applying the patch to the chest or forearm of a patient to treat Alzheimer's disease.

The invention and the manner and process of making and using it, are now described in such full, clear, concise, and exact terms as to enable any person skilled in the art to which it pertains, to make and use the same. It is to be understood that the foregoing describes preferred embodiments of the present invention and that modifications may be made therein without departing from the spirit or scope of the present invention as set forth in the claims. To particularly point out and distinctly claim the subject matter regarded as invention, the following claims conclude this specification.

What is claimed is:

1. A compound of formula:

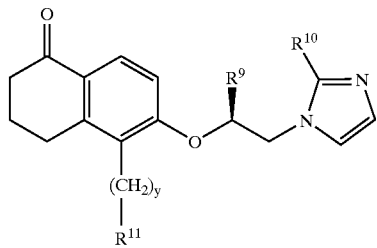

III wherein:

$R^9$ is heteroaryl;

$R^{10}$ is hydrogen, $C_1$–$C_6$ alkyl, or $C_1$–$C_6$ substituted alkyl;

y is 0, 1, 2, or 3;

$R^{11}$ is —O-substituted alkyl, —O-aryl, —O-substituted aryl, —O-aryl-heteroaryl, —O-heteroaryl, —O-substituted heteroaryl, —O-phenyl-O—$CF_3$, —O-phenyl-O-phenyl, —S-aryl, —S-substituted aryl, —S-arylalkyl, —S(O)z-substituted alkyl, —S(O)z-substituted arylalkyl, —S(O)z-heteroaryl, —S(O)z-heteroarylalkyl, —S(O)z-substituted heteroaryl, —SO-alkyl, —$SO_2$-alkyl, —SO-aryl, —$SO_2$-aryl, —SO-substituted aryl, —$SO_2$-substituted aryl, —SO-arylalkyl, —$SO_2$-arylalkyl, —S(O)z-phenyl-CONH—$R^{13}$, —$NHSO_2$—$R^{14}$, —NHCO—$R^{14}$, NHCO-heteroaryl-O-aryl, NHCO-heteroaryl-substituted aryl, NHCOC(substituted alkyl)$NHCO_2$-alkyl, —NHCO—C(substituted alkyl)amino, —$NHCO_2$-alkyl, —NH-aryl, —NH-substituted aryl, —NH-heteroaryl, —NH—$(CH_2)_2$—O-heteroaryl, —N(CO-alkyl) substituted aryl, -aryl-CO-alkyl,

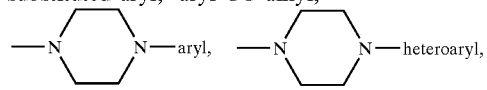

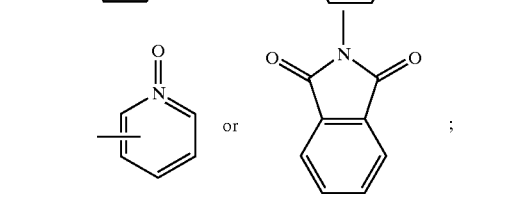

z is 0, 1 or 2;

$R^{13}$ is alkyl, substituted alkyl, alkenyl, alkynyl, cycloalkyl, or heteroarylalkyl;

$R^{14}$ is aryl, substituted aryl, arylalkyl, heteroaryl, heteroarylalkyl, or substituted heteroaryl;

provided that when $R^{11}$ is —O-aryl, —O-substituted aryl, —S-aryl, —S-arylalkyl, —S-substituted aryl, —NH-aryl, or —NH-substituted aryl that the aryl is not phenyl; and pharmaceutically acceptable salts, esters, amides, and prodrugs thereof.

2. A compound of claim 1 wherein $R^{11}$ is —NHCO—$R^{14}$ and $R^{14}$ is heteroaryl.

3. A compound of the formula:

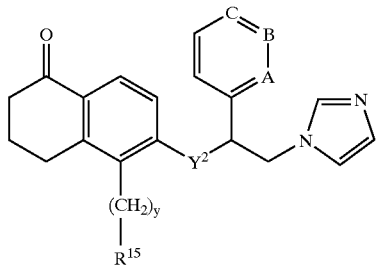

IV wherein:

y is 0, 1, 2, or 3;

$R^{15}$ is lower alkyl, lower alkenyl, alkoxy, substituted alkoxy, arylalkoxy, —O-cycloalkyl, —O-alkenyl, alkylthio, hydroxy, thiol, cyano, halogen, —$CF_3$, —$NO_2$, —$NH_2$, —NH-alkyl, —NH-dialkyl, —NHCO-alkyl, —$CO_2H$, —$CO_2$-alkyl, —$SO_3H$, —O-aryl, —O-substituted aryl, —O-heteroaryl, —O-substituted heteroaryl, —S-alkyl, —S-substituted alkyl, —S-cycloalkyl, —S-aryl, —S-substituted aryl, —S-heteroaryl, —S-substituted heteroaryl, —$SO_2NH_2$, —$SO_2$NH-alkyl, —SO-aryl, —$S_2$-aryl, —$SO_2$-substituted aryl, —$SO_2$-alkyl, —$SO_2$-heteroaryl, —$SO_2$-substituted heteroaryl, —$NHSO_2$-aryl, —NHCO-aryl, —NHCO-heteroaryl, —$NHCO_2$-alkyl, —NH-aryl, —NH-substituted aryl, aryl, substituted aryl, heteroaryl, and substituted heteroaryl;

$Y^2$ is $NR^{16}$, O, S, or $CR^{17}R^{17a}$;

$R^{16}$ is hydrogen, lower alkyl, aryl, arylalkyl, heteroaryl, or cycloalkyl;

$R^{17}$ and $R^{17a}$ are each independently hydrogen, lower alkyl, lower alkenyl, cycloalkyl, aryl, substituted aryl, arylalkyl, substituted arylalkyl, heteroaryl, substituted heteroaryl, heteroarylalkyl, substituted heteroarylalkyl, heterocycloalkyl, substituted heterocycloalkyl, heterocyclalkylalkyl, substituted heterocycloalkylalkyl, halogen, trifluoromethyl, —$OR^{19}$, $NR^{19}R^{19a}$, $NHSO_2R^{19}$, —$S(O)_zR^{19}$, —$SO_2NHR^{19}$, —$OCOR^{19}$, —$CH_2OR^{19}$, —$CH_2NR^{19}R^{19a}$, —$CH_2S(O)_zR^{19}$, —$CH_2NHSO_2R^{19}$, —$CH_2S(O)_zR^{19}$, —$CH_2SO_2NHR^{19}$, or —$CH_2OCOR^{19}$;

$R^{19}$ and $R^{19a}$ are each independently hydrogen, lower alkyl, aryl, arylalkyl, heteroaryl, or cycloalkyl;

wherein A is N while B and C are CH; and pharmaceutically acceptable salts, esters, amides, and prodrugs thereof.

4. A compound of the formula:

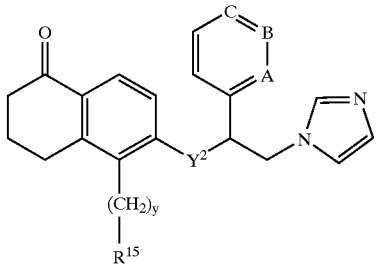

IV wherein:
y is 0, 1, 2, or 3;
$R^{15}$ is lower alkyl, lower alkenyl, alkoxy, substituted alkoxy, arylalkoxy, —O-cycloalkyl, —O-alkenyl, alkylthio, hydroxy, thiol, cyano, halogen, —CF$_3$, —NO$_2$, —NH$_2$, —NH-alkyl, —NH-dialkyl, —NHCO-alkyl, —CO$_2$H, —CO$_2$-alkyl, —SO$_3$H, —O-aryl, —O-substituted aryl, —O-heteroaryl, —O-substituted heteroaryl, —S-alkyl, —S-substituted alkyl, —S-cycloalkyl, —S-aryl, —S-substituted aryl, —S-heteroaryl, —S-substituted heteroaryl, —SO$_2$NH$_2$, —SO$_2$NH-alkyl, —SO-aryl, —SO$_2$-aryl, —SO$_2$-substituted aryl, —SO$_2$-alkyl, —SO$_2$-heteroaryl, —SO$_2$-substituted heteroaryl, —NHSO$_2$-aryl, —NHCO-aryl, —NHCO-heteroaryl, —NHCO$_2$-alkyl, —NH-aryl, —NH-substituted aryl, aryl, substituted aryl, heteroaryl, and substituted heteroaryl;
$Y^2$ is $NR^{16}$, O, S, or $CR^{17}R^{17a}$;
$R^{16}$ is hydrogen, lower alkyl, aryl, arylalkyl, heteroaryl, or cycloalkyl;
$R^{17}$ and $R^{17a}$ are each independently hydrogen, lower alkyl, lower alkenyl, cycloalkyl, aryl, substituted aryl, arylalkyl, substituted arylalkyl, heteroaryl, substituted heteroaryl, heteroarylalkyl, substituted heteroarylalkyl, heterocycloalkyl, substituted heterocycloalkyl, heterocyclalkylalkyl, substituted heterocycloalkylalkyl, halogen, trifluoromethyl, —OR$^{19}$, —NR$^{19}$R$^{19a}$, NHSO$_2$R$^{19}$, —S(O)$_z$R$^{19}$, —SO$_2$NHR$^{19}$, —OCOR$^{19}$, —CH$_2$OR$^{19}$, —CH$_2$NR$^{19}$R$^{19a}$, —CH$_2$S(O)$_z$R$^{19}$, —CH$_2$NHSO$_2$R$^{19}$, —CH$_2$S(O)$_z$R$^{19}$, —CH$_2$SO$_2$NHR$^{19}$, or —CH$_2$OCOR$^{19}$;
$R^{19}$ and $R^{19a}$ are each independently hydrogen, lower alkyl, aryl, arylalkyl, heteroaryl, or cycloalkyl;
wherein B is N while A and C are CH; and
pharmaceutically acceptable salts, esters, amides, and prodrugs thereof.

5. A compound of any one of claim 3 or claim 4 wherein $Y^2$ is O.

6. A compound of any one of claim 3 or claim 4 wherein y is 2 and $R^{15}$ is aryl or heteroaryl.

7. A compound of any one of claim 3 or claim 4 wherein y is 1.

8. A compound of any one of claim 3 or claim 4 wherein $R^{15}$ is —O-substituted aryl, —O-heteroaryl, —O-substituted heteroaryl, —S-alkyl, —S-substituted alkyl, —S-cycloalkyl, —S-aryl, —S-substituted aryl, —S-heteroaryl, —S-substituted heteroaryl, —SO$_2$NH$_2$, —SO$_2$NH-alkyl, —SO-aryl, —SO$_2$-aryl, —SO$_2$-substituted aryl, —SO$_2$-alkyl, —SO$_2$-heteroaryl, —SO$_2$-substituted heteroaryl, —NHSO$_2$-aryl, —NHCO-aryl, —NHCO-heteroaryl, —NHCO$_2$-alkyl, —NH-aryl, —NH-substituted aryl, aryl, substituted aryl, heteroaryl, or substituted heteroaryl.

9. A compound of any one of claim 3 or claim 4 wherein $R^{15}$ is aryl, heteroaryl, —SO$_2$-alkyl, —SO$_2$-heteroaryl, or —NHCO-heteroaryl.

10. A compound of any one of claim 3 or claim 4 wherein $R^{15}$ is —SO$_2$-alkyl, —SO$_2$-heteroaryl, or —NHCO-heteroaryl.

11. A compound of any one of claim 3 or claim 4 which is selected from the group consisting of
(±)-6-(2-Imidazolyl-1-(2-pyridyl)ethoxy)-5-(2-phenylethyl)-2,3,4-trihydronaphthalen-1-one;
(±)-6-(2-Imidazolyl-1-(3-pyridyl)ethoxy)-5-(2-phenylethyl)-2,3,4-trihydronaphthalen-1-one;
6-((S)-2-Imidazol-1-yl-1-pyridin-3-yl-ethoxy)-5-phenethyl-3,4-dihydro-2H-naphthalen-1-one;
6-((S)-2-Imidazol-1-yl-1-pyridin-3-yl-ethoxy)-5-(propane-2-sulfonylmethyl)-3,4-dihydro-2H-napthalen-1-one;
6-((S)-2-Imidazol-1-yl-1-pyridin-3-yl-ethoxy)-5-(pyridin-2-ylsulfonylmethyl)-3,4-dihydro-2H-napthalen-1-one;
6-((S)-2-Imidazol-1-yl-1-pyridin-3-ethoxy)-5-(2-pyridin-2-yl-ethyl)-3,4-dihydro-2H-naphthalen-1-one;
Isoquinoline-1-carboxylic acid [2-((S)-2-imidazol-1-yl-1-pyridin-3-yl-ethoxy)-5-oxo-5,6,7,8-tetrahydro-naphthalen-1-yl]-amide;
Pyrazine-2-carboxylic acid [2-((S)-2-imidazol-1-yl-1-pyridin-3-yl-ethoxy)-5-oxo-5,6,7,8-tetrahydro-naphthalen-1-yl]-amide; and
Cinnoline-4-carboxylic acid [2-((S)-2-imidazol-1-yl-1-pyridin-3-yl-ethoxy)-5-oxo-5,6,7,8-tetrahydro-naphthalen-1-yl]-amide.

12. A compound of any one of claim 3 or claim 4 which is selected from the group consisting of
6-((S)-2-Imidazol-1-yl-1-pyridin-3-yl-ethoxy)-5-(propane-2-sulfonylmethyl)-3,4-dihydro-2H-napthalen-1-one;
6-((S)-2-Imidazol-1-yl-1-pyridin-3-yl-ethoxy)-5-(pyridin-2-ylsulfonylmethyl)-3,4-dihydro-2H-napthalen-1-one;
Isoquinoline-1-carboxylic acid [2-((S)-2-imidazol-1-yl-1-pyridin-3-yl-ethoxy)-5-oxo-5,6,7,8-tetrahydro-naphthalen-1-yl]-amide; and
Pyrazine-2-carboxylic acid [2-((S)-2-imidazol-1-yl-1-pyridin-3-yl-ethoxy)-5-oxo-5,6,7,8-tetrahydro-naphthalen-1-yl]-amide.

* * * * *